US008124840B2

(12) United States Patent
Goddijn et al.

(10) Patent No.: US 8,124,840 B2
(45) Date of Patent: Feb. 28, 2012

(54) REGULATING METABOLISM BY MODIFYING THE LEVEL OF TREHALOSE-6-PHOSPHATE

(75) Inventors: Oscar Johannes Maria Goddijn, Leider (NL); Jan Pen, Leiden (NL); Josephus Christianus Maria Smeekens, Driebergen (NL)

(73) Assignee: Syngenta Mogen B.V., Leiden (NL)

( * ) Notice: Subject to any disclaimer, the term of this patent is extended or adjusted under 35 U.S.C. 154(b) by 0 days.

(21) Appl. No.: 11/818,157

(22) Filed: Jun. 13, 2007

(65) Prior Publication Data

US 2008/0138903 A1 Jun. 12, 2008

Related U.S. Application Data

(62) Division of application No. 10/682,456, filed on Oct. 9, 2003, now Pat. No. 7,247,770, which is a division of application No. 09/171,937, filed as application No. PCT/EP97/02497 on May 2, 1997, now Pat. No. 6,833,490.

(30) Foreign Application Priority Data

May 3, 1996 (EP) .................................... 96201225
Jul. 26, 1996 (EP) .................................... 96202128
Aug. 29, 1996 (EP) .................................... 96202395

(51) Int. Cl.
*C12N 15/82* (2006.01)
*C12N 15/29* (2006.01)
*C12N 15/09* (2006.01)
*C12N 15/00* (2006.01)

(52) U.S. Cl. ..... 800/284; 800/278; 435/468; 435/320.1; 536/23.1; 536/23.2; 536/23.6

(58) Field of Classification Search ........................ None
See application file for complete search history.

(56) References Cited

U.S. PATENT DOCUMENTS

| | | | |
|---|---|---|---|
| 5,422,254 A * | 6/1995 | Londesborough et al. | 435/97 |
| 6,130,368 A * | 10/2000 | Londesborough et al. | 800/298 |
| 6,133,034 A | 10/2000 | Strom et al. | |
| 6,833,490 B1 * | 12/2004 | Goddijn et al. | 800/284 |

FOREIGN PATENT DOCUMENTS

| | | |
|---|---|---|
| EP | 0438904 A1 | 7/1991 |
| EP | 0442592 A2 | 8/1991 |
| EP | 0451896 A1 | 10/1991 |
| EP | 0530978 A2 | 3/1993 |
| EP | 0577915 | 1/1994 |
| EP | 0784095 A2 | 7/1997 |
| WO | WO/93/17093 | 9/1993 |
| WO | WO/95/01446 | 1/1995 |
| WO | WO 95/24487 | 9/1995 |
| WO | WO/96/00789 | 1/1996 |
| WO | WO/96/17069 | 6/1996 |
| WO | WO 96/21030 | 7/1996 |
| WO | WO 97/26357 | 7/1997 |
| WO | WO 97/42327 | 11/1997 |

OTHER PUBLICATIONS

Vogel et al The Plant Journal 1998, 13:673-683, provided by Applicant IDS.*
Romero et al Planta, 1997 201:293-297.*
Goddijn et al., "Transgenic Tobacco Plants as a Model-System for the Production of Trehalose," Plant Physiology, vol. 108, No. 2, Jun. 1, 1995, p. 149.
Jang et al., "Sugar Sensing in Higher Plants," Plant Cell, vol. 6, Nov. 1990, pp. 1665-1679.
Lu et al., Cancer Research, vol. 52, Jul. 1992, pp. 3718-3725.
Holmstrom et al., "Drought tolerance in plants," Nature, vol. 379, Feb. 22, 1996, pp. 683-684.
Blaquez et al., "Trehalose-6-phosphate, a new regulator of yeast glycolysis that inhibits hexokinases," Febs Letter, vol. 329, No. 1, 2, 1993, pp. 51-54.
Holmann et al., Molecular Microbiology, vol. 20, No. 5, 1996, pp. 981-991.
Luyten et al., Dissertation Abstracts International, vol. 58, No. 1C, 1996, p. 105, Order No. AARC537180 Abstract.
Kaasen et al., Gene, vol. 145, 1994, pp. 9-15.
Newman et al., "11536 Arabidopsis thaliana cDNA clone 151A11T7," EMBL Sequence Database, Release 43, Mar. 25, 1995, Accession No. T76758.
Newman et al., "13527 Arabidopsis thaliana cDNA clone 170D15T7," EMBL Sequence Database, Release 44, Jun. 4, 1995, Accession No. R65023.
Thevelein et al., "Trehalose synthase: guard to the gate of glycolysis in yeast?" Trends in Biochemical Sciences, vol. 20, No. 1, Jan. 1995, pp. 3-10.
De Virgillio et al., Eur. J. Biochem., vol. 212, 1993, pp. 315-323.
Foyer et al., Plant Physiology, vol. 6, No. 5, Nov. 1, 1994, pp. 637-650.
Kossmann et al., Plant Journal, vol. 6, No. 5, Nov. 1, 1994, pp. 637-650.
Hajirezaei et al., Plant, vol. 192, 1994, pp. 16-30.
Trethewey et al., International Conf on the Transport of Photoassimilates, Canterbury, England, UK, Aug. 13-17, 1995, Journal of Experimental Botany, 47 (Spec. Issue),1996.
Vogel et al., Plant Journal, vol. 13, No. 5, 1998, pp. 673-683.
Avonce et al., "The Arabidopsis Trehalose-6-P Synthase *AtTPS1* Gene is a Regulator of Glucose, Abscisic Acid, and Stress Signaling," *Plant Physiol*., 2004, 136(3):3649-3659.
Ge et al., "Overexpression of the Trehalose-6-Phophate Phosphatase gene OsTPP1 Confers Stress Tolerance in Rice and Results in the Activation of Stress Responsive Genes," *Planta*, 2008, 228(1):191-201 (abstract only).
Miranda et al., "A Bifunctional TPS-TPP Enzyme from Yeast Confers Tolerance to Multiple and Extreme Abiotic-Stress Conditions in Transgenic Arabidopsis," *Planta*, 2007, 226(6):1411-1421 (abstract only).

* cited by examiner

*Primary Examiner* — Brent T Page

(57) ABSTRACT

Method for the inhibition of carbon flow in the glycolytic direction in a cell by increasing the intracellular availability of trehalose-6-phosphate.

15 Claims, 42 Drawing Sheets

```
LINEUP of: TPSPLANT  from: 1  to: 595   April 19, 1996 14:01  ..

           1                                                  50
Tpsyeast   MTTDNAKAQL TSSSGGNIIV VSNRLPVTIT KNSSTGQYEY AMSSGGLVTA

           51                                                100
Tpsyeast   LEGLKKTYTF KWFGWPGLEI PDDEKDQVRK DLLEKFNAVP IFLSDEIADL

           101                                               150
Tpssel8                                                        .
Tpsyeast   HYNGFSNSIL WPLFHYHPGE INFDENAWLA YNEANQTFTN EIAKTMNHND

           151                                               200
Tpsrice2                                                YRSLPVR
Tpssun10                                  GWFLHTPFPS SEVYKTLPMR
Tpssel43                                  GWFLHTPFPS SEIYRTLPLR
Tpssel8    IMWVHDYHLC LVPQMIRQKL PDVQI..... GFFLHTAFPS SEVFRCLAAR
Tpsyeast   LIWVHDYHLM LVPEMLRVKI HEKQLQNVKV GWFLHTPFPS SEIYRILPVR

           201                                               250
Tpsrice2   DEILKSLLNC DLIGFHTFDY ARHFLSCCSR MLGIEYQSKR GYIGLDYFGR
Tpssun10   NELLKGLLNA DLIGFHTYDY ARHFLTCCSR MFGLDHQLKR GYIFLEYNGR
Tpssel43   AELLQGVLGA DLVGFHTYDY ARHFVS.... ..AMHTDTRA GRHSQGVEDQ
Tpssel8    KELLDGMLGA NLVAFQTPEY AHHFLQ.... ..XVQSHXSL LKQPR.....
Tpsyeast   QEILKGVLSC DLVGFHTYDY ARHFLSSVQR VLNVNTLPNG VEYQGRFVNV

           251                                               300
Tpsrice2   TVGIKIMPVG INMTQLQTQI RLPDLEWRVA NSGSSLMGRL SCSVWMIWTY
Ricetps                     EWRV SELQQQFEGK .......TVL ....LGVDDM
Tpssun10   SIEIKIKASG IHVGRMESYL SQPDTRLQVQ EVK..KEIVL ....LGVDDL
Tpssel43   GKITRVAA.. FPVDRFGAIY RRVETDAVKK HMQELSQVLL S*GYVGVDRL
Tpssel8    ......KA.. FS.XRFVNVW ...SX..MQE ALRXVKKVIV ARDKLTTSR.
Tpsyeast   GAFPIGIDVD KFTDGLKKES VQKRIQQLKE TFKGCKIIV. .....GVDRL

           301                                               350
Tpsatal3                                                     .G
Tpsatal56                        N EELRGKVVLV QITNPARSS. .........G
Tpsrice2   LR..GLI*KF LRFEQMLRTH PKWQPRQFWC RFKPRVVVGR TLXYSXDXXV
Ricetps    DIFKGINLKL LAFENMLRTH PKWQGRAVLV QIANPARGK. .........G
Tpssun10   DIFKGVNFKV LALEKLLKSH PSWQGRVVLV QILNPSR.R. .........C
Tpssel43   DMIKGIPQKL LAFEKFLEEN SEWRDKVVLV QIAVPTRTD. .........V
Tpssel8    .....VREKL LSYELFLNKN PQWRDKVVLI QVATSTTEDS ELAATXYPKL
Tpsyeast   DYIKGVPQKL HAMEVFLNEH PEWRGKVVLV QVAVPSRGDV EEYQYLRSVV
```

Fig. 3 (part 1)

```
            351                                                   400
  Tpsatal3  IDVEEIRGEI EESCRRING. EFGKXGYQPI IYIDXPVSIN EINAYXHIAE
 Tpsatal56  KDVQDVEKQI NXIADEINSK FGRPGGYKPI VFVNGPVSTL DKVAYYAISE
  Tpsrice2  QXVMTFQAGI SL
   Ricetps  KDLEAIQAEI HESCKRING. EFGQSGYSPV VFIDRDVSSV EEDCLLHNSR
  Tpssun10  QDVDEINAEI RTVCERINN. ELGSPGYQPV VLIDGPVSLS EKAAYYVIAD
  Tpssel43  LEYQKLTSQV HEIVGRING. RFGSLTAVPI HHLDRSMKFP ELCALYAITD
   Tpssel8  LHVLTLCTRR SHTPTRLPQ. ARHCVLAVPR TSLDRRCSCN QLF.......
 Tpsyeast   NELVG..... .....RING. QFGTVEFVPI HFMHKSIPFE ELISLYAVSD

            401                                                   450
  Tpsatal3  CVVVTAVRDG MNLTPYEYIV CRQGLLGSES DFSGPKKSML ....VASXFI
 Tpsatal56  CVVVNXVRDG MNLVPYKYTV TRQGSPALDA ALGFGEDDVR KSVIIVSEFI
Tpsatal142                                   AVVDSSPR TSTLVVSEFI
  Tpsrice3                                        GPK KSMLVVSEFI
   Ricetps  MCGGDCC*GW D*LDTIWIYC L*GRGLTXHQ R
  Tpssun10  MAIVTPLRDG MNLV
  Tpssel43  VLLVTSLRDG MNFV
   Tpssel8  ........DG MNLV
  Tpsyeast  VCLVSSTRDG MNLVSYEYIA CQEE..... .........K KGSLILSEFT

            451                                                   500
  Tpsatal3  WMXPFRLXGA IRVNPW
 Tpsatal56  GCXP.SLSGA IXVNPWNIXA V
Tpsatal142  GCSP.SLSGA IRVNPWDVDA VAEAVNSALK MSETEKQLRH EKHYHYISTH
  Tpsrice3  GCSP.SLSGA IRVNPWNIEA TAEALNEAIS MSERXKQLRH EKHYRYVSTH
  Tpsyeast  GAAQ.SLNGA IIVNPWNTDD LSDAINEALT LPDVKKEVNW EKLYKYISKY

            501                                                   550
Tpsatal142  DVGYWAKSFM QDLERACRDH YSKRCWGIGF GLGFRVLSLSP SFRKLS
  Tpsrice3  DVAYWSKSFV QDLERACKDH FRKPCWGIGX GFRXR
  Tpsyeast  TSAFWGENFV HELYSTSSSS TSSSATKN** TRCK*DDRLF LVRFSLPSLL

            551                                          595
  Tpsyeast  FTFFILYIKL YK*HN*NATR PLLFVNACL* RC*LKLRK*F FHRIG
```

Fig. 3 (part 2)

ALIGNMENT TOBACCO TPS GENES WITH YEAST TPS1

```
              1              15 16           30 31          45 46          60 61          75 76          90
1 TPS840      ---GHIDPZRNC-SE RVMLZCVKQQF--EG KTVLLGADDLDIFKG MNLKLLAMEQMINIT PSGKGRLCWSKIANP TRGKGVDFDEIQAEI   84
2 TPS630      IIWGSFSNLDLP-ET EAKVFGTRQQFNHQG RTLLLGVDDMDIFKG ISLKLLAMEQLLLQH PEKQGKVVLVQIANP ARGKGKDVKEVQEET   89
3 TPS825      IHMGQLQNVMSLXDT GKKAKELKEKY--EG KIVMLGIDDMDMFKG IGLKFLAMGRILDEN PVLRGKVVLVXXXXX XXXXXXXXXXXXXXX   88
4 yeastTPS1   -DVDKFTDGLKKESV QKRIQQLKETF--KG CKIIVGVDRLDYIKG VPQKLEAMEVFLNEH PEWRGKVVLVQVAVP SRGDVEEYQYLRSVV   87

              91             105 106         120 121         135 136         150 151         165 166         180
1 TPS840      SESCKRINKQFGKPG YEPIVYIDRPVSSSE RMAYYSIAGCVVVTA VSDGMNLF        137
2 TPS630      SLTVKRINEAFGRPG YEPVILIDKPLKFYE RIAYYVVAECCLVTA VSDGMNLV        142
3 TPS825      XXXXXXINKKYGKPG YKPIVCINGPVSTQD KIAHYAVXECVVVNA VRDGMN--        139
4 yeastTPS1   NELVGRINGQFGTVE FVPIHFMHKSIPFEE LISLYAVSDVCLVSS TRDGMNLV        140
```

FIG. 4

Alignment sunflower bipartite with yeast TPS2

```
             1            15 16            30 31            45 46            60 61            75 76            90
1 bipsunfl   --------------- --------------- --------------- --------------- --MHIKDALPAAVEV FYVGALRADVG-PTE    27
2 yeastTPS2  MTTTAQDNSPKKRQR IINCVTQLPYKIQLG ESNDDWKISATTGNS ALYSSLEYLQFDSTE YEQHVVGWTGEITRT ERNLFTREAKEKPQD    90
             91          105 106          120 121          135 136          150 151          165 166          180
1 bipsunfl   QDD------------ VSRTILLDRFN----- --CVAVFVPTS---- ------KWDQYYHCF CKQYLWPIFEYKVPA SDVKSVPNSRDSWNA    88
2 yeastTPS2  LDDDPLYLTKEQING LTTTIQDHMKSDKEA KTDTTQTAPVTNNVH PVWLLRKNQSRWRNY AEKVIWETFEYILNP SNEGEQ--EKNWWYD   178
             181         195 196          210 211          225 226          240 241          255 256          270
1 bipsunfl   YVHVNKEFSQKVMEA VTNASNYVWIHDYHL MTLPTFLRRDFCR-- FKIGFFLHSPFPSSE VYKTLPMRNEIIKGL LNADLIGFHTYDYAR   176
2 yeastTPS2  YVKFNEAYAQKIGEV YRKG-DIIWIHDYYL LILPQLLRMKFNDES IIIGYFHHAPWPSNE YFRCLPRRKQILDGL VGANRICFQNESFSR   267
             271         285 286          300 301          315 316          330 331          345 346          360
1 bipsunfl   HFLTCCSRMFGLDHQ LKRG------YIFLE YNGRSIEIKIKASGI HVGRMESYLSQPDTR LQVQELKKRFEGKIV LLGVDDLDIFKGVNF   260
2 yeastTPS2  HFVSSCRRLLDATAK KSKNSSDSDQYQVSV YGG-DVLVDSLPIGV NTTQILKDAFTKDID SKVLSIKQAYQNKKI IIGRDRLDSVRGVVQ   356
             361         375 376          390 391          405 406          420 421          435 436          450
1 bipsunfl   KVLALEKLLKSEHSW QGRVVLVQILNPARA R-CQDVDEINAEIRT VCERINNELGSPGYQ PVVLIDGPVSLSEKA AYYAIADMAIVTPLR   349
2 yeastTPS2  KLRAFETFLAMYPEW RDQVVLIQVSSPTAN RNSPQTIRLEQQVNE LVNSINSEYGNLNFS PVQHYYMRIPKDVYL SLLRVADLCLITSVR   446
             451         465 466          480 481          495 496          510 511          525 526          540
1 bipsunfl   DGMNLIPYEYVVSRQ SVNDPNPNTPKKSML VVSEFIGCSLSLTGA IRVNPWDELETAEAL YDALMAPDDHKETAH MKQYQYIISHDVANW   439
2 yeastTPS2  DGMNTTALEYVTVKS HMSN---FLCYGNFL ILSEFSGSSNVLKDA IVVNPWDSVAVAKSI NMALKLDKEEKSNLE SKLWKEVP--TIQDW   531
             541         555 556          570 571          585 586          600 601          615 616          630
1 bipsunfl   ARSFFQDLEQACIDH SRKRCMNLGFGLDTR VVLFDEKFSKLDIDV IENAYSMAQNRAILL DYDGTVTPSISK--- -SPTEAVISMINKLC   525
2 yeastTPS2  TNKFLSSLKEKASSD DD------------- --VERKMTPALNRFV ILENYKQAKRRLFLF DYDGTLTPIVKDPAA AIPSARLYTILQKLC   606
             631         645 646          660 661          675 676          690 691          705 706          720
1 bipsunfl   NDPKNMVFIVSGRSR ENLGSWFG-ACEKPA IAAEHGYFIRWAGDQ EWETCARENNVGWME MAEPVMNLYTETTDG SYIEKKETAMVWHYE   614
2 yeastTPS2  ADPHNQIWIISGRDQ KFLNKWLGGKLPQLG LSAEHGCFMKDVSCQ DWVNLTEKVDMSWQV RVNEVMEEFTTRTPG SFIERKKVALTWHYR   696
             721         735 736          750 751          765 766          780 781          795 796          810
1 bipsunfl   DADKDLGLEQAKELL DELENVLANEPVEVK RGQYIVEVKPQVPHX LPSCYDIHRERFVES FNLNFFKYECNYRGS XKGIVAEKIFAFMAE   704
2 yeastTPS2  RTVPELGEFHAKELK EKLLSFTDDFDLEVM DGKANIEVRPRFVNK GEIVKRLVWEQHGKP QDMLKGISEKLPKDE MPDFVLCLGDDFTDE   786
             811         825 826          840 841          855 856          870 871          885 886          900
1 bipsunfl   -KGKQADFVLSVGDD RS-DED--------M FVAIGDGIKK----G RITNNN---SVFTCV VGEK---PSAAEYFL D--------ETKDVS   766
2 yeastTPS2  DMFRQLNTIETCWKE KYPDQKNQWGNYGFY PVTVGSASKKTVAKA HLTDPQQVLETLGLL VGDVSLFQSAGTVDL DSRGHVKNSESSLKS   876
             901         915 916          930 931          945 946          960 961          975 976          990
1 bipsunfl   MMLEKLGCLSNQG-- -----     779
2 yeastTPS2  KLASKAYVMKRSASY TGAKV     896
```

Fig. 6

ALIGNMENT PLANT TPS GENES WITH YEAST TPS1

```
              1             15 16           30 31           45 46           60 61           75 76           90
1 TPS1arab    KQHMKELKERFTDRK VMLGVDRLDMIKGIP QKILAFEKFLEENAN WRDKVVLLKIAVPTR PDVPEYQTLTSQVEE IVGRIIGRIGTLTAV   90
2 TPS1yeast   --RIQQLKETFKGCK IIVGVDRLDYIKGVP QKLEAMEVFLNEHPE WRGKVVLVQVAVPSR GDVEEYQYLRSVVNE LVGRINGQFGTVEFV   88
3 ESTrice     EWRVSELQQQFEGKT VLLGVDDMDIFKGIN LKLLAFENMLRTHPK WQGRAVLVQIANPAR GKGKDLEAIQAEIEE SCKRINGEFGQSGYS   90

              91           105 106          120 121          135 136          150 151          165 166          180
1 TPS1arab    PIHHLDRSLDFHALC ALYAVTDVALVTSLR DGMNLV          126
2 TPS1yeast   PIHFMHKSIPFEELI SLYAVSDVCLVSSTR DGMNL-          123
3 ESTrice     PVVFIDRDVSSVEED CL------------- ------          107
```

FIG. 7

ALIGNMENT HUMAN TPS GENE WITH YEAST TPS1

```
                1             15 16         30 31         45 46         60 61         75 76         90
1 humTPS        DVMWMHDYHLMVLPT FLR-----RRFNRLR MGFFLHSPFPSSEIY RILPVREEILKAILC ADIVGFHTFDYARHF LSCCSRMLGLEYQSK   85
2 yeastTPS1     DLIWVHDYHLMLVPE MLRVKIHEKQLQNVK VGWFLHTPFPSSEIY RILPVRQEILKGVLS CDLVGFHTYDYARHF LSSVQRVLNVNTLPN   90

                91            105 106       120 121       135 136         150 151         165 166         180
1 humTPS        RGYIGLEYYGRTVGI KIMPVGIHMGHIESM KKLAAKELMLKALKQ QFEGKTVLLGADDLD IFKGINIKLLAMEQM LKQHPKWQGQAVLVQ   175
2 yeastTPS1     ----GVEYQGRFVNV GAFPIGIDVDKFTDG LKKESVQKRIQQLKE TFKGCKIIVGVDRLD YIKGVPQKLHAMEVF LNEHPEWRGKVVLVQ   176

                181           195 196       210 211       225 226         240 241         255 256         270
1 humTPS        IANPTRGKGVDFEEI QAEISESCKRINKQF GKPGYEPIVYIDRPV SSSERMAYYSIAECV VVTAVSDGMNFV   247
2 yeastTPS1     VAVPSRGDVEEYQYL RSVVNELVGRINGQF GTVEFVPIHFMHKSI PFEELISLYAVSDVC LVSSTRDGMNLV   248
```

FIG. 8

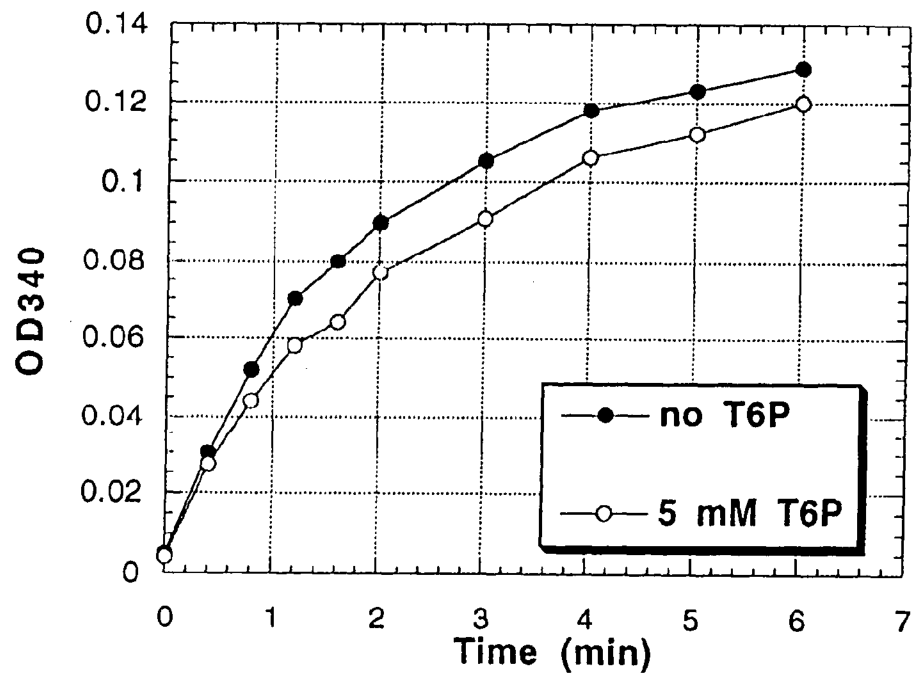
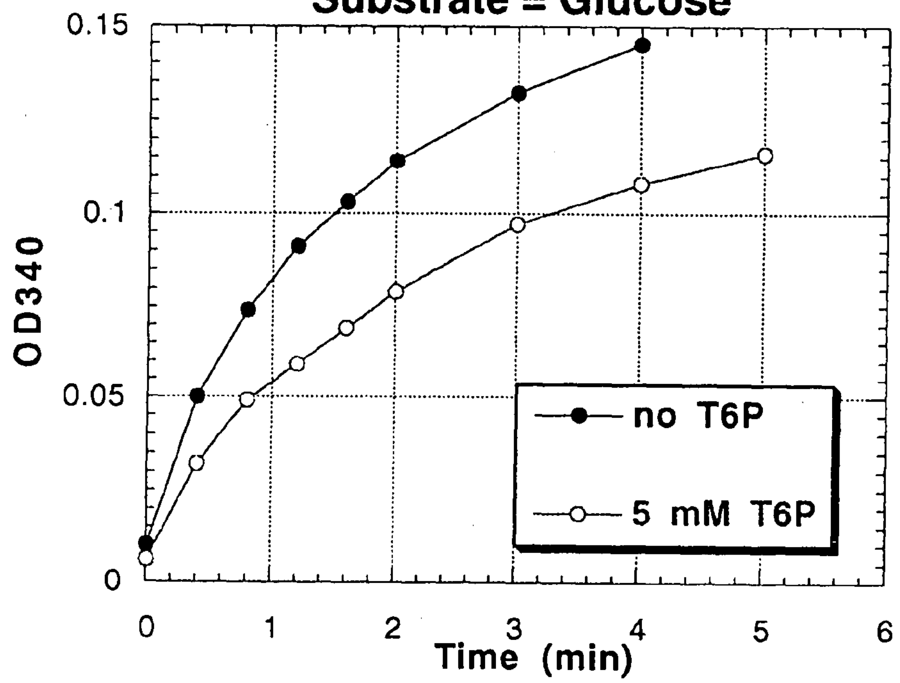
Fig. 12

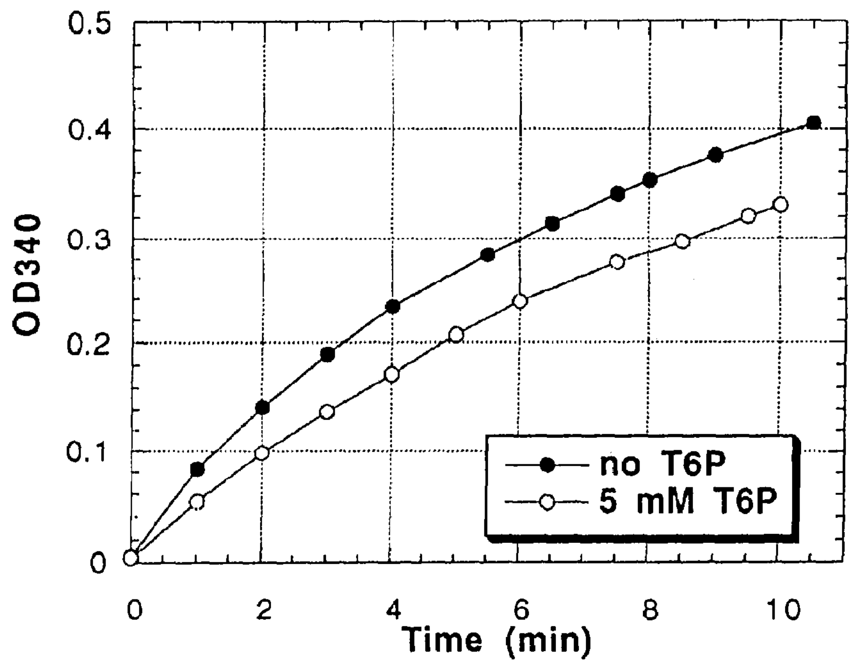
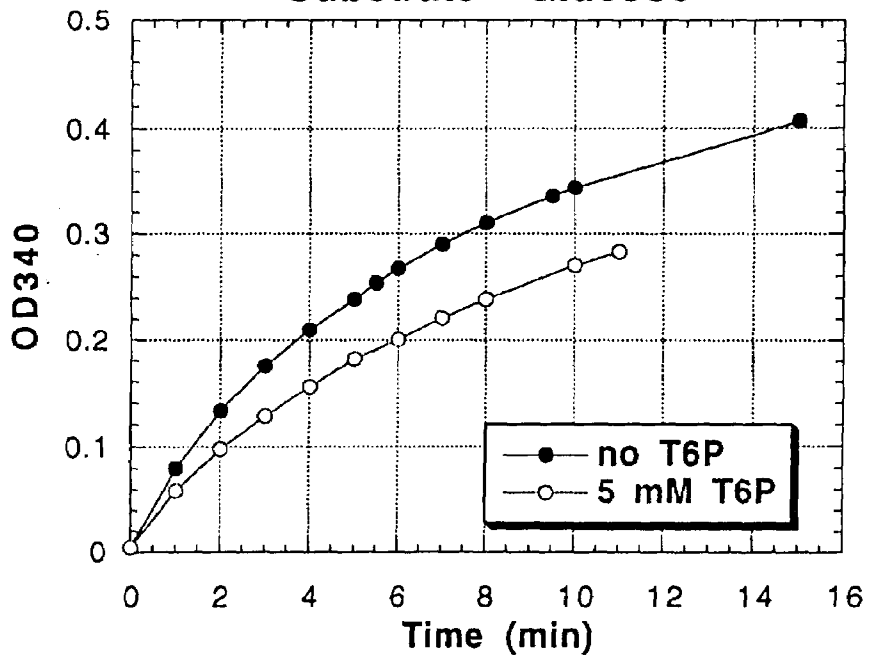
Fig. 15

TPP CONTROL TPS

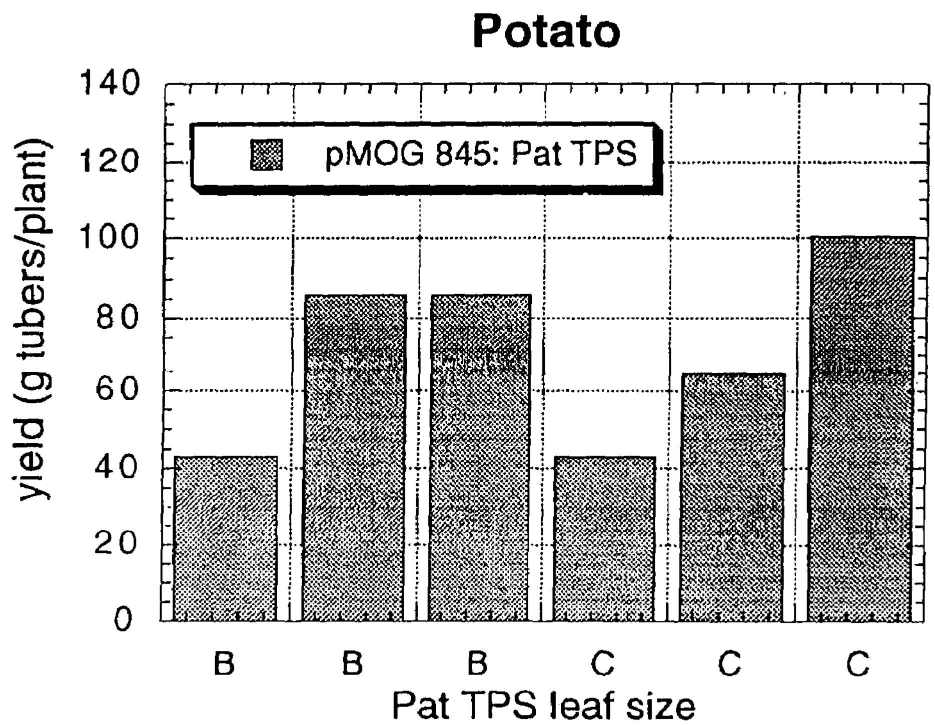
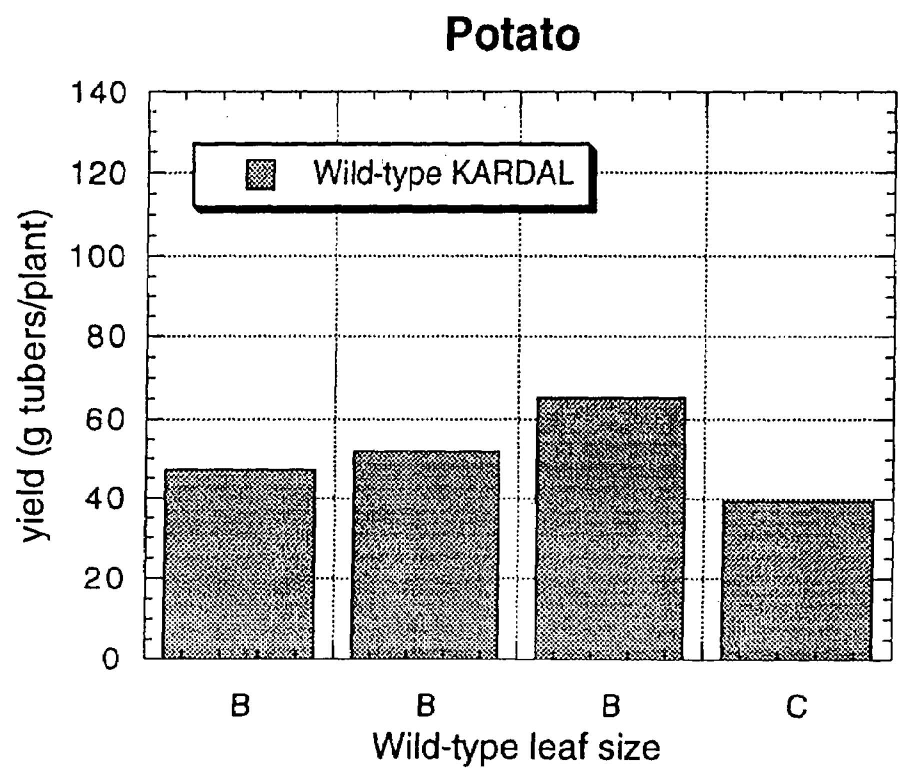
Fig. 27

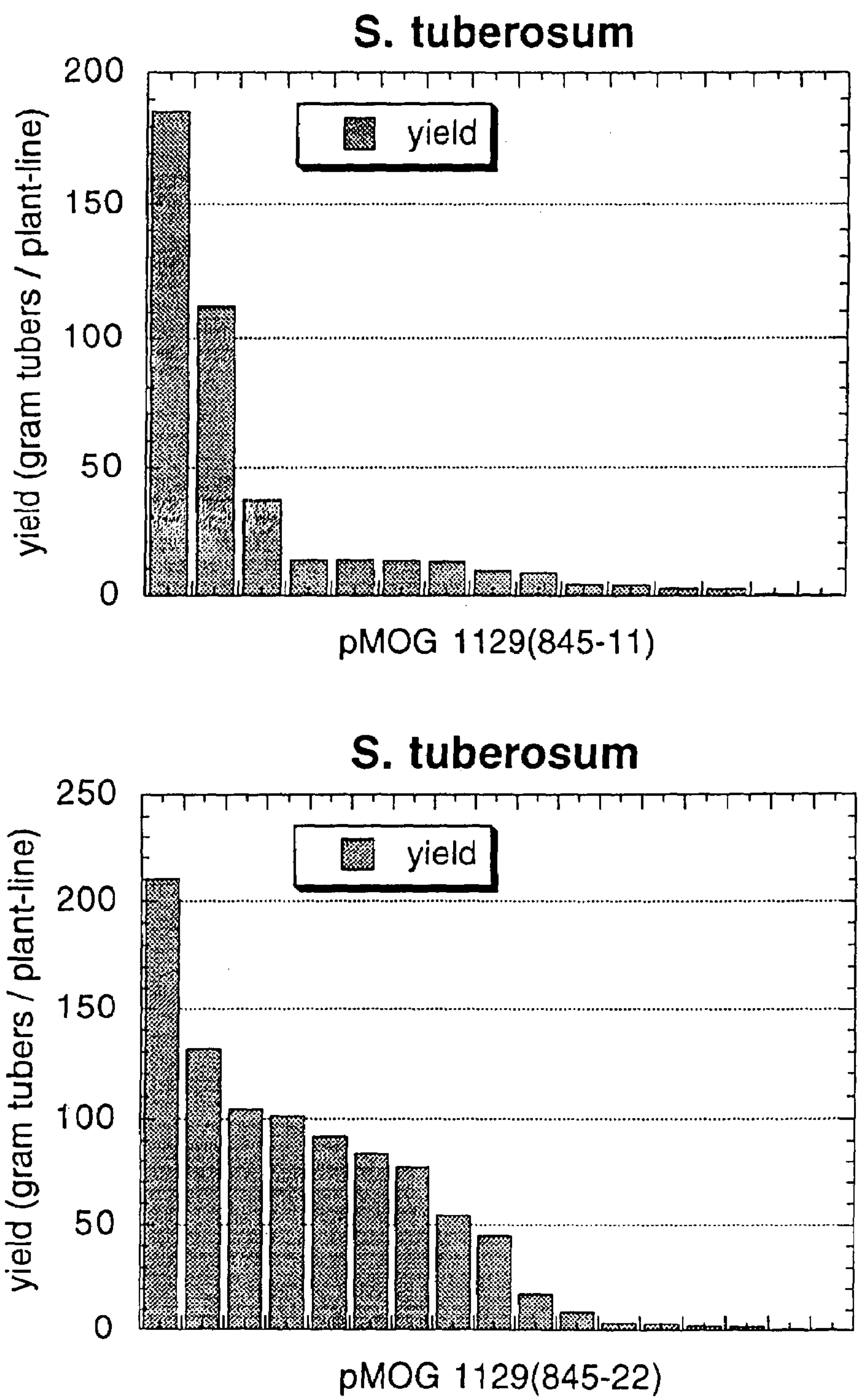
Fig. 28 (part 1)

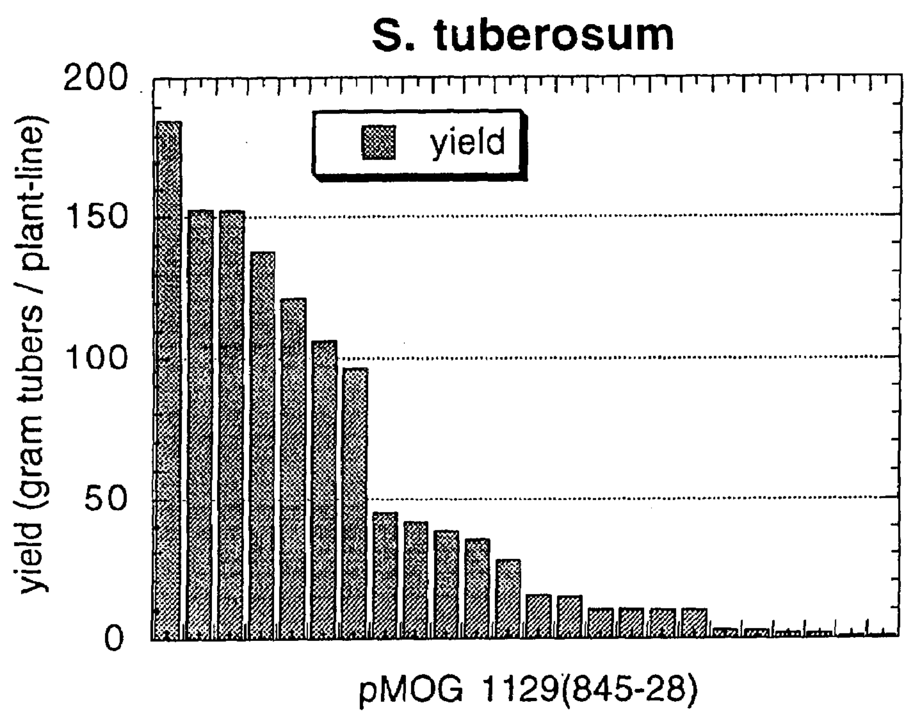
Fig. 28 (part 2)

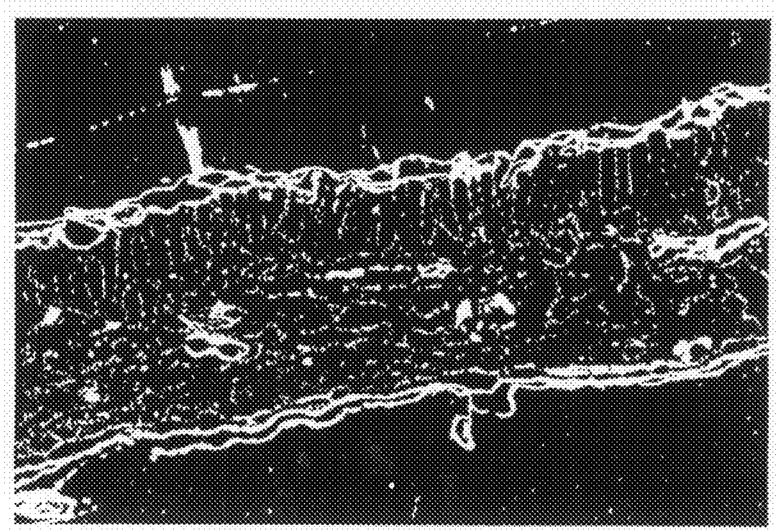
TPS TRANSGENIC TOBACCO LEAF
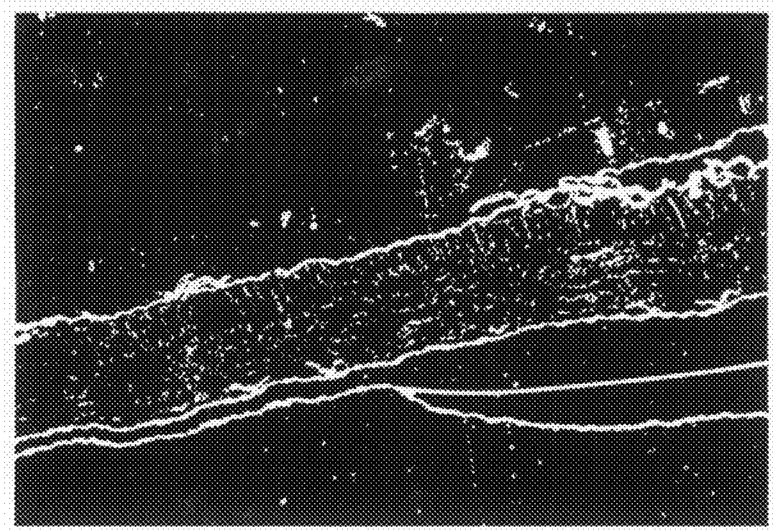
TPP TRANSGENIC TOBACCO LEAF
Fig. 29

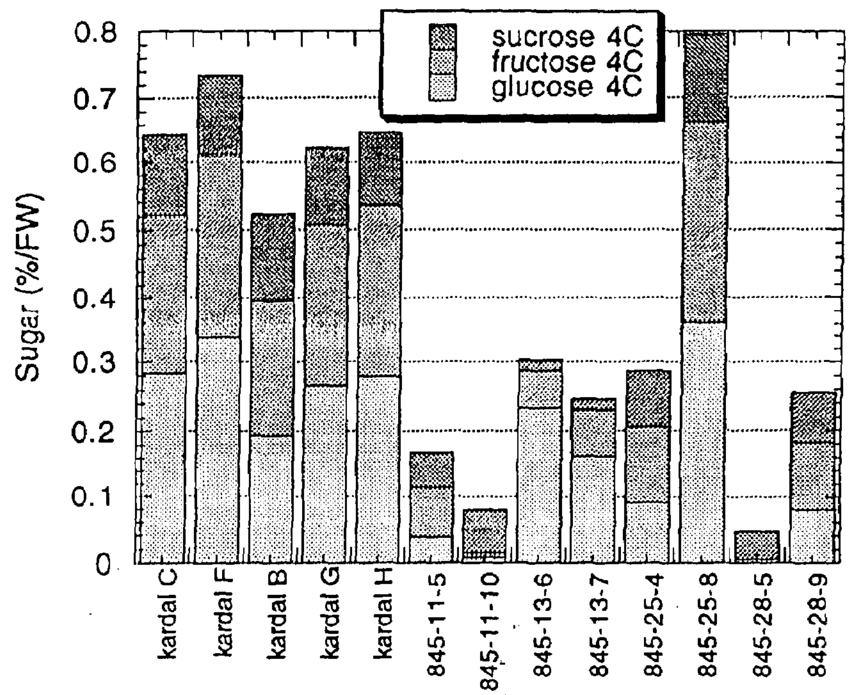
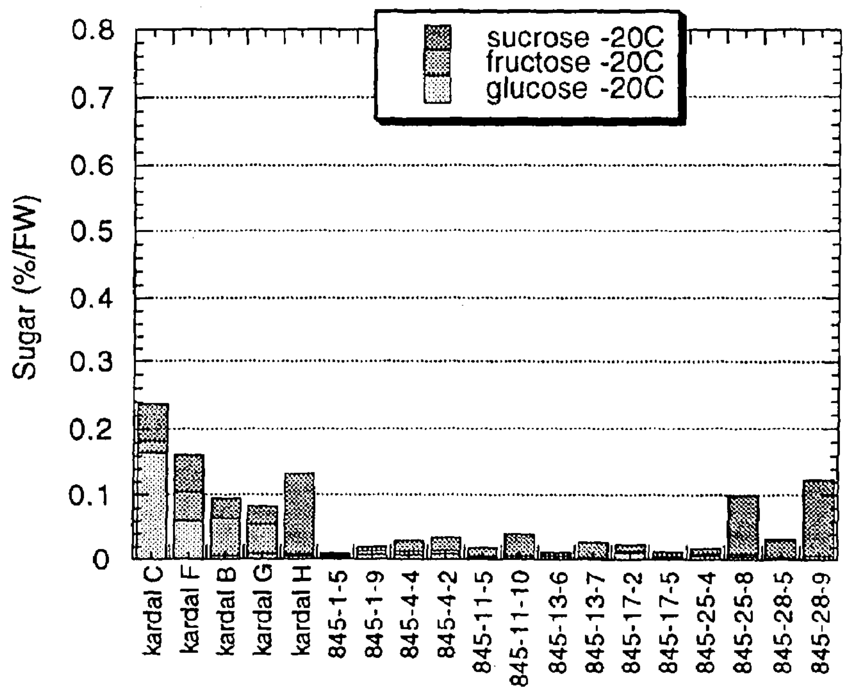
Fig. 30

SEQUENCE LISTING

```
(1) GENERAL INFORMATION:

   (iii) NUMBER OF SEQUENCES: 57


(2) INFORMATION FOR SEQ ID NO: 1:

     (i) SEQUENCE CHARACTERISTICS:
          (A) LENGTH: 1450 base pairs
          (B) TYPE: nucleic acid
          (C) STRANDEDNESS: double
          (D) TOPOLOGY: linear

    (ii) MOLECULE TYPE: DNA (genomic)

   (iii) HYPOTHETICAL: NO
```

```
    (ix) FEATURE:
          (A) NAME/KEY: CDS
          (B) LOCATION: 21..1450

    (xi) SEQUENCE DESCRIPTION: SEQ ID NO: 1:

ATAAAACTCT CCCCGGGACC ATG ACT ATG AGT CGT TTA GTC GTA GTA TCT         50
                      Met Thr Met Ser Arg Leu Val Val Val Ser
                        1               5                  10

AAC CGG ATT GCA CCA CCA GAC GAG CAC GCC GCC AGT GCC GGT GGC CTT       98
Asn Arg Ile Ala Pro Pro Asp Glu His Ala Ala Ser Ala Gly Gly Leu
                 15                  20                  25

GCC GTT GGC ATA CTG GGG GCA CTG AAA GCC GCA GGC GGA CTG TGG TTT      146
Ala Val Gly Ile Leu Gly Ala Leu Lys Ala Ala Gly Gly Leu Trp Phe
             30                  35                  40

GGC TGG AGT GGT GAA ACA GGG AAT GAG GAT CAG CCG CTA AAA AAG GTG      194
Gly Trp Ser Gly Glu Thr Gly Asn Glu Asp Gln Pro Leu Lys Lys Val
         45                  50                  55

AAA AAA GGT AAC ATT ACG TGG GCC TCT TTT AAC CTC AGC GAA CAG GAC      242
Lys Lys Gly Asn Ile Thr Trp Ala Ser Phe Asn Leu Ser Glu Gln Asp
     60                  65                  70

CTT GAC GAA TAC TAC AAC CAA TTC TCC AAT GCC GTT CTC TGG CCC GCT      290
Leu Asp Glu Tyr Tyr Asn Gln Phe Ser Asn Ala Val Leu Trp Pro Ala
 75                  80                  85                  90

TTT CAT TAT CGG CTC GAT CTG GTG CAA TTT CAG CGT CCT GCC TGG GAC      338
Phe His Tyr Arg Leu Asp Leu Val Gln Phe Gln Arg Pro Ala Trp Asp
                 95                 100                 105

GGC TAT CTA CGC GTA AAT GCG TTG CTG GCA GAT AAA TTA CTG CCG CTG      386
Gly Tyr Leu Arg Val Asn Ala Leu Leu Ala Asp Lys Leu Leu Pro Leu
            110                 115                 120

TTG CAA GAC GAT GAC ATT ATC TGG ATC CAC GAT TAT CAC CTG TTG CCA      434
Leu Gln Asp Asp Asp Ile Ile Trp Ile His Asp Tyr His Leu Leu Pro
        125                 130                 135

TTT GCG CAT GAA TTA CGC AAA CGG GGA GTG AAT AAT CGC ATT GGT TTC      482
Phe Ala His Glu Leu Arg Lys Arg Gly Val Asn Asn Arg Ile Gly Phe
    140                 145                 150

TTT CTG CAT ATT CCT TTC CCG ACA CCG GAA ATC TTC AAC GCG CTG CCG      530
Phe Leu His Ile Pro Phe Pro Thr Pro Glu Ile Phe Asn Ala Leu Pro
155                 160                 165                 170

ACA TAT GAC ACC TTG CTT GAA CAG CTT TGT GAT TAT GAT TTG CTG GGT      578
Thr Tyr Asp Thr Leu Leu Glu Gln Leu Cys Asp Tyr Asp Leu Leu Gly
                175                 180                 185

TTC CAG ACA GAA AAC GAT CGT CTG GCG TTC CTG GAT TGT CTT TCT AAC      626
Phe Gln Thr Glu Asn Asp Arg Leu Ala Phe Leu Asp Cys Leu Ser Asn
            190                 195                 200

CTG ACC CGC GTC ACG ACA CGT AGC GCA AAA AGC CAT ACA GCC TGG GGC      674
Leu Thr Arg Val Thr Thr Arg Ser Ala Lys Ser His Thr Ala Trp Gly
        205                 210                 215

AAA GCA TTT CGA ACA GAA GTC TAC CCG ATC GGC ATT GAA CCG AAA GAA      722
Lys Ala Phe Arg Thr Glu Val Tyr Pro Ile Gly Ile Glu Pro Lys Glu
    220                 225                 230

ATA GCC AAA CAG GCT GCC GGG CCA CTG CCG CCA AAA CTG GCG CAA CTT      770
Ile Ala Lys Gln Ala Ala Gly Pro Leu Pro Pro Lys Leu Ala Gln Leu
235                 240                 245                 250

AAA GCG GAA CTG AAA AAC GTA CAA AAT ATC TTT TCT GTC GAA CGG CTG      818
Lys Ala Glu Leu Lys Asn Val Gln Asn Ile Phe Ser Val Glu Arg Leu
                255                 260                 265

GAT TAT TCC AAA GGT TTG CCA GAG CGT TTT CTC GCC TAT GAA GCG TTG      866
Asp Tyr Ser Lys Gly Leu Pro Glu Arg Phe Leu Ala Tyr Glu Ala Leu
            270                 275                 280

CTG GAA AAA TAT CCG CAG CAT CAT GGT AAA ATT CGT TAT ACC CAG ATT      914
```

```
Leu Glu Lys Tyr Pro Gln His His Gly Lys Ile Arg Tyr Thr Gln Ile
        285                 290                 295

GCA CCA ACG TCG CGT GGT GAT GTG CAA GCC TAT CAG GAT ATT CGT CAT      962
Ala Pro Thr Ser Arg Gly Asp Val Gln Ala Tyr Gln Asp Ile Arg His
    300                 305                 310

CAG CTC GAA AAT GAA GCT GGA CGA ATT AAT GGT AAA TAC GGG CAA TTA     1010
Gln Leu Glu Asn Glu Ala Gly Arg Ile Asn Gly Lys Tyr Gly Gln Leu
315                 320                 325                 330

GGC TGG ACG CCG CTT TAT TAT TTG AAT CAG CAT TTT GAC CGT AAA TTA     1058
Gly Trp Thr Pro Leu Tyr Tyr Leu Asn Gln His Phe Asp Arg Lys Leu
                335                 340                 345

CTG ATG AAA ATA TTC CGC TAC TCT GAC GTG GGC TTA GTG ACG CCA CTG     1106
Leu Met Lys Ile Phe Arg Tyr Ser Asp Val Gly Leu Val Thr Pro Leu
            350                 355                 360

CGT GAC GGG ATG AAC CTG GTA GCA AAA GAG TAT GTT GCT GCT CAG GAC     1154
Arg Asp Gly Met Asn Leu Val Ala Lys Glu Tyr Val Ala Ala Gln Asp
        365                 370                 375

CCA GCC AAT CCG GGC GTT CTT GTT CTT TCG CAA TTT GCG GGA GCG GCA     1202
Pro Ala Asn Pro Gly Val Leu Val Leu Ser Gln Phe Ala Gly Ala Ala
    380                 385                 390

AAC GAG TTA ACG TCG GCG TTA ATT GTT AAC CCC TAC GAT CGT GAC GAA     1250
Asn Glu Leu Thr Ser Ala Leu Ile Val Asn Pro Tyr Asp Arg Asp Glu
395                 400                 405                 410

GTT GCA GCT GCG CTG GAT CGT GCA TTG ACT ATG TCG CTG GCG GAA CGT     1298
Val Ala Ala Ala Leu Asp Arg Ala Leu Thr Met Ser Leu Ala Glu Arg
                415                 420                 425

ATT TCC CGT CAT GCA GAA ATG CTG GAC GTT ATC GTG AAA AAC GAT ATT     1346
Ile Ser Arg His Ala Glu Met Leu Asp Val Ile Val Lys Asn Asp Ile
            430                 435                 440

AAC CAC TGG CAG GAG TGC TTC ATT AGC GAC CTA AAG CAG ATA GTT CCG     1394
Asn His Trp Gln Glu Cys Phe Ile Ser Asp Leu Lys Gln Ile Val Pro
        445                 450                 455

CGA AGC GCG GAA AGC CAG CAG CGC GAT AAA GTT GCT ACC TTT CCA AAG     1442
Arg Ser Ala Glu Ser Gln Gln Arg Asp Lys Val Ala Thr Phe Pro Lys
    460                 465                 470

CTC TGC AG                                                          1450
Leu Cys
475
```

(2) INFORMATION FOR SEQ ID NO: 2:

(i) SEQUENCE CHARACTERISTICS:
(A) LENGTH: 476 amino acids
(B) TYPE: amino acid
(D) TOPOLOGY: linear (ii) MOLECULE TYPE: protein (xi) SEQUENCE DESCRIPTION: SEQ ID NO: 2:

```
Met Thr Met Ser Arg Leu Val Val Val Ser Asn Arg Ile Ala Pro Pro
  1               5                  10                  15

Asp Glu His Ala Ala Ser Ala Gly Gly Leu Ala Val Gly Ile Leu Gly
             20                  25                  30

Ala Leu Lys Ala Ala Gly Gly Leu Trp Phe Gly Trp Ser Gly Glu Thr
         35                  40                  45

Gly Asn Glu Asp Gln Pro Leu Lys Lys Val Lys Lys Gly Asn Ile Thr
     50                  55                  60

Trp Ala Ser Phe Asn Leu Ser Glu Gln Asp Leu Asp Glu Tyr Tyr Asn
 65                  70                  75                  80

Gln Phe Ser Asn Ala Val Leu Trp Pro Ala Phe His Tyr Arg Leu Asp
                 85                  90                  95
```

```
Leu Val Gln Phe Gln Arg Pro Ala Trp Asp Gly Tyr Leu Arg Val Asn
            100                 105                 110

Ala Leu Leu Ala Asp Lys Leu Leu Pro Leu Leu Gln Asp Asp Asp Ile
        115                 120                 125

Ile Trp Ile His Asp Tyr His Leu Leu Pro Phe Ala His Glu Leu Arg
    130                 135                 140

Lys Arg Gly Val Asn Asn Arg Ile Gly Phe Phe Leu His Ile Pro Phe
145                 150                 155                 160

Pro Thr Pro Glu Ile Phe Asn Ala Leu Pro Thr Tyr Asp Thr Leu Leu
                165                 170                 175

Glu Gln Leu Cys Asp Tyr Asp Leu Leu Gly Phe Gln Thr Glu Asn Asp
            180                 185                 190

Arg Leu Ala Phe Leu Asp Cys Leu Ser Asn Leu Thr Arg Val Thr Thr
        195                 200                 205

Arg Ser Ala Lys Ser His Thr Ala Trp Gly Lys Ala Phe Arg Thr Glu
    210                 215                 220

Val Tyr Pro Ile Gly Ile Glu Pro Lys Glu Ile Ala Lys Gln Ala Ala
225                 230                 235                 240

Gly Pro Leu Pro Pro Lys Leu Ala Gln Leu Lys Ala Glu Leu Lys Asn
                245                 250                 255

Val Gln Asn Ile Phe Ser Val Glu Arg Leu Asp Tyr Ser Lys Gly Leu
            260                 265                 270

Pro Glu Arg Phe Leu Ala Tyr Glu Ala Leu Leu Glu Lys Tyr Pro Gln
        275                 280                 285

His His Gly Lys Ile Arg Tyr Thr Gln Ile Ala Pro Thr Ser Arg Gly
    290                 295                 300

Asp Val Gln Ala Tyr Gln Asp Ile Arg His Gln Leu Glu Asn Glu Ala
305                 310                 315                 320

Gly Arg Ile Asn Gly Lys Tyr Gly Gln Leu Gly Trp Thr Pro Leu Tyr
                325                 330                 335

Tyr Leu Asn Gln His Phe Asp Arg Lys Leu Leu Met Lys Ile Phe Arg
            340                 345                 350

Tyr Ser Asp Val Gly Leu Val Thr Pro Leu Arg Asp Gly Met Asn Leu
        355                 360                 365

Val Ala Lys Glu Tyr Val Ala Ala Gln Asp Pro Ala Asn Pro Gly Val
    370                 375                 380

Leu Val Leu Ser Gln Phe Ala Gly Ala Ala Asn Glu Leu Thr Ser Ala
385                 390                 395                 400

Leu Ile Val Asn Pro Tyr Asp Arg Asp Glu Val Ala Ala Ala Leu Asp
                405                 410                 415

Arg Ala Leu Thr Met Ser Leu Ala Glu Arg Ile Ser Arg His Ala Glu
            420                 425                 430

Met Leu Asp Val Ile Val Lys Asn Asp Ile Asn His Trp Gln Glu Cys
        435                 440                 445

Phe Ile Ser Asp Leu Lys Gln Ile Val Pro Arg Ser Ala Glu Ser Gln
    450                 455                 460

Gln Arg Asp Lys Val Ala Thr Phe Pro Lys Leu Cys
465                 470                 475
```

(2) INFORMATION FOR SEQ ID NO: 3:

(i) SEQUENCE CHARACTERISTICS:
(A) LENGTH: 835 base pairs
(B) TYPE: nucleic acid
(C) STRANDEDNESS: double

```
        (D) TOPOLOGY: linear

   (ii) MOLECULE TYPE: DNA (genomic)

  (iii) HYPOTHETICAL: NO

   (ix) FEATURE:
        (A) NAME/KEY: CDS
        (B) LOCATION: 18..818

   (xi) SEQUENCE DESCRIPTION: SEQ ID NO: 3:

ATAAAACTCT CCCCGGG ATG ACA GAA CCG TTA ACC GAA ACC CCT GAA CTA        50
                   Met Thr Glu Pro Leu Thr Glu Thr Pro Glu Leu
                    1               5                  10

TCC GCG AAA TAT GCC TGG TTT TTT GAT CTT GAT GGA ACG CTG GCG GAA       98
Ser Ala Lys Tyr Ala Trp Phe Phe Asp Leu Asp Gly Thr Leu Ala Glu
            15                  20                  25

ATC AAA CCG CAT CCC GAT CAG GTC GTC GTG CCT GAC AAT ATT CTG CAA      146
Ile Lys Pro His Pro Asp Gln Val Val Val Pro Asp Asn Ile Leu Gln
        30                  35                  40

GGA CTA CAG CTA CTG GCA ACC GCA AGT GAT GGT GCA TTG GCA TTG ATA      194
Gly Leu Gln Leu Leu Ala Thr Ala Ser Asp Gly Ala Leu Ala Leu Ile
    45                  50                  55

TCA GGG CGC TCA ATG GTG GAG CTT GAC GCA CTG GCA AAA CCT TAT CGC      242
Ser Gly Arg Ser Met Val Glu Leu Asp Ala Leu Ala Lys Pro Tyr Arg
 60                  65                  70                  75

TTC CCG TTA GCG GGC GTG CAT GGG GCG GAG CGC CGT GAC ATC AAT GGT      290
Phe Pro Leu Ala Gly Val His Gly Ala Glu Arg Arg Asp Ile Asn Gly
                80                  85                  90

AAA ACA CAT ATC GTT CAT CTG CCG GAT GCG ATT GCG CGT GAT ATT AGC      338
Lys Thr His Ile Val His Leu Pro Asp Ala Ile Ala Arg Asp Ile Ser
            95                 100                 105

GTG CAA CTG CAT ACA GTC ATC GCT CAG TAT CCC GGC GCG GAG CTG GAG      386
Val Gln Leu His Thr Val Ile Ala Gln Tyr Pro Gly Ala Glu Leu Glu
        110                 115                 120

GCG AAA GGG ATG GCT TTT GCG CTG CAT TAT CGT CAG GCT CCG CAG CAT      434
Ala Lys Gly Met Ala Phe Ala Leu His Tyr Arg Gln Ala Pro Gln His
    125                 130                 135

GAA GAC GCA TTA ATG ACA TTA GCG CAA CGT ATT ACT CAG ATC TGG CCA      482
Glu Asp Ala Leu Met Thr Leu Ala Gln Arg Ile Thr Gln Ile Trp Pro
140                 145                 150                 155

CAA ATG GCG TTA CAG CAG GGA AAG TGT GTT GTC GAG ATC AAA CCG AGA      530
Gln Met Ala Leu Gln Gln Gly Lys Cys Val Val Glu Ile Lys Pro Arg
                160                 165                 170

GGT ACC AGT AAA GGT GAG GCA ATT GCA GCT TTT ATG CAG GAA GCT CCC      578
Gly Thr Ser Lys Gly Glu Ala Ile Ala Ala Phe Met Gln Glu Ala Pro
            175                 180                 185

TTT ATC GGG CGA ACG CCC GTA TTT CTG GGC GAT GAT TTA ACC GAT GAA      626
Phe Ile Gly Arg Thr Pro Val Phe Leu Gly Asp Asp Leu Thr Asp Glu
        190                 195                 200

TCT GGC TTC GCA GTC GTT AAC CGA CTG GGC GGA ATG TCA GTA AAA ATT      674
Ser Gly Phe Ala Val Val Asn Arg Leu Gly Gly Met Ser Val Lys Ile
    205                 210                 215

GGC ACA GGT GCA ACT CAG GCA TCA TGG CGA CTG GCG GGT GTG CCG GAT      722
Gly Thr Gly Ala Thr Gln Ala Ser Trp Arg Leu Ala Gly Val Pro Asp
220                 225                 230                 235

GTC TGG AGC TGG CTT GAA ATG ATA ACC ACC GCA TTA CAA CAA AAA AGA      770
Val Trp Ser Trp Leu Glu Met Ile Thr Thr Ala Leu Gln Gln Lys Arg
                240                 245                 250

GAA AAT AAC AGG AGT GAT GAC TAT GAG TCG TTT AGT CGT AGT ATC TAA      818
Glu Asn Asn Arg Ser Asp Asp Tyr Glu Ser Phe Ser Arg Ser Ile
            255                 260                 265
```

CCGGATTGCA CCTGCAG 835

(2) INFORMATION FOR SEQ ID NO: 4:

(i) SEQUENCE CHARACTERISTICS:
(A) LENGTH: 266 amino acids
(B) TYPE: amino acid
(D) TOPOLOGY: linear (ii) MOLECULE TYPE: protein (xi) SEQUENCE DESCRIPTION: SEQ ID NO: 4:

```
Met Thr Glu Pro Leu Thr Glu Thr Pro Glu Leu Ser Ala Lys Tyr Ala
  1               5                  10                  15

Trp Phe Phe Asp Leu Asp Gly Thr Leu Ala Glu Ile Lys Pro His Pro
             20                  25                  30

Asp Gln Val Val Val Pro Asp Asn Ile Leu Gln Gly Leu Gln Leu Leu
         35                  40                  45

Ala Thr Ala Ser Asp Gly Ala Leu Ala Leu Ile Ser Gly Arg Ser Met
     50                  55                  60

Val Glu Leu Asp Ala Leu Ala Lys Pro Tyr Arg Phe Pro Leu Ala Gly
 65                  70                  75                  80

Val His Gly Ala Glu Arg Arg Asp Ile Asn Gly Lys Thr His Ile Val
                 85                  90                  95

His Leu Pro Asp Ala Ile Ala Arg Asp Ile Ser Val Gln Leu His Thr
            100                 105                 110

Val Ile Ala Gln Tyr Pro Gly Ala Glu Leu Glu Ala Lys Gly Met Ala
        115                 120                 125

Phe Ala Leu His Tyr Arg Gln Ala Pro Gln His Glu Asp Ala Leu Met
    130                 135                 140

Thr Leu Ala Gln Arg Ile Thr Gln Ile Trp Pro Gln Met Ala Leu Gln
145                 150                 155                 160

Gln Gly Lys Cys Val Val Glu Ile Lys Pro Arg Gly Thr Ser Lys Gly
                165                 170                 175

Glu Ala Ile Ala Ala Phe Met Gln Glu Ala Pro Phe Ile Gly Arg Thr
            180                 185                 190

Pro Val Phe Leu Gly Asp Asp Leu Thr Asp Glu Ser Gly Phe Ala Val
        195                 200                 205

Val Asn Arg Leu Gly Gly Met Ser Val Lys Ile Gly Thr Gly Ala Thr
    210                 215                 220

Gln Ala Ser Trp Arg Leu Ala Gly Val Pro Asp Val Trp Ser Trp Leu
225                 230                 235                 240

Glu Met Ile Thr Thr Ala Leu Gln Gln Lys Arg Glu Asn Asn Arg Ser
                245                 250                 255

Asp Asp Tyr Glu Ser Phe Ser Arg Ser Ile
            260                 265
```

(2) INFORMATION FOR SEQ ID NO: 5:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (iii) HYPOTHETICAL: NO (xi) SEQUENCE DESCRIPTION: SEQ ID NO: 5:

AAGCTTATGT TGCCATATAG AGTAGAT 27

(2) INFORMATION FOR SEQ ID NO: 6:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: cDNA (iii) HYPOTHETICAL: NO (xi) SEQUENCE DESCRIPTION: SEQ ID NO: 6:

GTAGTTGCCA TGGTGCAAAT GTTCATATG 29

(2) INFORMATION FOR SEQ ID NO: 7:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: modified base, Inosine
(B) LOCATION: 4
(D) OTHER INFORMATION: /note= N is Inosine (ix) FEATURE:
(A) NAME/KEY: modified base, Inosine
(B) LOCATION: 6
(D) OTHER INFORMATION: /note= N is Inosine (ix) FEATURE:
(A) NAME/KEY: modified base, Inosine
(B) LOCATION: 9
(D) OTHER INFORMATION: /note= N is Inosine (ix) FEATURE:
(A) NAME/KEY: modified base, Inosine
(B) LOCATION: 15
(D) OTHER INFORMATION: /note= N is Inosine (xi) SEQUENCE DESCRIPTION: SEQ ID NO: 7:

GAYNTNATAT GGRTNCAYGA YTAYCA 26

(2) INFORMATION FOR SEQ ID NO: 8:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: modified base, Inosine
(B) LOCATION: 2
(D) OTHER INFORMATION: /note= N is Inosine (ix) FEATURE:
(A) NAME/KEY: modified base, Inosine (B) LOCATION: 5
(D) OTHER INFORMATION: /note= N is Inosine (ix) FEATURE:
(A) NAME/KEY: modified base, Inosine
(B) LOCATION: 8
(D) OTHER INFORMATION: /note= N is Inosine (ix) FEATURE:
(A) NAME/KEY: modified base, Inosine
(B) LOCATION: 14
(D) OTHER INFORMATION: /note= N is Inosine (ix) FEATURE:
(A) NAME/KEY: modified base, Inosine
(B) LOCATION: 20
(D) OTHER INFORMATION: /note= N is Inosine (ix) FEATURE:
(A) NAME/KEY: modified base, Inosine
(B) LOCATION: 23
(D) OTHER INFORMATION: /note= N is Inosine (xi) SEQUENCE DESCRIPTION: SEQ ID NO: 8:

TNGGNTKNTT YYTNCAYAYN CCNTTYCC 28

(2) INFORMATION FOR SEQ ID NO: 9:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: modified base, Inosine
(B) LOCATION: 3
(D) OTHER INFORMATION: /note= N is Inosine (ix) FEATURE:
(A) NAME/KEY: modified base, Inosine
(B) LOCATION: 6
(D) OTHER INFORMATION: /note= N is Inosine (ix) FEATURE:
(A) NAME/KEY: modified base, Inosine
(B) LOCATION: 15
(D) OTHER INFORMATION: /note= N is Inosine (ix) FEATURE:
(A) NAME/KEY: modified base, Inosine
(B) LOCATION: 21
(D) OTHER INFORMATION: /note= N is Inosine (xi) SEQUENCE DESCRIPTION: SEQ ID NO: 9:

GYNACNARRT TCATNCCRTC NC 22

(2) INFORMATION FOR SEQ ID NO: 10:

(i) SEQUENCE CHARACTERISTICS:
(A) LENGTH: 743 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Homo sapiens (ix) FEATURE:
(A) NAME/KEY: CDS
(B) LOCATION: 1..743
(D) OTHER INFORMATION: /partial (xi) SEQUENCE DESCRIPTION: SEQ ID NO: 10:

```
GAC GTG ATG TGG ATG CAC GAC TAC CAT TTG ATG GTG TTG CCT ACG TTC       48
Asp Val Met Trp Met His Asp Tyr His Leu Met Val Leu Pro Thr Phe
  1               5                  10                  15

TTG AGG AGG CGG TTC AAT CGT TTG AGA ATG GGG TTT TTC CTT CAC AGT       96
Leu Arg Arg Arg Phe Asn Arg Leu Arg Met Gly Phe Phe Leu His Ser
             20                  25                  30

CCA TTT CCC TCA TCT GAG ATT TAC AGG ACA CTT CCT GTT AGA GAG GAA      144
Pro Phe Pro Ser Ser Glu Ile Tyr Arg Thr Leu Pro Val Arg Glu Glu
         35                  40                  45

ATA CTC AAG GCT TTG CTC TGT GCT GAC ATT GTT GGA TTC CAC ACT TTT      192
Ile Leu Lys Ala Leu Leu Cys Ala Asp Ile Val Gly Phe His Thr Phe
     50                  55                  60

GAC TAC GCG AGA CAC TTC CTC TCT TGT TGC AGT CGG ATG TTG GGT TTA      240
Asp Tyr Ala Arg His Phe Leu Ser Cys Cys Ser Arg Met Leu Gly Leu
 65                  70                  75                  80

GAG TAT CAG TCT AAA AGA GGT TAT ATA GGG TTA GAA TAC TAT GGA CGG      288
Glu Tyr Gln Ser Lys Arg Gly Tyr Ile Gly Leu Glu Tyr Tyr Gly Arg
                 85                  90                  95

ACA GTA GGC ATC AAG ATT ATG CCC GTC GGG ATA CAT ATG GGT CAT ATT      336
Thr Val Gly Ile Lys Ile Met Pro Val Gly Ile His Met Gly His Ile
            100                 105                 110

GAG TCC ATG AAG AAA CTT GCA GCG AAA GAG TTG ATG CTT AAG GCG CTA      384
Glu Ser Met Lys Lys Leu Ala Ala Lys Glu Leu Met Leu Lys Ala Leu
        115                 120                 125

AAG CAG CAA TTT GAA GGG AAA ACT GTG TTG CTT GGT GCC GAT GAC CTG      432
Lys Gln Gln Phe Glu Gly Lys Thr Val Leu Leu Gly Ala Asp Asp Leu
    130                 135                 140

GAT ATT TTC AAA GGT ATA AAC TTA AAG CTT CTA GCT ATG GAA CAG ATG      480
Asp Ile Phe Lys Gly Ile Asn Leu Lys Leu Leu Ala Met Glu Gln Met
145                 150                 155                 160

CTC AAA CAG CAC CCC AAG TGG CAA GGG CAG GCT GTG TTG GTC CAG ATT      528
Leu Lys Gln His Pro Lys Trp Gln Gly Gln Ala Val Leu Val Gln Ile
                165                 170                 175

GCA AAT CCT ACG AGG GGT AAA GGA GTA GAT TTT GAG GAA ATA CAG GCT      576
Ala Asn Pro Thr Arg Gly Lys Gly Val Asp Phe Glu Glu Ile Gln Ala
            180                 185                 190

GAG ATA TCG GAA AGC TGT AAG AGA ATC AAT AAG CAA TTC GGC AAG CCT      624
Glu Ile Ser Glu Ser Cys Lys Arg Ile Asn Lys Gln Phe Gly Lys Pro
        195                 200                 205

GGA TAT GAG CCT ATA GTT TAT ATT GAT AGG CCC GTG TCA AGC AGT GAA      672
Gly Tyr Glu Pro Ile Val Tyr Ile Asp Arg Pro Val Ser Ser Ser Glu
    210                 215                 220

CGC ATG GCA TAT TAC AGT ATT GCA GAA TGT GTT GTT GTC ACG GCT GTG      720
Arg Met Ala Tyr Tyr Ser Ile Ala Glu Cys Val Val Val Thr Ala Val
225                 230                 235                 240

AGC GAC GGC ATG AAC TTC GTC TC                                        743
Ser Asp Gly Met Asn Phe Val
                245
```

(2) INFORMATION FOR SEQ ID NO: 11:

(i) SEQUENCE CHARACTERISTICS:
(A) LENGTH: 247 amino acids (B) TYPE: amino acid
(D) TOPOLOGY: linear (ii) MOLECULE TYPE: protein (xi) SEQUENCE DESCRIPTION: SEQ ID NO: 11:

```
Asp Val Met Trp Met His Asp Tyr His Leu Met Val Leu Pro Thr Phe
  1               5                  10                  15

Leu Arg Arg Arg Phe Asn Arg Leu Arg Met Gly Phe Phe Leu His Ser
             20                  25                  30

Pro Phe Pro Ser Ser Glu Ile Tyr Arg Thr Leu Pro Val Arg Glu Glu
         35                  40                  45

Ile Leu Lys Ala Leu Leu Cys Ala Asp Ile Val Gly Phe His Thr Phe
     50                  55                  60

Asp Tyr Ala Arg His Phe Leu Ser Cys Cys Ser Arg Met Leu Gly Leu
 65                  70                  75                  80

Glu Tyr Gln Ser Lys Arg Gly Tyr Ile Gly Leu Glu Tyr Tyr Gly Arg
                 85                  90                  95

Thr Val Gly Ile Lys Ile Met Pro Val Gly Ile His Met Gly His Ile
            100                 105                 110

Glu Ser Met Lys Lys Leu Ala Ala Lys Glu Leu Met Leu Lys Ala Leu
        115                 120                 125

Lys Gln Gln Phe Glu Gly Lys Thr Val Leu Leu Gly Ala Asp Asp Leu
    130                 135                 140

Asp Ile Phe Lys Gly Ile Asn Leu Lys Leu Leu Ala Met Glu Gln Met
145                 150                 155                 160

Leu Lys Gln His Pro Lys Trp Gln Gly Gln Ala Val Leu Val Gln Ile
                165                 170                 175

Ala Asn Pro Thr Arg Gly Lys Gly Val Asp Phe Glu Glu Ile Gln Ala
            180                 185                 190

Glu Ile Ser Glu Ser Cys Lys Arg Ile Asn Lys Gln Phe Gly Lys Pro
        195                 200                 205

Gly Tyr Glu Pro Ile Val Tyr Ile Asp Arg Pro Val Ser Ser Ser Glu
    210                 215                 220

Arg Met Ala Tyr Tyr Ser Ile Ala Glu Cys Val Val Val Thr Ala Val
225                 230                 235                 240

Ser Asp Gly Met Asn Phe Val
                245
```

(2) INFORMATION FOR SEQ ID NO: 12:

(i) SEQUENCE CHARACTERISTICS:
(A) LENGTH: 395 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Nicotiana tabacum
(B) STRAIN: Samsun NN
(F) TISSUE TYPE: Leaf (ix) FEATURE:
(A) NAME/KEY: CDS
(B) LOCATION: 1..395
(D) OTHER INFORMATION: /partial (xi) SEQUENCE DESCRIPTION: SEQ ID NO: 12:

```
GCG AAA CCG GTG ATG AAA CTT TAC AGG GAA GCA ACT GAC GGA TCA TAT       48
Ala Lys Pro Val Met Lys Leu Tyr Arg Glu Ala Thr Asp Gly Ser Tyr
  1               5                  10                  15

ATA GAA ACT AAA GAG AGT GCA TTA GTG TGG CAC CAT CAT GAT GCA GAC       96
Ile Glu Thr Lys Glu Ser Ala Leu Val Trp His His His Asp Ala Asp
             20                  25                  30

CCT GAC TTT GGC TCC TGC CAG GCA AAG GAA TTG TTG GAT CAT TTG GAA      144
Pro Asp Phe Gly Ser Cys Gln Ala Lys Glu Leu Leu Asp His Leu Glu
         35                  40                  45

AGC GTA CTT GCA AAT GAA CCT GCA GTT GTT AAG AGG GGC CAA CAT ATT      192
Ser Val Leu Ala Asn Glu Pro Ala Val Val Lys Arg Gly Gln His Ile
     50                  55                  60

GTT GAA GTC AAG CCA CAA GGT GTG ACC AAA GGA TTA GTT TCA GAG AAG      240
Val Glu Val Lys Pro Gln Gly Val Thr Lys Gly Leu Val Ser Glu Lys
 65                  70                  75                  80

GTT CTC TCG ATG ATG GTT GAT AGT GGG AAA CCG CCC GAT TTT GTT ATG      288
Val Leu Ser Met Met Val Asp Ser Gly Lys Pro Pro Asp Phe Val Met
                 85                  90                  95

TGC ATT GGA GAT GAT AGG TCA GAC GAA GAC ATG TTT GAG AGC ATA TTA      336
Cys Ile Gly Asp Asp Arg Ser Asp Glu Asp Met Phe Glu Ser Ile Leu
            100                 105                 110

AGC ACC GTA TCC AGT CTG TCA GTC ACT GCT GCC CCT GAT GTC TTT GCC      384
Ser Thr Val Ser Ser Leu Ser Val Thr Ala Ala Pro Asp Val Phe Ala
        115                 120                 125

TGC ACC GTC GG                                                       395
Cys Thr Val
    130
```

(2) INFORMATION FOR SEQ ID NO: 13:

(i) SEQUENCE CHARACTERISTICS:
(A) LENGTH: 131 amino acids
(B) TYPE: amino acid
(D) TOPOLOGY: linear (ii) MOLECULE TYPE: protein (xi) SEQUENCE DESCRIPTION: SEQ ID NO: 13:

```
Ala Lys Pro Val Met Lys Leu Tyr Arg Glu Ala Thr Asp Gly Ser Tyr
  1               5                  10                  15

Ile Glu Thr Lys Glu Ser Ala Leu Val Trp His His His Asp Ala Asp
             20                  25                  30

Pro Asp Phe Gly Ser Cys Gln Ala Lys Glu Leu Leu Asp His Leu Glu
         35                  40                  45

Ser Val Leu Ala Asn Glu Pro Ala Val Val Lys Arg Gly Gln His Ile
     50                  55                  60

Val Glu Val Lys Pro Gln Gly Val Thr Lys Gly Leu Val Ser Glu Lys
 65                  70                  75                  80

Val Leu Ser Met Met Val Asp Ser Gly Lys Pro Pro Asp Phe Val Met
                 85                  90                  95

Cys Ile Gly Asp Asp Arg Ser Asp Glu Asp Met Phe Glu Ser Ile Leu
            100                 105                 110

Ser Thr Val Ser Ser Leu Ser Val Thr Ala Ala Pro Asp Val Phe Ala
        115                 120                 125

Cys Thr Val
    130
```

(2) INFORMATION FOR SEQ ID NO: 14:

```
     (i) SEQUENCE CHARACTERISTICS:
          (A) LENGTH: 491 base pairs
          (B) TYPE: nucleic acid
          (C) STRANDEDNESS: double
          (D) TOPOLOGY: linear

    (ii) MOLECULE TYPE: cDNA to mRNA

   (iii) HYPOTHETICAL: NO

    (iv) ANTI-SENSE: NO

    (vi) ORIGINAL SOURCE:
          (A) ORGANISM: Nicotiana tabacum
          (B) STRAIN: Samsun NN
          (F) TISSUE TYPE: Leaf

    (ix) FEATURE:
          (A) NAME/KEY: CDS
          (B) LOCATION: 1..491
          (D) OTHER INFORMATION: /partial

    (xi) SEQUENCE DESCRIPTION: SEQ ID NO: 14:

GGG CTG TCG GCG GAA CAC GGC TAT TTC TTG AGG ACG AGT CAA GAT GAA       48
Gly Leu Ser Ala Glu His Gly Tyr Phe Leu Arg Thr Ser Gln Asp Glu
  1               5                  10                  15

GAA TGG GAA ACA TGT GTA CCA CCA GTG GAA TGT TGT TGG AAA GAA ATA       96
Glu Trp Glu Thr Cys Val Pro Pro Val Glu Cys Cys Trp Lys Glu Ile
             20                  25                  30

GCT GAG CCT GTT ATG CAA CTT TAC ACT GAG ACT ACT GAT GGA TCA GTT      144
Ala Glu Pro Val Met Gln Leu Tyr Thr Glu Thr Thr Asp Gly Ser Val
         35                  40                  45

ATT GAA GAT AAG GAA ACA TCA ATG GTC TGG TCT TAC GAG GAT GCG GAT      192
Ile Glu Asp Lys Glu Thr Ser Met Val Trp Ser Tyr Glu Asp Ala Asp
     50                  55                  60

CCT GAT TTT GGA TCA TGT CAG GCT AAG GAA CTT CTT GAT CAC CTA GAA      240
Pro Asp Phe Gly Ser Cys Gln Ala Lys Glu Leu Leu Asp His Leu Glu
 65                  70                  75                  80

AGT GTA CTA GCT AAT GAA CCG GTC ACT GTC AGG AGT GGA CAG AAT ATA      288
Ser Val Leu Ala Asn Glu Pro Val Thr Val Arg Ser Gly Gln Asn Ile
                 85                  90                  95

GTG GAA GTT AAG CCC CAG GGT GTA TCC AAA GGG CTT GTT GCC AAG CGC      336
Val Glu Val Lys Pro Gln Gly Val Ser Lys Gly Leu Val Ala Lys Arg
            100                 105                 110

CTG CTT TCC GCA ATG CAA GAG AAA GGA ATG TCA CCA GAT TTT GTC CTT      384
Leu Leu Ser Ala Met Gln Glu Lys Gly Met Ser Pro Asp Phe Val Leu
        115                 120                 125

TGC ATA GGA GAT GAC CGA TCG GAT GAA GAC ATG TTC GAG GTG ATC ATG      432
Cys Ile Gly Asp Asp Arg Ser Asp Glu Asp Met Phe Glu Val Ile Met
    130                 135                 140

AGC TCG ATG TCT GGC CCG TCC ATG GCT CCA ACA GCT GAA GTC TTT GCC      480
Ser Ser Met Ser Gly Pro Ser Met Ala Pro Thr Ala Glu Val Phe Ala
145                 150                 155                 160

TGC ACC GTC GG                                                       491
Cys Thr Val


(2) INFORMATION FOR SEQ ID NO: 15:

     (i) SEQUENCE CHARACTERISTICS:
          (A) LENGTH: 163 amino acids
          (B) TYPE: amino acid
          (D) TOPOLOGY: linear

    (ii) MOLECULE TYPE: protein

    (xi) SEQUENCE DESCRIPTION: SEQ ID NO: 15:

Gly Leu Ser Ala Glu His Gly Tyr Phe Leu Arg Thr Ser Gln Asp Glu
```

```
 1               5                  10                  15

Glu Trp Glu Thr Cys Val Pro Pro Val Glu Cys Cys Trp Lys Glu Ile
             20                  25                  30

Ala Glu Pro Val Met Gln Leu Tyr Thr Glu Thr Thr Asp Gly Ser Val
         35                  40                  45

Ile Glu Asp Lys Glu Thr Ser Met Val Trp Ser Tyr Glu Asp Ala Asp
     50                  55                  60

Pro Asp Phe Gly Ser Cys Gln Ala Lys Glu Leu Leu Asp His Leu Glu
 65                  70                  75                  80

Ser Val Leu Ala Asn Glu Pro Val Thr Val Arg Ser Gly Gln Asn Ile
                 85                  90                  95

Val Glu Val Lys Pro Gln Gly Val Ser Lys Gly Leu Val Ala Lys Arg
            100                 105                 110

Leu Leu Ser Ala Met Gln Glu Lys Gly Met Ser Pro Asp Phe Val Leu
        115                 120                 125

Cys Ile Gly Asp Asp Arg Ser Asp Glu Asp Met Phe Glu Val Ile Met
    130                 135                 140

Ser Ser Met Ser Gly Pro Ser Met Ala Pro Thr Ala Glu Val Phe Ala
145                 150                 155                 160

Cys Thr Val
```

(2) INFORMATION FOR SEQ ID NO: 16:

(i) SEQUENCE CHARACTERISTICS:
(A) LENGTH: 361 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Nicotiana tabacum
(B) STRAIN: Samsun NN
(F) TISSUE TYPE: Leaf (xi) SEQUENCE DESCRIPTION: SEQ ID NO: 16:

```
TTTGATTATG ATGGGACGCT GCTGTCGGAG GAGAGTGTGG ACAAAACCCC GAGTGAAGAT     60

GACATCTCAA TTCTGAATGG TTTATGCAGT GATCCAAAGA ACGTAGTCTT TATCGTGAGT    120

GGCAGAGGAA AGGATACACT TAGCAAGTGG TTCTCTCCGT GTCCGAGACT CGGCCTATCA    180

GCAGAACATG GATATTTCAC TAGGTGGAGT AAGGATTCCG AGTGGGAATC TCGTCCATAG    240

CTGCAGACCT TGACTGGAAA AAAATAGTGT TGCCTATTAT GGAGCGCTAC ACAGAGCACA    300

GATGGTTCGT CGATAGAACA GAAGGAAACC TCGTGTTGGC TCATCAAATG CTGGCCCCGA    360

A                                                                    361
```

(2) INFORMATION FOR SEQ ID NO: 17:

(i) SEQUENCE CHARACTERISTICS:
(A) LENGTH: 118 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Nicotiana tabacum
(B) STRAIN: Samsun NN
(F) TISSUE TYPE: Leaf (xi) SEQUENCE DESCRIPTION: SEQ ID NO: 17:

```
GGAAACCCAC AGGATGTAAG CAAAGTTTTA GTTTTTGAGA TCTCTTGGCA TCAAGCAAAG     60

TAGAGGGAAG TCACCCGATT CGTGCTGTGC GTAGGGATGA CAGATCGGAC GACTTAGA      118
```

(2) INFORMATION FOR SEQ ID NO: 18:

(i) SEQUENCE CHARACTERISTICS:
(A) LENGTH: 417 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Nicotiana tabacum
(B) STRAIN: Samsun NN
(F) TISSUE TYPE: Leaf (xi) SEQUENCE DESCRIPTION: SEQ ID NO: 18:

```
TTGTGGCCGA TGTTCCACTA CATGTTGCCG TTCTCACCTG ACCATGGAGG CCGCTTTGAT     60

CGCTCTATGT GGGAAGCATA TGTTTCTGCC AACAAGTTGT TTTCACAAAA AGTAGTTGAG    120

GTTCTTAATC CTGAGGATGA CTTTGTCTGG ATTCATGATT ATCATTTGAT GGTGTTGCCA    180

ACGTTCTTGA GGAGGCGGTT CAATCGTTTG AGAATGGGGT TTTTCCTTCA CAGTCCATTC    240

CTTCATCTGA GATTTACAGG ACACTTCCTG TTAGAGAGGA AATACTCAAG GCTTTGCTCT    300

GTGCTGACAT TGTTGGATTC CACACTTTTG ACTACGCGAG ACACTTCCTC TCTTGTTGCA    360

GTCGATTTTG GGTAGAGTAC AGTCTAAAAA AAGTTATATT GGGTTAAAAT ACTATGG       417
```

(2) INFORMATION FOR SEQ ID NO: 19:

(i) SEQUENCE CHARACTERISTICS:
(A) LENGTH: 411 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Nicotiana tabacum
(B) STRAIN: Samsun NN
(F) TISSUE TYPE: Leaf (xi) SEQUENCE DESCRIPTION: SEQ ID NO: 19:

```
GGGTCATATT GATCCATGAA GAAATTGCAG CGAAAGAGTG ATGCTTTAAT GCGTAAAGCA     60

GCAATTTGAA GGGAAAACTG TGTTGTTAGG TGCCGATGAC CTGGATATTT TCAAAGGTAT    120

GAACTTAAAG CTTCTAGCTA TGGAACAGAT GCTCAAACAT CACCCCAAGT GGCAAGGGCA    180

GGCTGTGTTG GTCCAAGATT GCAAATCCTA CGAGGGGTAA AGGAGTAGAT TTTGACGAAA    240

TACGGCTGAG ACATCGGAAA GCTGTAAGAG AATCAATAAG CAATTCGGCA AGCCTGGATA    300
```

```
TGAGCCTATA GTTTATATTG ATAGGCCCGT GTCAAGCAGT GAACGCATGG CATATTACAG    360

TATTGCAGGA TGTGTTGTGG TCACGCTGTG AGCGATGGCA TGAATCTGTT C             411
```

(2) INFORMATION FOR SEQ ID NO: 20:

(i) SEQUENCE CHARACTERISTICS:
(A) LENGTH: 405 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Nicotiana tabacum
(B) STRAIN: Samsun NN
(F) TISSUE TYPE: Leaf (xi) SEQUENCE DESCRIPTION: SEQ ID NO: 20:

```
TGGGGTGGTT CCTGCATACG CCGTTTCCTT CTTCTGAGAT ATATAAAACT TTGCCTATTC     60

GCGAAAGATC TTACAGCTCT CTTGAATTCA ATTTGATTGG GTTCCACACT TTTGACTATG    120

CAGGCACTTC CTCTCGTGTT GCAGTCGGAT GTTAGGTATT TCTTATGATC AAAAAGGGGT    180

TACATAGGCC TCGATATTAT GGCAGGACTG TAATATAAAA ATTCTGCCAG CGGGTATTCA    240

TATGGGGCAG CTTCAGCAAG TCTTGAGTCT TCCTGAAACG GAGGCAAAAT CTCGGAACTC    300

GTGCAGCATT TAATCATCAG GGGGAGGACA TTGTTGCTGG GATTGATGAC TGGACATATT    360

TAAAGGCTCA TTTGAATTTA TTACCATGGA ACAACTCTAT TGCAC                    405
```

(2) INFORMATION FOR SEQ ID NO: 21:

(i) SEQUENCE CHARACTERISTICS:
(A) LENGTH: 427 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Nicotiana tabacum
(B) STRAIN: Samsun NN
(F) TISSUE TYPE: Leaf (xi) SEQUENCE DESCRIPTION: SEQ ID NO: 21:

```
ATCATATGGG GCAGCTTCAG CAATCTTGAT CTTCCTGAAA CGGAGGCAAA AGTCTTCGGA     60

ACTCGGCAGC AGTTTAATCA TCAGGGGAGG ACATTGTTGC TGGGAGTTGA TGACATGGAC    120

ATATTTAAAG GCATCAGTTT GAAGTTATTA GCAATGGAAC AACTTCTATT GCAGCACCCG    180

GAGAAGCAGG GGAAGGTTGT TTTGGTGCAG ATAGCCAATC CTGCTAGAGG CAAAGGAAAA    240

GATGTCAAAG AAGTGCAGGA AGAAACTCAT TGACGGTGAA GCGAATTAAT GAAGCATTTG    300

GAAGACCTGG GTACGAACCA GTTATCTTGA TTGATAAGCC ACTAAAGTTT TATGAAAGGA    360

TTGCTTATTA TGTTGTTGCA GAGTGTTGCC TAGTCACTGC TGTCAGCGAT GGCATGAACC    420

TCGTCTC                                                              427
```

(2) INFORMATION FOR SEQ ID NO: 22:

(i) SEQUENCE CHARACTERISTICS:
(A) LENGTH: 315 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Nicotiana tabacum
(B) STRAIN: Samsun NN
(F) TISSUE TYPE: Leaf (xi) SEQUENCE DESCRIPTION: SEQ ID NO: 22:

```
GATGTGGATG CATGACTACC AATCCAAGAG GGGGTATATT GGTCTTGACT ATTATGGTAA     60
ACTGTGACCA TTAAAATCCT TCCAGTTGGT ATTCACATGG GACAACTCCA AAATGTTATG    120
TCACTACAGA CACGGGAAAG AAAGCAAAGG AGTTGAAAGA AAAATATGAG GGGAAAATTG    180
TGATGTTAGG TATTGATGAT ATGGACATGT TTAAAGGAAT TGGTCTAAAG TTTCTGGCAA    240
TGGGGAGGCT TCTAGATGAA AACCCTGTCT TGAGGGGTAA AGTGGTATTG GTTCAATCAC    300
CAGGCCTGGA AATTA                                                     315
```

(2) INFORMATION FOR SEQ ID NO: 23:

(i) SEQUENCE CHARACTERISTICS:
(A) LENGTH: 352 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Nicotiana tabacum
(B) STRAIN: Samsun NN
(F) TISSUE TYPE: Leaf (xi) SEQUENCE DESCRIPTION: SEQ ID NO: 23:

```
AGAAGTAAAG GGAGTGAGTC CCCGAGGTTC AAAAAGAGGT CAACAGAATT GCAGTGAAAT     60
TAATAAAAAA TATGGCAAAC CGGGGTACAA GCCGATTGTT TGTATCAATG GTCCAGTTTC    120
GACACAAGAC AAGATTGCAC ATTATGCGGT CTTGAGTGTG TTGTTGTTAA TGCTGTTAGA    180
GATGGGATGA ACTTGGTGCC TTATGAGTAT ACGGTCTTTA GGCAGGGCAG CGATAATTTG    240
GATAAGGCCT TGCAGCTAGA TGGTCCTACT GCTTCCAGAA AGAGTGTGAT TATTGTCTTG    300
AATTCGTTGG GTGCTCGCCA TCTTTAGTGG CGCCATCCGC GTCAACCCCT GG            352
```

(2) INFORMATION FOR SEQ ID NO: 24:

(i) SEQUENCE CHARACTERISTICS:
(A) LENGTH: 2640 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO

```
(iv) ANTI-SENSE: NO

(vi) ORIGINAL SOURCE:
      (A) ORGANISM: Helianthus annuus
      (F) TISSUE TYPE: Leaf

(ix) FEATURE:
      (A) NAME/KEY: CDS
      (B) LOCATION: 171..2508

(ix) FEATURE:
      (A) NAME/KEY: unsure
      (B) LOCATION: replace(2141..2151, "ccatnnntta")

(ix) FEATURE:
      (A) NAME/KEY: unsure
      (B) LOCATION: replace(2237..2243, "actnaaa")

(xi) SEQUENCE DESCRIPTION: SEQ ID NO: 24:

GGATCCTGCG GTTTCATCAC ACAATATGAT ACTGTTACAT CTGATGCCCC TTCAGATGTC     60

CCAAATAGGT TGATTGTCGT ATCGAATCAG TTACCCATAA TCGCTAGGCT AAGACTAACG    120

ACAATGGAGG GTCCTTTTGG GATTTCACTT GGGACGAGAG TTCGATTTAC ATG CAC       176
                                                      Met His
                                                        1

ATC AAA GAT GCA TTA CCC GCA GCC GTT GAG GTT TTC TAT GTT GGC GCA      224
Ile Lys Asp Ala Leu Pro Ala Ala Val Glu Val Phe Tyr Val Gly Ala
        5                  10                  15

CTA AGG GCT GAC GTT GGC CCT ACC GAA CAA GAT GAC GTG TCA AAG ACA      272
Leu Arg Ala Asp Val Gly Pro Thr Glu Gln Asp Asp Val Ser Lys Thr
    20                  25                  30

TTG CTC GAT AGG TTT AAT TGC GTT GCG GTT TTT GTC CCT ACT TCA AAA      320
Leu Leu Asp Arg Phe Asn Cys Val Ala Val Phe Val Pro Thr Ser Lys
 35                  40                  45                  50

TGG GAC CAA TAT TAT CAC TGC TTT TGT AAG CAG TAT TTG TGG CCG ATA      368
Trp Asp Gln Tyr Tyr His Cys Phe Cys Lys Gln Tyr Leu Trp Pro Ile
                55                  60                  65

TTT CAT TAC AAG GTT CCC GCT TCT GAC GTC AAG AGT GTC CCG AAT AGT      416
Phe His Tyr Lys Val Pro Ala Ser Asp Val Lys Ser Val Pro Asn Ser
            70                  75                  80

CGG GAT TCA TGG AAC GCT TAT GTT CAC GTG AAC AAA GAG TTT TCC CAG      464
Arg Asp Ser Trp Asn Ala Tyr Val His Val Asn Lys Glu Phe Ser Gln
        85                  90                  95

AAG GTG ATG GAG GCA GTA ACC AAT GCT AGC AAT TAT GTA TGG ATA CAT      512
Lys Val Met Glu Ala Val Thr Asn Ala Ser Asn Tyr Val Trp Ile His
    100                 105                 110

GAC TAC CAT TTA ATG ACG CTA CCG ACT TTC TTG AGG CGG GAT TTT TGT      560
Asp Tyr His Leu Met Thr Leu Pro Thr Phe Leu Arg Arg Asp Phe Cys
115                 120                 125                 130

CGT TTT AAA ATC GGT TTT TTT CTG CAT AGC CCG TTT CCT TCC TCG GAG      608
Arg Phe Lys Ile Gly Phe Phe Leu His Ser Pro Phe Pro Ser Ser Glu
                135                 140                 145

GTT TAC AAG ACC CTA CCA ATG AGA AAC GAG CTC TTG AAG GGT CTG TTA      656
Val Tyr Lys Thr Leu Pro Met Arg Asn Glu Leu Leu Lys Gly Leu Leu
            150                 155                 160

AAT GCT GAT CTT ATC GGG TTC CAT ACA TAC GAT TAT GCC CGT CAT TTT      704
Asn Ala Asp Leu Ile Gly Phe His Thr Tyr Asp Tyr Ala Arg His Phe
        165                 170                 175

CTA ACG TGT TGT AGT CGA ATG TTT GGT TTG GAT CAT CAG TTG AAA AGG      752
Leu Thr Cys Cys Ser Arg Met Phe Gly Leu Asp His Gln Leu Lys Arg
    180                 185                 190

GGG TAC ATT TTC TTG GAA TAT AAT GGA AGG AGC ATT GAG ATC AAG ATA      800
Gly Tyr Ile Phe Leu Glu Tyr Asn Gly Arg Ser Ile Glu Ile Lys Ile
195                 200                 205                 210
```

```
AAG GCG AGC GGG ATT CAT GTT GGT CGA ATG GAG TCG TAC TTG AGT CAG      848
Lys Ala Ser Gly Ile His Val Gly Arg Met Glu Ser Tyr Leu Ser Gln
            215                 220                 225

CCC GAT ACA AGA TTA CAA GTT CAA GAA CTA AAA AAA CGT TTC GAA GGG      896
Pro Asp Thr Arg Leu Gln Val Gln Glu Leu Lys Lys Arg Phe Glu Gly
        230                 235                 240

AAA ATC GTG CTA CTT GGA GTT GAT GAT TTG GAT ATA TTC AAA GGT GTG      944
Lys Ile Val Leu Leu Gly Val Asp Asp Leu Asp Ile Phe Lys Gly Val
    245                 250                 255

AAC TTC AAG GTT TTA GCG TTG GAG AAG TTA CTT AAA TCA CAC CCG AGT      992
Asn Phe Lys Val Leu Ala Leu Glu Lys Leu Leu Lys Ser His Pro Ser
    260                 265                 270

TGG CAA GGG CGT GTG GTT TTG GTG CAA ATC TTG AAT CCC GCT CGC GCG     1040
Trp Gln Gly Arg Val Val Leu Val Gln Ile Leu Asn Pro Ala Arg Ala
275                 280                 285                 290

CGT TGC CAA GAC GTC GAT GAG ATC AAT GCC GAG ATA AGA ACA GTC TGT     1088
Arg Cys Gln Asp Val Asp Glu Ile Asn Ala Glu Ile Arg Thr Val Cys
                295                 300                 305

GAA AGA ATC AAT AAC GAA CTG GGA AGC CCG GGA TAC CAG CCC GTT GTG     1136
Glu Arg Ile Asn Asn Glu Leu Gly Ser Pro Gly Tyr Gln Pro Val Val
            310                 315                 320

TTA ATT GAT GGG CCC GTT TCG TTA AGT GAA AAA GCT GCT TAT TAT GCT     1184
Leu Ile Asp Gly Pro Val Ser Leu Ser Glu Lys Ala Ala Tyr Tyr Ala
        325                 330                 335

ATC GCC GAT ATG GCA ATT GTT ACA CCG TTA CGT GAC GGC ATG AAT CTT     1232
Ile Ala Asp Met Ala Ile Val Thr Pro Leu Arg Asp Gly Met Asn Leu
    340                 345                 350

ATC CCG TAC GAG TAC GTC GTT TCC CGA CAA AGT GTT AAT GAC CCA AAT     1280
Ile Pro Tyr Glu Tyr Val Val Ser Arg Gln Ser Val Asn Asp Pro Asn
355                 360                 365                 370

CCC AAT ACT CCA AAA AAG AGC ATG CTA GTG GTC TCC GAG TTC ATC GGG     1328
Pro Asn Thr Pro Lys Lys Ser Met Leu Val Val Ser Glu Phe Ile Gly
                375                 380                 385

TGT TCA CTA TCT TTA ACC GGG GCC ATA CGG GTC AAC CCA TGG GAT GAG     1376
Cys Ser Leu Ser Leu Thr Gly Ala Ile Arg Val Asn Pro Trp Asp Glu
            390                 395                 400

TTG GAG ACA GCA GAA GCA TTA TAC GAC GCA CTC ATG GCT CCT GAT GAC     1424
Leu Glu Thr Ala Glu Ala Leu Tyr Asp Ala Leu Met Ala Pro Asp Asp
        405                 410                 415

CAT AAA GAA ACC GCC CAC ATG AAA CAG TAT CAA TAC ATT ATC TCC CAT     1472
His Lys Glu Thr Ala His Met Lys Gln Tyr Gln Tyr Ile Ile Ser His
    420                 425                 430

GAT GTA GCT AAC TGG GCT CGT AGC TTC TTT CAA GAT TTA GAG CAA GCG     1520
Asp Val Ala Asn Trp Ala Arg Ser Phe Phe Gln Asp Leu Glu Gln Ala
435                 440                 445                 450

TGC ATC GAT CAT TCT CGT AAA CGA TGC ATG AAT TTA GGA TTT GGG TTA     1568
Cys Ile Asp His Ser Arg Lys Arg Cys Met Asn Leu Gly Phe Gly Leu
                455                 460                 465

GAT ACT AGA GTC GTT CTT TTT GAT GAG AAG TTT AGC AAG TTG GAT ATA     1616
Asp Thr Arg Val Val Leu Phe Asp Glu Lys Phe Ser Lys Leu Asp Ile
            470                 475                 480

GAT GTC TTG GAG AAT GCT TAT TCC ATG GCT CAA AAT CGG GCC ATA CTT     1664
Asp Val Leu Glu Asn Ala Tyr Ser Met Ala Gln Asn Arg Ala Ile Leu
        485                 490                 495

TTG GAC TAT GAC GGC ACT GTT ACT CCA TCT ATC AGT AAA TCT CCA ACT     1712
Leu Asp Tyr Asp Gly Thr Val Thr Pro Ser Ile Ser Lys Ser Pro Thr
    500                 505                 510

GAA GCT GTT ATC TCC ATG ATC AAC AAA CTG TGC AAT GAT CCA AAG AAC     1760
Glu Ala Val Ile Ser Met Ile Asn Lys Leu Cys Asn Asp Pro Lys Asn
515                 520                 525                 530
```

```
ATG GTG TTC ATC GTT AGT GGA CGC AGT AGA GAA AAT CTT GGC AGT TGG      1808
Met Val Phe Ile Val Ser Gly Arg Ser Arg Glu Asn Leu Gly Ser Trp
                535                 540                 545

TTC GGC GCG TGT GAG AAA CCC GCC ATT GCA GCT GAG CAC GGA TAC TTT      1856
Phe Gly Ala Cys Glu Lys Pro Ala Ile Ala Ala Glu His Gly Tyr Phe
            550                 555                 560

ATA AGG TGG GCG GGT GAT CAA GAA TGG GAA ACG TGC GCA CGT GAG AAT      1904
Ile Arg Trp Ala Gly Asp Gln Glu Trp Glu Thr Cys Ala Arg Glu Asn
        565                 570                 575

AAT GTC GGG TGG ATG GAA ATG GCT GAG CCG GTT ATG AAT CTT TAT ACA      1952
Asn Val Gly Trp Met Glu Met Ala Glu Pro Val Met Asn Leu Tyr Thr
    580                 585                 590

GAA ACT ACT GAC GGT TCG TAT ATT GAA AAG AAA GAA ACT GCA ATG GTT      2000
Glu Thr Thr Asp Gly Ser Tyr Ile Glu Lys Lys Glu Thr Ala Met Val
595                 600                 605                 610

TGG CAC TAT GAA GAT GCT GAT AAA GAT CTT GGG TTG GAG CAG GCT AAG      2048
Trp His Tyr Glu Asp Ala Asp Lys Asp Leu Gly Leu Glu Gln Ala Lys
                615                 620                 625

GAA CTG TTG GAC CAT CTT GAA AAC GTG CTC GCT AAT GAG CCC GTT GAA      2096
Glu Leu Leu Asp His Leu Glu Asn Val Leu Ala Asn Glu Pro Val Glu
            630                 635                 640

GTG AAA CGA GGT CAA TAC ATT GTA GAA GTT AAA CCA CAG GTA CCC CAT      2144
Val Lys Arg Gly Gln Tyr Ile Val Glu Val Lys Pro Gln Val Pro His
        645                 650                 655

GGG TTA CCT TCT TGT TAT GAC ATT CAT AGG CAC AGA TTT GTA GAA TCT      2192
Gly Leu Pro Ser Cys Tyr Asp Ile His Arg His Arg Phe Val Glu Ser
    660                 665                 670

TTT AAC TTA AAT TTC TTT AAA TAT GAA TGC AAT TAT AGG GGG TCA CTG      2240
Phe Asn Leu Asn Phe Phe Lys Tyr Glu Cys Asn Tyr Arg Gly Ser Leu
675                 680                 685                 690

AAA GGT ATA GTT GCA GAG AAG ATT TTT GCG TTC ATG GCT GAA AAG GGA      2288
Lys Gly Ile Val Ala Glu Lys Ile Phe Ala Phe Met Ala Glu Lys Gly
                695                 700                 705

AAA CAG GCT GAT TTC GTG TTG AGC GTT GGA GAT GAT AGA AGT GAT GAA      2336
Lys Gln Ala Asp Phe Val Leu Ser Val Gly Asp Asp Arg Ser Asp Glu
            710                 715                 720

GAC ATG TTT GTG GCC ATT GGG GAT GGA ATA AAA AAG GGT CGG ATA ACT      2384
Asp Met Phe Val Ala Ile Gly Asp Gly Ile Lys Lys Gly Arg Ile Thr
        725                 730                 735

AAC AAC AAT TCA GTG TTT ACA TGC GTA GTG GGA GAG AAA CCG AGT GCA      2432
Asn Asn Asn Ser Val Phe Thr Cys Val Val Gly Glu Lys Pro Ser Ala
    740                 745                 750

GCT GAG TAC TTT TTA GAC GAG ACG AAA GAT GTT TCA ATG ATG CTC GAG      2480
Ala Glu Tyr Phe Leu Asp Glu Thr Lys Asp Val Ser Met Met Leu Glu
755                 760                 765                 770

AAG CTC GGG TGT CTC AGC AAC CAA GGA T GATGATCCGG AAGCTTCTCG          2528
Lys Leu Gly Cys Leu Ser Asn Gln Gly
                775

TGATCTTTAT GAGTTAAAAG TTTTCGACTT TTTCTTCATC AAGATTCATG GGAAAGTTGT    2588

TCAATATGAA CTTGTGTTTC TTGGTTCTGG ATTTTAGGGA GTCTATGGAT CC            2640
```

(2) INFORMATION FOR SEQ ID NO: 25:

(i) SEQUENCE CHARACTERISTICS:
(A) LENGTH: 779 amino acids
(B) TYPE: amino acid
(D) TOPOLOGY: linear (ii) MOLECULE TYPE: protein (xi) SEQUENCE DESCRIPTION: SEQ ID NO: 25:

```
Met His Ile Lys Asp Ala Leu Pro Ala Ala Val Glu Val Phe Tyr Val
1               5                   10                  15

Gly Ala Leu Arg Ala Asp Val Gly Pro Thr Glu Gln Asp Asp Val Ser
            20                  25                  30

Lys Thr Leu Leu Asp Arg Phe Asn Cys Val Ala Val Phe Val Pro Thr
        35                  40                  45

Ser Lys Trp Asp Gln Tyr Tyr His Cys Phe Cys Lys Gln Tyr Leu Trp
    50                  55                  60

Pro Ile Phe His Tyr Lys Val Pro Ala Ser Asp Val Lys Ser Val Pro
65                  70                  75                  80

Asn Ser Arg Asp Ser Trp Asn Ala Tyr Val His Val Asn Lys Glu Phe
                85                  90                  95

Ser Gln Lys Val Met Glu Ala Val Thr Asn Ala Ser Asn Tyr Val Trp
            100                 105                 110

Ile His Asp Tyr His Leu Met Thr Leu Pro Thr Phe Leu Arg Arg Asp
        115                 120                 125

Phe Cys Arg Phe Lys Ile Gly Phe Phe Leu His Ser Pro Phe Pro Ser
    130                 135                 140

Ser Glu Val Tyr Lys Thr Leu Pro Met Arg Asn Glu Leu Leu Lys Gly
145                 150                 155                 160

Leu Leu Asn Ala Asp Leu Ile Gly Phe His Thr Tyr Asp Tyr Ala Arg
                165                 170                 175

His Phe Leu Thr Cys Cys Ser Arg Met Phe Gly Leu Asp His Gln Leu
            180                 185                 190

Lys Arg Gly Tyr Ile Phe Leu Glu Tyr Asn Gly Arg Ser Ile Glu Ile
        195                 200                 205

Lys Ile Lys Ala Ser Gly Ile His Val Gly Arg Met Glu Ser Tyr Leu
    210                 215                 220

Ser Gln Pro Asp Thr Arg Leu Gln Val Gln Glu Leu Lys Lys Arg Phe
225                 230                 235                 240

Glu Gly Lys Ile Val Leu Leu Gly Val Asp Asp Leu Asp Ile Phe Lys
                245                 250                 255

Gly Val Asn Phe Lys Val Leu Ala Leu Glu Lys Leu Leu Lys Ser His
            260                 265                 270

Pro Ser Trp Gln Gly Arg Val Val Leu Val Gln Ile Leu Asn Pro Ala
        275                 280                 285

Arg Ala Arg Cys Gln Asp Val Asp Glu Ile Asn Ala Glu Ile Arg Thr
    290                 295                 300

Val Cys Glu Arg Ile Asn Asn Glu Leu Gly Ser Pro Gly Tyr Gln Pro
305                 310                 315                 320

Val Val Leu Ile Asp Gly Pro Val Ser Leu Ser Glu Lys Ala Ala Tyr
                325                 330                 335

Tyr Ala Ile Ala Asp Met Ala Ile Val Thr Pro Leu Arg Asp Gly Met
            340                 345                 350

Asn Leu Ile Pro Tyr Glu Tyr Val Val Ser Arg Gln Ser Val Asn Asp
        355                 360                 365

Pro Asn Pro Asn Thr Pro Lys Lys Ser Met Leu Val Val Ser Glu Phe
    370                 375                 380

Ile Gly Cys Ser Leu Ser Leu Thr Gly Ala Ile Arg Val Asn Pro Trp
385                 390                 395                 400

Asp Glu Leu Glu Thr Ala Glu Ala Leu Tyr Asp Ala Leu Met Ala Pro
                405                 410                 415

Asp Asp His Lys Glu Thr Ala His Met Lys Gln Tyr Gln Tyr Ile Ile
            420                 425                 430
```

```
Ser His Asp Val Ala Asn Trp Ala Arg Ser Phe Phe Gln Asp Leu Glu
        435                 440                 445

Gln Ala Cys Ile Asp His Ser Arg Lys Arg Cys Met Asn Leu Gly Phe
    450                 455                 460

Gly Leu Asp Thr Arg Val Val Leu Phe Asp Glu Lys Phe Ser Lys Leu
465                 470                 475                 480

Asp Ile Asp Val Leu Glu Asn Ala Tyr Ser Met Ala Gln Asn Arg Ala
                485                 490                 495

Ile Leu Leu Asp Tyr Asp Gly Thr Val Thr Pro Ser Ile Ser Lys Ser
            500                 505                 510

Pro Thr Glu Ala Val Ile Ser Met Ile Asn Lys Leu Cys Asn Asp Pro
        515                 520                 525

Lys Asn Met Val Phe Ile Val Ser Gly Arg Ser Arg Glu Asn Leu Gly
    530                 535                 540

Ser Trp Phe Gly Ala Cys Glu Lys Pro Ala Ile Ala Ala Glu His Gly
545                 550                 555                 560

Tyr Phe Ile Arg Trp Ala Gly Asp Gln Glu Trp Glu Thr Cys Ala Arg
                565                 570                 575

Glu Asn Asn Val Gly Trp Met Glu Met Ala Glu Pro Val Met Asn Leu
            580                 585                 590

Tyr Thr Glu Thr Thr Asp Gly Ser Tyr Ile Glu Lys Lys Glu Thr Ala
        595                 600                 605

Met Val Trp His Tyr Glu Asp Ala Asp Lys Asp Leu Gly Leu Glu Gln
    610                 615                 620

Ala Lys Glu Leu Leu Asp His Leu Glu Asn Val Leu Ala Asn Glu Pro
625                 630                 635                 640

Val Glu Val Lys Arg Gly Gln Tyr Ile Val Glu Val Lys Pro Gln Val
                645                 650                 655

Pro His Gly Leu Pro Ser Cys Tyr Asp Ile His Arg His Arg Phe Val
            660                 665                 670

Glu Ser Phe Asn Leu Asn Phe Phe Lys Tyr Glu Cys Asn Tyr Arg Gly
        675                 680                 685

Ser Leu Lys Gly Ile Val Ala Glu Lys Ile Phe Ala Phe Met Ala Glu
    690                 695                 700

Lys Gly Lys Gln Ala Asp Phe Val Leu Ser Val Gly Asp Asp Arg Ser
705                 710                 715                 720

Asp Glu Asp Met Phe Val Ala Ile Gly Asp Gly Ile Lys Lys Gly Arg
                725                 730                 735

Ile Thr Asn Asn Asn Ser Val Phe Thr Cys Val Val Gly Glu Lys Pro
            740                 745                 750

Ser Ala Ala Glu Tyr Phe Leu Asp Glu Thr Lys Asp Val Ser Met Met
        755                 760                 765

Leu Glu Lys Leu Gly Cys Leu Ser Asn Gln Gly
    770                 775
```

(2) INFORMATION FOR SEQ ID NO: 26:

(i) SEQUENCE CHARACTERISTICS:
(A) LENGTH: 2130 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO

```
    (iv) ANTI-SENSE: NO

    (vi) ORIGINAL SOURCE:
         (A) ORGANISM: Helianthus annuus

    (ix) FEATURE:
         (A) NAME/KEY: CDS
         (B) LOCATION: 171..2130
         (D) OTHER INFORMATION: /partial

    (xi) SEQUENCE DESCRIPTION: SEQ ID NO: 26:

GGATCCTGCG GTTTCATCAC ACAATATGAT ACTGTTACAT CTGATGCCCC TTCAGATGTC     60

CCAAATAGGT TGATTGTCGT ATCGAATCAG TTACCCATAA TCGCTAGGCT AAGACTAACG    120

ACAATGGAGG GTCCTTTTGG GATTTCACTT GGGACGAGAG TTCGATTTAC ATG CAC       176
                                                      Met His
                                                        1

ATC AAA GAT GCA TTA CCC GCA GCC GTT GAG GTT TTC TAT GTT GGC GCA      224
Ile Lys Asp Ala Leu Pro Ala Ala Val Glu Val Phe Tyr Val Gly Ala
          5                  10                  15

CTA AGG GCT GAC GTT GGC CCT ACC GAA CAA GAT GAC GTG TCA AAG ACA      272
Leu Arg Ala Asp Val Gly Pro Thr Glu Gln Asp Asp Val Ser Lys Thr
     20                  25                  30

TTG CTC GAT AGG TTT AAT TGC GTT GCG GTT TTT GTC CCT ACT TCA AAA      320
Leu Leu Asp Arg Phe Asn Cys Val Ala Val Phe Val Pro Thr Ser Lys
 35                  40                  45                  50

TGG GAC CAA TAT TAT CAC TGC TTT TGT AAG CAG TAT TTG TGG CCG ATA      368
Trp Asp Gln Tyr Tyr His Cys Phe Cys Lys Gln Tyr Leu Trp Pro Ile
                 55                  60                  65

TTT CAT TAC AAG GTT CCC GCT TCT GAC GTC AAG AGT GTC CCG AAT AGT      416
Phe His Tyr Lys Val Pro Ala Ser Asp Val Lys Ser Val Pro Asn Ser
             70                  75                  80

CGG GAT TCA TGG AAC GCT TAT GTT CAC GTG AAC AAA GAG TTT TCC CAG      464
Arg Asp Ser Trp Asn Ala Tyr Val His Val Asn Lys Glu Phe Ser Gln
         85                  90                  95

AAG GTG ATG GAG GCA GTA ACC AAT GCT AGC AAT TAT GTA TGG ATA CAT      512
Lys Val Met Glu Ala Val Thr Asn Ala Ser Asn Tyr Val Trp Ile His
    100                 105                 110

GAC TAC CAT TTA ATG ACG CTA CCG ACT TTC TTG AGG CGG GAT TTT TGT      560
Asp Tyr His Leu Met Thr Leu Pro Thr Phe Leu Arg Arg Asp Phe Cys
115                 120                 125                 130

CGT TTT AAA ATC GGT TTT TTT CTG CAT AGC CCG TTT CCT TCC TCG GAG      608
Arg Phe Lys Ile Gly Phe Phe Leu His Ser Pro Phe Pro Ser Ser Glu
                135                 140                 145

GTT TAC AAG ACC CTA CCA ATG AGA AAC GAG CTC TTG AAG GGT CTG TTA      656
Val Tyr Lys Thr Leu Pro Met Arg Asn Glu Leu Leu Lys Gly Leu Leu
            150                 155                 160

AAT GCT GAT CTT ATC GGG TTC CAT ACA TAC GAT TAT GCC CGT CAT TTT      704
Asn Ala Asp Leu Ile Gly Phe His Thr Tyr Asp Tyr Ala Arg His Phe
        165                 170                 175

CTA ACG TGT TGT AGT CGA ATG TTT GGT TTG GAT CAT CAG TTG AAA AGG      752
Leu Thr Cys Cys Ser Arg Met Phe Gly Leu Asp His Gln Leu Lys Arg
    180                 185                 190

GGG TAC ATT TTC TTG GAA TAT AAT GGA AGG AGC ATT GAG ATC AAG ATA      800
Gly Tyr Ile Phe Leu Glu Tyr Asn Gly Arg Ser Ile Glu Ile Lys Ile
195                 200                 205                 210

AAG GCG AGC GGG ATT CAT GTT GGT CGA ATG GAG TCG TAC TTG AGT CAG      848
Lys Ala Ser Gly Ile His Val Gly Arg Met Glu Ser Tyr Leu Ser Gln
                215                 220                 225

CCC GAT ACA AGA TTA CAA GTT CAA GAA CTA AAA AAA CGT TTC GAA GGG      896
Pro Asp Thr Arg Leu Gln Val Gln Glu Leu Lys Lys Arg Phe Glu Gly
            230                 235                 240
```

-continued

```
AAA ATC GTG CTA CTT GGA GTT GAT GAT TTG GAT ATA TTC AAA GGT GTG      944
Lys Ile Val Leu Leu Gly Val Asp Asp Leu Asp Ile Phe Lys Gly Val
        245                 250                 255

AAC TTC AAG GTT TTA GCG TTG GAG AAG TTA CTT AAA TCA CAC CCG AGT      992
Asn Phe Lys Val Leu Ala Leu Glu Lys Leu Leu Lys Ser His Pro Ser
    260                 265                 270

TGG CAA GGG CGT GTG GTT TTG GTG CAA ATC TTG AAT CCC GCT CGC GCG     1040
Trp Gln Gly Arg Val Val Leu Val Gln Ile Leu Asn Pro Ala Arg Ala
275                 280                 285                 290

CGT TGC CAA GAC GTC GAT GAG ATC AAT GCC GAG ATA AGA ACA GTC TGT     1088
Arg Cys Gln Asp Val Asp Glu Ile Asn Ala Glu Ile Arg Thr Val Cys
                295                 300                 305

GAA AGA ATC AAT AAC GAA CTG GGA AGC CCG GGA TAC CAG CCC GTT GTG     1136
Glu Arg Ile Asn Asn Glu Leu Gly Ser Pro Gly Tyr Gln Pro Val Val
            310                 315                 320

TTA ATT GAT GGG CCC GTT TCG TTA AGT GAA AAA GCT GCT TAT TAT GCT     1184
Leu Ile Asp Gly Pro Val Ser Leu Ser Glu Lys Ala Ala Tyr Tyr Ala
        325                 330                 335

ATC GCC GAT ATG GCA ATT GTT ACA CCG TTA CGT GAC GGC ATG AAT CTT     1232
Ile Ala Asp Met Ala Ile Val Thr Pro Leu Arg Asp Gly Met Asn Leu
    340                 345                 350

ATC CCG TAC GAG TAC GTC GTT TCC CGA CAA AGT GTT AAT GAC CCA AAT     1280
Ile Pro Tyr Glu Tyr Val Val Ser Arg Gln Ser Val Asn Asp Pro Asn
355                 360                 365                 370

CCC AAT ACT CCA AAA AAG AGC ATG CTA GTG GTC TCC GAG TTC ATC GGG     1328
Pro Asn Thr Pro Lys Lys Ser Met Leu Val Val Ser Glu Phe Ile Gly
                375                 380                 385

TGT TCA CTA TCT TTA ACC GGG GCC ATA CGG GTC AAC CCA TGG GAT GAG     1376
Cys Ser Leu Ser Leu Thr Gly Ala Ile Arg Val Asn Pro Trp Asp Glu
            390                 395                 400

TTG GAG ACA GCA GAA GCA TTA TAC GAC GCA CTC ATG GCT CCT GAT GAC     1424
Leu Glu Thr Ala Glu Ala Leu Tyr Asp Ala Leu Met Ala Pro Asp Asp
        405                 410                 415

CAT AAA GAA ACC GCC CAC ATG AAA CAG TAT CAA TAC ATT ATC TCC CAT     1472
His Lys Glu Thr Ala His Met Lys Gln Tyr Gln Tyr Ile Ile Ser His
    420                 425                 430

GAT GTA GCT AAC TGG GCT CGT AGC TTC TTT CAA GAT TTA GAG CAA GCG     1520
Asp Val Ala Asn Trp Ala Arg Ser Phe Phe Gln Asp Leu Glu Gln Ala
435                 440                 445                 450

TGC ATC GAT CAT TCT CGT AAA CGA TGC ATG AAT TTA GGA TTT GGG TTA     1568
Cys Ile Asp His Ser Arg Lys Arg Cys Met Asn Leu Gly Phe Gly Leu
                455                 460                 465

GAT ACT AGA GTC GTT CTT TTT GAT GAG AAG TTT AGC AAG TTG GAT ATA     1616
Asp Thr Arg Val Val Leu Phe Asp Glu Lys Phe Ser Lys Leu Asp Ile
            470                 475                 480

GAT GTC TTG GAG AAT GCT TAT TCC ATG GCT CAA AAT CGG GCC ATA CTT     1664
Asp Val Leu Glu Asn Ala Tyr Ser Met Ala Gln Asn Arg Ala Ile Leu
        485                 490                 495

TTG GAC TAT GAC GGC ACT GTT ACT CCA TCT ATC AGT AAA TCT CCA ACT     1712
Leu Asp Tyr Asp Gly Thr Val Thr Pro Ser Ile Ser Lys Ser Pro Thr
    500                 505                 510

GAA GCT GTT ATC TCC ATG ATC AAC AAA CTG TGC AAT GAT CCA AAG AAC     1760
Glu Ala Val Ile Ser Met Ile Asn Lys Leu Cys Asn Asp Pro Lys Asn
515                 520                 525                 530

ATG GTG TTC ATC GTT AGT GGA CGC AGT AGA GAA AAT CTT GGC AGT TGG     1808
Met Val Phe Ile Val Ser Gly Arg Ser Arg Glu Asn Leu Gly Ser Trp
                535                 540                 545

TTC GGC GCG TGT GAG AAA CCC GCC ATT GCA GCT GAG CAC GGA TAC TTT     1856
Phe Gly Ala Cys Glu Lys Pro Ala Ile Ala Ala Glu His Gly Tyr Phe
            550                 555                 560
```

```
ATA AGG TGG GCG GGT GAT CAA GAA TGG GAA ACG TGC GCA CGT GAG AAT      1904
Ile Arg Trp Ala Gly Asp Gln Glu Trp Glu Thr Cys Ala Arg Glu Asn
        565                 570                 575

AAT GTC GGG TGG ATG GAA ATG GCT GAG CCG GTT ATG AAT CTT TAT ACA      1952
Asn Val Gly Trp Met Glu Met Ala Glu Pro Val Met Asn Leu Tyr Thr
    580                 585                 590

GAA ACT ACT GAC GGT TCG TAT ATT GAA AAG AAA GAA ACT GCA ATG GTT      2000
Glu Thr Thr Asp Gly Ser Tyr Ile Glu Lys Lys Glu Thr Ala Met Val
595                 600                 605                 610

TGG CAC TAT GAA GAT GCT GAT AAA GAT CTT GGG TTG GAG CAG GCT AAG      2048
Trp His Tyr Glu Asp Ala Asp Lys Asp Leu Gly Leu Glu Gln Ala Lys
                615                 620                 625

GAA CTG TTG GAC CAT CTT GAA AAC GTG CTC GCT AAT GAG CCC GTT GAA      2096
Glu Leu Leu Asp His Leu Glu Asn Val Leu Ala Asn Glu Pro Val Glu
            630                 635                 640

GTG AAA CGA GGT CAA TAC ATT GTA GAA GTT AAA C                        2130
Val Lys Arg Gly Gln Tyr Ile Val Glu Val Lys
        645                 650
```

(2) INFORMATION FOR SEQ ID NO: 27:

(i) SEQUENCE CHARACTERISTICS:
(A) LENGTH: 653 amino acids
(B) TYPE: amino acid
(D) TOPOLOGY: linear (ii) MOLECULE TYPE: protein (xi) SEQUENCE DESCRIPTION: SEQ ID NO: 27:

```
Met His Ile Lys Asp Ala Leu Pro Ala Ala Val Glu Val Phe Tyr Val
  1               5                  10                  15

Gly Ala Leu Arg Ala Asp Val Gly Pro Thr Glu Gln Asp Asp Val Ser
             20                  25                  30

Lys Thr Leu Leu Asp Arg Phe Asn Cys Val Ala Val Phe Val Pro Thr
         35                  40                  45

Ser Lys Trp Asp Gln Tyr Tyr His Cys Phe Cys Lys Gln Tyr Leu Trp
     50                  55                  60

Pro Ile Phe His Tyr Lys Val Pro Ala Ser Asp Val Lys Ser Val Pro
 65                  70                  75                  80

Asn Ser Arg Asp Ser Trp Asn Ala Tyr Val His Val Asn Lys Glu Phe
                 85                  90                  95

Ser Gln Lys Val Met Glu Ala Val Thr Asn Ala Ser Asn Tyr Val Trp
            100                 105                 110

Ile His Asp Tyr His Leu Met Thr Leu Pro Thr Phe Leu Arg Arg Asp
        115                 120                 125

Phe Cys Arg Phe Lys Ile Gly Phe Phe Leu His Ser Pro Phe Pro Ser
    130                 135                 140

Ser Glu Val Tyr Lys Thr Leu Pro Met Arg Asn Glu Leu Leu Lys Gly
145                 150                 155                 160

Leu Leu Asn Ala Asp Leu Ile Gly Phe His Thr Tyr Asp Tyr Ala Arg
                165                 170                 175

His Phe Leu Thr Cys Cys Ser Arg Met Phe Gly Leu Asp His Gln Leu
            180                 185                 190

Lys Arg Gly Tyr Ile Phe Leu Glu Tyr Asn Gly Arg Ser Ile Glu Ile
        195                 200                 205

Lys Ile Lys Ala Ser Gly Ile His Val Gly Arg Met Glu Ser Tyr Leu
    210                 215                 220

Ser Gln Pro Asp Thr Arg Leu Gln Val Gln Glu Leu Lys Lys Arg Phe
225                 230                 235                 240
```

```
Glu Gly Lys Ile Val Leu Leu Gly Val Asp Asp Leu Asp Ile Phe Lys
                245                 250                 255

Gly Val Asn Phe Lys Val Leu Ala Leu Glu Lys Leu Leu Lys Ser His
            260                 265                 270

Pro Ser Trp Gln Gly Arg Val Val Leu Val Gln Ile Leu Asn Pro Ala
        275                 280                 285

Arg Ala Arg Cys Gln Asp Val Asp Glu Ile Asn Ala Glu Ile Arg Thr
    290                 295                 300

Val Cys Glu Arg Ile Asn Asn Glu Leu Gly Ser Pro Gly Tyr Gln Pro
305                 310                 315                 320

Val Val Leu Ile Asp Gly Pro Val Ser Leu Ser Glu Lys Ala Ala Tyr
                325                 330                 335

Tyr Ala Ile Ala Asp Met Ala Ile Val Thr Pro Leu Arg Asp Gly Met
            340                 345                 350

Asn Leu Ile Pro Tyr Glu Tyr Val Val Ser Arg Gln Ser Val Asn Asp
        355                 360                 365

Pro Asn Pro Asn Thr Pro Lys Lys Ser Met Leu Val Val Ser Glu Phe
    370                 375                 380

Ile Gly Cys Ser Leu Ser Leu Thr Gly Ala Ile Arg Val Asn Pro Trp
385                 390                 395                 400

Asp Glu Leu Glu Thr Ala Glu Ala Leu Tyr Asp Ala Leu Met Ala Pro
                405                 410                 415

Asp Asp His Lys Glu Thr Ala His Met Lys Gln Tyr Gln Tyr Ile Ile
            420                 425                 430

Ser His Asp Val Ala Asn Trp Ala Arg Ser Phe Phe Gln Asp Leu Glu
        435                 440                 445

Gln Ala Cys Ile Asp His Ser Arg Lys Arg Cys Met Asn Leu Gly Phe
    450                 455                 460

Gly Leu Asp Thr Arg Val Val Leu Phe Asp Glu Lys Phe Ser Lys Leu
465                 470                 475                 480

Asp Ile Asp Val Leu Glu Asn Ala Tyr Ser Met Ala Gln Asn Arg Ala
                485                 490                 495

Ile Leu Leu Asp Tyr Asp Gly Thr Val Thr Pro Ser Ile Ser Lys Ser
            500                 505                 510

Pro Thr Glu Ala Val Ile Ser Met Ile Asn Lys Leu Cys Asn Asp Pro
        515                 520                 525

Lys Asn Met Val Phe Ile Val Ser Gly Arg Ser Arg Glu Asn Leu Gly
    530                 535                 540

Ser Trp Phe Gly Ala Cys Glu Lys Pro Ala Ile Ala Ala Glu His Gly
545                 550                 555                 560

Tyr Phe Ile Arg Trp Ala Gly Asp Gln Glu Trp Glu Thr Cys Ala Arg
                565                 570                 575

Glu Asn Asn Val Gly Trp Met Glu Met Ala Glu Pro Val Met Asn Leu
            580                 585                 590

Tyr Thr Glu Thr Thr Asp Gly Ser Tyr Ile Glu Lys Lys Glu Thr Ala
        595                 600                 605

Met Val Trp His Tyr Glu Asp Ala Asp Lys Asp Leu Gly Leu Glu Gln
    610                 615                 620

Ala Lys Glu Leu Leu Asp His Leu Glu Asn Val Leu Ala Asn Glu Pro
625                 630                 635                 640

Val Glu Val Lys Arg Gly Gln Tyr Ile Val Glu Val Lys
                645                 650
```

(2) INFORMATION FOR SEQ ID NO: 28:

(i) SEQUENCE CHARACTERISTICS:
(A) LENGTH: 390 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Helianthus annuus (ix) FEATURE:
(A) NAME/KEY: CDS
(B) LOCATION: 3..258
(D) OTHER INFORMATION: /partial (xi) SEQUENCE DESCRIPTION: SEQ ID NO: 28:

```
TT GCA GAG AAG ATT TTT GCG TTC ATG GCT GAA AAG GGA AAA CAG GCT        47
   Ala Glu Lys Ile Phe Ala Phe Met Ala Glu Lys Gly Lys Gln Ala
     1               5                  10                  15

GAT TTC GTG TTG AGC GTT GGA GAT GAT AGA AGT GAT GAA GAC ATG TTT       95
Asp Phe Val Leu Ser Val Gly Asp Asp Arg Ser Asp Glu Asp Met Phe
                 20                  25                  30

GTG GCC ATT GGG GAT GGA ATA AAA AAG GGT CGG ATA ACT AAC AAC AAT      143
Val Ala Ile Gly Asp Gly Ile Lys Lys Gly Arg Ile Thr Asn Asn Asn
             35                  40                  45

TCA GTG TTT ACA TGC GTA GTG GGA GAG AAA CCG AGT GCA GCT GAG TAC      191
Ser Val Phe Thr Cys Val Val Gly Glu Lys Pro Ser Ala Ala Glu Tyr
         50                  55                  60

TTT TTA GAC GAG ACG AAA GAT GTT TCA ATG ATG CTC GAG AAG CTC GGG      239
Phe Leu Asp Glu Thr Lys Asp Val Ser Met Met Leu Glu Lys Leu Gly
     65                  70                  75

TGT CTC AGC AAC CAA GGA T GATGATCCGG AAGCTTCTCG TGATCTTTAT           288
Cys Leu Ser Asn Gln Gly
 80                  85

GAGTTAAAAG TTTTCGACTT TTTCTTCATC AAGATTCATG GGAAAGTTGT TCAATATGAA    348

CTTGTGTTTC TTGGTTCTGG ATTTTAGGGA GTCTATGGAT CC                       390
```

(2) INFORMATION FOR SEQ ID NO: 29:

(i) SEQUENCE CHARACTERISTICS:
(A) LENGTH: 85 amino acids
(B) TYPE: amino acid
(D) TOPOLOGY: linear (ii) MOLECULE TYPE: protein (xi) SEQUENCE DESCRIPTION: SEQ ID NO: 29:

```
Ala Glu Lys Ile Phe Ala Phe Met Ala Glu Lys Gly Lys Gln Ala Asp
  1               5                  10                  15

Phe Val Leu Ser Val Gly Asp Asp Arg Ser Asp Glu Asp Met Phe Val
             20                  25                  30

Ala Ile Gly Asp Gly Ile Lys Lys Gly Arg Ile Thr Asn Asn Asn Ser
         35                  40                  45

Val Phe Thr Cys Val Val Gly Glu Lys Pro Ser Ala Ala Glu Tyr Phe
     50                  55                  60

Leu Asp Glu Thr Lys Asp Val Ser Met Met Leu Glu Lys Leu Gly Cys
 65                  70                  75                  80

Leu Ser Asn Gln Gly
```

85

(2) INFORMATION FOR SEQ ID NO: 30:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: modified base, Inosine
(B) LOCATION: 4
(D) OTHER INFORMATION: /note= N is Inosine (ix) FEATURE:
(A) NAME/KEY: modified base, Inosine
(B) LOCATION: 10
(D) OTHER INFORMATION: /note= N is Inosine (ix) FEATURE:
(A) NAME/KEY: modified base, Inosine
(B) LOCATION: 13
(D) OTHER INFORMATION: /note= N is Inosine (ix) FEATURE:
(A) NAME/KEY: modified base, Inosine
(B) LOCATION: 19
(D) OTHER INFORMATION: /note= N is Inosine (ix) FEATURE:
(A) NAME/KEY: modified base, Inosine
(B) LOCATION: 22
(D) OTHER INFORMATION: /note= N is Inosine (xi) SEQUENCE DESCRIPTION: SEQ ID NO: 30:

CCANGGRTTN ACNCKDNTNG CNCC 24

(2) INFORMATION FOR SEQ ID NO: 31:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: modified base, Inosine
(B) LOCATION: 6
(D) OTHER INFORMATION: /note= A is Inosine (ix) FEATURE:
(A) NAME/KEY: modified base, Inosine
(B) LOCATION: 9
(D) OTHER INFORMATION: /note= A is Inosine (ix) FEATURE:
(A) NAME/KEY: modified base, Inosine
(B) LOCATION: 12
(D) OTHER INFORMATION: /note= A is Inosine (ix) FEATURE:
(A) NAME/KEY: modified base, Inosine
(B) LOCATION: 18
(D) OTHER INFORMATION: /note= A is Inosine (ix) FEATURE:
(A) NAME/KEY: modified base, Inosine
(B) LOCATION: 21
(D) OTHER INFORMATION: /note= A is Inosine (xi) SEQUENCE DESCRIPTION: SEQ ID NO: 31:

ATHGTNGTNW SNAAYMRNYT NCC 23

(2) INFORMATION FOR SEQ ID NO: 32:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: modified base, Inosine
(B) LOCATION: 3
(D) OTHER INFORMATION: /note= N is Inosine (ix) FEATURE:
(A) NAME/KEY: modified base, Inosine
(B) LOCATION: 9
(D) OTHER INFORMATION: /note= N is Inosine (ix) FEATURE:
(A) NAME/KEY: modified base, Inosine
(B) LOCATION: 12
(D) OTHER INFORMATION: /note= N is Inosine (xi) SEQUENCE DESCRIPTION: SEQ ID NO: 32:

YTNTGGCCNA TNTTYCAYTA 20

(2) INFORMATION FOR SEQ ID NO: 33:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: modified base, Inosine
(B) LOCATION: 6
(D) OTHER INFORMATION: /note= N is Inosine (ix) FEATURE:
(A) NAME/KEY: modified base, Inosine
(B) LOCATION: 9
(D) OTHER INFORMATION: /note= N is Inosine (ix) FEATURE:
(A) NAME/KEY: modified base, Inosine
(B) LOCATION: 18
(D) OTHER INFORMATION: /note= N is Inosine (xi) SEQUENCE DESCRIPTION: SEQ ID NO: 33:

TGRTCNARNA RYTCYTTNGC 20

(2) INFORMATION FOR SEQ ID NO: 34:

(i) SEQUENCE CHARACTERISTICS:
(A) LENGTH: 20 base pairS
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: modified base, Inosine
(B) LOCATION: 6
(D) OTHER INFORMATION: /note= N is Inosine (ix) FEATURE:
(A) NAME/KEY: modified base, Inosine
(B) LOCATION: 18
(D) OTHER INFORMATION: /note= N is Inosine (xi) SEQUENCE DESCRIPTION: SEQ ID NO: 34:

TCRTCNGTRA ARTCRTCNCC 20

(2) INFORMATION FOR SEQ ID NO: 35:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: modified base, Inosine
(B) LOCATION: 15
(D) OTHER INFORMATION: /note= N is Inosine (ix) FEATURE:
(A) NAME/KEY: modified base, Inosine
(B) LOCATION: 18
(D) OTHER INFORMATION: /note= N is Inosine (xi) SEQUENCE DESCRIPTION: SEQ ID NO: 35:

TTYGAYTAYG AYGGNACNYT 20

(2) INFORMATION FOR SEQ ID NO: 36:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: modified base, Inosine
(B) LOCATION: 3
(D) OTHER INFORMATION: /note= N is Inosine (ix) FEATURE:
(A) NAME/KEY: modified base, Inosine
(B) LOCATION: 6
(D) OTHER INFORMATION: /note= N is Inosine (ix) FEATURE:
(A) NAME/KEY: modified base, Inosine
(B) LOCATION: 12
(D) OTHER INFORMATION: /note= N is Inosine (xi) SEQUENCE DESCRIPTION: SEQ ID NO: 36:

GGNYTNWBNG CNGARCAYGG 20

(2) INFORMATION FOR SEQ ID NO: 37:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: modified base, Inosine
(B) LOCATION: 3
(D) OTHER INFORMATION: /note= N is Inosine (ix) FEATURE:
(A) NAME/KEY: modified base, Inosine
(B) LOCATION: 6
(D) OTHER INFORMATION: /note= N is Inosine (ix) FEATURE:
(A) NAME/KEY: modified base, Inosine
(B) LOCATION: 12
(D) OTHER INFORMATION: /note= N is Inosine (ix) FEATURE:
(A) NAME/KEY: modified base, Inosine
(B) LOCATION: 15
(D) OTHER INFORMATION: /note= N is Inosine (xi) SEQUENCE DESCRIPTION: SEQ ID NO: 37:

ATNGCNAARC CNGTNATGAA 20

(2) INFORMATION FOR SEQ ID NO: 38:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: modified base, Inosine
(B) LOCATION: 3
(D) OTHER INFORMATION: /note= N is Inosine (ix) FEATURE:
(A) NAME/KEY: modified base, Inosine
(B) LOCATION: 6
(D) OTHER INFORMATION: /note= N is Inosine (ix) FEATURE:
(A) NAME/KEY: modified base, Inosine
(B) LOCATION: 12
(D) OTHER INFORMATION: /note= N is Inosine (ix) FEATURE:

(A) NAME/KEY: modified base, Inosine
(B) LOCATION: 18
(D) OTHER INFORMATION: /note= N is Inosine (xi) SEQUENCE DESCRIPTION: SEQ ID NO: 38:

```
CCNACNGTRC ANGCRAANAC                                          20
```

(2) INFORMATION FOR SEQ ID NO: 39:

(i) SEQUENCE CHARACTERISTICS:
(A) LENGTH: 2982 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Arabidopsis thaliana (ix) FEATURE:
(A) NAME/KEY: CDS
(B) LOCATION: 64..2889

(xi) SEQUENCE DESCRIPTION: SEQ ID NO: 39:

```
ATAAACTTCC TCGCGGCCGC CAGTGTGAGT AATTTAGTTT TGGTTCTGTT TTGGTGTGAG     60

CGT ATG CCT GGA AAT AAG TAC AAC TGC AGT TCT TCT CAT ATC CCA CTC      108
    Met Pro Gly Asn Lys Tyr Asn Cys Ser Ser Ser His Ile Pro Leu
      1               5                  10                  15

TCT CGA ACA GAA CGC CTC TTG AGA GAT AGA GAG CTT AGA GAG AAG AGG      156
Ser Arg Thr Glu Arg Leu Leu Arg Asp Arg Glu Leu Arg Glu Lys Arg
                 20                  25                  30

AAG AGC AAC CGA GCT CGT AAT CCT AAT GAC GTT GCT GGC AGT TCC GAG      204
Lys Ser Asn Arg Ala Arg Asn Pro Asn Asp Val Ala Gly Ser Ser Glu
             35                  40                  45

AAC TCT GAG AAT GAC TTG CGT TTA GAA GGT GAC AGT TCA AGG CAG TAT      252
Asn Ser Glu Asn Asp Leu Arg Leu Glu Gly Asp Ser Ser Arg Gln Tyr
         50                  55                  60

GTT GAA CAG TAC TTG GAA GGG GCT GCT GCT GCA ATG GCG CAC GAT GAT      300
Val Glu Gln Tyr Leu Glu Gly Ala Ala Ala Ala Met Ala His Asp Asp
     65                  70                  75

GCG TGT GAG AGG CAA GAA GTT AGG CCT TAT AAT AGG CAA CGA CTA CTT      348
Ala Cys Glu Arg Gln Glu Val Arg Pro Tyr Asn Arg Gln Arg Leu Leu
 80                  85                  90                  95

GTA GTG GCT AAC AGG CTC CCA GTT TCT CCC GTG AGA AGA GGT GAA GAT      396
Val Val Ala Asn Arg Leu Pro Val Ser Pro Val Arg Arg Gly Glu Asp
                100                 105                 110

TCA TGG TCT CTT GAG ATC AGT GCT GGT GGT CTA GTC AGT GCT CTC TTA      444
Ser Trp Ser Leu Glu Ile Ser Ala Gly Gly Leu Val Ser Ala Leu Leu
            115                 120                 125

GGT GTA AAG GAA TTT GAG GCC AGA TGG ATA GGA TGG GCT GGA GTT AAT      492
Gly Val Lys Glu Phe Glu Ala Arg Trp Ile Gly Trp Ala Gly Val Asn
        130                 135                 140

GTG CCT GAT GAG GTT GGA CAG AAG GCA CTT AGC AAA GCT TTG GCT GAG      540
Val Pro Asp Glu Val Gly Gln Lys Ala Leu Ser Lys Ala Leu Ala Glu
    145                 150                 155

AAG AGG TGT ATT CCC GTG TTC CTT GAT GAA GAG ATT GTT CAT CAG TAC      588
Lys Arg Cys Ile Pro Val Phe Leu Asp Glu Glu Ile Val His Gln Tyr
160                 165                 170                 175

TAT AAT GGT TAC TGC AAC AAT ATT CTG TGG CCT CTG TTT CAC TAC CTT      636
Tyr Asn Gly Tyr Cys Asn Asn Ile Leu Trp Pro Leu Phe His Tyr Leu
```

```
            180                 185                 190

GGA CTT CCG CAA GAA GAT CGG CTT GCC ACA ACC AGA AGC TTT CAG TCC      684
Gly Leu Pro Gln Glu Asp Arg Leu Ala Thr Thr Arg Ser Phe Gln Ser
        195                 200                 205

CAA TTT GCT GCA TAC AAG AAG GCA AAC CAA ATG TTC GCT GAT GTT GTA      732
Gln Phe Ala Ala Tyr Lys Lys Ala Asn Gln Met Phe Ala Asp Val Val
    210                 215                 220

AAT GAG CAC TAT GAA GAG GGA GAT GTC GTC TGG TGC CAT GAC TAT CAT      780
Asn Glu His Tyr Glu Glu Gly Asp Val Val Trp Cys His Asp Tyr His
    225                 230                 235

CTT ATG TTC CTT CCT AAA TGC CTT AAG GAG TAC AAC AGT AAG ATG AAA      828
Leu Met Phe Leu Pro Lys Cys Leu Lys Glu Tyr Asn Ser Lys Met Lys
240                 245                 250                 255

GTT GGA TGG TTT CTC CAT ACA CCA TTC CCT TCG TCT GAG ATA CAC AGG      876
Val Gly Trp Phe Leu His Thr Pro Phe Pro Ser Ser Glu Ile His Arg
            260                 265                 270

ACA CTT CCA TCA CGA TCA GAG CTC CTT CGG TCA GTT CTT GCT GCT GAT      924
Thr Leu Pro Ser Arg Ser Glu Leu Leu Arg Ser Val Leu Ala Ala Asp
        275                 280                 285

TTA GTT GGC TTC CAT ACA TAT GAC TAT GCA AGG CAC TTT GTG AGT GCG      972
Leu Val Gly Phe His Thr Tyr Asp Tyr Ala Arg His Phe Val Ser Ala
    290                 295                 300

TGC ACT CGT ATT CTT GGA CTT GAA GGA ACA CCT GAG GGA GTT GAG GAT     1020
Cys Thr Arg Ile Leu Gly Leu Glu Gly Thr Pro Glu Gly Val Glu Asp
    305                 310                 315

CAA GGC AGG CTC ACT CGT GTA GCT GCT TTT CCA ATT GGC ATA GAT TCT     1068
Gln Gly Arg Leu Thr Arg Val Ala Ala Phe Pro Ile Gly Ile Asp Ser
320                 325                 330                 335

GAT CGG TTT ATA CGA GCA CTT GAG GTC CCC GAA GTC AAA CAA CAC ATG     1116
Asp Arg Phe Ile Arg Ala Leu Glu Val Pro Glu Val Lys Gln His Met
            340                 345                 350

AAG GAA TTG AAA GAA AGA TTT ACT GAC AGA AAG GTG ATG TTA GGT GTT     1164
Lys Glu Leu Lys Glu Arg Phe Thr Asp Arg Lys Val Met Leu Gly Val
        355                 360                 365

GAT CGT CTT GAC ATG ATC AAA GGG ATT CCA CAA AAG ATT CTG GCA TTC     1212
Asp Arg Leu Asp Met Ile Lys Gly Ile Pro Gln Lys Ile Leu Ala Phe
    370                 375                 380

GAA AAA TTT CTC GAG GAA AAT GCA AAC TGG CGT GAT AAA GTG GTC TTA     1260
Glu Lys Phe Leu Glu Glu Asn Ala Asn Trp Arg Asp Lys Val Val Leu
    385                 390                 395

TTG AAA ATT GCG GTG CCA ACA AGA CCT GAC GTT CCT GAG TAT CAA ACA     1308
Leu Lys Ile Ala Val Pro Thr Arg Pro Asp Val Pro Glu Tyr Gln Thr
400                 405                 410                 415

CTC ACA AGC CAA GTT CAT GAA ATT GTT GGC CGC ATT ATT GGT CGT CTC     1356
Leu Thr Ser Gln Val His Glu Ile Val Gly Arg Ile Ile Gly Arg Leu
            420                 425                 430

GGG ACA CTG ACT GCA GTT CCA ATA CAT CAT CTG GAT CGG TCT CTG GAC     1404
Gly Thr Leu Thr Ala Val Pro Ile His His Leu Asp Arg Ser Leu Asp
        435                 440                 445

TTT CAT GCT TTA TGT GCA CTT TAT GCC GTC ACA GAT GTT GCG CTT GTA     1452
Phe His Ala Leu Cys Ala Leu Tyr Ala Val Thr Asp Val Ala Leu Val
    450                 455                 460

ACA TCT TTG AGA GAT GGG ATG AAT CTT GTC AGT TAT GAG TTT GTT GCT     1500
Thr Ser Leu Arg Asp Gly Met Asn Leu Val Ser Tyr Glu Phe Val Ala
    465                 470                 475

TGC CAA GAG GCC AAA AAG GGC GTC CTC ATT CTC AGT GAA TTT GCA GGT     1548
Cys Gln Glu Ala Lys Lys Gly Val Leu Ile Leu Ser Glu Phe Ala Gly
480                 485                 490                 495

GCT GCA CAG TCT CTG GGT GCT GGA GCT ATT CTT GTG AAT CCT TGG AAC     1596
Ala Ala Gln Ser Leu Gly Ala Gly Ala Ile Leu Val Asn Pro Trp Asn
```

```
                500                 505                 510

ATC ACA GAA GTT GCT GCC TCC ATT GGA CAA GCC CTA AAC ATG ACA GCT      1644
Ile Thr Glu Val Ala Ala Ser Ile Gly Gln Ala Leu Asn Met Thr Ala
            515                 520                 525

GAA GAA AGA GAG AAA AGA CAT CGC CAT AAT TTT CAT CAT GTC AAA ACT      1692
Glu Glu Arg Glu Lys Arg His Arg His Asn Phe His His Val Lys Thr
        530                 535                 540

CAC ACT GCT CAA GAA TGG GCT GAA ACT TTT GTC AGT GAA CTA AAT GAC      1740
His Thr Ala Gln Glu Trp Ala Glu Thr Phe Val Ser Glu Leu Asn Asp
    545                 550                 555

ACT GTA ATT GAG GCG CAA CTA CGA ATT AGT AAA GTC CCA CCA GAG CTT      1788
Thr Val Ile Glu Ala Gln Leu Arg Ile Ser Lys Val Pro Pro Glu Leu
560                 565                 570                 575

CCA CAG CAT GAT GCA ATT CAA CGG TAT TCA AAG TCC AAC AAC AGG CTT      1836
Pro Gln His Asp Ala Ile Gln Arg Tyr Ser Lys Ser Asn Asn Arg Leu
                580                 585                 590

CTA ATC CTG GGT TTC AAT GCA ACA TTG ACT GAA CCA GTG GAT AAT CAA      1884
Leu Ile Leu Gly Phe Asn Ala Thr Leu Thr Glu Pro Val Asp Asn Gln
            595                 600                 605

GGG AGA AGA GGT GAT CAA ATA AAG GAG ATG GAT CTT AAT CTA CAC CCT      1932
Gly Arg Arg Gly Asp Gln Ile Lys Glu Met Asp Leu Asn Leu His Pro
        610                 615                 620

GAG CTT AAA GGG CCC TTA AAG GCA TTA TGC AGT GAT CCA AGT ACA ACC      1980
Glu Leu Lys Gly Pro Leu Lys Ala Leu Cys Ser Asp Pro Ser Thr Thr
    625                 630                 635

ATA GTT GTT CTG AGC GGA AGC AGC AGA AGT GTT TTG GAC AAA AAC TTT      2028
Ile Val Val Leu Ser Gly Ser Ser Arg Ser Val Leu Asp Lys Asn Phe
640                 645                 650                 655

GGA GAG TAT GAC ATG TGG CTG GCA GCA GAA AAT GGG ATG TTC CTA AGG      2076
Gly Glu Tyr Asp Met Trp Leu Ala Ala Glu Asn Gly Met Phe Leu Arg
                660                 665                 670

CTT ACG AAT GGA GAG TGG ATG ACT ACA ATG CCA GAA CAC TTG AAC ATG      2124
Leu Thr Asn Gly Glu Trp Met Thr Thr Met Pro Glu His Leu Asn Met
            675                 680                 685

GAA TGG GTT GAT AGC GTA AAG CAT GTT TTC AAG TAC TTC ACT GAG AGA      2172
Glu Trp Val Asp Ser Val Lys His Val Phe Lys Tyr Phe Thr Glu Arg
        690                 695                 700

ACT CCC AGG TCA CAC TTT GAA ACT CGC GAT ACT TCG CTT ATT TGG AAC      2220
Thr Pro Arg Ser His Phe Glu Thr Arg Asp Thr Ser Leu Ile Trp Asn
    705                 710                 715

TAC AAA TAT GCA GAT ATC GAA TTC GGG AGA CTT CAA GCA AGA GAT TTG      2268
Tyr Lys Tyr Ala Asp Ile Glu Phe Gly Arg Leu Gln Ala Arg Asp Leu
720                 725                 730                 735

TTA CAA CAC TTA TGG ACA GGT CCA ATC TCT AAT GCA TCA GTT GAT GTT      2316
Leu Gln His Leu Trp Thr Gly Pro Ile Ser Asn Ala Ser Val Asp Val
                740                 745                 750

GTC CAA GGA AGC CGC TCT GTG GAA GTC CGT GCA GTT GGT GTC ACA AAG      2364
Val Gln Gly Ser Arg Ser Val Glu Val Arg Ala Val Gly Val Thr Lys
            755                 760                 765

GGA GCT GCA ATT GAT CGT ATT CTA GGA GAG ATA GTG CAT AGC AAG TCG      2412
Gly Ala Ala Ile Asp Arg Ile Leu Gly Glu Ile Val His Ser Lys Ser
        770                 775                 780

ATG ACT ACA CCA ATC GAT TAC GTC TTG TGC ATT GGT CAT TTC TTG GGG      2460
Met Thr Thr Pro Ile Asp Tyr Val Leu Cys Ile Gly His Phe Leu Gly
    785                 790                 795

AAG GAC GAA GAT GTT TAC ACT TTC TTC GAA CCA GAA CTT CCA TCC GAC      2508
Lys Asp Glu Asp Val Tyr Thr Phe Phe Glu Pro Glu Leu Pro Ser Asp
800                 805                 810                 815

ATG CCA GCC ATT GCA CGA TCC AGA CCA TCA TCT GAC AGT GGA GCC AAG      2556
Met Pro Ala Ile Ala Arg Ser Arg Pro Ser Ser Asp Ser Gly Ala Lys
```

```
                820                 825                 830

TCA TCA TCA GGA GAC CGA AGA CCA CCT TCA AAG TCG ACA CAT AAC AAC     2604
Ser Ser Ser Gly Asp Arg Arg Pro Pro Ser Lys Ser Thr His Asn Asn
            835                 840                 845

AAC AAA AGT GGA TCA AAA TCC TCA TCA TCC TCT AAC TCT AAC AAC AAC     2652
Asn Lys Ser Gly Ser Lys Ser Ser Ser Ser Ser Asn Ser Asn Asn Asn
        850                 855                 860

AAC AAG TCC TCA CAG AGA TCT CTT CAG TCA GAG AGA AAA AGT GGA TCC     2700
Asn Lys Ser Ser Gln Arg Ser Leu Gln Ser Glu Arg Lys Ser Gly Ser
    865                 870                 875

AAC CAT AGC TTA GGA AAC TCA AGA CGT CCT TCA CCA GAG AAG ATC TCA     2748
Asn His Ser Leu Gly Asn Ser Arg Arg Pro Ser Pro Glu Lys Ile Ser
880                 885                 890                 895

TGG AAT GTG CTT GAC CTC AAA GGA GAG AAC TAC TTC TCT TGC GCT GTG     2796
Trp Asn Val Leu Asp Leu Lys Gly Glu Asn Tyr Phe Ser Cys Ala Val
                900                 905                 910

GGT CGT ACT CGC ACC AAT GCT AGA TAT CTC CTT GGC TCA CCT GAC GAC     2844
Gly Arg Thr Arg Thr Asn Ala Arg Tyr Leu Leu Gly Ser Pro Asp Asp
            915                 920                 925

GTC GTT TGC TTC CTT GAG AAG CTC GCT GAC ACC ACT TCC TCA CCT TAA     2892
Val Val Cys Phe Leu Glu Lys Leu Ala Asp Thr Thr Ser Ser Pro
        930                 935                 940

TATCCCGAGA CAGTGTCAAG TGAGTTCATG TAACCCAATA AAAACTATTG TTTTGTAACA   2952

AAAAGCAGCC ATTACCAGAC TCTTTAGTGG                                    2982
```

(2) INFORMATION FOR SEQ ID NO: 40:

(i) SEQUENCE CHARACTERISTICS:
(A) LENGTH: 942 amino acids
(B) TYPE: amino acid
(D) TOPOLOGY: linear (ii) MOLECULE TYPE: protein (xi) SEQUENCE DESCRIPTION: SEQ ID NO: 40:

```
Met Pro Gly Asn Lys Tyr Asn Cys Ser Ser Ser His Ile Pro Leu Ser
  1               5                  10                  15

Arg Thr Glu Arg Leu Leu Arg Asp Arg Glu Leu Arg Glu Lys Arg Lys
            20                  25                  30

Ser Asn Arg Ala Arg Asn Pro Asn Asp Val Ala Gly Ser Ser Glu Asn
        35                  40                  45

Ser Glu Asn Asp Leu Arg Leu Glu Gly Asp Ser Ser Arg Gln Tyr Val
     50                  55                  60

Glu Gln Tyr Leu Glu Gly Ala Ala Ala Ala Met Ala His Asp Asp Ala
 65                  70                  75                  80

Cys Glu Arg Gln Glu Val Arg Pro Tyr Asn Arg Gln Arg Leu Leu Val
                 85                  90                  95

Val Ala Asn Arg Leu Pro Val Ser Pro Val Arg Arg Gly Glu Asp Ser
            100                 105                 110

Trp Ser Leu Glu Ile Ser Ala Gly Gly Leu Val Ser Ala Leu Leu Gly
        115                 120                 125

Val Lys Glu Phe Glu Ala Arg Trp Ile Gly Trp Ala Gly Val Asn Val
    130                 135                 140

Pro Asp Glu Val Gly Gln Lys Ala Leu Ser Lys Ala Leu Ala Glu Lys
145                 150                 155                 160

Arg Cys Ile Pro Val Phe Leu Asp Glu Glu Ile Val His Gln Tyr Tyr
                165                 170                 175

Asn Gly Tyr Cys Asn Asn Ile Leu Trp Pro Leu Phe His Tyr Leu Gly
```

```
            180                 185                 190

Leu Pro Gln Glu Asp Arg Leu Ala Thr Thr Arg Ser Phe Gln Ser Gln
        195                 200                 205

Phe Ala Ala Tyr Lys Lys Ala Asn Gln Met Phe Ala Asp Val Val Asn
    210                 215                 220

Glu His Tyr Glu Glu Gly Asp Val Val Trp Cys His Asp Tyr His Leu
225                 230                 235                 240

Met Phe Leu Pro Lys Cys Leu Lys Glu Tyr Asn Ser Lys Met Lys Val
                245                 250                 255

Gly Trp Phe Leu His Thr Pro Phe Pro Ser Ser Glu Ile His Arg Thr
            260                 265                 270

Leu Pro Ser Arg Ser Glu Leu Leu Arg Ser Val Leu Ala Ala Asp Leu
        275                 280                 285

Val Gly Phe His Thr Tyr Asp Tyr Ala Arg His Phe Val Ser Ala Cys
    290                 295                 300

Thr Arg Ile Leu Gly Leu Glu Gly Thr Pro Glu Gly Val Glu Asp Gln
305                 310                 315                 320

Gly Arg Leu Thr Arg Val Ala Ala Phe Pro Ile Gly Ile Asp Ser Asp
                325                 330                 335

Arg Phe Ile Arg Ala Leu Glu Val Pro Glu Val Lys Gln His Met Lys
            340                 345                 350

Glu Leu Lys Glu Arg Phe Thr Asp Arg Lys Val Met Leu Gly Val Asp
        355                 360                 365

Arg Leu Asp Met Ile Lys Gly Ile Pro Gln Lys Ile Leu Ala Phe Glu
    370                 375                 380

Lys Phe Leu Glu Glu Asn Ala Asn Trp Arg Asp Lys Val Val Leu Leu
385                 390                 395                 400

Lys Ile Ala Val Pro Thr Arg Pro Asp Val Pro Glu Tyr Gln Thr Leu
                405                 410                 415

Thr Ser Gln Val His Glu Ile Val Gly Arg Ile Ile Gly Arg Leu Gly
            420                 425                 430

Thr Leu Thr Ala Val Pro Ile His His Leu Asp Arg Ser Leu Asp Phe
        435                 440                 445

His Ala Leu Cys Ala Leu Tyr Ala Val Thr Asp Val Ala Leu Val Thr
    450                 455                 460

Ser Leu Arg Asp Gly Met Asn Leu Val Ser Tyr Glu Phe Val Ala Cys
465                 470                 475                 480

Gln Glu Ala Lys Lys Gly Val Leu Ile Leu Ser Glu Phe Ala Gly Ala
                485                 490                 495

Ala Gln Ser Leu Gly Ala Gly Ala Ile Leu Val Asn Pro Trp Asn Ile
            500                 505                 510

Thr Glu Val Ala Ala Ser Ile Gly Gln Ala Leu Asn Met Thr Ala Glu
        515                 520                 525

Glu Arg Glu Lys Arg His Arg His Asn Phe His His Val Lys Thr His
    530                 535                 540

Thr Ala Gln Glu Trp Ala Glu Thr Phe Val Ser Glu Leu Asn Asp Thr
545                 550                 555                 560

Val Ile Glu Ala Gln Leu Arg Ile Ser Lys Val Pro Pro Glu Leu Pro
                565                 570                 575

Gln His Asp Ala Ile Gln Arg Tyr Ser Lys Ser Asn Asn Arg Leu Leu
            580                 585                 590

Ile Leu Gly Phe Asn Ala Thr Leu Thr Glu Pro Val Asp Asn Gln Gly
        595                 600                 605
```

```
Arg Arg Gly Asp Gln Ile Lys Glu Met Asp Leu Asn Leu His Pro Glu
    610                 615                 620

Leu Lys Gly Pro Leu Lys Ala Leu Cys Ser Asp Pro Ser Thr Thr Ile
625                 630                 635                 640

Val Val Leu Ser Gly Ser Ser Arg Ser Val Leu Asp Lys Asn Phe Gly
                645                 650                 655

Glu Tyr Asp Met Trp Leu Ala Ala Glu Asn Gly Met Phe Leu Arg Leu
            660                 665                 670

Thr Asn Gly Glu Trp Met Thr Thr Met Pro Glu His Leu Asn Met Glu
        675                 680                 685

Trp Val Asp Ser Val Lys His Val Phe Lys Tyr Phe Thr Glu Arg Thr
    690                 695                 700

Pro Arg Ser His Phe Glu Thr Arg Asp Thr Ser Leu Ile Trp Asn Tyr
705                 710                 715                 720

Lys Tyr Ala Asp Ile Glu Phe Gly Arg Leu Gln Ala Arg Asp Leu Leu
                725                 730                 735

Gln His Leu Trp Thr Gly Pro Ile Ser Asn Ala Ser Val Asp Val Val
            740                 745                 750

Gln Gly Ser Arg Ser Val Glu Val Arg Ala Val Gly Val Thr Lys Gly
        755                 760                 765

Ala Ala Ile Asp Arg Ile Leu Gly Glu Ile Val His Ser Lys Ser Met
    770                 775                 780

Thr Thr Pro Ile Asp Tyr Val Leu Cys Ile Gly His Phe Leu Gly Lys
785                 790                 795                 800

Asp Glu Asp Val Tyr Thr Phe Phe Glu Pro Glu Leu Pro Ser Asp Met
                805                 810                 815

Pro Ala Ile Ala Arg Ser Arg Pro Ser Ser Asp Ser Gly Ala Lys Ser
            820                 825                 830

Ser Ser Gly Asp Arg Arg Pro Pro Ser Lys Ser Thr His Asn Asn Asn
        835                 840                 845

Lys Ser Gly Ser Lys Ser Ser Ser Ser Ser Asn Ser Asn Asn Asn Asn
    850                 855                 860

Lys Ser Ser Gln Arg Ser Leu Gln Ser Glu Arg Lys Ser Gly Ser Asn
865                 870                 875                 880

His Ser Leu Gly Asn Ser Arg Arg Pro Ser Pro Glu Lys Ile Ser Trp
                885                 890                 895

Asn Val Leu Asp Leu Lys Gly Glu Asn Tyr Phe Ser Cys Ala Val Gly
            900                 905                 910

Arg Thr Arg Thr Asn Ala Arg Tyr Leu Leu Gly Ser Pro Asp Asp Val
        915                 920                 925

Val Cys Phe Leu Glu Lys Leu Ala Asp Thr Thr Ser Ser Pro
```

(2) INFORMATION FOR SEQ ID NO: 41:

(i) SEQUENCE CHARACTERISTICS:
- (A) LENGTH: 300 base pairs
- (B) TYPE: nucleic acid
- (C) STRANDEDNESS: double
- (D) TOPOLOGY: linear (ii) MOLECULE TYPE: cDNA to mRNA (iii) HYPOTHETICAL: NO (iv) ANTI-SENSE: NO (vi) ORIGINAL SOURCE:
- (A) ORGANISM: Oryza sativa (xi) SEQUENCE DESCRIPTION: SEQ ID NO: 41:

```
ATAAACTTCC TCGGACCAAA GAAGAGCATG TTGGTTGTGT CGGAGTTTAT TGGTTGCTCA     60

CCTTCACTGA GTGGAGCCAT TCGTGTTAAC CCGTGGAATA TCGAGGCAAC TGCAGAGGCA    120

CTGAATGAGG CCATCTCAAT GTCAGAGCGT AAAAGCAGCT GAGGCACGAA AAACATTACC    180

GTTATGTCAG CACCCATGAT GTTGCATATT GGTCTAAGAG CTTTGTACAG GACCTGGAGA    240

GGGCTTGCAA GGATCACTTT AGGAAACCAT GCTGGGGCAT TGGATTGGAT TTCGCTCAGG    300
```

(2) INFORMATION FOR SEQ ID NO: 42:

(i) SEQUENCE CHARACTERISTICS:
(A) LENGTH: 627 base pairs
(B) TYPE: nucleic acid
(C) STRANDEDNESS: double
(D) TOPOLOGY: /note = stopcodon (ii) MOLECULE TYPE: cDNA to mRNA (iii) HYPOTHETICAL: NO (iv) ANTI-SENSE: NO (vi) ORIGINAL SOURCE:
(A) ORGANISM: Selaginella lepidophylla (ix) FEATURE:
(A) NAME/KEY: CDS
(B) LOCATION: 4..627
(D) OTHER INFORMATION: /partial (ix) FEATURE:
(A) NAME/KEY: unsure
(B) LOCATION: 337..339

(xi) SEQUENCE DESCRIPTION: SEQ ID NO: 42:

```
ATT ATG TGG GTG CAT GAT TAC CAC CTC TGT CTG GTC CCT CAG ATG ATC       48
    Met Trp Val His Asp Tyr His Leu Cys Leu Val Pro Gln Met Ile
      1               5                  10                  15

CGC CAA AAG CTG CCA GAT GTG CAG ATT GGC TTC TTC CTC CAC ACC GCT       96
Arg Gln Lys Leu Pro Asp Val Gln Ile Gly Phe Phe Leu His Thr Ala
                20                  25                  30

TTT CCC TCG TCA GAG GTC TTC CGC TGC TTG GCC GCA CGA AAG GAG CTG      144
Phe Pro Ser Ser Glu Val Phe Arg Cys Leu Ala Ala Arg Lys Glu Leu
            35                  40                  45

CTG GAC GGC ATG CTT GGT GCC AAC TTG GTT GCT TTC CAG ACG CCA GAG      192
Leu Asp Gly Met Leu Gly Ala Asn Leu Val Ala Phe Gln Thr Pro Glu
        50                  55                  60

TAT GCA CAC CAC TTC CTC CAG ACG TGC AGT CGC ATT TCT CTG CTG AAG      240
Tyr Ala His His Phe Leu Gln Thr Cys Ser Arg Ile Ser Leu Leu Lys
     65                  70                  75

CAA CCG AGG AAG GCG TTC AGC TCG TTT CGT CAA TGT CTG GTC ATA ATG      288
Gln Pro Arg Lys Ala Phe Ser Ser Phe Arg Gln Cys Leu Val Ile Met
 80                  85                  90                  95

CAA GAA GCG CTA CGA GGG TCA AGA AGG TCA TCG TTG CGC GTG ACA AGC      336
Gln Glu Ala Leu Arg Gly Ser Arg Arg Ser Ser Leu Arg Val Thr Ser
                100                 105                 110

TGA CAA CAT CGC GTG TAC GCG AGA AGC TTC TGT CGT ACG AGC TGT TCT      384
Xaa Gln His Arg Val Tyr Ala Arg Ser Phe Cys Arg Thr Ser Cys Ser
            115                 120                 125

TGA ACA AGA ACC CAC AGT GGA GGG ACA AGG TCG TTC TCA TTC AGG TTG      432
Xaa Thr Arg Thr His Ser Gly Gly Thr Arg Ser Phe Ser Phe Arg Leu
        130                 135                 140

CGA CCT CCA CGA CTG AGG ATT CTG AGC TTG CTG CGA CCG TAT CCG AAA      480
Arg Pro Pro Arg Leu Arg Ile Leu Ser Leu Leu Arg Pro Tyr Pro Lys
    145                 150                 155
```

```
TTG TTA CAC GTA TTG ACG CTG TGC ACT CGA CGC TCA CAC ACA CCC ACT      528
Leu Leu His Val Leu Thr Leu Cys Thr Arg Arg Ser His Thr Pro Thr
160                 165                 170                 175

CGT CTT CCT CAG GCA AGA CAT TGC GTT CTC GCA GTA CCT CGC ACT TCT      576
Arg Leu Pro Gln Ala Arg His Cys Val Leu Ala Val Pro Arg Thr Ser
                180                 185                 190

CTC GAT CGC CGA TGC TCT TGC AAT CAA CTG TTC GAT GGC ATG AAC CTC      624
Leu Asp Arg Arg Cys Ser Cys Asn Gln Leu Phe Asp Gly Met Asn Leu
            195                 200                 205

GTC                                                                  627
Val
```

(2) INFORMATION FOR SEQ ID NO: 43:

(i) SEQUENCE CHARACTERISTICS:
(A) LENGTH: 208 amino acids
(B) TYPE: amino acid
(D) TOPOLOGY: linear (ii) MOLECULE TYPE: protein (xi) SEQUENCE DESCRIPTION: SEQ ID NO: 43:

```
Met Trp Val His Asp Tyr His Leu Cys Leu Val Pro Gln Met Ile Arg
  1               5                  10                  15

Gln Lys Leu Pro Asp Val Gln Ile Gly Phe Phe Leu His Thr Ala Phe
            20                  25                  30

Pro Ser Ser Glu Val Phe Arg Cys Leu Ala Ala Arg Lys Glu Leu Leu
        35                  40                  45

Asp Gly Met Leu Gly Ala Asn Leu Val Ala Phe Gln Thr Pro Glu Tyr
    50                  55                  60

Ala His His Phe Leu Gln Thr Cys Ser Arg Ile Ser Leu Leu Lys Gln
 65                  70                  75                  80

Pro Arg Lys Ala Phe Ser Ser Phe Arg Gln Cys Leu Val Ile Met Gln
                85                  90                  95

Glu Ala Leu Arg Gly Ser Arg Arg Ser Ser Leu Arg Val Thr Ser Xaa
            100                 105                 110

Gln His Arg Val Tyr Ala Arg Ser Phe Cys Arg Thr Ser Cys Ser Xaa
        115                 120                 125

Thr Arg Thr His Ser Gly Gly Thr Arg Ser Phe Ser Phe Arg Leu Arg
    130                 135                 140

Pro Pro Arg Leu Arg Ile Leu Ser Leu Leu Arg Pro Tyr Pro Lys Leu
145                 150                 155                 160

Leu His Val Leu Thr Leu Cys Thr Arg Arg Ser His Thr Pro Thr Arg
                165                 170                 175

Leu Pro Gln Ala Arg His Cys Val Leu Ala Val Pro Arg Thr Ser Leu
            180                 185                 190

Asp Arg Arg Cys Ser Cys Asn Gln Leu Phe Asp Gly Met Asn Leu Val
        195                 200                 205
```

(2) INFORMATION FOR SEQ ID NO: 44:

(i) SEQUENCE CHARACTERISTICS:
(A) LENGTH: 645 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Selaginella lepidophylla (xi) SEQUENCE DESCRIPTION: SEQ ID NO: 44:

```
GGGTGGTTCT TGCACACGCC GTTTCCCTCG TCTGAGATTT ACAGAACGCT GCCGCTGCGG     60

GCCGAGCTGC TCCAAGGCGT CTTAGGCGCG GACTTAGTGG GGTTCCACAC ATACGACTAT    120

GCAAGGCACT TTGTTAGCGC GATGCACACG GATACTCGGG CTGGAAGGCA CTCCCAGGGT    180

GTCGAGGATC AAGGGAAGAT CACGCGAGTG GCTGCCTTCC CCGTGGATCG ATTCGGAGCG    240

ATTTATCGAC GCGTAGAGAC CGATGCGGTC AAGAAACACA TGCAAGAGCT GAGCCAGGTT    300

TTGCTGTCGT AAGGTTATGT TGGGGTGGAT AGGCTTGACA TGATTAAAGG AATTCCACAG    360

AAGCTGCTAG CCTTTGAAAA ATTCCTCGAG GAGAACTCCG AGTGGCGTGA TAAGGTCGTC    420

CTGGTGCAAA TCGCGGTGCC GACTAGAACG GACGTCCTCG AGTACCAAAA GCTTACGAGC    480

CAGGTTCACG AGATTGTTGG TCGCATAAAT GGACGTTTCG GCTCCTTGAC GGCTGTTCCT    540

ATCCATCACC TCGATCGGTC CATGAAATTT CCGGAGCTTT GTGCGTTATA TGCAATCACT    600

GATGTCCTGC TCGTGACATC CCTGCGCGAC GGCATGAACT TCGTC                    645
```

(2) INFORMATION FOR SEQ ID NO: 45:

(i) SEQUENCE CHARACTERISTICS:
(A) LENGTH: 498 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Arabidopsis thaliana (xi) SEQUENCE DESCRIPTION: SEQ ID NO: 45:

```
GCCGTTGTGG ATTCATCGCC TCGCACAAGC ACTCTTGTCG TGTCTGAGTT TATTGGATGC     60

TCACCTTCTT TGAGTGGTGC CATTAGGGTG AATCCATGGG ATGTGGATGC TGTTGCTGAA    120

GCGGTAAACT CGGCTCTTAA AATAGTGAGA CTGAGAAGCA ACTACGGCAT GAGAAACATT    180

ATCATTATAT TAGCACTCAT GATGTTGGTT ATTGGGCAAA GAGCTTTATG CAGGATCTTG    240

AGAGAGCGTG CCGAGATCAT TATAGTAAAC GTTGTTGGGG GATTGGTTTT GGCTTGGGGT    300

TCAGAGTTTT GTCACTCTCT CCAAGTTTTA GGAAGCTATC TGTGGACACA TTTGTTCCAG    360

TTTATAGGAA AACCACAGAG AGGGCTAATA TTCTTTTATA ATGGTACTCT TTGTTCCGAA    420

AGCTCATTGT TCAAGATCCA GCAACGGGTT CCTTGTCCTA AGCCCCTTAA GGCCCCATAA    480

CCGGTGTTTT TTAGTGAG                                                  498
```

(2) INFORMATION FOR SEQ ID NO: 46:

(i) SEQUENCE CHARACTERISTICS:
(A) LENGTH: 463 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Arabidopsis thaliana (xi) SEQUENCE DESCRIPTION: SEQ ID NO: 46:

```
GCCGTTGTGG ATTCATCGCC TCGCACAAGC ACTCTTGTCG TGTCTGAGTT TATTGGATGC     60

TCACCTTCTT TGAGTGGTGC CATTGGGTGA ATCCATGGGA TGTGGATGCT GTTGCTGAAG    120

CGGTAAACTC GGCTCTTAAA ATGAGTGAGA CTGAGAAGCA ACTACGGCAT GAGAAACATT    180

ATCATTATAT TAGCACTCAT GATGTTGGTT ATTGGGCAAA GAGCTTTATG CAGGATCTTG    240

AGAGAGCGTG CCGAGATCAT TATAGTAAAC GTTGTTGGGG GATTGGTTTT GGTTTGGGGT    300

TCAGAGTTTT TGTCACTCTC TCCAAGTTTA GGAAGCTATC TTGGGACAAT TGTTCCAGTT    360

TTTAGGGAAA ACACAGGGAA GGTTATTTCC TTGATTATAA TGGACCTTGT CCAAGCCCCA    420

TTTTTAAGGC CCAGGAACCG GGTTTTTTTT TCTTAAAGCC CCT                      463
```

(2) INFORMATION FOR SEQ ID NO: 47:

(i) SEQUENCE CHARACTERISTICS:
(A) LENGTH: 394 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Arabidopsis thaliana (xi) SEQUENCE DESCRIPTION: SEQ ID NO: 47:

```
GGTATTGATG TAGAGGAAAT ACGTGGTGAA ATCGAAGAAA GCTGCAGGAG GATCAATGGA     60

GAGTTTGGGA AACCGGATAT CAACCTATCA TATATATTGA TACCCGGTTT CGATTAATGA    120

AATAAATGCT TATACCATAT TGCTGAGTGC GTGGTCGTTA CAGCTGTTAG AGATGGTATG    180

AACCTTACTC CCTACGAATA TATCGTTTGT AGACAAGGTT TACTTGGGTC TGAATCAGAC    240

TTTAGTGGCC CAAAGAAGAG CATGTTGGTT GCATCAAGTT TATTTGGATG TCCCCTTTCG    300

CTTAGTGGGG CTATACGCGT AAACCCATGG AACCGTTGAA GCTACTTGAG GAGCCTTAAT    360

TAGGCCCCTC AAATATGCTG GAACACTACG GATG                                394
```

(2) INFORMATION FOR SEQ ID NO: 48:

(i) SEQUENCE CHARACTERISTICS:
(A) LENGTH: 428 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Arabidopsis thaliana (xi) SEQUENCE DESCRIPTION: SEQ ID NO: 48:

```
AAGTCCGTTG TGGATTCACG CCTCGCACAA GCACTCTTGT CGTGTCTAGT TTATTGGATG     60

CTCACCTTCT TTAGTGGTGC CATTAGGGTG AATCCATGGA TGTGGATGCT GTTGCTGAAG    120
```

CGGTAAACTC GGCTCTTAAA ATAGTGAGAC TGAGAAGCAA CTACGGCATG AGAAACATTA 180

TCATTATATT AGCACTCATG ATGTTGGTTA TTGGGCAAAG AGCTTTATGC AGGACTTAGA 240

GAGCGTGCCG AGATCATTAT AGTAAACGTT GTTGGGGGAT TGGTTTTGGT TTGGGGTTCA 300

AGTTTTGTCA CTCTCTCCAA GTTTTAGGAA GCTATCTTGT GGACACATTG TTCCAGTTTA 360

TAGAAACACA GGGAAGGGGC TATATTCTTG TTTAAATGGG ACCCCTTGTC CCTAAAAGTC 420

CCATTTGT 428

(2) INFORMATION FOR SEQ ID NO: 49:

(i) SEQUENCE CHARACTERISTICS:
(A) LENGTH: 481 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Arabidopsis thaliana (xi) SEQUENCE DESCRIPTION: SEQ ID NO: 49:

CAAACGAAGA GCTTCGTGGG AAAGTGGTTC TCGTGCAGAT TACTAATCCT GCTCGTAGTT 60

CAGGTAAGGA TGTTCAAGAT GTAGAGAAAC AGATAAATTT ATTGCTGATG AGATCAATTC 120

TAAATTTGGG AGACCTGGTG GTTATAAGCC TATTGTTTTG TAATGGACCT GTTAGTACTT 180

TGGATAAAGT TGCTTATTAC GCGATCTCGG AGTGTGTTGT CGTGAATCTG TGAGAGATGG 240

GATGAATTTG GTGCCTTATA AGTACACAGT GACTCGGCAA GGGAGCCCTG CTTTGGATGC 300

AGCTTTGGTT TTGGGGAGGA TGATGTTAGG AAGAGTGTGA TTATTGTTTC TGAGGTTCAA 360

CCGGTTGTCC TCCATCTCTA GTGGTGCGAT CCCTTTTAAT CCGTGGACAT CGATCAGCAC 420

TTACGCCATG AGCTTCAAAT CCGGTTTCCG CAAAGGGAAA ATTGCCCCGA GCTTAAGGCC 480

A 481

(2) INFORMATION FOR SEQ ID NO: 50:

(i) SEQUENCE CHARACTERISTICS:
(A) LENGTH: 395 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Arabidopsis thaliana (xi) SEQUENCE DESCRIPTION: SEQ ID NO: 50:

AGACCTGGTG GTTATAAGCC TATTGTGTTT GTCAATGGAC CTGTTAGTAC TTTGGATAAA 60

TTGCTTATTA CGCGATCTCG GAGTGTGTTG TCGTGAATCT GTGAGAGATG GGATGAATTT 120

GGTGCCTTAT AAGTACACAG TGACTCGGCA AGGGAGCCCT GCTTTGGATG CAGCTTTAGG 180

TTTTGGGGAG GATGATGTTA GGAAGAGTGT GATTATTGTT TCTAGTTCAT CGGTTGTCTC 240

CATCTCTGAG TGGTGCGATC CGTTAATCCG TGGAACATCG TGCAGTCACT AAACGCCATG 300

AGCCTGCAAT ACGATGTCGC AAAGGGAAAA TCTTTGCCAC CAGAAGCATC ATAAGTACAT 360

AAAGCCTCAC AATTGCCTAT TTGGGCCGGG GTTTT 395

(2) INFORMATION FOR SEQ ID NO: 51:

(i) SEQUENCE CHARACTERISTICS:
(A) LENGTH: 431 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Oryza sativa (ix) FEATURE:
(A) NAME/KEY: misc_feature
(B) LOCATION: 1
(D) OTHER INFORMATION: /standard_name= "GENBANK ID: D22143"

(xi) SEQUENCE DESCRIPTION: SEQ ID NO: 51:

GGGAATGGAG GGTCTCCGAG CTGCAGCAGC AATTTGAGGG GAAGACTGTG TTGCTCGGTG 60

TGGATGACAT GGATATCTTC AAGGGTATCA ACTTGAAGCT TCTTGCCTTC GAGAATATGT 120

TGAGGACACA TCCCAAGTGG CAGGGGCGGG CAGTGTTGGT GCAAATTGCT AATCCGGCCC 180

GTGGAAAGGG TAAGGATCTT GAAGCCATCC AGGCTGAGAT TCATGAGAGC TGCAAGAGGA 240

TTAATGGAGA GTTTGGCCAG TCAGGATACA GCCCTGTTGT CTTCATTGAC CGTGATGTGT 300

CAAGTGTGGA GGAAGATTGC CTACTACACA ATAGCAGAAT GTGTGGTGGT GACTGCTGTT 360

AGGGATGGGA TTGACTTGAC ACCATATGGA TATATTGTCT GTAGGGCAGG GGTCTTACTC 420

ACATCAGAGG T 431

(2) INFORMATION FOR SEQ ID NO: 52:

(i) SEQUENCE CHARACTERISTICS:
(A) LENGTH: 496 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Oryza sativa (ix) FEATURE:
(A) NAME/KEY: misc_feature
(B) LOCATION: 1
(D) OTHER INFORMATION: /standard_name= "GENBANK ID: D40048"

(xi) SEQUENCE DESCRIPTION: SEQ ID NO: 52:

CTACCGTTCC CTCCCTGTTC GCGACGAGAT CCTCAAATCA CTGCTAAACT GCGATCTGAT 60

TGGGTTCCAC ACCTTTGATT ACGCGCGGCA TTTCCTGTCC TGCTGCAGCC GGATGCTGGG 120

GATCGAGTAC CAGTCGAAGA GGGGATATAT CGGTCTCGAT TACTTTGGCC GCACTGTTGG 180

GATAAAGATC ATGCCTGTTG GGATTAACAT GACGCAGCTG CAGACGCAGA TCCGGCTGCC 240

```
TGATCTTGAG TGGCGTGTCG CGAACTCCGG AAGCAGTTTG ATGGGAAGAC TGTCATGCTC    300

GGTGTGGATG ATATGGACAT ATTTAAGGGG ATTAATCTGA AAGTTCTTGC GTTTTGAGCA    360

GATGCTGAGG ACACACCCAA AATGGCAGCC AAGGCAGTTT TGGTGCAGAT TCAAACCAAG    420

GGTGGTTGTT GGGAGGACTT AGGTACAGCT AGATATGAGT TCAGGGGTAA TGACATTTCA    480

GGCGGTATTT CCTTGG                                                    496
```

(2) INFORMATION FOR SEQ ID NO: 53:

(i) SEQUENCE CHARACTERISTICS:
(A) LENGTH: 288 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Oryza sativa (xi) SEQUENCE DESCRIPTION: SEQ ID NO: 53:

```
GGACCAAAGA AGAGCATGTT GGTTGTGTCG GAGTTTATTG GTTGCTCACC TTCACTGAGT     60

GGAGCCATTC GTGTTAACCC GTGGAATATC GAGGCAACTG CAGAGGCACT GAATGAGGCC    120

ATCTCAATGT CAGAGCGTAA AAGCAGCTGA GGCACGAAAA ACATTACCGT TATGTCAGCA    180

CCCATGATGT TGCATATTGG TCTAAGAGCT TTGTACAGGA CCTGGAGAGG GCTTGCAAGG    240

ATCACTTTAG GAAACCATGC TGGGGCATTG GATTGGATTT CGCTCAGG                 288
```

(2) INFORMATION FOR SEQ ID NO: 54:

(i) SEQUENCE CHARACTERISTICS:
(A) LENGTH: 2207 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Solanum tuberosum
(B) STRAIN: Kardal (ix) FEATURE:
(A) NAME/KEY: CDS
(B) LOCATION: 161..1906

(ix) FEATURE:
(A) NAME/KEY: misc_feature
(B) LOCATION: 842..850
(D) OTHER INFORMATION: /function= "putative glycosylationsite"

(xi) SEQUENCE DESCRIPTION: SEQ ID NO: 54:

```
CTTTTCTGAG TAATAACATA GGCATTGATT TTTTTTCAAT TAATAACACC TGCAAACATT     60

CCCATTGCCG GCATTCTCTG TTCTTACAAA AAAAAACATT TTTTTGTTCA CATAAATTAG    120

TTATGGCATC AGTATTGAAC CCTTTAACTT GTTATACAAT ATG GGT AAA GCT ATA      175
                                            Met Gly Lys Ala Ile
                                              1               5
```

-continued

```
ATT TTT ATG ATT TTT ACT ATG TCT ATG AAT ATG ATT AAA GCT GAA ACT      223
Ile Phe Met Ile Phe Thr Met Ser Met Asn Met Ile Lys Ala Glu Thr
                10                  15                  20

TGC AAA TCC ATT GAT AAG GGT CCT GTA ATC CCA ACA ACC CCT TTA GTG      271
Cys Lys Ser Ile Asp Lys Gly Pro Val Ile Pro Thr Thr Pro Leu Val
            25                  30                  35

ATT TTT CTT GAA AAA GTT CAA GAA GCT GCT CTT CAA ACT TAT GGC CAT      319
Ile Phe Leu Glu Lys Val Gln Glu Ala Ala Leu Gln Thr Tyr Gly His
        40                  45                  50

AAA GGG TTT GAT GCT AAA CTG TTT GTT GAT ATG TCA CTG AGA GAG AGT      367
Lys Gly Phe Asp Ala Lys Leu Phe Val Asp Met Ser Leu Arg Glu Ser
    55                  60                  65

CTT TCA GAA ACA GTT GAA GCT TTT AAT AAG CTT CCA AGA GTT GTG AAT      415
Leu Ser Glu Thr Val Glu Ala Phe Asn Lys Leu Pro Arg Val Val Asn
 70                  75                  80                  85

GGT TCA ATA TCA AAA AGT GAT TTG GAT GGT TTT ATA GGT AGT TAC TTG      463
Gly Ser Ile Ser Lys Ser Asp Leu Asp Gly Phe Ile Gly Ser Tyr Leu
                90                  95                 100

AGT AGT CCT GAT AAG GAT TTG GTT TAT GTT GAG CCT ATG GAT TTT GTG      511
Ser Ser Pro Asp Lys Asp Leu Val Tyr Val Glu Pro Met Asp Phe Val
            105                 110                 115

GCT GAG CCT GAA GGC TTT TTG CCA AAG GTG AAG AAT TCT GAG GTG AGG      559
Ala Glu Pro Glu Gly Phe Leu Pro Lys Val Lys Asn Ser Glu Val Arg
        120                 125                 130

GCA TGG GCA TTG GAG GTG CAT TCA CTT TGG AAG AAT TTA AGT AGG AAA      607
Ala Trp Ala Leu Glu Val His Ser Leu Trp Lys Asn Leu Ser Arg Lys
    135                 140                 145

GTG GCT GAT CAT GTA TTG GAA AAA CCA GAG TTG TAT ACT TTG CTT CCA      655
Val Ala Asp His Val Leu Glu Lys Pro Glu Leu Tyr Thr Leu Leu Pro
150                 155                 160                 165

TTG AAA AAT CCA GTT ATT ATA CCG GGA TCG CGT TTT AAG GAG GTT TAT      703
Leu Lys Asn Pro Val Ile Ile Pro Gly Ser Arg Phe Lys Glu Val Tyr
                170                 175                 180

TAT TGG GAT TCT TAT TGG GTA ATA AGG GGT TTG TTA GCA AGC AAA ATG      751
Tyr Trp Asp Ser Tyr Trp Val Ile Arg Gly Leu Leu Ala Ser Lys Met
            185                 190                 195

TAT GAA ACT GCA AAA GGG ATT GTG ACT AAT CTG GTT TCT CTG ATA GAT      799
Tyr Glu Thr Ala Lys Gly Ile Val Thr Asn Leu Val Ser Leu Ile Asp
        200                 205                 210

CAA TTT GGT TAT GTT CTT AAC GGT GCA AGA GCA TAC TAC AGT AAC AGA      847
Gln Phe Gly Tyr Val Leu Asn Gly Ala Arg Ala Tyr Tyr Ser Asn Arg
    215                 220                 225

AGT CAG CCT CCT GTC CTG GCC ACG ATG ATT GTT GAC ATA TTC AAT CAG      895
Ser Gln Pro Pro Val Leu Ala Thr Met Ile Val Asp Ile Phe Asn Gln
230                 235                 240                 245

ACA GGT GAT TTA AAT TTG GTT AGA AGA TCC CTT CCT GCT TTG CTC AAG      943
Thr Gly Asp Leu Asn Leu Val Arg Arg Ser Leu Pro Ala Leu Leu Lys
                250                 255                 260

GAG AAT CAT TTT TGG AAT TCA GGA ATA CAT AAG GTG ACT ATT CAA GAT      991
Glu Asn His Phe Trp Asn Ser Gly Ile His Lys Val Thr Ile Gln Asp
            265                 270                 275

GCT CAG GGA TCA AAC CAC AGC TTG AGT CGG TAC TAT GCT ATG TGG AAT     1039
Ala Gln Gly Ser Asn His Ser Leu Ser Arg Tyr Tyr Ala Met Trp Asn
        280                 285                 290

AAG CCC CGT CCA GAA TCG TCA ACT ATA GAC AGT GAA ACA GCT TCC GTA     1087
Lys Pro Arg Pro Glu Ser Ser Thr Ile Asp Ser Glu Thr Ala Ser Val
    295                 300                 305

CTC CCA AAT ATA TGT GAA AAA AGA GAA TTA TAC CGT GAA CTG GCA TCA     1135
Leu Pro Asn Ile Cys Glu Lys Arg Glu Leu Tyr Arg Glu Leu Ala Ser
310                 315                 320                 325
```

```
GCT GCT GAA AGT GGA TGG GAT TTC AGT TCA AGA TGG ATG AGC AAC GGA     1183
Ala Ala Glu Ser Gly Trp Asp Phe Ser Ser Arg Trp Met Ser Asn Gly
                330                 335                 340

TCT GAT CTG ACA ACA ACT AGT ACA ACA TCA ATT CTA CCA GTT GAT TTG     1231
Ser Asp Leu Thr Thr Thr Ser Thr Thr Ser Ile Leu Pro Val Asp Leu
            345                 350                 355

AAT GCA TTC CTT CTG AAG ATG GAA CTT GAC ATT GCC TTT CTA GCA AAT     1279
Asn Ala Phe Leu Leu Lys Met Glu Leu Asp Ile Ala Phe Leu Ala Asn
        360                 365                 370

CTT GTT GGA GAA AGT AGC ACG GCT TCA CAT TTT ACA GAA GCT GCT CAA     1327
Leu Val Gly Glu Ser Ser Thr Ala Ser His Phe Thr Glu Ala Ala Gln
    375                 380                 385

AAT AGA CAG AAG GCT ATA AAC TGT ATC TTT TGG AAC GCA GAG ATG GGG     1375
Asn Arg Gln Lys Ala Ile Asn Cys Ile Phe Trp Asn Ala Glu Met Gly
390                 395                 400                 405

CAA TGG CTT GAT TAC TGG CTT ACC AAC AGC GAC ACA TCT GAG GAT ATT     1423
Gln Trp Leu Asp Tyr Trp Leu Thr Asn Ser Asp Thr Ser Glu Asp Ile
                410                 415                 420

TAT AAA TGG GAA GAT TTG CAC CAG AAC AAG AAG TCA TTT GCC TCT AAT     1471
Tyr Lys Trp Glu Asp Leu His Gln Asn Lys Lys Ser Phe Ala Ser Asn
            425                 430                 435

TTT GTT CCG CTG TGG ACT GAA ATT TCT TGT TCA GAT AAT AAT ATC ACA     1519
Phe Val Pro Leu Trp Thr Glu Ile Ser Cys Ser Asp Asn Asn Ile Thr
        440                 445                 450

ACT CAG AAA GTA GTT CAA AGT CTC ATG AGC TCG GGC TTG CTT CAG CCT     1567
Thr Gln Lys Val Val Gln Ser Leu Met Ser Ser Gly Leu Leu Gln Pro
    455                 460                 465

GCA GGG ATT GCA ATG ACC TTG TCT AAT ACT GGA CAG CAA TGG GAT TTT     1615
Ala Gly Ile Ala Met Thr Leu Ser Asn Thr Gly Gln Gln Trp Asp Phe
470                 475                 480                 485

CCG AAT GGT TGG CCC CCC CTT CAA CAC ATA ATC ATT GAA GGT CTC TTA     1663
Pro Asn Gly Trp Pro Pro Leu Gln His Ile Ile Ile Glu Gly Leu Leu
                490                 495                 500

AGG TCT GGA CTA GAA GAG GCA AGA ACC TTA GCA AAA GAC ATT GCT ATT     1711
Arg Ser Gly Leu Glu Glu Ala Arg Thr Leu Ala Lys Asp Ile Ala Ile
            505                 510                 515

CGC TGG TTA AGA ACT AAC TAT GTG ACT TAC AAG AAA ACC GGT GCT ATG     1759
Arg Trp Leu Arg Thr Asn Tyr Val Thr Tyr Lys Lys Thr Gly Ala Met
        520                 525                 530

TAT GAA AAA TAT GAT GTC ACA AAA TGT GGA GCA TAT GGA GGT GGT GGT     1807
Tyr Glu Lys Tyr Asp Val Thr Lys Cys Gly Ala Tyr Gly Gly Gly Gly
    535                 540                 545

GAA TAT ATG TCC CAA ACG GGT TTC GGA TGG TCA AAT GGC GTT GTA CTG     1855
Glu Tyr Met Ser Gln Thr Gly Phe Gly Trp Ser Asn Gly Val Val Leu
550                 555                 560                 565

GCA CTT CTA GAG GAA TTT GGA TGG CCT GAA GAT TTG AAG ATT GAT TGC     1903
Ala Leu Leu Glu Glu Phe Gly Trp Pro Glu Asp Leu Lys Ile Asp Cys
                570                 575                 580

TAATGAGCAA GTAGAAAAGC CAAATGAAAC ATCATTGAGT TTTATTTTCT TCTTTTGTTA   1963

AAATAAGCTG CAATGGTTTG CTGATAGTTT ATGTTTTGTA TTACTATTTC ATAAGGTTTT   2023

TGTACCATAT CAAGTGATAT TACCATGAAC TATGTCGTTC GGACTCTTCA AATCGGATTT   2083

TGCAAAAATA ATGCAGTTTT GGAGAATCCG ATAACATAGA CCATGTATGG ATCTAAATTG   2143

TAAACAGCTT ACTATATTAA GTAAAAGAAA GATGATTCCT CTGCTTTAAA AAAAAAAAAA   2203

AAAA                                                                2207
```

(2) INFORMATION FOR SEQ ID NO: 55:

(i) SEQUENCE CHARACTERISTICS:

```
        (A) LENGTH: 581 amino acids
        (B) TYPE: amino acid
        (D) TOPOLOGY: linear

    (ii) MOLECULE TYPE: protein

    (xi) SEQUENCE DESCRIPTION: SEQ ID NO: 55:

Met Gly Lys Ala Ile Ile Phe Met Ile Phe Thr Met Ser Met Asn Met
  1               5                  10                  15

Ile Lys Ala Glu Thr Cys Lys Ser Ile Asp Lys Gly Pro Val Ile Pro
             20                  25                  30

Thr Thr Pro Leu Val Ile Phe Leu Glu Lys Val Gln Glu Ala Ala Leu
         35                  40                  45

Gln Thr Tyr Gly His Lys Gly Phe Asp Ala Lys Leu Phe Val Asp Met
     50                  55                  60

Ser Leu Arg Glu Ser Leu Ser Glu Thr Val Glu Ala Phe Asn Lys Leu
 65                  70                  75                  80

Pro Arg Val Val Asn Gly Ser Ile Ser Lys Ser Asp Leu Asp Gly Phe
                 85                  90                  95

Ile Gly Ser Tyr Leu Ser Ser Pro Asp Lys Asp Leu Val Tyr Val Glu
            100                 105                 110

Pro Met Asp Phe Val Ala Glu Pro Glu Gly Phe Leu Pro Lys Val Lys
        115                 120                 125

Asn Ser Glu Val Arg Ala Trp Ala Leu Glu Val His Ser Leu Trp Lys
    130                 135                 140

Asn Leu Ser Arg Lys Val Ala Asp His Val Leu Glu Lys Pro Glu Leu
145                 150                 155                 160

Tyr Thr Leu Leu Pro Leu Lys Asn Pro Val Ile Ile Pro Gly Ser Arg
                165                 170                 175

Phe Lys Glu Val Tyr Tyr Trp Asp Ser Tyr Trp Val Ile Arg Gly Leu
            180                 185                 190

Leu Ala Ser Lys Met Tyr Glu Thr Ala Lys Gly Ile Val Thr Asn Leu
        195                 200                 205

Val Ser Leu Ile Asp Gln Phe Gly Tyr Val Leu Asn Gly Ala Arg Ala
    210                 215                 220

Tyr Tyr Ser Asn Arg Ser Gln Pro Pro Val Leu Ala Thr Met Ile Val
225                 230                 235                 240

Asp Ile Phe Asn Gln Thr Gly Asp Leu Asn Leu Val Arg Arg Ser Leu
                245                 250                 255

Pro Ala Leu Leu Lys Glu Asn His Phe Trp Asn Ser Gly Ile His Lys
            260                 265                 270

Val Thr Ile Gln Asp Ala Gln Gly Ser Asn His Ser Leu Ser Arg Tyr
        275                 280                 285

Tyr Ala Met Trp Asn Lys Pro Arg Pro Glu Ser Ser Thr Ile Asp Ser
    290                 295                 300

Glu Thr Ala Ser Val Leu Pro Asn Ile Cys Glu Lys Arg Glu Leu Tyr
305                 310                 315                 320

Arg Glu Leu Ala Ser Ala Ala Glu Ser Gly Trp Asp Phe Ser Ser Arg
                325                 330                 335

Trp Met Ser Asn Gly Ser Asp Leu Thr Thr Thr Ser Thr Thr Ser Ile
            340                 345                 350

Leu Pro Val Asp Leu Asn Ala Phe Leu Leu Lys Met Glu Leu Asp Ile
        355                 360                 365

Ala Phe Leu Ala Asn Leu Val Gly Glu Ser Ser Thr Ala Ser His Phe
    370                 375                 380
```

```
Thr Glu Ala Ala Gln Asn Arg Gln Lys Ala Ile Asn Cys Ile Phe Trp
385                 390                 395                 400

Asn Ala Glu Met Gly Gln Trp Leu Asp Tyr Trp Leu Thr Asn Ser Asp
                405                 410                 415

Thr Ser Glu Asp Ile Tyr Lys Trp Glu Asp Leu His Gln Asn Lys Lys
            420                 425                 430

Ser Phe Ala Ser Asn Phe Val Pro Leu Trp Thr Glu Ile Ser Cys Ser
        435                 440                 445

Asp Asn Asn Ile Thr Thr Gln Lys Val Val Gln Ser Leu Met Ser Ser
    450                 455                 460

Gly Leu Leu Gln Pro Ala Gly Ile Ala Met Thr Leu Ser Asn Thr Gly
465                 470                 475                 480

Gln Gln Trp Asp Phe Pro Asn Gly Trp Pro Pro Leu Gln His Ile Ile
                485                 490                 495

Ile Glu Gly Leu Leu Arg Ser Gly Leu Glu Glu Ala Arg Thr Leu Ala
            500                 505                 510

Lys Asp Ile Ala Ile Arg Trp Leu Arg Thr Asn Tyr Val Thr Tyr Lys
        515                 520                 525

Lys Thr Gly Ala Met Tyr Glu Lys Tyr Asp Val Thr Lys Cys Gly Ala
    530                 535                 540

Tyr Gly Gly Gly Gly Glu Tyr Met Ser Gln Thr Gly Phe Gly Trp Ser
545                 550                 555                 560

Asn Gly Val Val Leu Ala Leu Leu Glu Glu Phe Gly Trp Pro Glu Asp
                565                 570                 575

Leu Lys Ile Asp Cys
            580
```

(2) INFORMATION FOR SEQ ID NO: 56:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (iii) HYPOTHETICAL: NO (xi) SEQUENCE DESCRIPTION: SEQ ID NO: 56:

```
CTCAGATCTG GCCACAAA                                                18
```

(2) INFORMATION FOR SEQ ID NO: 57:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (iii) HYPOTHETICAL: NO (xi) SEQUENCE DESCRIPTION: SEQ ID NO: 57:

```
GTGCTCGTCT GCAGGTGC                                                18
```

REGULATING METABOLISM BY MODIFYING THE LEVEL OF TREHALOSE-6-PHOSPHATE

This is a division of U.S. application Ser. No. 10/682,456, filed Oct. 9, 2003, and issued as U.S. Pat. No. 7,247,770 on Jul. 24, 2007, which is a division of U.S. application Ser. No. 09/171,937, filed Apr. 28, 1999, and issued as U.S. Pat. No. 6,833,490 on Dec. 21, 2004, which is a national stage application of International Application No. PCT/EP97/02497, filed May 2, 1997, which claims priority to Netherlands Application No. 96201225, filed May 3, 1996, Netherlands Application No. 96202128, filed Jul. 26, 1996, and Netherlands Application No. 96202395, filed May 3, 1996.

FIELD OF THE INVENTION

Glycolysis has been one of the first metabolic processes described in biochemical detail in the literature. Although the general flow of carbohydrates in organisms is known and although all enzymes of the glycolytic pathway(s) are elucidated, the signal which determines the induction of metabolism by stimulating glycolysis has not been unravelled. Several hypotheses, especially based on the situation in yeast have been put forward, but none has been proven beyond doubt.

Influence on the direction of the carbohydrate partitioning does not only influence directly the cellular processes of glycolysis and carbohydrate storage, but it can also be used to influence secondary or derived processes such as cell division, biomass generation and accumulation of storage compounds, thereby determining growth and productivity.

Especially in plants, often the properties of a tissue are directly influenced by the presence of carbohydrates, and the steering of carbohydrate partitioning can give substantial differences.

The growth, development and yield of plants depends on the energy which such plants can derive from $CO_2$-fixation during photosynthesis.

Photosynthesis primarily takes place in leaves and to a lesser extent in the stem, while other plant organs such as roots, seeds or tubers do not essentially contribute to the photoassimilation process. These tissues are completely dependent on photosynthetically active organs for their growth and nutrition. This then means that there is a flux of products derived from photosynthesis (collectively called "photosynthate") to photosynthetically inactive parts of the plants.

The photosynthetically active parts are denominated as "sources" and they are defined as net exporters of photosynthate. The photosynthetically inactive parts are denominated as "sinks" and they are defined as net importers of photosynthate.

It is assumed that both the efficiency of photosynthesis, as well as the carbohydrate partitioning in a plant are essential. Newly developing tissues like young leaves or other parts like root and seed are completely dependent on photosynthesis in the sources. The possibility of influencing the carbohydrate partitioning would have great impact on the phenotype of a plant, e.g. its height, the internodium distance, the size and form of a leaf and the size and structure of the root system.

Furthermore, the distribution of the photoassimilation products is of great importance for the yield of plant biomass and products. An example is the development in wheat over the last century. Its photosynthetic capacity has not changed considerably but the yield of wheat grain has increased substantially, i.e. the harvest index (ratio harvestable biomass/total biomass) has increased. The underlying reason is that the sink-to-source ratio was changed by conventional breeding, such that the harvestable sinks, i.e. seeds, portion increased. However, the mechanism which regulates the distribution of assimilation products and consequently the formation of sinks and sources is yet unknown. The mechanism is believed to be located somewhere in the carbohydrate metabolic pathways and their regulation. In the recent research it has become apparent that hexokinases may play a major role in metabolite signalling and control of metabolic flow. A number of mechanisms for the regulation of the hexokinase activity have been postulated (Graham et al. (1994), The Plant Cell 6: 761; Jang & Sheen (1994), The Plant Cell 6, 1665; Rose et al. Eur. J. Biochem. 199, 511-518, 1991; Blazquez et al. (1993), FEBS 329, 51; Koch, Annu. Rev. Plant Physiol. Plant. Mol. Biol. (1996) 47, 509; Jang et al. (1997), The Plant Cell 9, 5, one of these theories of hexokinase regulation, postulated in yeast mentions trehalose and its related monosaccharides (Thevelein & Hohmann (1995). TIBS 20, 3). However, it is hard to see that this would be an universal mechanism, as trehalose synthesis is believed to be restricted to certain species.

Thus, there still remains a need for the elucidation of the signal which can direct the modification of the development and/or composition of cells, tissue and organs in vivo.

SUMMARY OF THE INVENTION

It has now been found that modification of the development and/or composition of cells, tissue and organs in vivo is possible by introducing the enzyme trehalose-6-phosphate synthase (TPS) and/or trehalose-6-phosphatase phosphate (TPP) thereby inducing a change in metabolic pathways of the saccharide trehalose-6-phosphate (T-6-P) resulting in an alteration of the intracellular availability of T-6-P. Introduction of TPS thereby inducing an increase in the intracellular concentration of T-6-P causes inhibition of carbon flow in the glycolytic direction, stimulation of the photosynthesis, inhibition of growth stimulation of sink-related activity and an increase in storage of resources. Introduction of TPP thereby introducing a decrease in the intracellular concentration of T-6-P causes stimulation of carbon flow in the glycolytic direction, increase in biomass and a decrease in photosynthetic activity.

The levels of T-6-P may be influenced by genetic engineering of an organism with gene constructs able to influence the level of T-6-P or by exogenously (orally, topically, parenterally etc.) supplying compounds able to influence these levels.

The gene constructs that can be used in this invention are constructs harbouring the gene for trehalose phosphate synthase (TPS) the enzyme that is able to catalyze the reaction from glucose-6-phosphate and UDP-glucose to T-6-P. On the other side a construct coding for the enzyme trehalose-phosphate phosphatase (TPP) which catalyzes the reaction from T-6-P to trehalose will, upon expression, give a decrease of the amount of T-6-P.

Alternatively, gene constructs harbouring antisense TPS or TPP can be used to regulate the intracellular availability of T-6-P.

Furthermore, it was recently reported that an intracellular phospho-alpha-(1,1)-glucosidase, TreA, from *Bacillus subtilis* was able to hydrolyse T-6-P into glucose and glucose-6-phosphate (Schŏck et al., Gene, 170, 77-80, 1996). A similar enzyme has already been described for *E. coli* (Rimmele and Boos (1996), J. Bact. 176 (18), 5654-).

For overexpression heterologous or homologous gene constructs have to be used. It is believed that the endogenous T-6-P forming and/or degrading enzymes are under allosteric regulation and regulation through covalent modification. This regulation may be circumvented by using heterologous genes.

Alternatively, mutation of heterologous or homologous genes may be used to abolish regulation.

The invention also gives the ability to modify source-sink relations and resource allocation in plants. The whole carbon economy of the plant, including assimilate production in source tissues and utilization in source tissues can be modified, which may lead to increased biomass yield of harvested products. Using this approach, increased yield potential can be realized, as well as improved harvest index and product quality. These changes in source tissues can lead to changes in sink tissues by for instance increased export of photosynthase. Conversely changes in sink tissue can lead to change in source tissue.

Specific expression in a cell organelle, a tissue or other part of an organism enables the general effects that have been mentioned above to be directed to specific local applications. This specific expression can be established by placing the genes coding for TPS, TPP or the antisense genes for TPS or TPP under control of a specific promoter.

Specific expression also enables the simultaneous expression of both TPS and TPP enzymes in different tissues thereby increasing the level of T-6-P and decreasing the level of T-6-P locally.

By using specific promoters it is also possible to construct a temporal difference. For this purpose promoters can be used that are specifically active during a certain period of the organogenesis of the plant parts. In this way it is possible to first influence the amount of organs which will be developed and then enable these organs to be filled with storage material like starch, oil or proteins.

Alternatively, inducible promoters may be used to selectively switch on or off the expression of the genes of the invention. Induction can be achieved by for instance pathogens, stress, chemicals or light/dark stimuli.

DEFINITIONS

Hexokinase activity is the enzymatic activity found in cells which catalyzes the reaction of hexose to hexose-6-phosphate. Hexoses include glucose, fructose, galactose or any other $C_6$ sugar. It is acknowledged that there are many isoenzymes which all can play a part in said biochemical reaction. By catalyzing this reaction hexokinase forms a key enzyme in hexose (glucose) signalling.

Hexose signalling is the regulatory mechanism by which a cell senses the availability of hexose (glucose).

Glycolysis is the sequence of reactions that converts glucose into pyruvate with the concomitant production of ATP.

Cold sweetening is the accumulation of soluble sugars in potato tubers after harvest when stored at low temperatures.

Storage of resource material is the process in which the primary product glucose is metabolized into the molecular form which is fit for storage in the cell or in a specialized tissue. These forms can be divers. In the plant kingdom storage mostly takes place in the form of carbohydrates and polycarbohydrates such as starch, fructan and cellulose, or as the more simple mono- and di-saccharides like fructose, sucrose and maltose; in the form of oils such as arachic or oleic oil and in the form of proteins such as cruciferin, napin and seed storage proteins in rapeseed. In animal cells also polymeric carbohydrates such as glycogen are formed, but also a large amount of energy rich carbon compounds is transferred into fat and lipids.

Biomass is the total mass of biological material.

DESCRIPTION OF THE FIGURES

FIG. 4. Alignment of PCR amplified tobacco TPS cDNA fragments with the TPS encoding yeast TPS1 gene. Boxes indicate identity between amino-acids of all four listed sequences.

FIG. 6. Alignment of a fragment of the PCR amplified sunflower TPS/TPP bipartite cDNA (SEQ ID NO: 24) with the TPP encoding yeast TPS2 gene. Boxes indicate identity between amino-acids of both sequences.

FIG. 7. Alignment of a fragment of the *Arabidopsis* TPS1 and Rice EST clones with the TPS encoding yeast TPS1 gene. Boxes indicate identity between amino-acids of all three sequences.

FIG. 8. Alignment of a fragment of the PCR amplified human TPS cDNA (SEQ ID NO: 10) with the TPS encoding yeast TPS1 gene. Boxes indicate identity between amino-acids of both sequences.

FIG. 12. Hexokinase activity of a wild-type tobacco leaf extract (*Nicotiana tabacum* cv. SR1) with and without the addition of trehalose-6-phosphate. Fructose or glucose is used as substrate for the assay.

Data series 1: Tobacco plant extract

Data series 2: Tobacco plant extract+1 mM trehalose-6-phosphate

Data series 3: Commercial hexokinase extract from yeast (⅛ unit)

Figure 14:
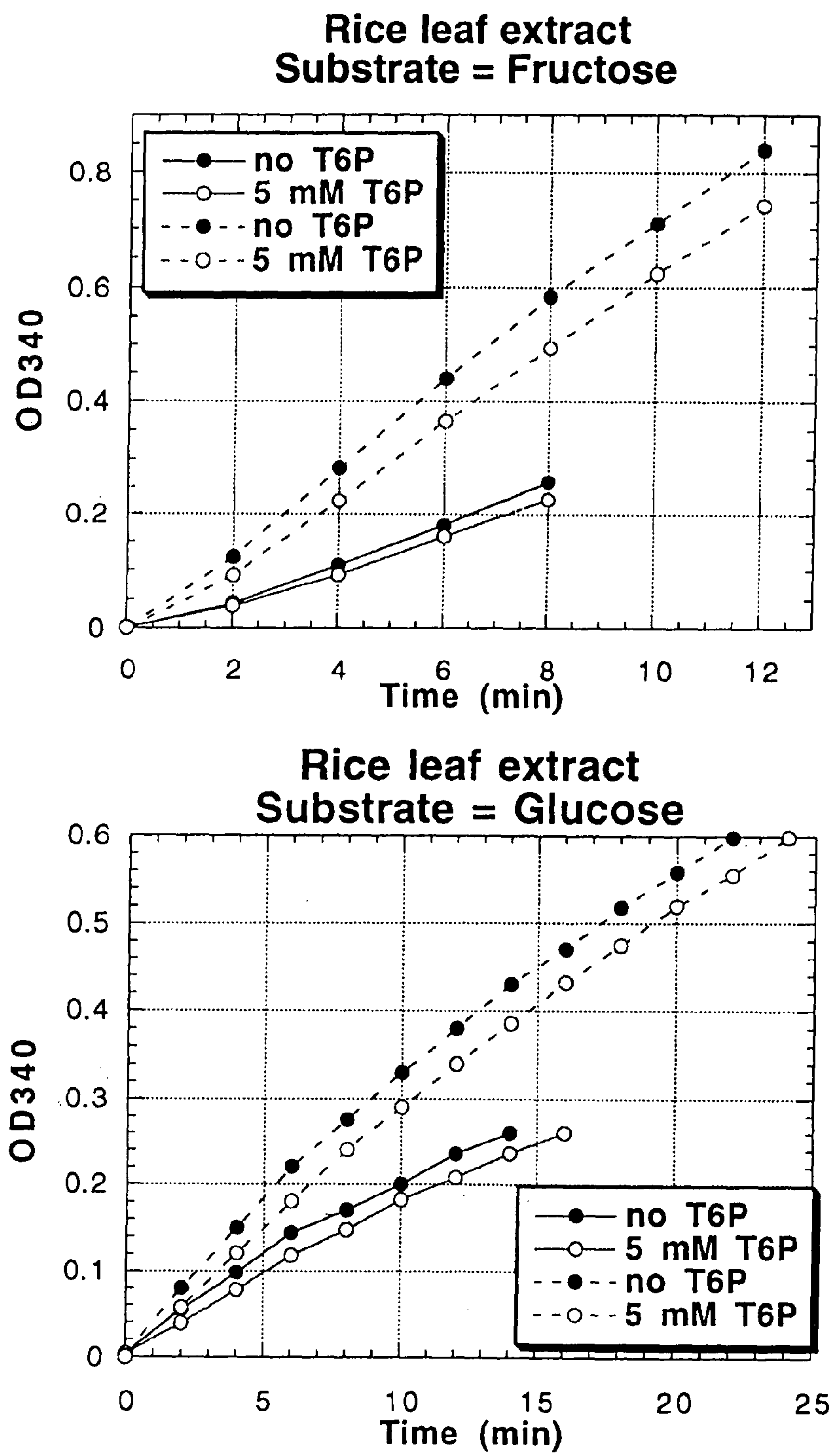

FIG. 14. Hexokinase activity of a wild-type rice leaf extract (*Oryza sativa*) extract with and without the addition of trehalose-6-phosphate. Experiments have been performed in duplicate using different amounts of extracts. Fructose or glucose is used as substrate for the assay.

FIG. 15. Hexokinase activity of a wild-type maize leaf extract (*Zea mais*) extract with and without the addition of trehalose-6-phosphate. Fructose or glucose is used as substrate for the assay.

Figure 16:
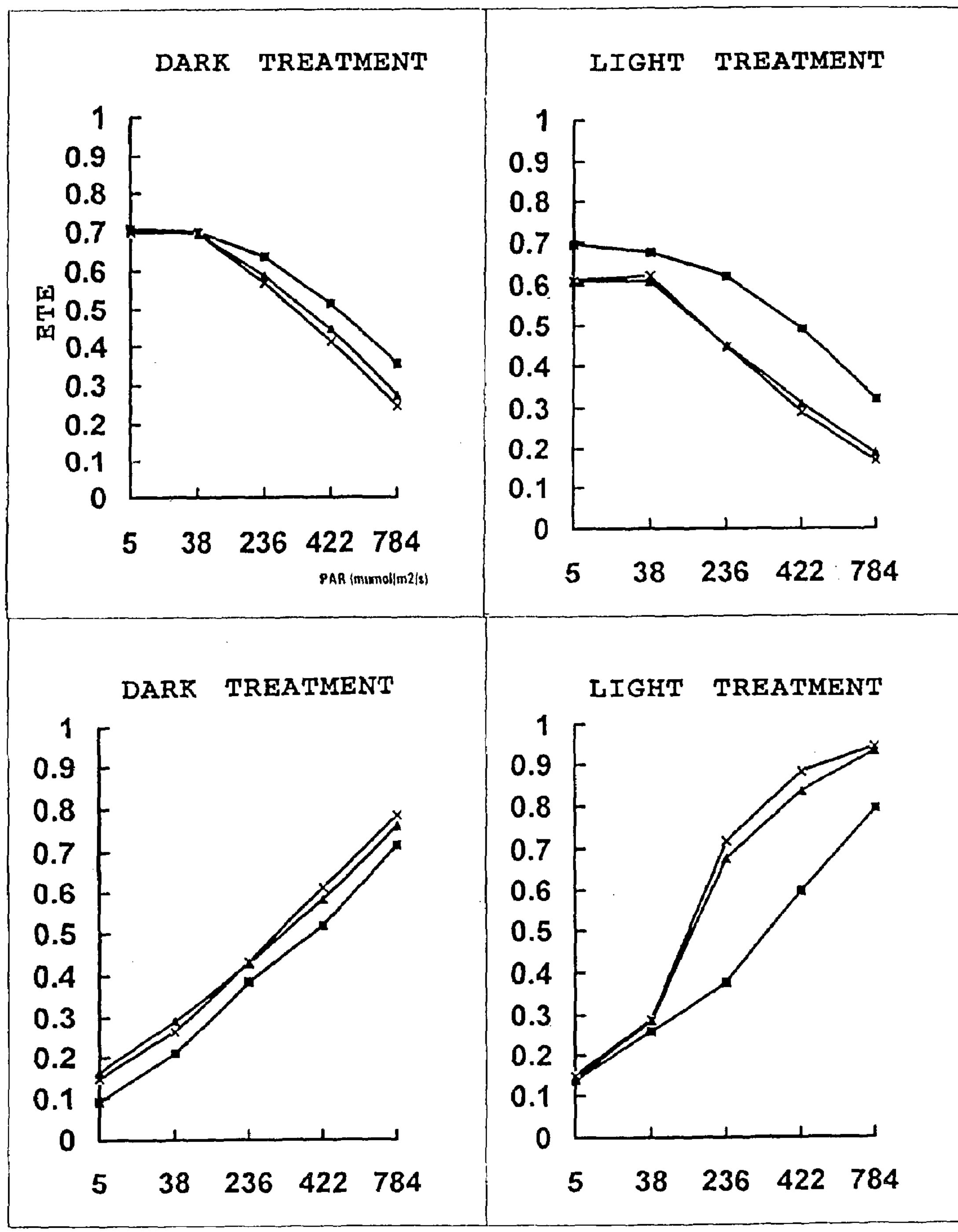

FIG. 16. Fluorescence characteristics of wild-type (triangle), PC-TPS (square) and 35S-TPP (cross) tobacco leaves. The upper two panels show the electron transport efficiency (ETE) at the indicated light intensities (PAR). Plants were measured after a dark-period (upper-left panel) and after a light-period (upper-right panel). The bottom panels show reduction of fluorescence due to assimilate accumulation (non-photochemical quenching). Left and right panel as above.

Figure 17:
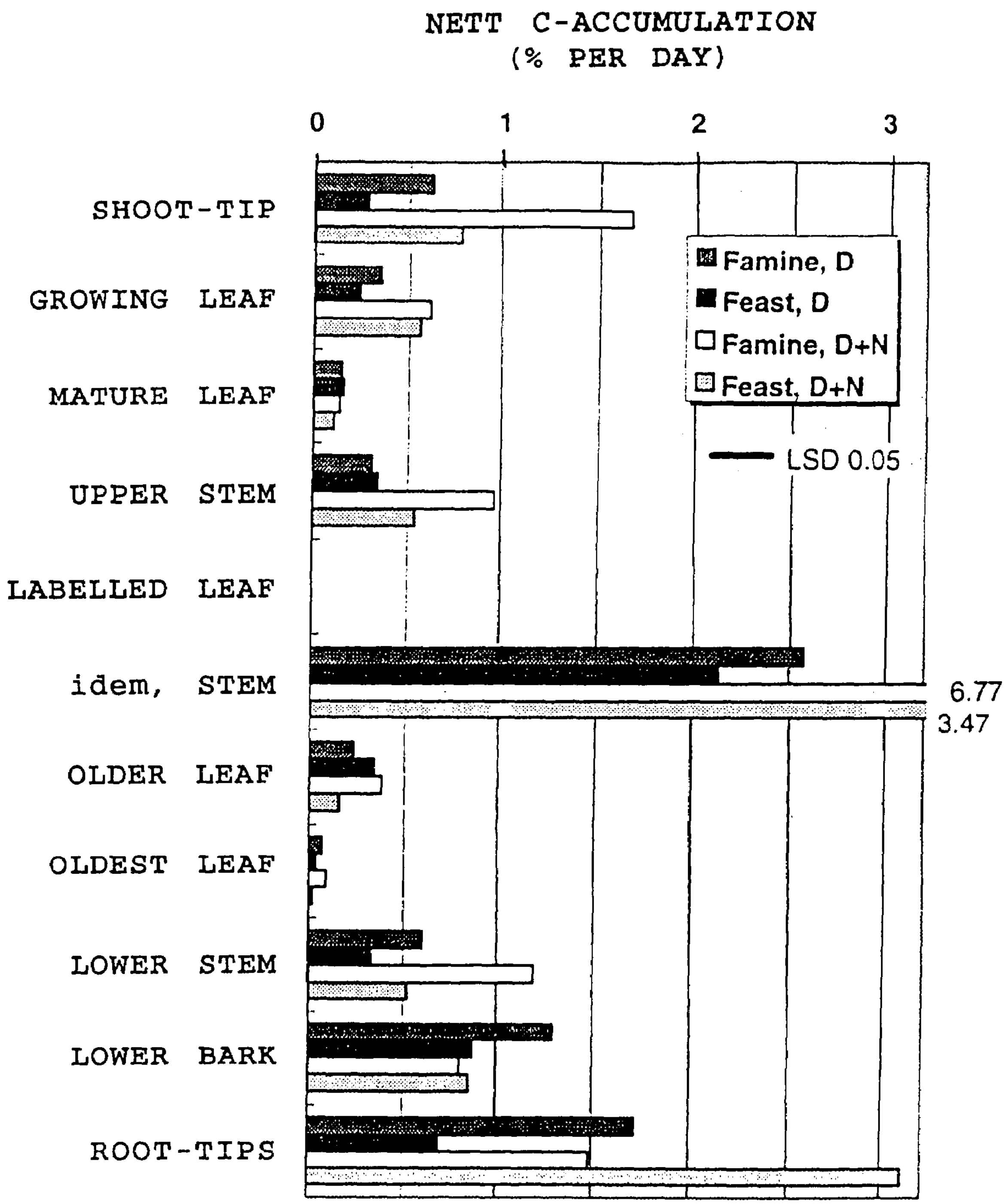

FIG. 17. Relative sink-activity of plant-parts of PC-TPS (Famine) and 35S-TPP (Feast) transgenic tobacco plants. Indicated is the nett C-accumulation expressed as percentage of total C-content, for various plant-parts after a period of light (D) or light+dark (D+N).

Figure 18:
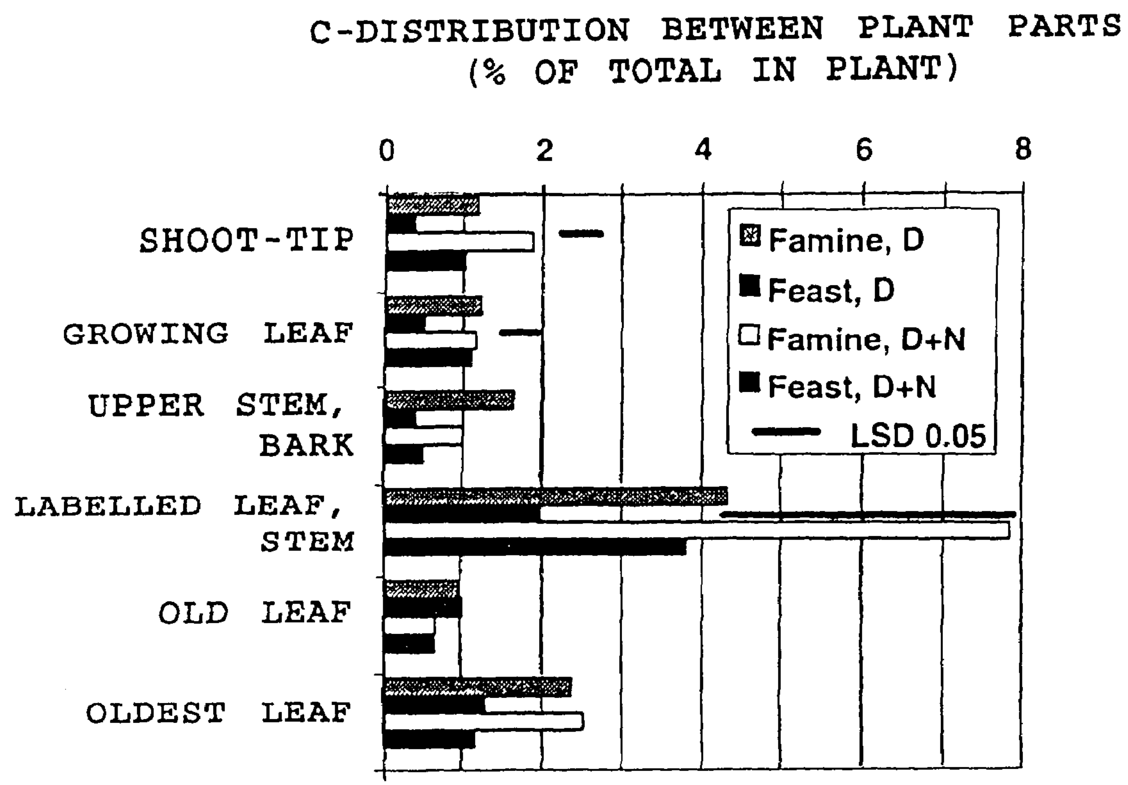

FIG. 18. Actual distribution of carbon in plant-parts of PC-TPS (Famine) and 35S-TPP (Feast) transgenic tobacco plants. Indicated is the nett C-accumulation expressed as percentage of total daily accumulated new C for various plant-parts after a period of light (D) or light+dark (D+N).

Figure 19:
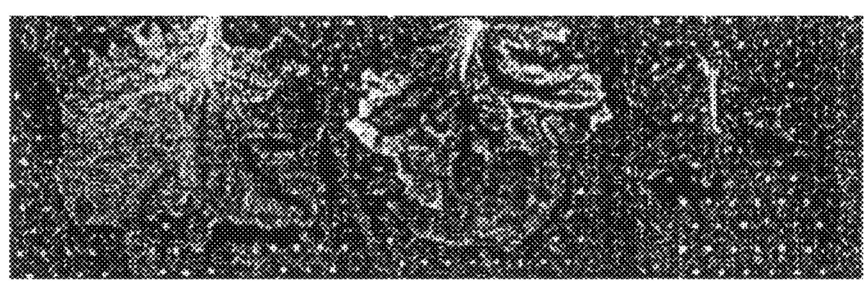

FIG. 19. Scanned images showing reduced and enhanced bolting in transgenic lettuce lines expressing PC-TPS or PC-TPP compared to wild-type plants. The lower panel shows leaf morphology and color.

FIGS. 20A-D. Profile of soluble sugars (FIGS. 20A and B) in extracts of transgenic lettuce (upper panel) and transgenic beet (lower panel) lines. In the upper panel controls are GUS-transgenic lines which are compared to lines transgenics for PC-TPS and PC-TPP. In lower panel all transgenic are PC-TPS. Starch profiles are depicted in FIGS. 20B and C.

Figure 21:
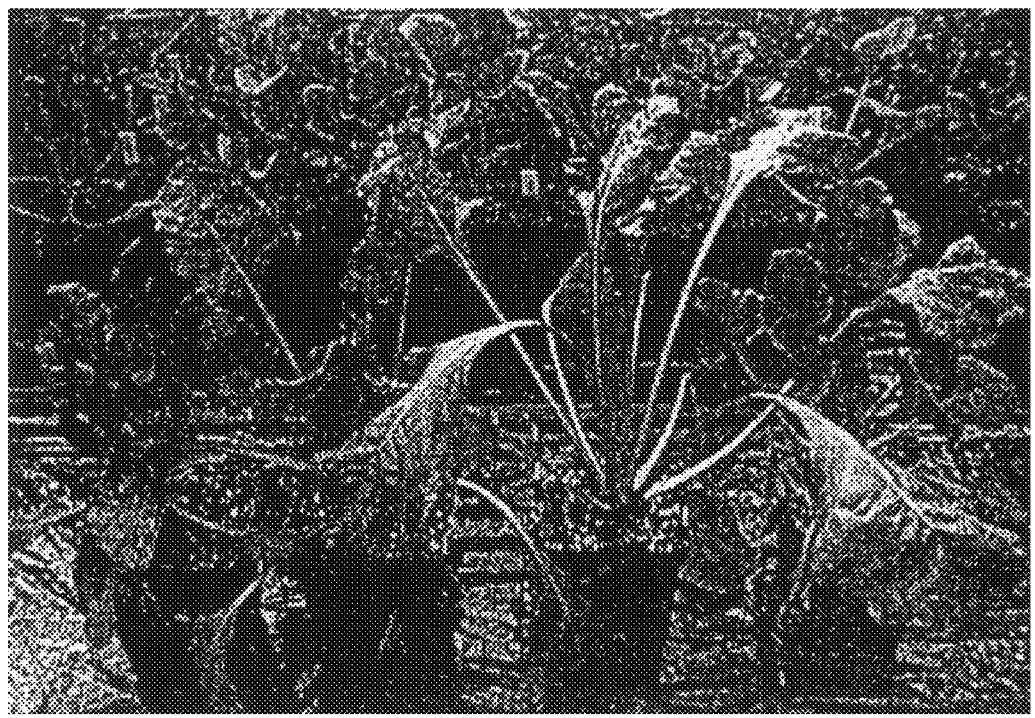

FIG. 21. Scanned image showing plant and leaf morphology of transgenic sugarbeet lines expressing PC-TPS (TPS) or PC-TPP (TPP) compared to wild-type plants (Control). TPS A-type has leaves which are comparable to wild-type while TPS D-type has clearly smaller leaves. The leaves of the TPP transgenic line have a lighter green color, a larger petiole and an increased size compared to the control.

Figure 22:
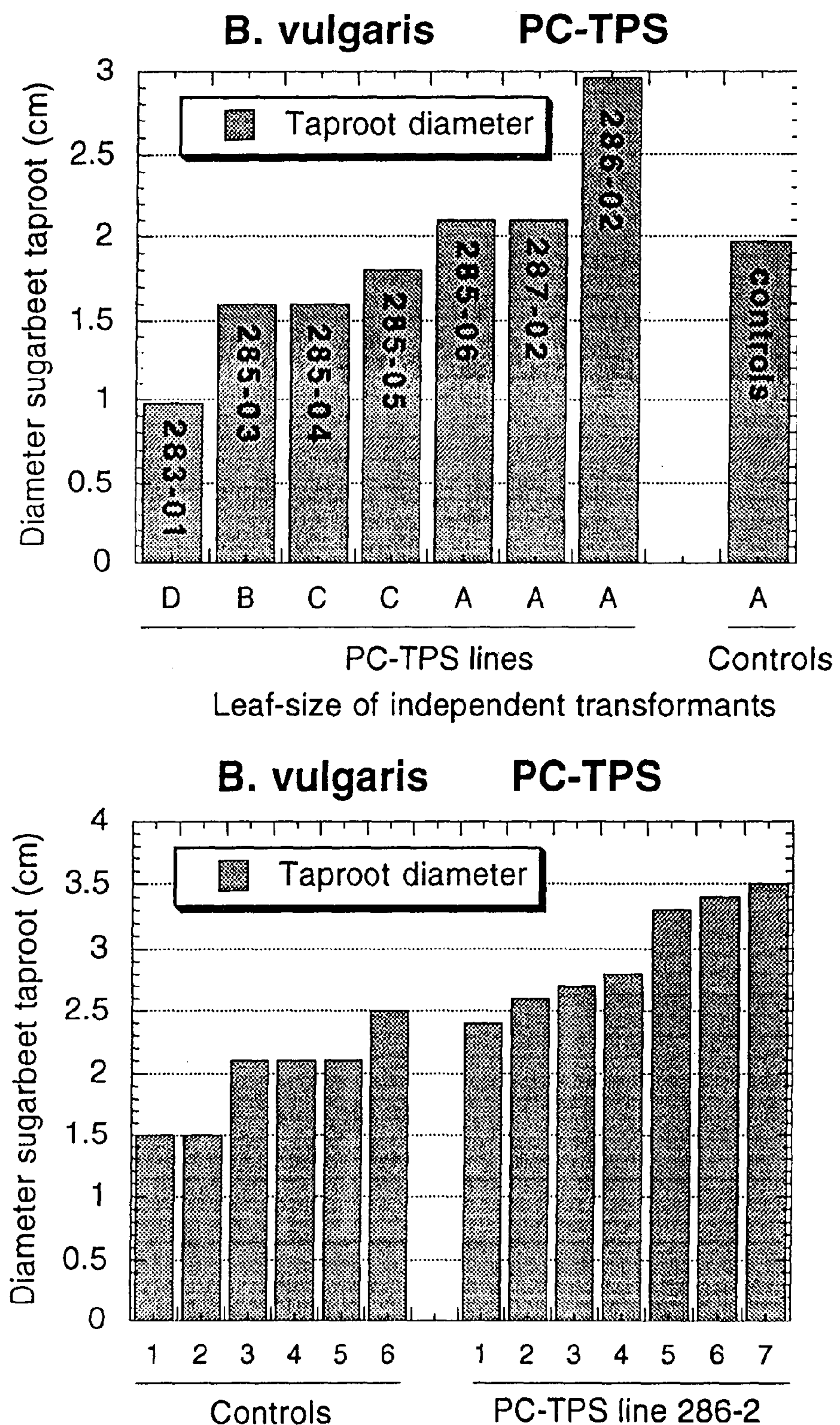

FIG. 22. Taproot diameter of transgenic sugarbeet lines (PC-TPS). In the upper panel A, B, C and D indicate decreasing leaf sizes as compared to control (A). In the lower panel individual clones of control and PC-TPS line 286-2 are shown.

Figure 23:
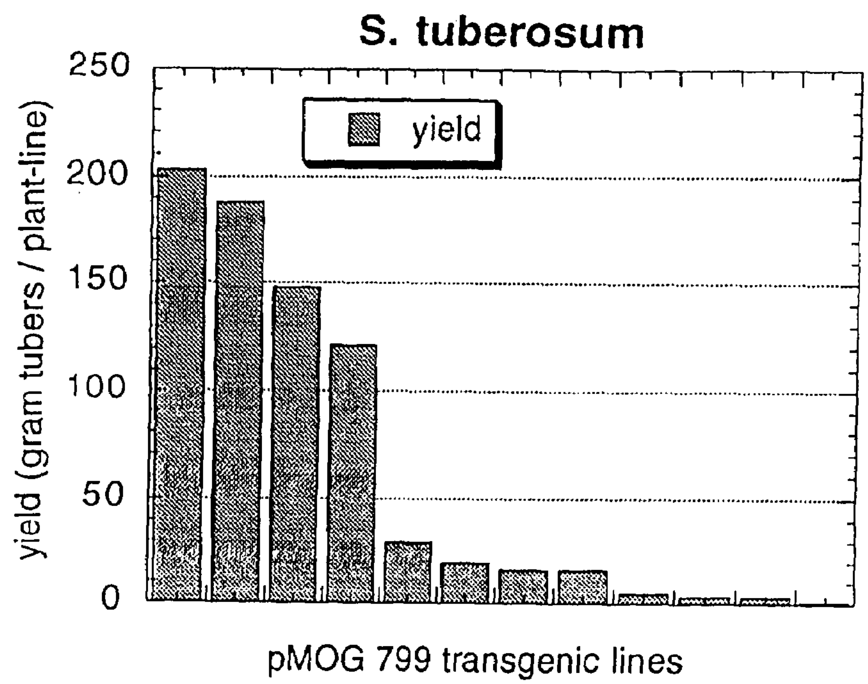

FIG. 23. Tuber yield of pMOG799 (35S TPS) transgenic potato lines.

Figure 24:
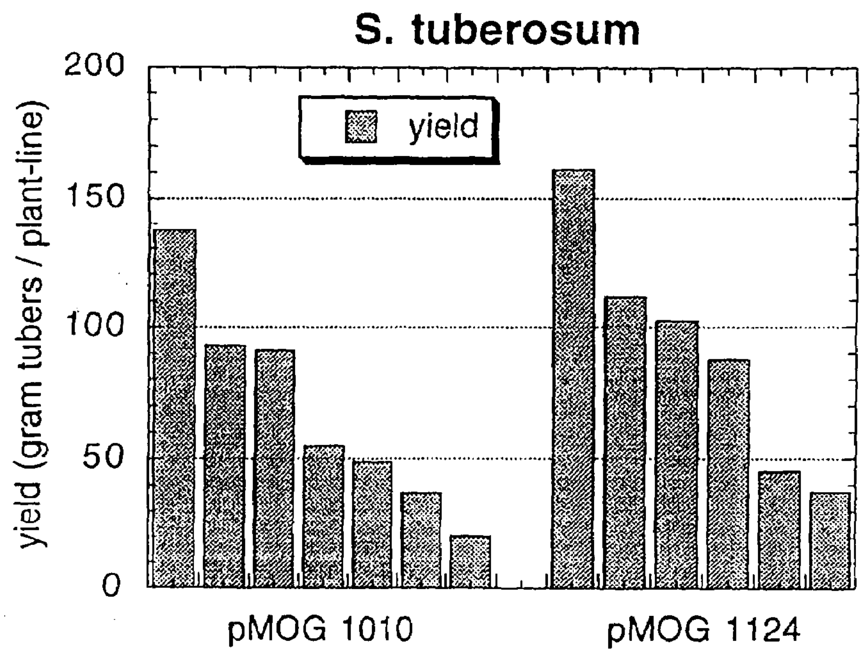

FIG. 24. Tuber yield of pMOG1010 (35S TPP) and pMOG1124 (PC-TPP) transgenic potato lines.

Figure 25:
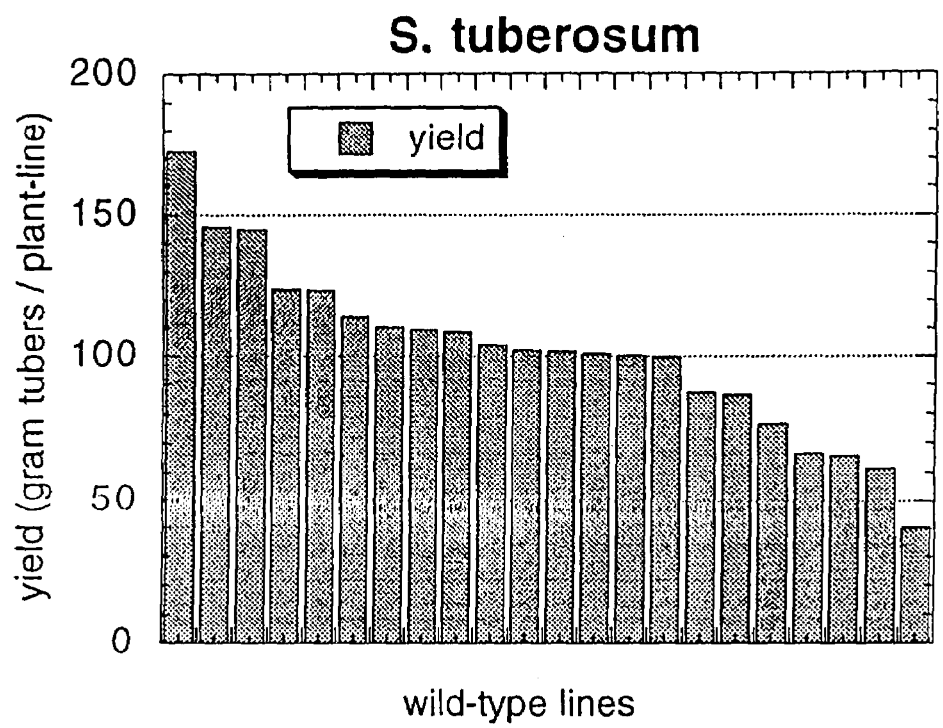

FIG. 25. Tuber yield of 22 independent wild-type *S. tuberosum* clones.

Figure 26:
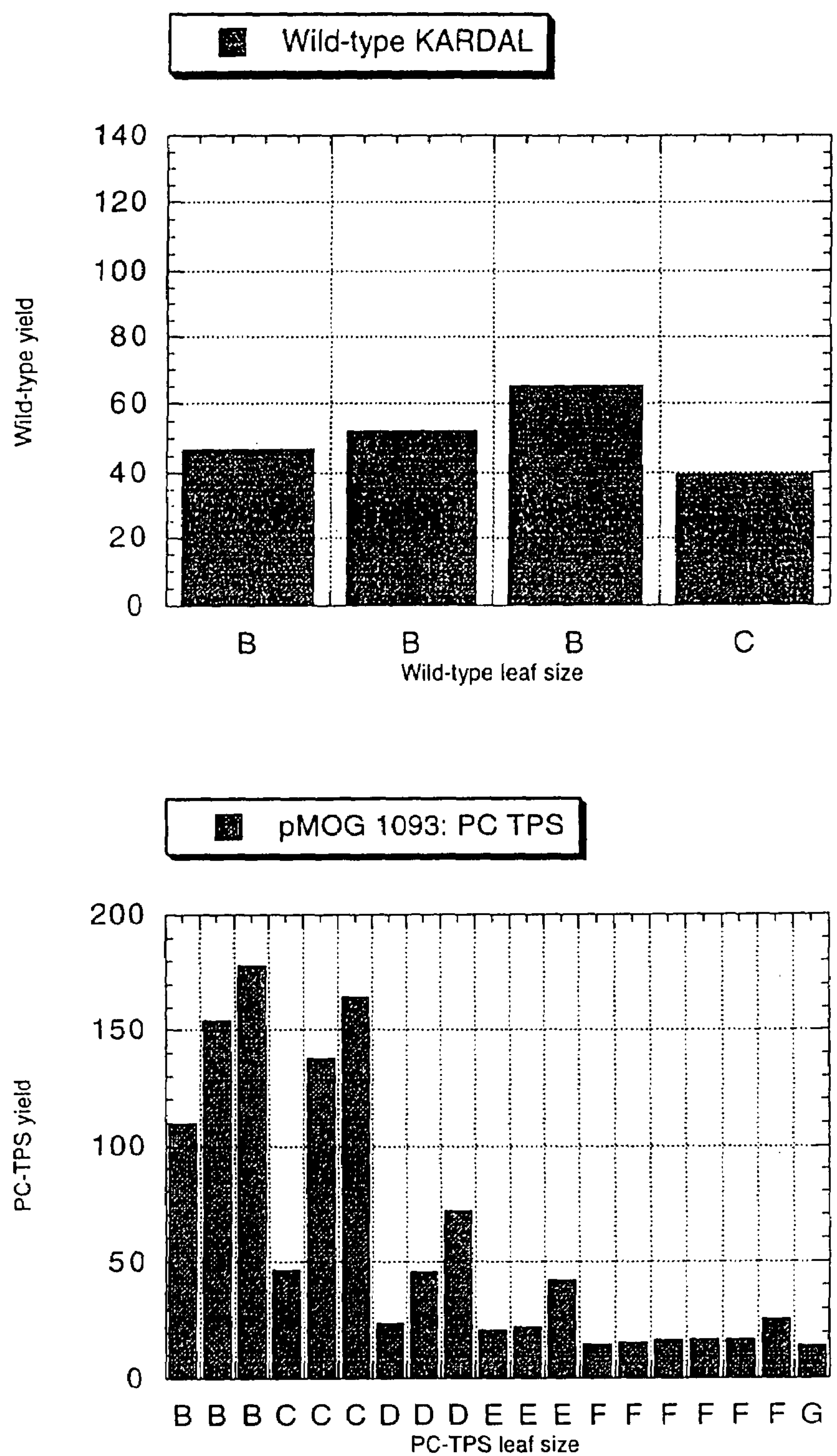

FIG. 26. Tuber yield of pMOG1093 (PC-TPS) transgenic potato lines in comparison to wild-type. B, C, D, E, F, G indicate decreasing leaf sizes as compared to wild-type (B/C).

Figure 1:
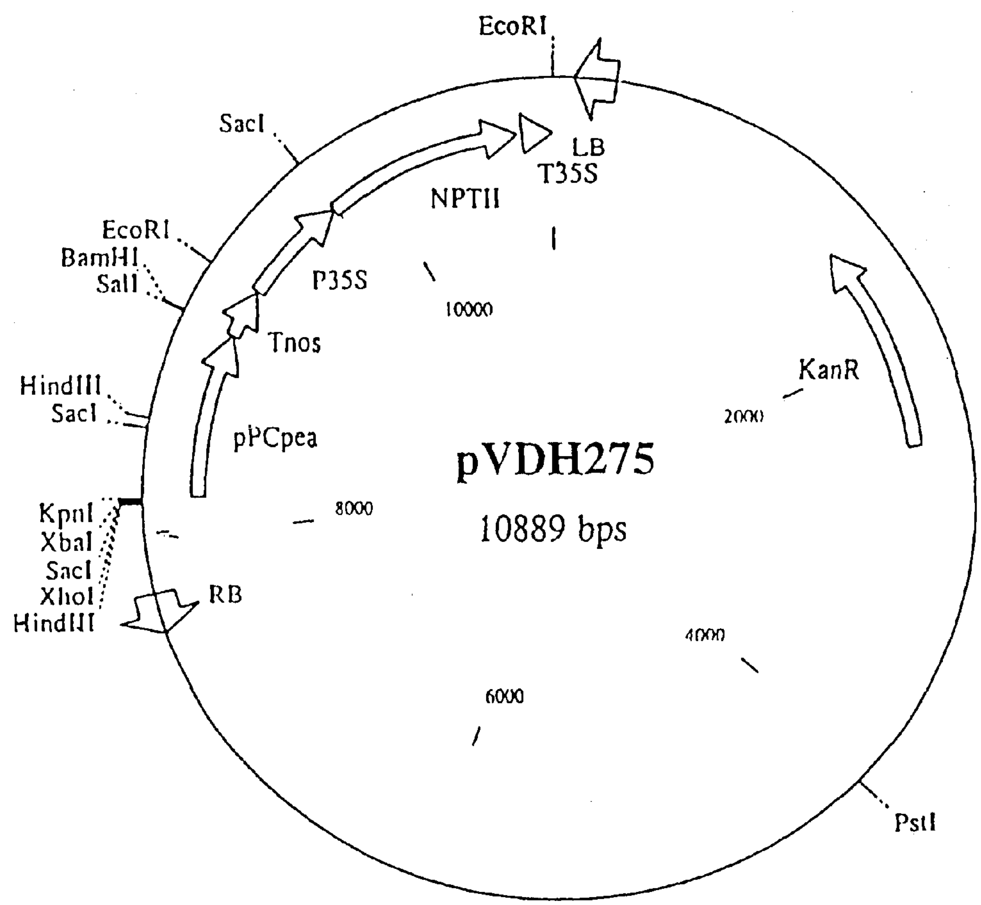
FIG. 1. Schematic representation of plasmid pVDH275 harbouring the neomycin-phosphotransferase gene (NPTII) flanked by the 35S cauliflower mosaic virus promoter (P35S) and terminator (T35S) as a selectable marker; an expression cassette comprising the pea plastocyanin promoter (pPCpea) and the nopaline synthase terminator (Tnos); right (RB) and left (LB) T-DNA border sequences and a bacterial kanamycin resistance (KanR) marker gene.
Figures 1, 20:
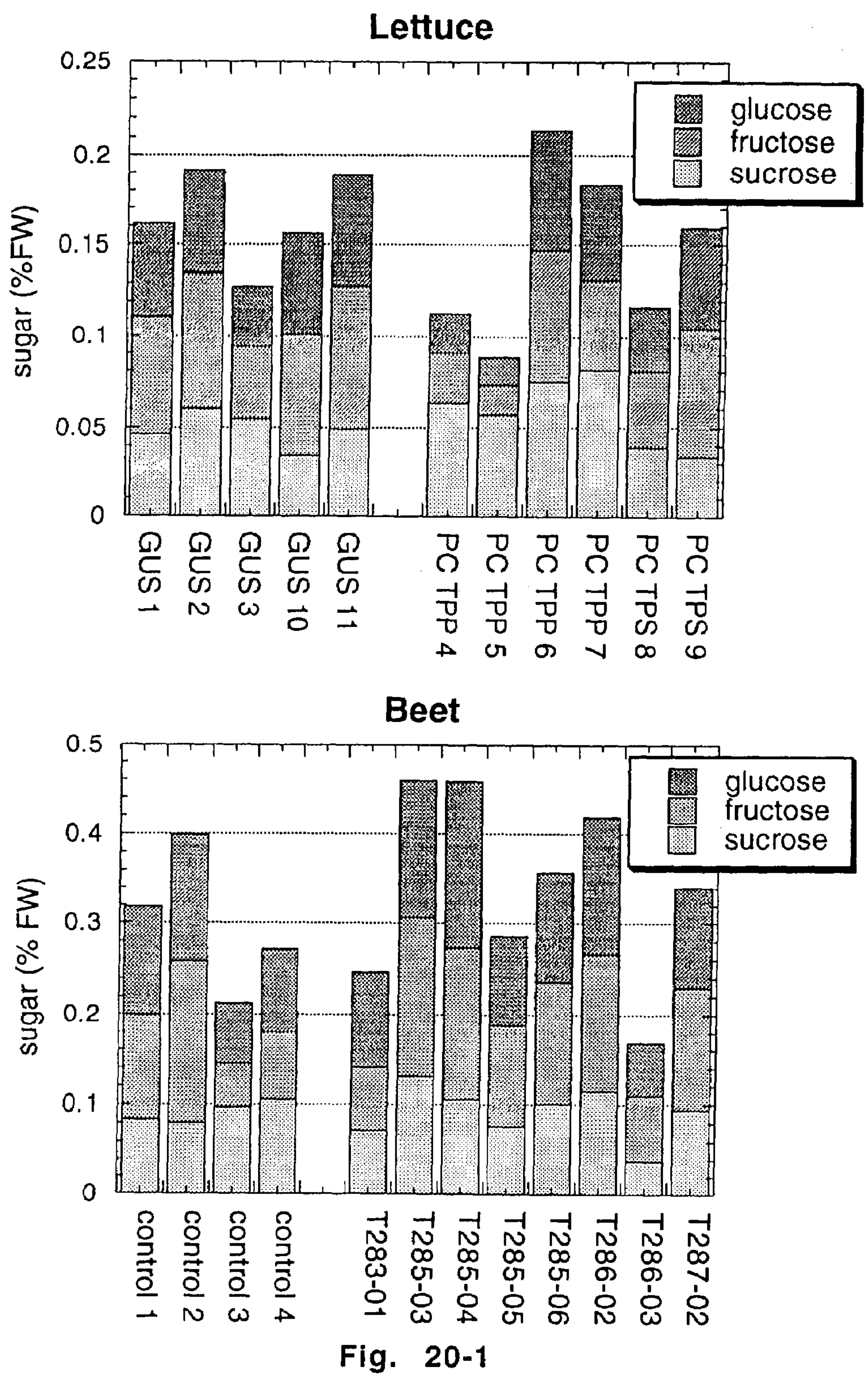
Figures 2, 20:
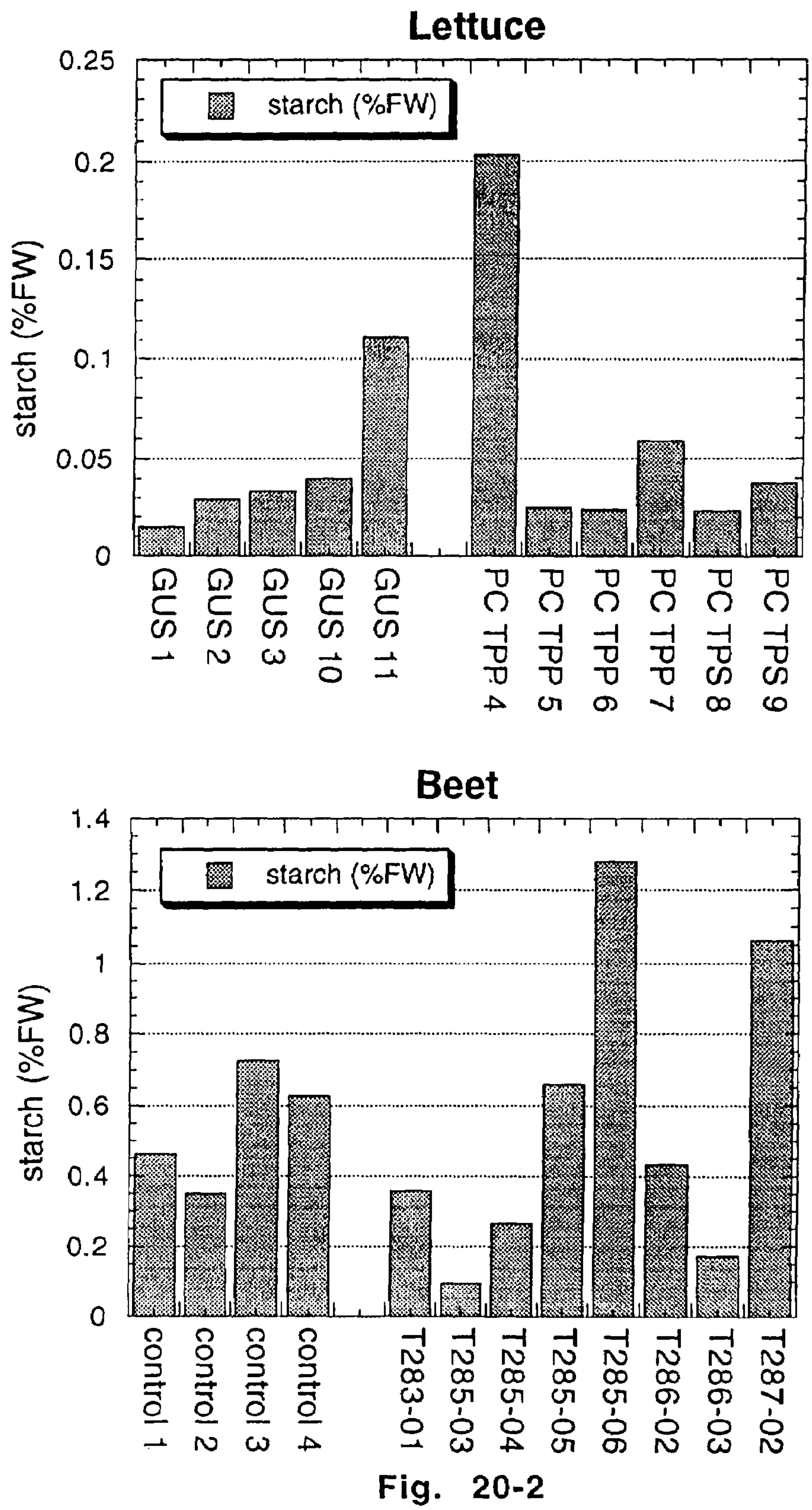
FIG. 2. Northern blot analysis of transgenic tobacco plants. Panel A depicts expression of otsA mRNA in leaves of individual pMOG799 transgenic tobacco plants. The control lane "C" contains total RNA from a non-transformed *N. tabacum* plant.

FIG. 27. Tuber yield of pMoG845 (Pat-TPS) transgenic potato lines (FIG. 27-1) in comparison to wild-type (FIG. 27-2). B, C indicate leaf sizes.

FIGS. 28A-C. Tuber yield of pMOG 1129 (845-11/22/28) transgenic potato lines.

FIGS. 29A-B. Scanned images showing cross section through leaves of TPP (FIG. 29B) and TPS (FIG. 29A) transgenic tobacco plants. Additional cell layers and increased cell size are visible in the TPS cross section.

FIG. 30. HPLC-PED analysis of tubers transgenic for $TPS_{E.coli}$ before and after storage at 4° C. Kardal C, F, B, G and H are non-transgenic control lines.

Figure 31:
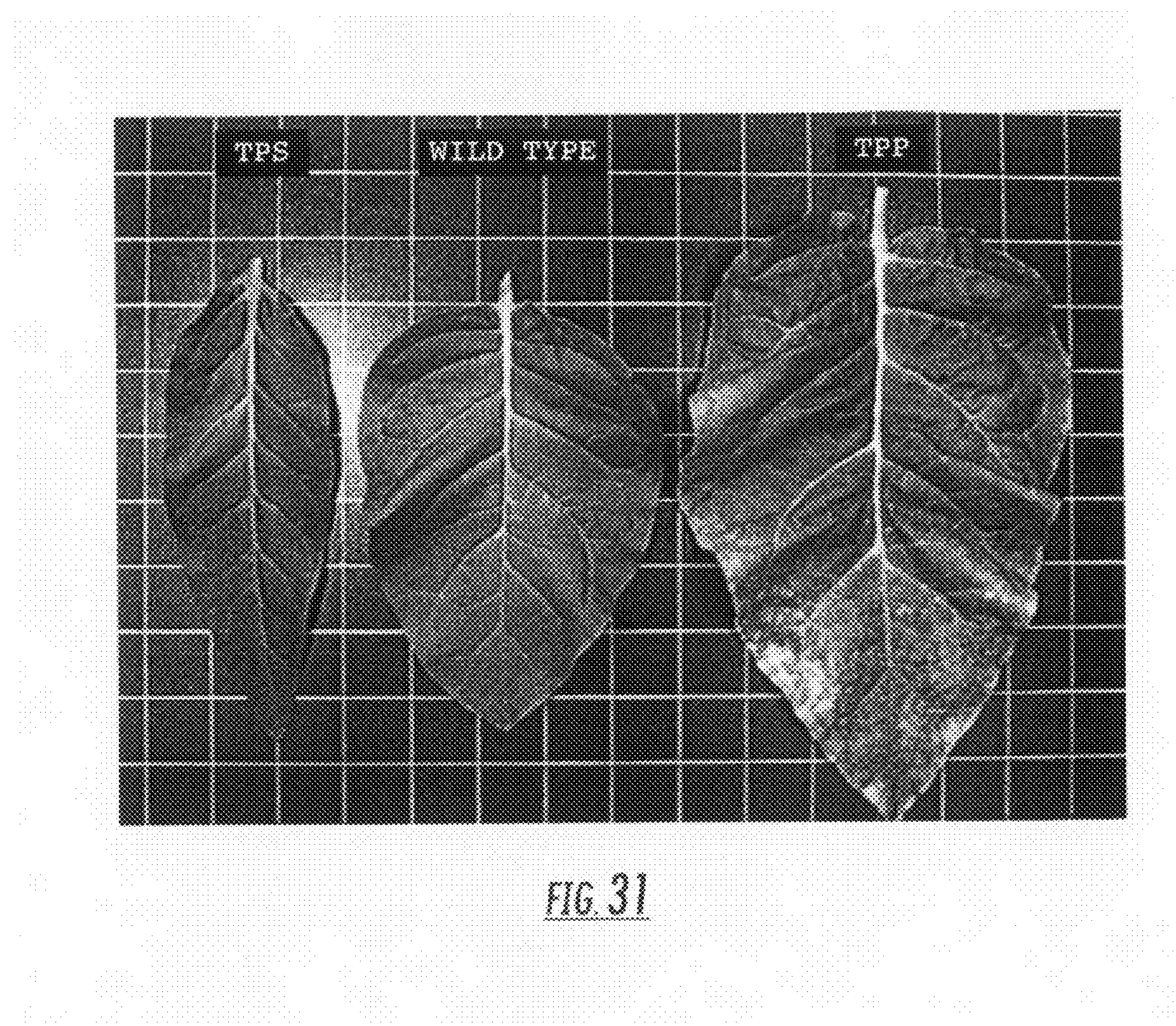

FIG. 31. Scanned images showing leaf morphology, color and size of tobacco lines transgenic for 35S TPS (upper leaf), wild-type (middle leaf) and transgenic for 35S TPP (bottom leaf).

FIGS. 32A-D. Metabolic profiling of 35S TPS (pMOG799), 35S TPP (pMOG1010), wild-type (WT), PC-TPS (pMOG1177) and PC-TPP (pMOG1124) transgenic tobacco lines. Shown are the levels of trehalose, soluble sugars FIGS. 32A and B, starch and chlorophyll FIGS. 32C and D.

Figure 33:
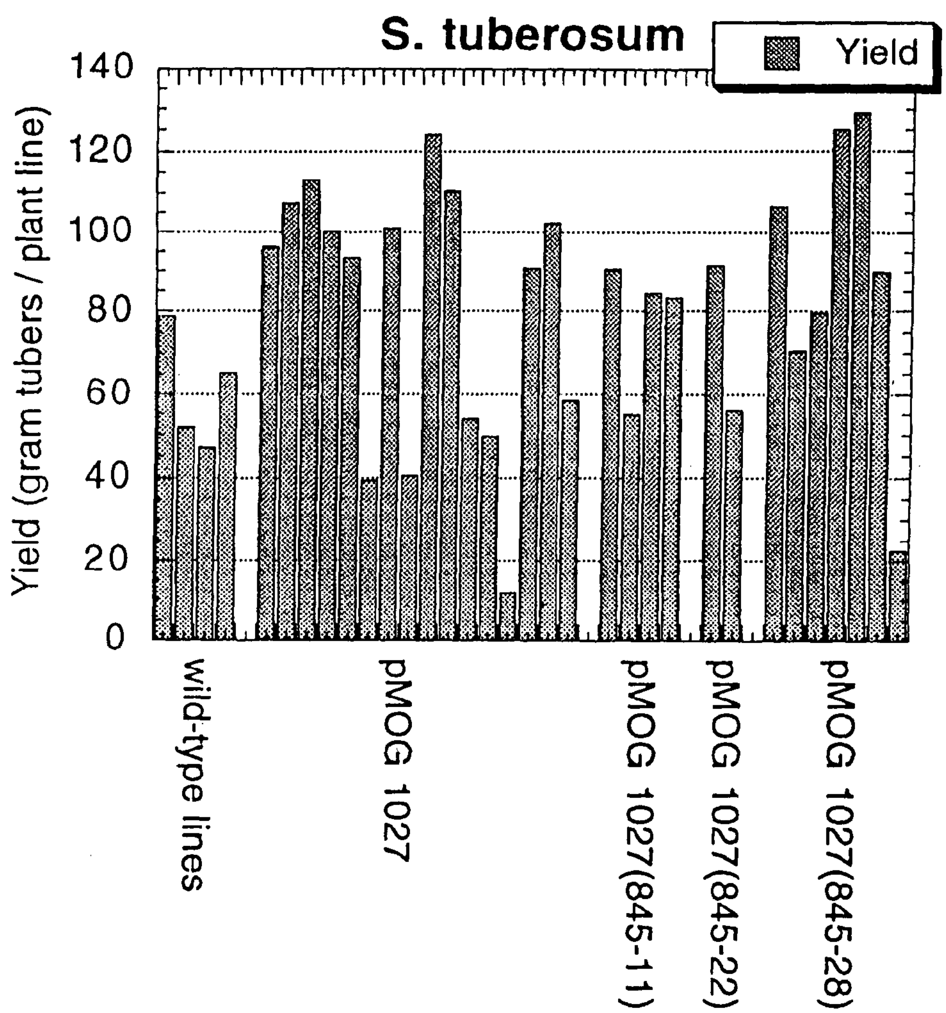

FIG. 33. Tuber yield of pMOG027 (35S as-trehalase) and pMOG1027(845-11/22/28) (35S as-trehalase pat TPS) transgenic potato lines in comparison to wild-type potato lines.

Figure 34:
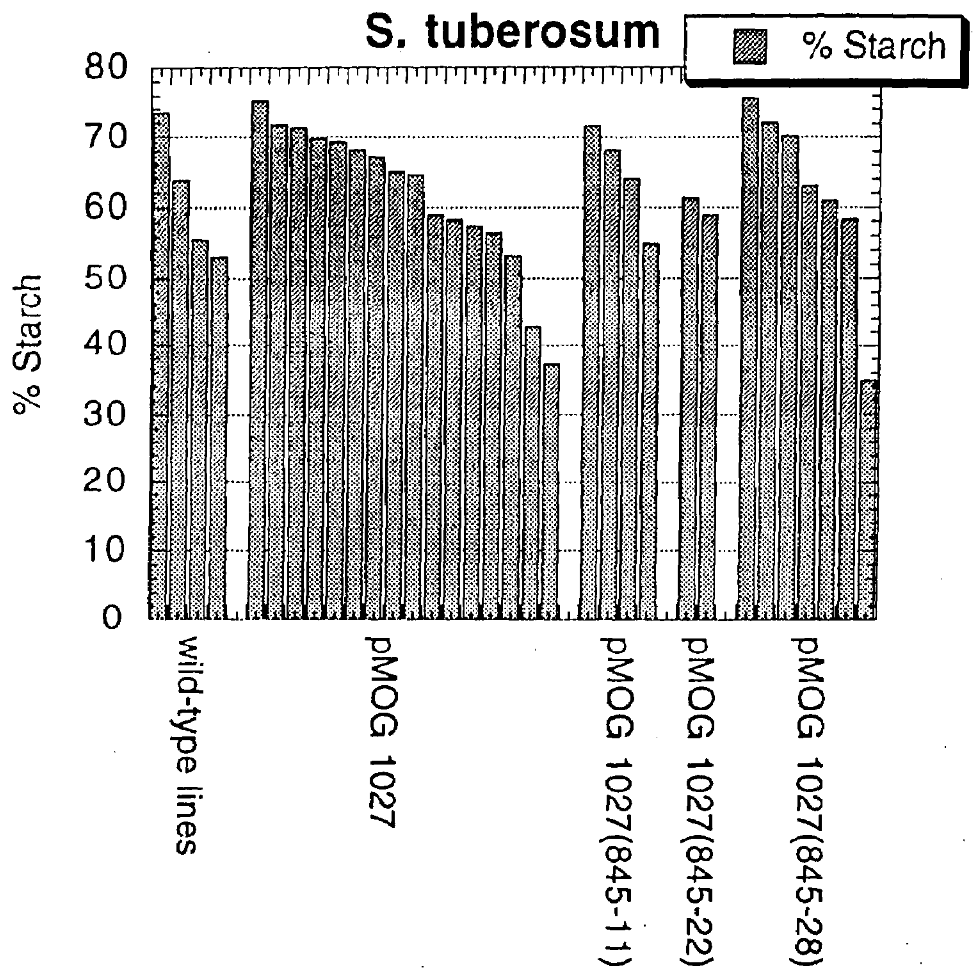

FIG. 34. Starch content of pMOG027 (35S as-trehalase) and pMOG1027 (845-11/22/28) (35S as-trehalase pat TPS) transgenic potato lines in comparison to wild-type potato lines. The sequence of all lines depicted is identical to FIG. 33.

FIGS. 35A-E. Yield of pMOG1028 (pat as-trehalase) and pMOG1028(845-11/22/28) (pat as-trehalase pat TPS) transgenic potato lines in comparison to wild-type potato lines.

Figures 1, 35:
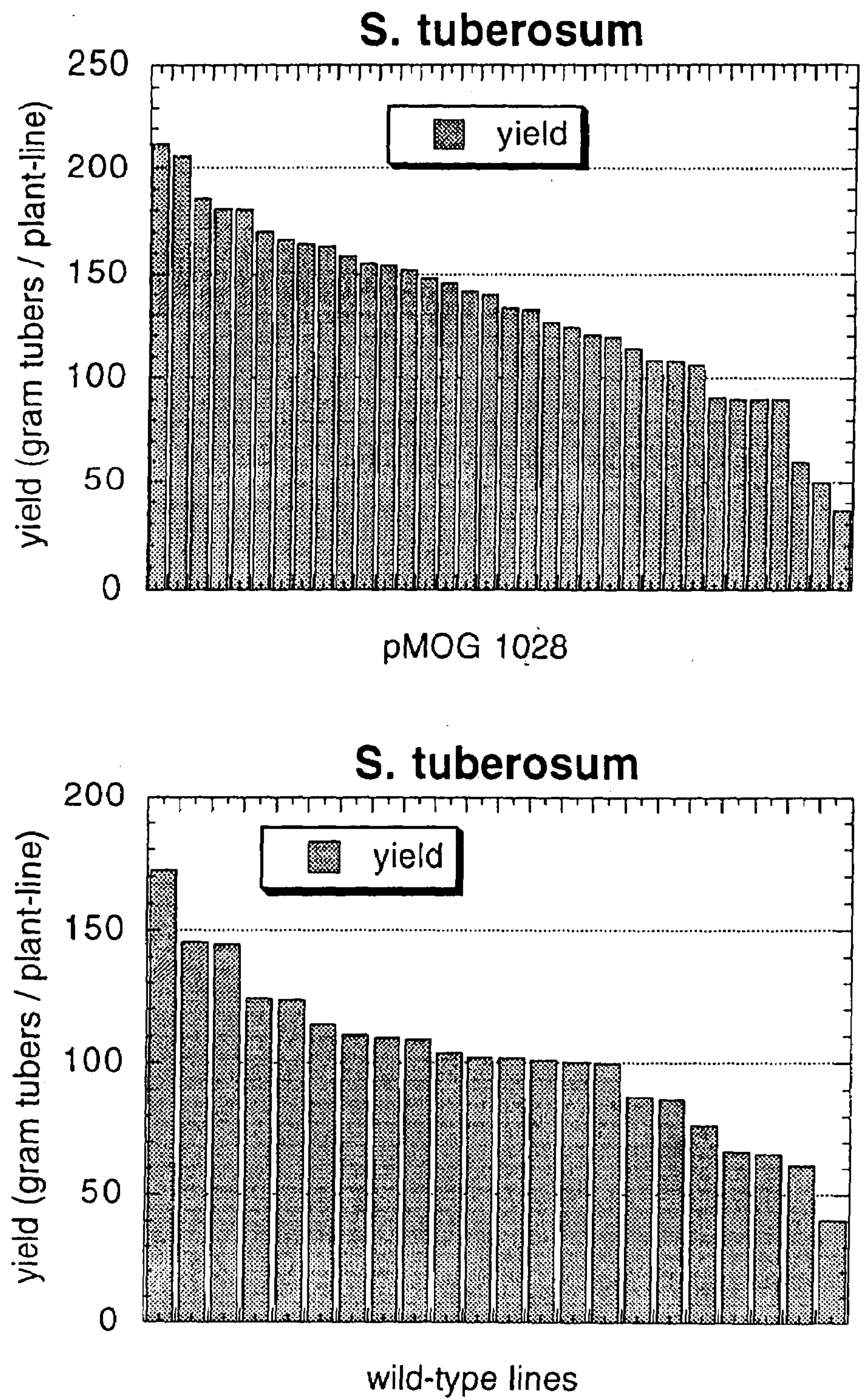
Figures 2, 35:
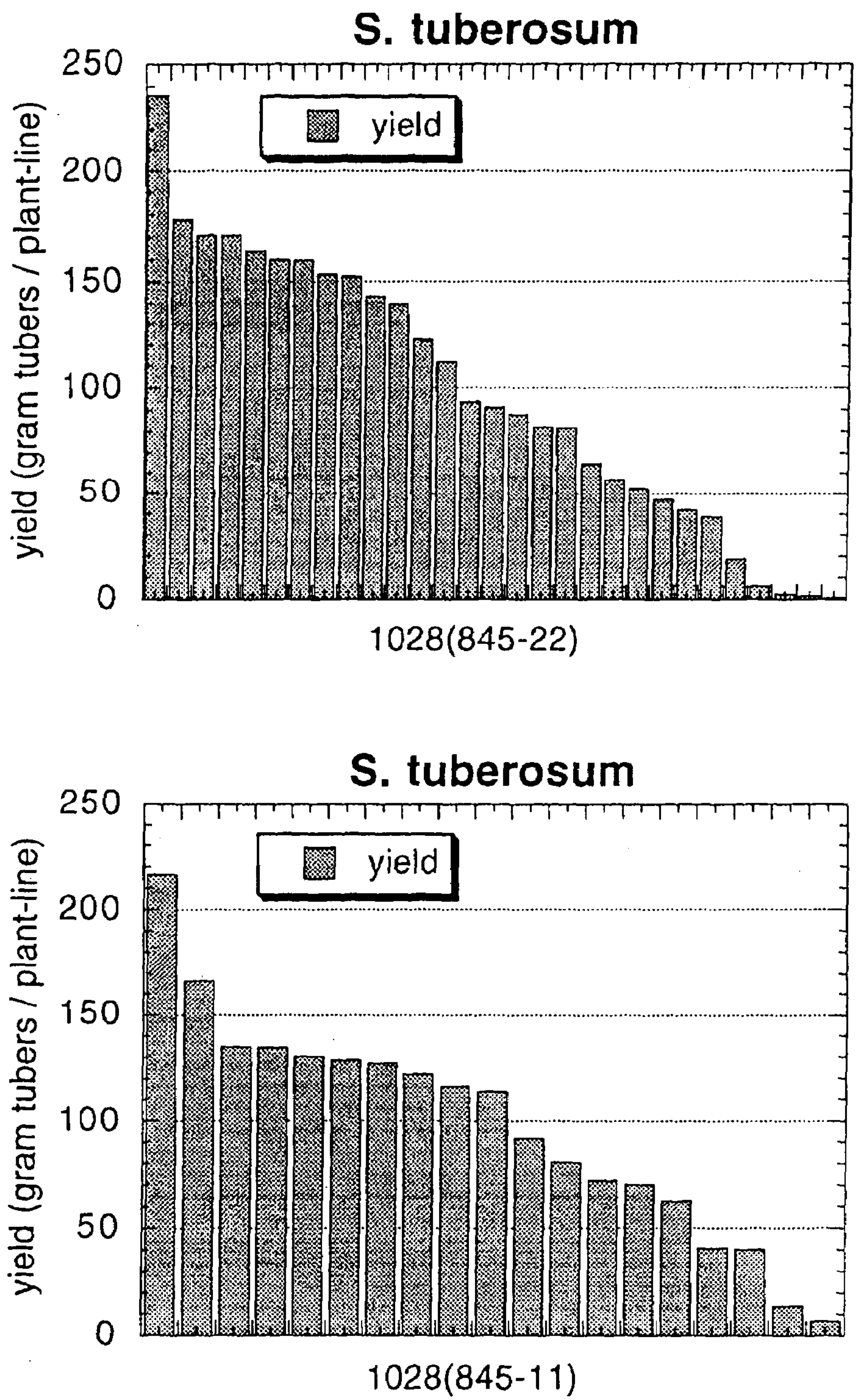
Figure 36:
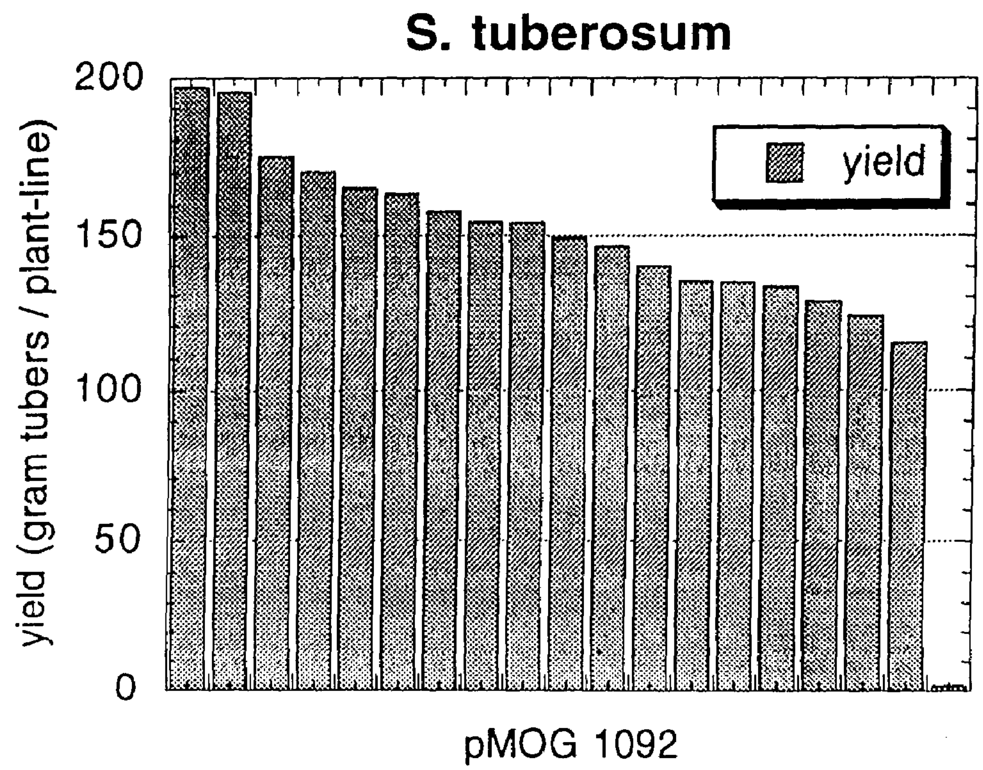

FIG. 36. Yield of pMOG1092 (PC as-trehalase) transgenic potato lines in comparison to wild-type potato lines as depicted in FIGS. 35A-E.

Figure 37:
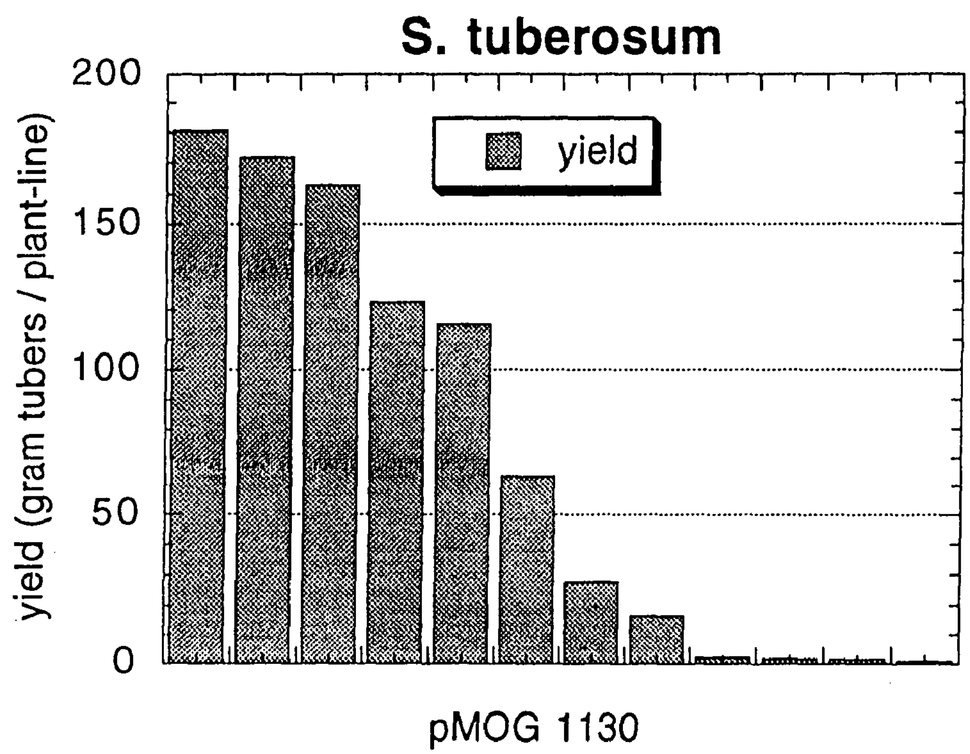

FIG. 37. Yield of pMOG1130 (PC as-trehalase PC TPS) transgenic potato lines in comparison to wild-type potato lines as depicted in FIGS. 35A-E.

DETAILED DESCRIPTION OF THE INVENTION

The invention is concerned with the finding that metabolism can be modified in vivo by the level of T-6-P. A decrease of the intracellular concentration of T-6-P stimulates glycolytic activity. On the contrary, an increase of the T-6-P concentration will inhibit glycolytic activity and stimulate photosynthesis.

These modifications established by changes in T-6-P levels are most likely a result of the signalling function of hexokinase, which activity is shown to be regulated by T-6-P. An increase in the flux through hexokinase (i.e. an increase in the amount of glucose) that is reacted in glucose-6-phosphate has been shown to inhibit photosynthetic activity in plants. Furthermore, an increase in the flux through hexokinase would not only stimulate the glycolysis, but also cell division activity.

Theory of Trehalose-6-Phosphate Regulation of Carbon Metabolism

In a normal plant cell formation of carbohydrates takes place in the process of photosynthesis in which $CO_2$ is fixed and reduced to phosphorylated hexoses with sucrose as an end-product. Normally this sucrose is transported out of the cell to cells or tissues which through uptake of this sucrose can use the carbohydrates as building material for their metabolism or are able to store the carbohydrates as e.g. starch. In this respect, in plants, cells that are able to photosynthesize and thus to produce carbohydrates are denominated as sources, while cells which consume or store the carbohydrates are called sinks.

In animal and most microbial cells no photosynthesis takes place and the carbohydrates have to be obtained from external sources, either by direct uptake from saccharides (e.g. yeasts and other micro-organisms) or by digestion of carbohydrates (animals). Carbohydrate transport usually takes place in these organisms in the form of glucose, which is actively transported over the cell membrane.

After entrance into the cell, one of the first steps in the metabolic pathway is the phosphorylation of glucose into glucose-6-phosphate catalyzed by the enzyme hexokinase. It has been demonstrated that in plants sugars which are phosphorylated by hexokinase (HXK) are controlling the expression of genes involved in photosynthesis (Jang & Sheen (1994), The Plant Cell 6, 1665). Therefore, it has been proposed that HXK may have a dual function and may act as a key sensor and signal transmitter of carbohydrate-mediated regulation of gene-expression. It is believed that this regulation normally signals the cell about the availability of starting product, i.e. glucose. Similar effects are observed by the introduction of TPS or TPP which influence the level of T-6-P. Moreover, it is shown that in vitro T-6-P levels affect hexokinase activity. By increasing the level of T-6-P, the cell perceives a signal that there is a shortage of carbohydrate input. Conversely, a decrease in the level of T-6-P results in a signal that there is plenty of glucose, resulting in the down-regulation of photosynthesis: it signals that substrate for glycolysis and consequently energy supply for processes as cell growth and cell division is sufficiently available. This signaling is thought to be initiated by the increased flux through hexokinase (J. J. Van Oosten, public lecture at Rijks Universiteit Utrecht dated Apr. 19, 1996).

The theory that hexokinase signalling in plants can be regulated through modulation of the level of trehalose-6-phosphate would imply that all plants require the presence of an enzyme system able to generate and break-down the signal molecule trehalose-6-phosphate. Although trehalose is commonly found in a wide variety of fungi, bacterial, yeasts and algae, as well as in some invertebrates only a very limited range of vascular plants have been proposed to be able to synthesize this sugar (Elbein (1974), Adv. Carboh. Chem. Biochem. 30, 227). A phenomenon which was not understood until now is that despite the apparent lack of trehalose synthesizing enzymes, all plants do seem to contain trehalases, enzymes which are able to break down trehalose into two glucose molecules.

Indirect evidence for the presence of a metabolic pathway for trehalose is obtained by experiments presented herein with trehalase inhibitors such as Validamycin A or transformation with anti-sense trehalase.

Production of trehalose would be hampered if its intermediate T-6-P would influence metabolic activity too much. Preferably, in order to accumulate high levels of trehalose without affecting partitioning and allocation of metabolites by the action of trehalose-6-phosphate, one should overexpress a bipartite TPS/TPP enzyme. Such an enzyme would resemble a genetic constitution as found in yeast, where the TPS2 gene product harbours a TPS and TPP homologous region when compared with the *E. coli* otsA and otsB gene (Kaasen et al. (1994), Gene 145, 9). Using such an enzyme, trehalose-6-phosphate will not become freely available to other cell components. Another example of such a bipartite enzyme is given by Zentella & Iturriaga (Plant Physiol. (1996), 111 Abstract 88) who isolated a 3.2 kb cDNA from *Selaginella lepidophylla* encoding a putative trehalose-6-phosphate synthase/phosphatase. It is also envisaged that construction of a truncated TPS-TPP gene product, whereby only the TPS activity would be retained, would be as powerful for synthesis of T-6-P as the otsA gene of *E. coli*, also when used in homologous systems.

On a molecular level we have data that indicate that next to *Selaginella* also trehalose synthesizing genes are present in *Arabidopsis*, tobacco, rice and sunflower. Using degenerated primers, based on conserved sequences between $TPS_{E.coli}$ and $TPS_{yeast}$, we have been able to identify genes encoding putative trehalose-6-phosphate generating enzymes in sunflower and tobacco. Sequence comparison revealed significant homology between these sequences, the TPS genes from yeast and *E. coli*, and EST (expressed sequences tags) sequences from *Arabidopsis* and rice (see also Table 6b which contains the EST numbers of homologous EST's found).

Recently an *Arabidopsis* gene has been elucidated (disclosed in GENBANK Acc. No. Y08568, depicted in SEQ ID NO: 39) that on basis of its homology can be considered as a bipartite enzyme. These data indicate that, in contrast to current beliefs, most plants do contain genes which encode trehalose-phosphate-synthases enabling them to synthesize T-6-P. As proven by the accumulation of trehalose in TPS expressing plants, plants also contain phosphatases, non-specific or specific, able to dephosphorylate the T-6-P into trehalose. The presence of trehalase in all plants may be to effectuate turnover of trehalose.

Furthermore, we also provide data that T-6-P is involved in regulating carbohydrate pathways in human tissue. We have elucidated a human TPS gene (depicted in SEQ ID NO: 10) which shows homology with the TPS genes of yeast, *E. coli* and plants. Furthermore, we show data that also the activity of hexokinase is influenced in mammalian (mouse) tissue.

Generation of the "plenty" signal by decreasing the intracellular concentration of trehalose-6-phosphate through expression of the enzyme TPP (or inhibition of the enzyme TPS) will signal all cell systems to increase glycolytic carbon flow and inhibit photosynthesis. This is nicely shown in the experimental part, where, for instance in Experiment 2 transgenic tobacco plants are described in which the enzyme TPP is expressed having increased leaf size, increased branching and a reduction of the amount of chlorophyll. However, since the "plenty" signal is generated in the absence of sufficient supply of glucose, the pool of carbohydrates in the cell is rapidly depleted.

Thus, assuming that the artificial "plenty" signal holds on, the reduction in carbohydrates will finally become limiting for growth and cell division, i.e. the cells will use up all their storage carbohydrates and will be in a "hunger"-stage. Thus, leaves are formed with a low amount of stored carbohydrates. On the other hand, plants that express a construct with a gene coding for TPS, which increases the intracellular amount of T-6-P, showed a reduction of leaf size, while also the leaves were darker green, and contained an increased amount of chlorophyll.

In yeast, a major role of glucose-induced signalling is to switch metabolism from a neogenetic/respirative mode to a fermentative mode. Several signalling pathways are involved in this phenomenon (Thevelein and Hohmann, (1995) TIBS 20, 3). Besides the possible role of hexokinase signalling, the RAS-cyclic-AMP (cAMP) pathway has been shown to be activated by glucose. Activation of the RAS-cAMP pathway by glucose requires glucose phosphorylation, but no further glucose metabolism. So far, this pathway has been shown to activate trehalase and 6-phosphofructo-2-kinase (thereby stimulating glycolysis), while fructose-1,6-bisphosphatase is inhibited (thereby preventing gluconeogenesis), by cAMP-dependent protein phosphorylation. This signal transduction route and the metabolic effects it can bring about can thus be envisaged as one that acts in parallels with the hexokinase signalling pathway, that is shown to be influenced by the level of trehalose-6-phosphate.

As described in our invention, transgenic plants expressing as-trehalase reveal similar phenomena, like dark-green leaves, enhanced yield, as observed when expressing a TPS gene. It also seems that expression of as-trehalase in double-constructs enhances the effects that are caused by the expression of TPS. Trehalase activity has been shown to be present in e.g. plants, insects, animals, fungi and bacteria while only in a limited number of species, trehalose is accumulated.

Up to now, the role of trehalase in plants is unknown although this enzyme is present in almost all plant-species. It has been proposed to be involved in plant pathogen interactions and/or plant defense responses. We have isolated a potato trehalase gene and show that inhibition of trehalase activity in potato leaf and tuber tissues leads to an increase in tuber-yield. Fruit-specific expression of as-trehalase in tomato combined with TPS expression dramatically alters fruit development.

According to one embodiment of the invention, accumulation of T-6-P is brought about in cells in which the capacity of producing T-6-P has been introduced by introduction of an expressible gene construct encoding trehalose-phosphate-synthase (TPS). Any trehalose phosphate synthase gene under the control of regulatory elements necessary for expression of DNA in cells, either specifically or constitutively, may be used, as long as it is capable of producing a trehalose phosphate synthase capable of T-6-P production in said cells. One example of an open reading frame according to the invention is one encoding a TPS-enzyme as represented in SEQ ID NO: 2. Other examples are the open reading frames as represented in SEQ ID NO's: 10, 18-23, 41 and 45-53. As is illustrated by the above-mentioned sequences it is well known that more than one DNA sequence may encode an identical enzyme, which fact is caused by the degeneracy of the genetic code. If desired, the open reading frame encoding the trehalose phosphate synthase activity may be adapted to codon usage in the host of choice, but this is not a requirement.

The isolated nucleic acid sequence represented by for instance SEQ ID NO: 2, may be used to identify trehalose phosphate synthase genes in other organisms and subsequently isolating and cloning them, by PCR techniques and/or by hybridizing DNA from other sources with a DNA- or RNA fragment obtainable from the *E. coli* gene. Preferably, such DNA sequences are screened by hybridizing under more or less stringent conditions (influenced by factors such as temperature and ionic strength of the hybridization mixture). Whether or not conditions are stringent also depends on the nature of the hybridization, i.e. DNA:DNA, DNA:RNA, RNA:RNA, as well as the length of the shortest hybridizing fragment. Those of skill in the art are readily capable of establishing a hybridization regime stringent enough to isolate TPS genes, while avoiding non-specific hybridization. As genes involved in trehalose synthesis from other sources become available these can be used in a similar way to obtain an expressible trehalose phosphate synthase gene according to the invention. More detail is given in the experimental section.

Sources for isolating trehalose phosphate synthase activities include microorganisms (e.g. bacteria, yeast, fungi), plants, animals, and the like. Isolated DNA sequences encoding trehalose phosphate synthase activity from other sources may be used likewise in a method for producing T-6-P according to the invention. As an example, genes for producing T-6-P from yeast are disclosed in WO 93/17093.

The invention also encompasses nucleic acid sequences which have been obtained by modifying the nucleic acid sequence represented in SEQ ID NO: 1 by mutating one or more codons so that it results in amino acid changes in the encoded protein, as long as mutation of the amino acid sequence does not entirely abolish trehalose phosphate synthase activity.

According to another embodiment of the invention the trehalose-6-phosphate in a cell can be converted into trehalose by trehalose phosphate phosphatase encoding genes under control of regulatory elements necessary for the expression of DNA in cells. A preferred open reading frame according to the invention is one encoding a TPP-enzyme as represented in SEQ ID NO: 4 (Kaasen et al. (1994) Gene, 145, 9). It is well known that more than one DNA sequence may encode an identical enzyme, which fact is caused by the degeneracy of the genetic code. If desired, the open reading frame encoding the trehalose phosphate phosphatase activity may be adapted to codon usage in the host of choice, but this is not a requirement.

The isolated nucleic acid sequence represented by SEQ ID NO: 3, may be used to identify trehalose phosphate phosphatase genes in other organisms and subsequently isolating and cloning them, by PCR techniques and/or by hybridizing DNA from other sources with a DNA- or RNA fragment obtainable from the *E. coli* gene. Preferably, such DNA sequences are screened by hybridizing under more or less stringent conditions (influenced by factors such as temperature and ionic strength of the hybridization mixture). Whether or not conditions are stringent also depends on the nature of the hybridization, i.e. DNA:DNA, DNA:RNA, RNA:RNA, as well as the length of the shortest hybridizing fragment. Those of skill in the art are readily capable of establishing a hybridization regime stringent enough to isolate TPP genes, while avoiding aspecific hybridization. As genes involved in trehalose synthesis from other sources become available these can be used in a similar way to obtain an expressible trehalose phosphate phosphatase gene according to the invention. More detail is given in the experimental section.

Sources for isolating trehalose phosphate phosphatase activities include microorganisms (e.g. bacteria, yeast, fungi), plants, animals, and the like. Isolated DNA sequences encoding trehalose phosphate phosphatase activity from other sources may be used likewise.

The invention also encompasses nucleic acid sequences which have been obtained by modifying the nucleic acid sequence represented in SEQ ID NO: 3 by mutating one or more codons so that it results in amino acid changes in the encoded protein, as long as mutation of the amino acid sequence does not entirely abolish trehalose phosphate phosphatase activity.

Other enzymes with TPS or TPP activity are represented by the so-called bipartite enzymes. It is envisaged that the part of the sequence which is specifically coding for one of the two activities can be separated from the part of the bipartite enzyme coding for the other activity. One way to separate the activities is to insert a mutation in the sequence coding for the activity that is not selected, by which mutation the expressed protein is impaired or deficient of this activity and thus only performs the other function. This can be done both for the TPS- and TPP-activity coding sequence. Thus, the coding sequences obtained in such a way can be used for the formation of novel chimaeric open reading frames capable of expression of enzymes having either TPS or TPP activity.

According to another embodiment of the invention, especially plants can be genetically altered to produce and accumulate the above-mentioned enzymes in specific parts of the plant. Preferred sites of enzyme expression are leaves and storage parts of plants. In particular potato tubers are considered to be suitable plant parts. A preferred promoter to achieve selective TPS-enzyme expression in microtubers and tubers of potato is obtainable from the region upstream of the open reading frame of the patatin gene of potato.

Another suitable promoter for specific expression is the plastocyanin promoter, which is specific for photoassimilating parts of plants. Furthermore, it is envisaged that specific expression in plant parts can yield a favourable effect for plant growth and reproduction or for economic use of said plants. Promoters which are useful in this respect are: the E8-promoter (EP 0 409 629) and the 2A11-promoter (van Haaren and Houck (1993), Plant Mol. Biol., 221, 625) which are fruit-specific; the cruciferin promoter, the napin promoter and the ACP promoter which are seed-specific; the PAL-promoter; the chalcon-isomerase promoter which is flower-specific; the SSU promoter, and ferredoxin promoter, which are leaf-specific; the TobRb7 promoter which is root-specific, the RolC promoter which is specific for phloem and the HMG2 promoter (Enjuto et al. (1995). Plant Cell 7, 517) and the rice PCNA promoter (Kosugi et al. (1995), Plant J. 7, 877) which are specific for meristematic tissue.

Another option under this invention is to use inducible promoters. Promoters are known which are inducible by pathogens, by stress, by chemical or light/dark stimuli. It is envisaged that for induction of specific phenoma, for instance sprouting, bolting, seed setting, filling of storage tissues, it is beneficial to induce the activity of the genes of the invention by external stimuli. This enables normal development of the plant and the advantages of the inducibility of the desired phenomena at control. Promoters which qualify for use in such a regime are the pathogen inducible promoters described in DE 4446342 (fungus and auxin inducible PRP-1), WO 96/28561 (fungus inducible PRP-1), EP 0 586 612 (nematode inducible), EP 0 712 273 (nematode inducible), WO 96/34949 (fungus inducible), PCT/EP96/02437 (nematode inducible), EP 0 330 479 (stress inducible), U.S. Pat. No. 5,510,474 (stress inducible), WO 96/12814 (cold inducible), EP 0 494 724 (tetracycline inducible), EP 0 619 844 (ethylene inducible), EP 0 337 532 (salicylic acid inducible), WO 95/24491 (thiamine inducible) and WO 92/19724 (light inducible). Other chemical inducible promoters are described in EP 0 674 608, EP 637 339, EP 455 667 and U.S. Pat. No. 5,364,780.

According to another embodiment of the invention, cells are transformed with constructs which inhibit the function of the endogenously expressed TPS or TPP. Inhibition of undesired endogenous enzyme activity is achieved in a number of ways, the choice of which is not critical to the invention. One method of inhibition of gene expression is achieved through the so-called 'antisense approach.' Herein a DNA sequence is expressed which produces an RNA that is at least partially complementary to the RNA which encodes the enzymatic activity that is to be blocked. It is preferred to use homologous antisense genes as these are more efficient than heterologous genes.

An alternative method to block the synthesis of undesired enzymatic activities is the introduction into the genome of the plant host of an additional copy of an endogenous gene present in the plant host. It is often observed that such an additional copy of a gene silences the endogenous gene: this effect is referred to in the literature as the co-suppressive effect, or co-suppression. Details of the procedure of enhancing substrate availability are provided in the Examples of WO 95/01446, incorporated by reference herein.

Host cells can be any cells in which the modification of hexokinase-signalling can be achieved through alterations in the level of T-6-P. Thus, accordingly, all eukaryotic cells are subject to this invention. From an economic point of view the cells most suited for production of metabolic compounds are most suitable for the invention. These organisms are, amongst others, plants animals, yeast, fungi. However, also expression in specialized animal cells (like pancreatic beta-cells and fat cells) is envisaged.

Preferred plant hosts among the Spermatophytae are the Angiospermae, notably the Dicotyledoneae, comprising inter alia the Solanaceae as a representative family, and the Monocotyledoneae, comprising inter alia the Gramineae as a representative family. Suitable host plants, as defined in the context of the present invention include plants (as well as parts and cells of said plants) and their progeny which contain a modified level of T-6-P, for instance by using recombinant DNA techniques to cause or enhance production of TPS or TPP in the desired plant or plant organ. Crops according to the invention include those which have flowers such as cauliflower (*Brassica oleracea*), artichoke (*Cynara scolymus*), cut flowers like carnation (*Dianthus caryophyllus*), rose (*Rosa* spp), Chrysanthemum, Petunia, Alstromeria, Gerbera, Gladiolus, lily (*Lilium* spp), hop (*Humulus lupulus*), broccoli, potted plants like Rhododendron, Azalia, Dahlia, Begonia, Fuchsia, Geranium etc.; fruits such as apple (*Malus*, e.g. *domesticus*), banana (*Musa*, e.g. *Acuminata*), apricot (*Prunus armeniaca*), olive (*Oliva sativa*), pineapple (*Ananas comosus*), coconut (*Cocos nucifera*), mango (*Mangifera indica*), kiwi, avocado (*Persea americana*), berries (such as the currant, *Ribes*, e.g. *rubrum*), cherries (such as the sweet cherry, *Prunus*, e.g. *avium*), cucumber (*Cucumis*, e.g. *sativus*), grape (*Vitis*, e.g. *vinifera*), lemon (*Citrus limon*), melon (*Cucumis melo*), mustard (*Sinapis alba* and *Brassica nigra*), nuts (such as the walnut, *Juglans*, e.g. *regia*; peanut, *Arachis hypogeae*), orange (*Citrus*, e.g. *maxima*), peach (*Prunus*, e.g. *persica*), pear (*Pyra*, e.g. *Communis*), pepper (*Solanum*, e.g. *capsicum*), plum (*Prunus*, e.g. *domestica*), strawberry (*Fragaria*, e.g. *moschata*), tomato (*Lycopersicon*, e.g. *esculentum*); leaves, such as alfalfa (*Medicago sativa*), cabbages (such as *Brassica oleracea*), endive (*Cichoreum*, e.g. *endivia*), leek (*Allium porruin*), lettuce (*Lactuca sativa*), spinach (*Spinacia oleraceae*), tobacco (*Nicociana tabacum*), grasses like *Festuca, Poa*, rye-grass (such as *Lolium perenne, Lolium multiflorum* and *Arrenatherum* spp.), amenity grass, turf, seaweed, chicory (*Cichorium intybus*), tea (*Thea sinensis*), celery, parsley (*Pecroselinum crispum*), chevil and other herbs; roots, such as arrowroot (*Maranta arundinacea*), beet (*Beta vulgaris*), carrot (*Daucus carota*), cassaya (*Manihot esculenta*), ginseng (*Panax ginseng*), turnip (*Brassica rapa*), radish (*Raphanus sativus*), yam (*Dioscorea esculenta*), sweet potato (*Ipomoea batatas*), taro; seeds, such as beans (*Phaseolus vulgaris*), pea (*Pisum sativum*), soybean (*Glycin max*), wheat (*Triticum aestivum*), barley (*Hordeum vulgare*), corn (*Zea mays*), rice (*Oryza sativa*), bush beans and broad beans (*Vicia faba*), cotton (*Gossypium* spp.), coffee (*Coffea arabica* and *C. canephora*); tubers, such as kohlrabi (*Brassica oleraceae*), potato (*Solanum tuberosum*); bulbous plants as onion (*Allium cepa*), scallion, tulip (*Tulipa* spp.), daffodil (*Narcissus* spp.), garlic (*Allium sativum*); stems such as cork-oak, sugarcane (*Saccharum* spp.), sisal (*Sisal* spp.), flax (*Linum vulgare*), jute; trees like rubber tree, oak (*Quercus* spp.), beech (*Betula* spp.), alder (*Alnus* spp.), ashtree (*Acer* spp.), elm (*Ulmus* spp.), palms, ferns, ivies and the like.

Transformation of yeast and fungal or animal cells can be done through normal state-of-the art transformation techniques through commonly known vector systems like pBluescript, pUC and viral vector systems like RSV and SV40.

The method of introducing the expressible trehalose-phosphate synthase gene, the expressible trehalose-phosphate-phosphatase gene, or any other sense or antisense gene into a recipient plant cell is not crucial, as long as the gene is expressed in said plant cell.

Although some of the embodiments of the invention may not be practicable at present, e.g. because some plant species are as yet recalcitrant to genetic transformation, the practicing of the invention in such plant species is merely a matter of time and not a matter of principle, because the amenability to genetic transformation as such is of no relevance to the underlying embodiment of the invention.

Transformation of plant species is now routine for an impressive number of plant species, including both the Dicotyledoneae as well as the Monococyledoneae. In principle any transformation method may be used to introduce chimeric DNA according to the invention into a suitable ancestor cell. Methods may suitably be selected from the calcium/polyethylene glycol method for protoplasts (Krens et al. (1982), Nature 296, 72; Negrutiu et al. (1987), Plant Mol. Biol. 8, 363, electroporation of protoplasts (Shillito et al. (1985) Bio/Technol. 3, 1099), microinjection into plant material (Crossway et al. (1986), Mol. Gen. Genet. 202), (DNA or RNA-coated) particle bombardment of various plant material (Klein at al. (1987), Nature 327, 70), infection with (non-integrative) viruses, in planta *Agrobacterium tumefaciens* mediated gene transfer by infiltration of adult plants or transformation of mature pollen or microspores (EP 0 301 316) and the like. A preferred method according to the invention comprises *Agrobacterium*-mediated DNA transfer. Especially preferred is the use of the so-called binary vector technology as disclosed in EP A 120 516 and U.S. Pat. No. 4,940,838).

Although considered somewhat more recalcitrant towards genetic transformation, monocotyledonous plants are amenable to transformation and fertile transgenic plants can be regenerated from transformed cells or embryos, or other plant material. Presently, preferred methods for transformation of monocots are microprojectile bombardment of embryos, explants or suspension cells, and direct DNA uptake or (tissue) electroporation (Shimamoto et al. (1989), Nature 338, 274-276). Transgenic maize plants have been obtained by introducing the *Screptomyces hygroscopicus* bar-gene, which encodes phosphinothricin acetyltransferase (an enzyme which inactivates the herbicide phosphinothricin), into embryogenic cells of a maize suspension culture by microprojectile bombardment (Gordon-Kamm (1990), Plant Cell, 2, 603). The introduction of genetic material into aleurone protoplasts of other monocot crops such as wheat and barley has been reported (Lee (1989), Plant Mol. Biol. 13, 21). Wheat plants have been regenerated from embryogenic suspension culture by selecting embryogenic callus for the establishment of the embryogenic suspension cultures (Vasil (1990) Bio/Technol. 8, 429). The combination with transformation systems for these crops enables the application of the present invention to monocots.

Monocotyledonous plants, including commercially important crops such as rice and corn are also amenable to DNA transfer by *Agrobacterium* strains (vide WO 94/00977, EP 0 159 418 B 1; Gould et al. (1991) Plant. Physiol. 95, 426-434).

To obtain transgenic plants capable of constitutively expressing more than one chimeric gene, a number of alternatives are available including the following:

A. The use of DNA, e.g a T-DNA on a binary plasmid, with a number of modified genes physically coupled to a second selectable marker gene. The advantage of this method is that the chimeric genes are physically coupled and therefore migrate as a single Mendelian locus.

B. Cross-pollination of transgenic plants each already capable of expressing one or more chimeric genes, preferably coupled to a selectable marker gene, with pollen from a transgenic plant which contains one or more chimeric genes coupled to another selectable marker. Afterwards the seed, which is obtained by this crossing, maybe selected on the basis of the presence of the two selectable markers, or on the basis of the presence of the chimeric genes themselves. The plants obtained from the selected seeds can afterwards be used for further crossing. In principle the chimeric genes are not on a single locus and the genes may therefore segregate as independent loci.

C. The use of a number of a plurality chimeric DNA molecules, e.g. plasmids, each having one or more chimeric genes and a selectable marker. If the frequency of co-transformation is high, then selection on the basis of only one marker is sufficient. In other cases, the selection on the basis of more than one marker is preferred.

D. Consecutive transformation of transgenic plants already containing a first, second, (etc), chimeric gene with new chimeric DNA, optionally comprising a selectable marker gene. As in method B, the chimeric genes are in principle not on a single locus and the chimeric genes may therefore segregate as independent loci.

E. Combinations of the above mentioned strategies.

The actual strategy may depend on several considerations as maybe easily determined such as the purpose of the parental lines (direct growing, use in a breeding programme, use to produce hybrids) but is not critical with respect to the described invention.

It is known that practically all plants can be regenerated from cultured cells or tissues. The means for regeneration vary from species to species of plants, but generally a suspension of transformed protoplasts or a petri plate containing transformed explants is first provided. Shoots may be induced directly, or indirectly from callus via organogenesis or embryogenesis and subsequently rooted. Next to the selectable marker, the culture media will generally contain various amino acids and hormones, such as auxin and cytokinins. It is also advantageous to add glutamic acid and proline to the medium, especially for such species as corn and alfalfa. Efficient regeneration will depend on the medium, on the genotype and on the history of the culture. If these three variables are controlled regeneration is usually reproducible and repeatable. After stable incorporation of the transformed gene sequences into the transgenic plants, the traits conferred by them can be transferred to other plants by sexual crossing. Any of a number of standard breeding techniques can be used, depending upon the species to be crossed.

Suitable DNA sequences for control of expression of the plant expressible genes (including marker genes), such as transcriptional initiation regions, enhancers, non-transcribed leaders and the like, may be derived from any gene that is expressed in a plant cell. Also intended are hybrid promoters combining functional portions of various promoters, or synthetic equivalents thereof. Apart from constitutive promoters, inducible promoters, or promoters otherwise regulated in their expression pattern, e.g. developmentally or cell-type specific, may be used to control expression of the expressible genes according to the invention.

To select or screen for transformed cells, it is preferred to include a marker gene linked to the plant expressible gene according to the invention to be transferred to a plant cell. The choice of a suitable marker gene in plant transformation is well within the scope of the average skilled worker; some examples of routinely used marker genes are the neomycin phosphotransferase genes conferring resistance to kanamycin (EP-B 131 623), the glutathion-5-transferase gene from rat liver conferring resistance to glutathione derived herbicides (EP-A 256 223), glutamine synthetase conferring upon overexpression resistance to glutamine synthetase inhibitors such as phosphinothricin (WO 87/05327), the acetyl transferase gene from *Streptomyces* viridochromogenes conferring resistance to the selective agent phosphinothricin (EP-A 275 957), the gene encoding a 5-enolshikimate-3-phosphate synthase (EPSPS) conferring tolerance to N-phosphonomethylglycine, the bar gene conferring resistance against Bialaphos (e.g. WO 91/02071) and the like. The actual choice of the marker is not crucial as long as it is functional (i.e. selective) in combination with the plant cells of choice.

The marker gene and the gene of interest do not have to be linked, since co-transformation of unlinked genes (U.S. Pat. No. 4,399,216) is also an efficient process in plant transformation.

Preferred plant material for transformation, especially for dicotyledonous crops are leaf-discs which can be readily transformed and have good regenerative capability (Horsch et al. (1985), Science 227, 1229).

Specific use of the invention is envisaged in the following ways: as can be seen from the Examples the effects of the expression of TPP (which causes a decrease in the intracellular T-6-P concentration) are an increased leaf size, increased branching leading t6 an increase in the number of leaves, increase in total leaf biomass, bleaching of mature leaves, formation of more small flowers and sterility. These effects are specifically useful in the following cases: increased leaf size (and increase in the number of leaves) is economically important for leafy vegetables such as spinach, lettuce, leek, alfalfa, silage maize; for ground coverage and weed control by grasses and garden plants; for crops in which the leaves are used as product, such as tobacco, tea, hemp and roses (perfumes!); for the matting up of cabbage-like crops such as cauliflower.

An additional advantage of the fact that these leaves are stimulated in their metabolic activity is that they tend to burn all their intracellular resources, which means that they are low in starch-content. For plants meant for consumption a reduction in starch content is advantageous in the light of the present tendency for low-calorie foodstuffs. Such a reduction in starch content also has effects on taste and texture of the leaves. An increase in the protein/carbohydrate balance as can be produced by the expression of TPP is especially important for leafy crops as silage maize.

Increased branching, which is accompanied by a tendency to have stems with a larger diameter, can be advantageous in crops in which the stem is responsible for the generation of an economically attractive product. Examples in this category are all trees for the increased production of wood, which is also a starting material for paper production; crops like hemp, sisal, flax which are used for the production of rope and linen; crops like bamboo and sugarcane; rubber-tree, cork-oak; for the prevention of flattening in crops or crop parts, like grains, corn, legumes and strawberries.

A third phenomenon is increased bleaching of the leaves (caused by a decrease of photosynthetic activity). Less colourful leaves are preferred for crops such as chicory and asparagus. Also for cut flowers bleaching in the petals can be desired, for instance in *Alstromeria.*

An overall effect is the increase in biomass resulting from an increase in metabolic activity. This means that the biomass consists of metabolized compounds such as proteins and fats. Accordingly, there is an increased protein/carbohydrate balance in mature leaves which is an advantage for crops like silage maize, and all fodder which can be ensilaged. A similar increased protein/carbohydrate balance can be established in fruits, tubers and other edible plant parts.

Outside the plant kingdom an increased metabolism would be beneficial for protein production in microorganisms or eukaryotic cell cultures. Both production of endogenous but also of heterologous proteins will be enhanced which means that the production of heterologous proteins in cultures of yeast or other unicellular organisms can be enhanced in this way. For yeast this would give a more efficient fermentation, which would result in an increased alcohol yield, which of course is favourable in brewery processes, alcohol production and the like.

In animals or human beings it is envisaged that diseases caused by a defect in metabolism can be overcome by stable expression of TPP or TPS in the affected cells. In human cells, the increased glucose consumption of many tumour cells depends to a large extent on the overexpression of hexokinase (Rempel et al. (1996) FEBS Lett. 385, 233). It is envisaged that the flux of glucose into the metabolism of cancer cells can be influenced by the expression of trehalose-6-phosphate synthesizing enzymes. It has also been shown that the hexokinase activation is potentiated by the cAMP/PKA (protein kinase A pathway). Therefore, inactivation of this signal transduction pathway may affect glucose uptake and the proliferation of neoplasias. Enzyme activities in mammalian cells able to synthesize trehalose-6-phosphate and trehalose and degrade trehalose have been shown in e.g. rabbit kidney cortex cells (Sacktor (1968) Proc. Natl. Acad. Sci. USA 60, 1007).

Another example can be found in defects in insulin secretion in pancreatic beta-cells in which the production of glucose-6-phosphate catalyzed by hexokinase is the predominant reaction that couples rises in extracellular glucose levels to insulin secretion (Efrat et al. (1994), TIBS 19, 535). An increase in hexokinase activity caused by a decrease of intracellular T-6-P then will stimulate insulin production in cells which are deficient in insulin secretion.

Also in transgenic animals an increased protein/carbohydrate balance can be advantageous. Both the properties of on increased metabolism and an enhanced production of proteins are of large importance in farming in which animals should gain in flesh as soon as possible. Transformation of the enzyme TPP into meat-producing animals like chickens, cattle, sheep, turkeys, goats, fish, lobster, crab, shrimps, snails etc, will yield animals that grow faster and have a more proteinaceous meat.

In the same way this increased metabolism means an increase in the burn rate of carbohydrates and it thus prevents obesity.

More plant-specific effects from the decrease of intracellular T-6-P concentration are an increase in the number of flowers (although they do not seem to lead to the formation of seed). However, an increase in the number of flowers is advantageous for cutflower plants and pot flower plants and also for all plants suitable for horticulture.

A further effect of this flowering phenomenon is sterility, because the plants do not produce seed. Sterile plants are advantageous in hybrid breeding.

Another economically important aspect is the prohibiting of bolting of culture crops such as lettuce, endive and both recreational and fodder grasses. This is a beneficial property because it enables the crop to grow without having to spend metabolic efforts to flowering and seed production. Moreover, in crops like lettuce, endive and grasses the commercial product/application is non-bolted.

Specific expression of TPP in certain parts (sinks) of the plant can give additional beneficial effects. It is envisaged that expression of TPP by a promoter which is active early in e.g. seed forming enables an increased growth of the developing seed. A similar effect would be obtained by expressing TPP by a flower-specific promoter. To put it shortly: excessive growth of a certain plant part is possible if TPP is expressed by a suitable specific promoter. In fruits specific expression can lead to an increased growth of the skin in relation to the flesh. This enables improvement of the peeling of the fruit, which can be advantageous for automatic peeling industries.

Expression of TPP during the process of germination of oil-storing seeds prevents oil-degradations. In the process of germination, the glyoxylate cycle is very active. This metabolic pathway converts acetyl-CoA via malate into sucrose which can be transported and used as energy source during growth of the seedling. Key-enzymes in this process are malate synthase and isocitrate lyase. Expression of both enzymes is supposed to be regulated by hexokinase signalling. One of the indications for this regulation is that both 2-deoxyglucose and mannose are phosphorylated by hexokinase and able to transduce their signal, being reduction of malate synthase and isocitrate lyase expression, without being further metabolised. Expression of TPP in the seed, thereby decreasing the inhibition of hexokinase, thereby inhibiting malate synthase and isocitrate lyase maintains the storage of oil into the seeds and prevents germination.

In contrast to the effects of TPP the increase in T-6-P caused by the expression of TPS causes other effects as is illustrated in the Examples. From these it can be learnt that an increase in the amount of T-6-P causes dwarfing or stunted growth (especially at high expression of TPS), formation of more lancet-shaped leaves, darker colour due to an increase in chlorophyll and an increase in starch content. As is already acknowledged above, the introduction of an anti-sense trehalase construct will also stimulate similar effects as the introduction of TPS. Therefore, the applications which are shown or indicated for TPS will equally be established by using as-trehalase. Moreover, the use of double-constructs of TPS and as-trehalase enhances the effects of a single construct.

Dwarfing is a phenomenon that is desired in horticultural plants, of which the Japanese bonsai trees are a proverbial example. However, also creation of mini-flowers in plants like allseed, roses, Amaryllis, Hortensia, birch and palm will have economic opportunities. Next to the plant kingdom dwarfing is also desired in animals. It is also possible to induce bolting in culture crops such as lettuce. This is beneficial because it enables a rapid production of seed. Ideally the expression of TPS for this effect should be under control of an inducible promoter.

Loss of apical dominance also causes formation of multiple shoots which is of economic importance for instance in alfalfa.

A reduction in growth is furthermore desired for the industry of "veggie snacks", in which vegetables are considered to be consumed in the form of snacks. Cherry-tomatoes is an example of reduced size vegetables which are successful in the market. It can be envisaged that also other vegetables like cabbages, cauliflower, carrot, beet and sweet potato and fruits like apple, pear, peach, melon, and several tropical fruits like mango and banana would be marketable on miniature size.

Reduced growth is desired for all cells that are detrimental to an organism, such as cells of pathogens and cancerous cells. In this last respect a role can be seen in regulation of the growth by changing the level of T-6-P. An increase in the T-6-P level would reduce growth and metabolism of cancer tissue. One way to increase the intracellular level of T-6-P is to knock-out the TPP gene of such cells by introducing a specific recombination event which causes the introduction of a mutation in the endogenous TPP-genes. One way in which this could be done is the introduction of a DNA-sequence able of introducing a mutation in the endogenous gene via a cancer cell specific internalizing antibody. Another way is targeted microparticle bombardment with said DNA. Thirdly a cancer cell specific viral vectors having said DNA can be used.

The phenomenon of a darker green colour seen with an increased concentration of T-6-P, is a property which is desirable for pot flower plants and, in general, for species in horticulture and for recreational grasses.

Increase in the level of T-6-P also causes an increase in the storage carbohydrates such as starch and sucrose. This then would mean that tissues in which carbohydrates are stored would be able to store more material. This can be illustrated by the Examples where it is shown that in plants increased biomass of storage organs such as tubers and thickened roots as in beets (storage of sucrose) are formed.

Crops in which this would be very advantageous are potato, sugarbeet, carrot, chicory and sugarcane.

An additional economically important effect in potatoes is that after transformation with DNA encoding for the TPS gene (generating an increase in T-6-P) it has been found that the amount of soluble sugars decreases, even after harvest and storage of the tubers under cold conditions (4° C.). Normally even colder storage would be necessary to prevent early sprouting, but this results in excessive sweetening of the potatoes. Reduction of the amount of reducing sugars is of major importance for the food industry since sweetened potato tuber material is not suitable for processing because a Maillard reaction will take place between the reducing sugars and the amino-acids which results in browning.

In the same way also inhibition of activity of invertase can be obtained by transforming sugarbeets with a polynucleotide encoding for the enzyme TPS. Inhibition of invertase activity in sugarbeets after harvest is economically very important.

Also in fruits and seeds, storage can be altered. This does not only result in an increased storage capacity but in a change in the composition of the stored compounds. Crops in which improvements in yield in seed are especially important are maize, rice, cereals, pea, oilseed rape, sunflower, soybean and legumes. Furthermore, all fruitbearing plants are important for the application of developing a change in the amount and composition of stored carbohydrates. Especially for fruit the composition of stored products gives changes in solidity and firmness, which is especially important in soft fruits like tomato, banana, strawberry, peach, berries and grapes.

In contrast to the effects seen with the expression of TPP, the expression of TPS reduces the ratio of protein/carbohydrate in leaves. This effect is of importance in leafy crops such as fodder grasses and alfalfa. Furthermore, the leaves have a reduced biomass, which can be of importance in amenity grasses, but, more important, they have a relatively increased energy content. This property is especially beneficial for crops as onion, leek and silage maize.

Furthermore, also the viability of the seeds can be influenced by the level of intracellularly available T-6-P.

Combinations of expression of TPP in one part of a plant and TPS in an other part of the plant can synergize to increase the above-described effects. It is also possible to express the genes sequential during development by using specific promoters. Lastly, it is also possible to induce expression of either of the genes involved by placing the coding the sequence under control of an inducible promoter. It is envisaged that combinations of the methods of application as described will be apparent to the person skilled in the art.

The invention is further illustrated by the following examples. It is stressed that the Examples show specific embodiments of the inventions, but that it will be clear that variations on these examples and use of other plants or expression systems are covered by the invention.

EXPERIMENTAL

DNA Manipulations

All DNA procedures (DNA isolation from *E. coli*, restriction, ligation, transformation, etc.) are performed according to standard protocols (Sambrook et al. (1989) Molecular Cloning: a laboratory manual, 2nd ed. Cold Spring Harbor Laboratory Press, CSH, New York).

Strains

In all examples *E. coli* K-12 strain DH5α is used for cloning. The *Agrobacterium tumefaciens* strains used for plant transformation experiments are EHA 105 and MOG 101 (Hood et al. (1993) Trans. Research 2, 208).

Construction of *Agrobacterium* Strain MOG101

Construction of *Agrobacterium* strain MOG101 is described in WO 96/21030.

Cloning of the *E. coli* otsA Gene and Construction of pMOG799

In *E. coli* trehalose phosphate synthase (TPS) is encoded by the otsA gene located in the operon otsBA. The cloning and sequence determination of the otsA gene is described in detail in Example I of WO95/01446, herein incorporated by reference. To effectuate its expression in plant cells, the open reading frame has been linked to the transcriptional regulatory elements of the CaMV 5S RNA promoter, the translational enhancer of the ALMV leader, and the transcriptional terminator of the nos-gene, as described in greater detail in Example I of WO95/01446, resulting in pMOG799. A sample of an *E. coli* strain harbouring pMOG799 has been deposited under the Budapest Treaty at the Centraal Bureau voor Schimmelcultures, Oosterstraat 1, P.O. Box 273, 3740 AG Baarn, The Netherlands, on Monday 23 Aug. 1993: the Accession Number given by the International Depositary Institution is CBS 430.93.

Isolation of a Patatin Promoter/Construction of pMoG546

A patatin promoter fragment is isolated from chromosomal DNA of *Solanum_tuberosum* cv. Bintje using the polymerase chain reaction. A set of oligonucleotides, complementary to the sequence of the upstream region of Λpat21 patatin gene (Bevan et al. (1986) Nucl. Acids Res. 14, 5564), is synthesized consisting of the following sequences:

```
                                     (SEQ ID NO:5)
5' AAG CTT ATG TTG CCA TAT AGA GTA G 3'   PatB33.2

                                     (SEQ ID NO:6)
5' GTA GTT GCC ATG GTG CAA ATG TTC 3'     PatATG.2
```

These primers are used to PCR amplify a DNA fragment of 1123 bp, using chromosomal DNA isolated from potato cv. Bintje as a template. The amplified fragment shows a high degree of similarity to the Λpat21 patatin sequence and is cloned using EcoRI linkers into a pUC18 vector resulting in plasmid pMOG546.

Construction of pMOG845

Construction of pMOG845 is described in WO 96/21030.

Construction of pVDH318 Plastocvanin-TPS

Plasmid pMOG79B (described in WO95/01446) is digested with HindIII and ligated with the oligonucleotide duplex TCV11 and TCV12 (see construction of pMOG845). The resulting vector is digested with PstI and HindIII followed by the insertion of the PotPiII terminator resulting in pTCV118. Plasmid pTCV118 is digested with SmaI and HindIII yielding a DNA fragment comprising the TPS coding region and the PotPiII terminator. BglII linkers were added and the resulting fragment was inserted in the plant binary expression vector pVDH275 (FIG. 1) digested with BamHI, yielding pVDH318. pVDH275 is a derivative of pMOG23 (Sijmons et al. (1990), Bio/Technol. 8, 217) harbouring the NPTII selection marker under control of the 35S CaMV promoter and an expression cassette comprising the pea plastocyanin (PC) promoter and nos terminator sequences. The plastocyanin promoter present in pVDH275 has been described by Pwee & Gray (1993) Plant J. 3, 437. This promoter has been transferred to the binary vector using PCR amplification and primers which contain suitable cloning sites.

Cloning of the *E. coli* otsB Gene and Construction of pMOG100 (35S CaMV TPP)

A set of oligonucleotides, TPP I (5'CTCAGATCTGGCCACAAA 3') (SEQ ID NO: 56) and TPP II (5' GTGCTCGTCTGCAGGTGC 3') (SEQ ID NO: 57), was synthesized complementary to the sequence of the *E. coli* TPP gene (SEQ ID NO: 3). These primers were used to PCR amplify a DNA fragment of 375 bp harbouring the 3' part of the coding region of the *E. coli* TPP gene, introducing a PstI site 10 bp down-stream of the stop codon, using pMOG748 (WO 95/01446) as a template. This PCR fragment was digested with BglII and PstI and cloned into pMG445 (EP 0 449 376 A2 example 7a) and linearized with BglII and PstI. The resulting vector was digested with PstI and HindIII and a PotPiII terminator was inserted (see construction pMOG845). The previous described vector was digested with BglII and HindIII, the resulting 1325 bp fragment was isolated and cloned together with the 5'TPP PCRed fragment digested with SmaI and BglII into pUC18 linearized with SmaI and HindIII. The resulting vector was called pTCV124. This vector was linearized with EcoRI and SmaI and used to insert the 35S CaMV promoter (a 850 bp EcoRI-'NcoI' (the NcoI site was made blunt by treatment with mungbean nuclease) fragment isolated from pMOG18 containing the 35S CaMV double enhancer promoter). This vector was called pTCV127. From this vector a 2.8 kb EcoRI-HindIII fragment was isolated containing the complete 35S TPP expression cassette and cloned in binary vector pMOG800 resulting in vector pMOG1010.

Construction of pVDH321, Plastocyanin (PC) TPP

The BamHI site of plasmid pTCV124 was removed by BamHI digestion, filling-in and subsequent religation. Subsequent digestion with HindIII and EcoRI yields a DNA fragment comprising the TPP coding region and the PotPiII terminator. BamHI linkers were added and the resulting fragment was inserted in the plant binary expression vector pVDH275 (digested with BamHI) yielding pVDH321.

Construction of a Patatin TPP Expression Vector

Similar to the construction of the patatin TPS expression vector (see construction of pMOG845), a patatin TPP expression vector was constructed yielding a binary vector (pMOG1128) which, after transformation, can effectuate expression of TPP in a tuber-specific manner.

Construction of Other Expression Vectors

Similar to the construction of the above mentioned vectors, gene constructs can be made where different promoters are used, in combination with TPS, TPP or trehalase using binary vectors with the NPTII gene or the Hygromycin-resistance gene as selectable marker gene. A description of binary vector pMOG22 harbouring a HPT selection marker is given in Goddijn et al. (1993) Plant J. 4, 863.

Triparental Matings

The binary vectors are mobilized in triparental matings with the *E. coli* strain HB101 containing plasmid pRK2013 (Ditta et al. (1980) Proc. Natl. Acad. Sci. USA 77, 7347) into *Agrobacterium tumefaciens* strain MOG 101 or EHA 105 and used for transformation.

Transformation of Tobacco (*Nicotiana tabacum* cv. SR1 or cv, Samsun NN)

Tobacco was transformed by cocultivation of plant tissue with *Agrobacterium tumefaciens* strain MOG101 containing the binary vector of interest as described. Transformation was carried out using cocultivation of tobacco leaf disks as described by Horsch et al. (1985) Science 227, 1229. Transgenic plants are regenerated from shoots that grow on selection medium containing kanamycin, rooted and transferred to soil.

Transformation of Potato

Potato (*Solanum tuberosum* cv. Kardal) was transformed with the *Agrobacterium* strain EHA 105 containing the binary vector of interest. The basic culture medium was MS30R3 medium consisting of MS salts (Murashige and Skoog (1962) Physiol. Plant. 14, 473), R3 vitamins (Ooms et al. (1987) Theor. Appl. Genet. 73, 744), 30 g/l sucrose, 0.5 g/l MES with final pH 5.8 (adjusted with KOH) solidified when necessary with 8 g/l Daichin agar. Tubers of *Solanum tuberosum* cv. Kardal were peeled and surface sterilized by burning them in 96% ethanol for 5 seconds. The flames were extinguished in sterile water and cut slices of approximately 2 mm thickness. Disks were cut with a bore from the vascular tissue and incubated for 20 minutes in MS30R3 medium containing 1-5×$10^8$ bacteria/ml of *Agrobacterium* EHA 105 containing the binary vector. The tuber discs were washed with MS30R3 medium and transferred to solidified postculture medium (PM). PM consisted of M30R3 medium supplemented with 3.5 mg/l zeatin riboside and 0.03 mg/l indole acetic acid (IAA). After two days, discs were transferred to fresh PM medium with 200 mg/i cefotaxim and 100 mg/l vancomycin. Three days later, the tuber discs were transferred to shoot induction medium (SIM) which consisted of PM medium with 250 mg/l carbenicillin and 100 mg/l kanamycin. After 4-8 weeks, shoots emerging from the discs were excised and placed on rooting medium (MS30R3-medium with 100 mg/l cefotaxim, 50 mg/l vancomycin and 50 mg/l kanamycin). The shoots were propagated axenically by meristem cuttings.

Transformation of Lettuce

Transformation of lettuce, *Lattuca sativa* cv. Evola was performed according to Curtis et al. (1994) J. Exp. Bot. 45, 1441.

Transformation of Sugarbeet

Transformation of sugarbeet, *Beta vulgaris* (maintainer population) was performed according to Fry et al. (1991) Third International Congress of ISPMB, Tucson USA Abstract No. 384, or according to Krens et al. (1996), Plant Sci. 116, 97.

Transformation of *Lycopersicon esculentum*

Tomato transformation was performed according to Van Roekel et al. (1993) Plant Cell Rep. 12, 644.

Transformation of *Arabidopsis*

Transformation of *Arabidopsis thaliana* was carried out either by the method described by Clarke et al. (1992) Plant. Mol. Biol. Rep. 10, 178 or by the method described by Valvekens et al. (1988) Proc. Natl. Acad. Sci. USA, 85, 5536.

Induction of Micro-Tubers

Stem segments of in vitro potato plants harbouring an auxiliary meristem were transferred to micro-tuber inducing medium. Micro-tuber inducing medium contains 1 X MS-salts supplemented with R3 vitamins, 0.5 g/l MES (final pH=5.8, adjusted with KOH) and solidified with 8 g/l Daichin agar, 60 g/l sucrose and 2.5 mg/l kinetin. After 3 to 5 weeks of growth in the dark at 24° C., micro-tubers were formed.

Isolation of Validamycin A

Validamycin A has been found to be a highly specific inhibitor of trehalases from various sources ranging from ($IC_{50}$) $10^{-6}$M to $10^{-10}$M (Asano et al. (1987) J. Antibiot. 40, 526; Kameda et al. (1987) J. Antibiot 40, 563). Except for trehalase, it does not significantly inhibit any α- or β-glycohydrolase activity. Validamycin A was isolated from Solacol, a commercial agricultural formulation (Takeda Chem. Indust., Tokyo) as described by Kendall et al. (1990) Phytochemistry 29, 2525. The procedure involves ion-exchange chromatography (QAE-Sephadex A-25 (Pharmacia), bed vol. 10 ml, equilibration buffer 0.2 mM Na-Pi pH 7) from a 3% agricultural formulation of Solacol. Loading 1 ml of Solacol on the column and eluting with water in 7 fractions, practically all Validamycin was recovered in fraction 4. Based on a 100% recovery, using this procedure, the concentration of Validamycin A was adjusted to 1.$10^{-3}$ M in MS-medium, for use in trehalose accumulation tests. Alternatively, Validamycin A and B may be purified directly from *Streptomyces hygroscopicus* var. *limoneus*, as described by Iwasa et al. (1971) J. Antibiot. 24, 119, the content of which is incorporated herein by reference.

Carbohydrate Analysis

Carbohydrates were determined quantitatively by anion exchange chromatography with pulsed electrochemical detection. Extracts were prepared by extracting homogenized frozen material with 80% EtOH. After extraction for 15 minutes at room temperature, the soluble fraction is evaporated and dissolved in distilled water. Samples (25 μl) were analyzed on a Dionex DX-300 liquid chromatograph equipped with a 4×250 mm Dionex 35391 carbopac PA-1 column and a 4×50 mm Dionex 43096 carbopac PA-1 precolumn. Elution was with 100 mM NaOH at 1 ml/min followed by a NaAc gradient. Sugars were detected with a pulsed electrochemical detector (Dionex, PED). Commercially available carbohydrates (Sigma) were used as a standard.

Starch Analysis

Starch analysis was performed as described in: Aman et al. (1994) Methods in Carbohydrate Chemistry, Volume X (eds. BeMiller et al.), pp 111-115.

Expression Analysis

The expression of genes introduced in various plant species was monitored using Northern blot analysis.

Trehalose-6-Phosphate Phosphatase Assay

TPP was assayed at 37° C. by measuring the production of [$^{14}$C]trehalose from [$^{14}$C]trehalose-6-phosphate (Londesborough and Vuorio (1991) J. of Gen. Microbiol. 137, 323). Crude extracts were prepared in 25 mM Tris, HCl pH 7.4, containing 5.5 mM $MgCl_2$. Samples were diluted to a protein concentration of 1 mg/ml in extraction buffer containing 1 mg/ml BSA. Standard assay mixtures (50 μl final volume) contained 27.5 mM Tris, HCl pH 7.4, 5.5 mM $MgCl_2$, 1 mg/ml BSA and 0.55 mM T-6-P (specific activity 854 cpm/nmol). Reactions were initiated by the addition of 5 .mu.l enzyme and terminated after 1 hour by heating for 5 minutes in boiling water. AG1-X8 (formate) anion-exchange resin (BioRad) was added and the reaction mixtures were centrifuged after 20 minutes of equilibration at room temperature. The radioactivity in the supernatant of the samples (400 μl) was measured by liquid scintillation counting.

Preparation of Plant Extracts for Hexokinase Assays

Frozen plant material was grinded in liquid nitrogen and homogenized for 30 seconds with extraction buffer (EB: 100 mM HEPES pH7.0 (KOH), 1% (w/v) PVP, 5 mM $MgCl_2$, 1.5 mM EDTA, 0.1% v/v β-MeOH) including Proteinase Inhibitors Complete (Boehringer Mannheim). After centrifugation, proteins in the supernatant were precipitated using 80% ammoniumsulphate and dissolved in Tris-HCl pH 7.4 and the extract was dialyzed overnight against 100 mM Tris-HCl pH 7.4. Part of the sample was used in the hexokinase assay.

Hexokinase Assay

Hexokinase activity was measured in an assay containing 0.1 M Hepes-KOH pH 7.0, 4 mM $MgCl_2$, 5 mM ATP, 0.2 mM $NADP^+$, 10 U/ml Creatine Phosphate Kinase (dissolved in 50% glycerol, 0.1% BSA, 50 mM Hepes pH 7.0), 3.5 mM Creatine Phosphate, 7 U/ml Glucose-6-Phosphate Dehydrogenase and 2 mM Glucose by measuring the increase in OD at 340 nm at 25° C.

When 2 mM Fructose was used instead of glucose as substrate for the hexokinase reaction, 3.8 U/ml Phosphoglucose Isomerase was included. Alternatively, a hexokinase assay as described by Gancedo et al. (1977) J. Biol. Chem. 252, 4443 was used.

Example 1

Expression of the *E. coli* otsA Gene (TPS) in Tobacco and Potato

Transgenic tobacco plants were generated barbouring the otsA gene driven by the de35SCaMV promoter (pMOG799) or the plastocyanin promoter (pVDH318).

Transgenic potato plants were generated harbouring the otsA gene driven by the potato tuber-specific patatin promoter (pMOG845).

Tobacco leaf discs were transformed with the binary vector pMOG799 using *Agrobacterium tumefaciens*. Transgenic shoots were selected on kanamycin.

Leaves of some soil-grown plants did not fully expand in lateral direction, leading to a lancet-shaped morphology (FIG. 31).

Furthermore, apical dominance was reduced resulting in stunted growth and formation of several axillary shoots. Seven out of thirty-two plants showed severe growth reduction, reaching plant heights of 4-30 cm at the time of flowering (Table 1).

TABLE 1

Trehalose accumulation in leaf samples of otsA transgenic tobacco plants and their plant length at the time of flowering.

| plant-line | trehalose mg · g fresh weight | height cm |
|---|---|---|
| controls | 0.00 | 60-70 |
| 799-1 | 0.04 | ND |
| 799-3 | 0.02 | 10 |
| 799.5 | 0.08 | 4 |
| 799-15 | 0.055 | 30 |
| 799-24 | 0.02 | 12 |
| 799-26 | 0.05 | 25 |
| 799-32 | 0.055 | 30 |
| 799-40 | 0.11 | 25 |

ND: not determined

Control plants reached lengths of 60-70 cm at the time of flowering. Less seed was produced by transgenic lines with the stunted growth phenotype. Northern blot analysis confirmed that plants having the stunted growth phenotype expressed the otsA gene from *E. coli* (FIG. 2). In control plants no transcript could be detected. The functionality of the introduced gene was proven by carbohydrate analyses of leaf material from 32 transgenic greenhouse-grown tobacco plants, revealing the presence of 0.02 to 0.12 $mg \cdot g^{-1}$ fresh weight trehalose in plants reduced in length (Table 1) indicating that the product of the TPS-catalyzed reaction is dephosphorylated by plant phosphatases. Further proof for the accumulation of trehalose in tobacco was obtained by treating crude extracts with porcine trehalase. Prolonged incubation of a tobacco leaf extract with trehalase resulted in complete degradation of trehalose (data not shown). Trehalose was not detected in control plants or transgenic tobacco plants without an aberrant phenotype.

TABLE 1a

Primary PC-TPS tobacco transformants

| Plant-line | Leaf tw $cm^2$ | Leaf area $cm^2$ | No. of branches | Plant height cm | Leaf colour | Axillary shoots | Fw/area $g/cm^2$ | Dry matter % | Dry matter/area $g/cm^2$ |
|---|---|---|---|---|---|---|---|---|---|
| ctrl. 1 | 8.18 | 349.37 | 1 | | wt | | 0.023 | 7.21 | 0.0017 |
| ctrl. 2 | 10.5 | 418.89 | 1 | | wt | | 0.025 | 9.52 | 0.0024 |
| ctrl. 3 | 9.99 | 373.87 | 1 | | wt | | 0.027 | 12.91 | 0.0035 |
| ctrl. 4 | 9.91 | 362.92 | 1 | | wt | | 0.027 | 9.59 | 0.0026 |
| ctrl. 5 | 9.82 | 393.84 | 1 | | wt | | 0.025 | 11.51 | 0.0029 |
| average | | | | | | | 0.0254 | 10.148 | 0.0026 |
| 2 | 8.39 | 290 | 2 | 105 | wt | | 0.029 | 12.16 | 0.0035 |
| 3 | 9.34 | 296 | 1 | 123 | wt | | 0.032 | 12.21 | 0.0039 |
| 4 | 8.36 | 254 | 2 | 130 | wt | many | 0.033 | 10.05 | 0.0033 |
| 6 | 2.28 | 106 | 5 | 90 | wt | | 0.022 | 11.40 | 0.0025 |
| 8 | 5.21 | 133 | 4 | 100 | dark | many | 0.039 | 7.49 | 0.0029 |
| 10 | 8.08 | 258 | 2 | 165 | dark | many | 0.031 | 12.25 | 0.0038 |
| 11 | 2.61 | 64 | 12 | 95 | dark | many | 0.041 | 9.20 | 0.0038 |
| 13 | 2.83 | 92 | 1 | 150 | dark | many | 0.031 | 8.48 | 0.0026 |
| 16 | 5.86 | 209 | 3 | 130 | dark | many | 0.028 | 10.58 | 0.0030 |
| 17 | 5.15 | 224 | 2 | 155 | wt | | 0.023 | 11.65 | 0.0027 |
| 18 | 17.2 | 547 | 1 | 133 | wt | | 0.031 | 10.35 | 0.0033 |
| 19 | 2.13 | 63 | 4 | 80 | dark | many | 0.034 | 11.74 | 0.0040 |
| 20 | 3.44 | 113 | 4 | 90 | wt + Da | many | 0.030 | 8.14 | 0.0025 |
| 21 | 9.88 | 246 | 1 | 105 | dark | many | 0.040 | 8.50 | 0.0034 |
| 22 | 13.1 | 409 | 1 | 135 | wt | | 0.032 | 10.68 | 0.0034 |
| 23 | 2.50 | 73 | 6 | 55 | dark | many | 0.034 | 8.80 | 0.0030 |
| 24 | 8.76 | 286 | 2 | 130 | wt | | 0.031 | 15.07 | 0.0046 |
| 27 | 7.91 | 219 | 1 | 124 | wt | | 0.036 | 14.41 | 0.0052 |
| 28 | 10.0 | 269 | 2 | 117 | dark | many | 0.038 | 8.62 | 0.0032 |
| 29 | 4.17 | 142 | 1 | 85 | dark | many | 0.029 | 10.07 | 0.0030 |
| 30 | 10.2 | 343 | 1 | 160 | wt | | 0.030 | 9.56 | 0.0029 |
| 32 | 1.95 | 61 | 3 | 75 | dark | many | 0.032 | 8.21 | 0.0026 |
| 33 | 2.85 | 96 | 5 | 95 | wt + Da | many | 0.030 | 11.23 | 0.0033 |

TABLE 1a-continued

| Primary PC-TPS tobacco transformants | | | | | | | | | |
|---|---|---|---|---|---|---|---|---|---|
| Plant-line | Leaf tw $cm^2$ | Leaf area $cm^2$ | No. of branches | Plant height cm | Leaf colour | Axillary shoots | Fw/area $g/cm^2$ | Dry matter % | Dry matter/area $g/cm^2$ |
| 34 | 8.38 | 244 | 1 | 123 | wt | | 0.034 | 13.60 | 0.0047 |
| 35 | 5.59 | 173 | 3 | 126 | wt | | 0.032 | 14.49 | 0.0047 |
| 36 | 3.28 | 84 | 3 | 100 | dark | many | 0.039 | 11.28 | 0.0044 |
| 37 | 7.80 | 222 | 1 | 125 | wt + Da | many | 0.035 | 11.28 | 0.0040 |
| 39 | 3.70 | 131 | 2 | 123 | wt | | 0.028 | 17.84 | 0.0050 |
| 40 | 2.40 | 68.5 | 3 | 108 | dark | many | 0.035 | 9.58 | 0.0034 |
| average | | | | | | | 0.032 | 11.00 | 0.0035 |

Transgenic pVDH318 transgenic tobacco plants developed stunted growth and development of small leaves which were darker green and slightly thicker than control leaves, a phenotype similar to the pMOG799 transgenic plants (Table 1a). Further analysis of these leaves showed an increased fresh and dry weight per leaf-area compared to the controls (Tables 1a and 2). The dark green leaves indicate the presence of more chlorophyll in the transgenic leaves (Table 1b). Plants transgenic for pNOG799 (35STPS) and pMCG177 (PCTPS) were analyzed on soluble carbohydrates, chlorophyll, trehalose and starch (FIG. 32). pMOG1177 is functionally identical to pVDH318.

TABLE 1B

| Chlorophyll content of *N. tabacum* leaves ($T_0$) transgenic for PC-TPS | |
|---|---|
| Sample | Chlorophyll (mg/g leaf) |
| Control 1 | 0.59 |
| PC TPS 10-1 | 0.75 |
| PC TPS 10-2 | 0.80 |
| PC TPS 11 | 0.60 |
| PC TPS 13 | 0.81 |
| PC TPS 16 | 0.90 |
| PC TPS 19 | 0.64 |
| PC TPS 37 | 0.96 |

Note:
light conditions during growth will influence the determined levels of chlorophyll significantly. The calculated amounts of chlorophyll may thus only be compared between plants harvested and analyzed within one experiment!

TABLE 2

| Fresh weight and dry weight data of leaf material transgenic for plastocyanin-$TPS_{E. coli}$ *N. tabacum* cv. Samsun NN transgenic for PC-TPS | | |
|---|---|---|
| | Transgene | Control |
| Fresh weight (g) | 0.83 | 0.78 |
| Dry weight (g) | 0.072 | 0.079 |
| % dry matter | 8.70% | 10.10% |
| FW/area | 39 (139%) | 28 (100%) |
| DW/area | 3.46 (121%) | 2.87 (100%) |
| area (units) | 208 | 275 |

Calculation of the ratio between the length and width of the developing leaves clearly indicate that leaves of plants transgenic for PC-TPS are more lancet-shaped (Table 3).

Potato *Solanum tuberosum* cv. Xardal tuber discs were transformed with *Agrobacterium tumefaciens* EHA 105 harbouring the binary vector pMOG845, transgenics were obtained with transformation frequencies comparable to empty vector controls. All plants obtained were phenotypically indistinguishable from wild type plants indicating that use of a tissue specific promoter prevents the phenotypes observed in plants where a constitutive promoter drives the TPS gene. Micro-tubers were induced on stem segments of transgenic and wild-type plants cultured on microtuber-inducing medium supplemented with $10^{-3}$ M Validamycin A. As a control, microtubers were induced on medium without Validamycin A. Microtubers induced on medium with Validamycin A showed elevated levels of trehalose in comparison with microtubers grown on medium without Validamycin A (Table 4). The presence of small amounts of trehalose in wild-type plants indicates the presence of a functional trehalose biosynthetic pathway.

TABLE 3

| Tobacco plants (cv. Samsun NN) transgenic for pVDH318 | | | |
|---|---|---|---|
| Transformant | Length (cm) | Width (cm) | Ratio 1/w |
| control 1 | 12 | 8 | 1.50 |
| control 2 | 13 | 8.5 | 1.53 |
| control 3 | 12 | 7.5 | 1.60 |
| control 4 | 15 | 9 | 1.67 |
| control 5 | 25 | 16 | 1.56 |
| control 6 | 24 | 16.5 | 1.45 |
| control 7 | 28 | 20 | 1.40 |
| control 8 | 25 | 16 | 1.56 |
| control 9 | 26 | 19 | 1.37 |
| control 10 | 21 | 15 | 1.40 |
| 1318-28 | 16 | 8.5 | 1.88* |
| 1318-29 | 11 | 6.5 | 1.69 |
| 1318-30 | 19 | 14 | 1.36 |
| 1318-35 | 19 | 12 | 1.58 |
| 1318-39 | 21 | 16.5 | 1.27 |
| 1318-40 | 14 | 7 | 2.00* |
| 1318-34 | 21 | 13 | 1.62 |
| 1318-36 | 13.5 | 7 | 1.93* |
| 1318-37 | 17 | 9 | 1.89* |
| 1318-4 | 20.5 | 12 | 1.71 |
| 1318-23 | 14 | 4.5 | 3.78* |
| 1318-22 | 27 | 18 | 1.50 |
| 1318-19 | 9 | 4 | 2.25* |
| 1318-2 | 27 | 19 | 1.42 |
| 1318-15 | 11 | 5 | 2.20* |
| 1318-10 | 20 | 13 | 1.54 |
| 1318-3 | 25 | 18 | 1.39 |
| 1318-21 | 17 | 8.5 | 2.00* |
| 1318-16 | 20 | 10 | 2.00* |
| 1318-6 | 19 | 10.5 | 1.81 |
| 1318-20 | 13 | 5 | 2.60* |
| 1318-33 | 12 | 5 | 2.40* |
| 1318-27 | 23 | 20 | 1.15 |
| 1318-11 | 12 | 5 | 2.40 |
| 1318-8 | 18.5 | 6.5 | 2.85* |
| 1318-24 | 27 | 17 | 1.59 |
| 1318-13 | 15 | 7 | 2.14* |
| 1318-17 | 24 | 16 | 1.50 |
| 1318-18 | 23 | 16.5 | 1.39 |

*typical TPS phenotypes Ratio 1/w average of controls is 1.50

TABLE 4

| Trehalose (% fresh weight) | | |
|---|---|---|
| | +Validamycin A | −Validamycin A |
| 845-2 | 0.016 | — |
| 845-4 | — | — |
| 845-8 | 0.051 | — |
| 845-11 | 0.015 | — |
| 845-13 | 0.011 | — |
| 845-22 | 0.112 | — |
| 845-25 | 0.002 | — |
| 845-28 | 0.109 | — |
| wild type Kardal | 0.001 | — |

Example 2

Expression of the *E. coli* otaB Gene (TPP) in Tobacco

Transgenic tobacco plants were generated harbouring the otsogene driven by the double enhanced 35SCaMV promoter (pMOG1010) and the plastocyanin promoter (pVDH321).

Tobacco plants (cv. Samsun NN) transformed with pMOG1010 revealed in the greenhouse the development of very large leaves (leaf area increased on average up to approximately 140%) which started to develop chlorosis when fully developed (FIG. 31). Additionally, thicker stems were formed as compared to the controls, in some instances leading to bursting of the stems. In some cases, multiple stems were formed (branching) from the base of the plant (Table 5). Leaf samples of plants developing large leaves revealed 5-10 times enhanced trehalose-6-phosphate phosphatase activities compared to control plants proving functionality of the gene introduced. The dry and fresh weight/cm$^2$ of the abnormal large leaves was comparable to control leaves, indicating that the increase in size is due to an increase in dry matter and not to an increased water content. The inflorescence was also affected by the expression of TPP. Plants which had a stunted phenotype, probably caused by the constitutive expression of the TPP gene in all plant parts, developed many small flowers which did not fully mature and fell off or necrotized. The development of flowers and seed setting seems to be less affected in plants which were less stunted.

TABLE 5

Tobacco plants transgenic for pMOG1010, de35S CaMV TPP

| Line | Height (cm) | Leaf area cm$^2$ | Bleaching (5-severe) | Branching | Fw/cm$^2$ (g) | DW/cm$^2$ (g) | Inflorescence Norm./ | Stem diameter (mm) |
|---|---|---|---|---|---|---|---|---|
| 1 | 63 | 489 | 5 | + | 0.096 | 0.0031 | A | 13 |
| 2 | 90 | 472 | 3 | + | 0.076 | 0.0035 | A | 19 |
| 3 | 103 | 345 | 0 | | 0.072 | 0.0023 | N | 16 |
| 4 | 90 | 612 | 4 | + | 0.096 | 0.0039 | A | 5, 6, 7, 8, 14 |
| 5 | 104 | 618 | 1 | + | 0.08 | 0.0035 | N | 17 |
| 6 | 110 | 658 | 3 | + | 0.078 | 0.0035 | N/A | 19 |
| 7 | 120 | 427 | 0 | | 0.074 | 0.0037 | N | 18 |
| 8 | 90 | 472 | 2 | + | 0.076 | 0.0023 | A | 6, 7, 18 |
| 9 | 60 | 354 | 3 | + | 0.092 | 0.0031 | N | 9.13 |
| 10 | 103 | 342 | 0 | | 0.084 | 0.0025 | N | 16 |
| 11 | 110 | 523 | 1 | + | 0.076 | 0.0031 | A | 18 |
| 12 | 90 | 533 | 1 | + | 0.098 | 0.0023 | N | 5.16 |
| 13 | 53 | 432 | 4 | + | 0.084 | 0.0043 | A | 5, 6, 6, 14 |
| 14 | 125 | 335 | 0 | | 0.086 | 0.0023 | N | 17 |
| 15 | 85 | 251 | 0 | | 0.094 | 0.0031 | N | 14 |
| 16 | 64 | 352 | 0 | + | 0.076 | 0.0028 | A | 9.13 |
| 17 | 64 | 267 | 0 | | 0.11 | 0.0018 | N | 15 |
| 18 | 71 | 370 | 2 | | 0.086 | 0.0032 | A | 5, 7, 8, 14 |
| 19 | 92 | 672 | 4 | + | 0.076 | 0.0034 | N | 16 |
| 20 | | | | | | | | |
| 21 | 94 | 517 | 4 | + | 0.07 | 0.0044 | N | 17 |
| 22 | 96 | 659 | 3 | + | 0.082 | 0.0031 | N | 17 |
| 23 | 110 | 407 | 0 | | 0.082 | 0.0042 | N | 16 |
| 24 | 90 | 381 | 0 | | 0.1 | 0.0034 | A | 15 |
| 25 | 120 | 535 | 0 | | 0.076 | 0.003 | N | 16 |
| 26 | 42 | 511 | 5 | | 0.08 | 0.0038 | ? | 15 |
| 27 | 100 | 468 | 0 | | 0.086 | 0.0018 | N | 17 |
| 28 | 83 | 583 | 3 | | 0.072 | 0.0034 | N/A | 17 |
| 29 | 27 | 452 | 5 | + | 0.104 | 0.004 | ? | 7, 7, 15 |
| 30 | 23 | 479 | 4 | + | 0.076 | 0.0027 | ? | 6, 6, 7, 9, 14 |
| 31 | 103 | 308 | 1 | | 0.086 | 0.0027 | N | 14 |
| 32 | 48 | 286 | 0 | | 0.108 | 0.002 | N | 16 |
| 33 | 67 | 539 | 5 | + | 0.102 | 0.0056 | A | 18 |
| 34 | 40 | 311 | 5 | + | 0.084 | 0.0051 | A | 7, 7, 12 |

TABLE 6

| Primary PC-TPP tobacco transformants | | | | | | | | | | |
|---|---|---|---|---|---|---|---|---|---|---|
| Plant-line | Leaf fw (g) | Leaf area $cm^2$ | No. of branches | Plant height cm | Leaf colour | Bleaching | Fw/area | Dry matter % | Dry matter/ area |
| ctrl. 1 | 8.18 | 349.37 | | | | | 0.023 | 7.213 | |
| ctrl. 2 | 10.5 | 418.89 | | | | | 0.025 | 9.524 | |
| ctrl. 3 | 9.99 | 373.87 | | | | | 0.027 | 12.913 | |
| ctrl. 4 | 9.91 | 362.92 | | | | | 0.027 | 9.586 | |
| ctrl. 5 | 9.82 | 393.84 | | | | | 0.025 | 11.507 | |
| | | | | | | average | 0.0255 | 10.149 | 0.0026 |
| 11 | 11.5 | 338 | 3 | 114 | wt | | 0.0340 | 6.43 | 0.0022 |
| 12 | 20.1 | 742 | | | pale | bleaching | 0.0272 | 9.82 | 0.0027 |
| 14 | 9.61 | 345 | 1 | 150 | wt | | 0.0279 | 11.65 | 0.0032 |
| 16 | 5.99 | 234 | 5 | 54 | pale | bleaching | 0.0256 | 12.85 | 0.0033 |
| 17 | 9.10 | 314 | 3 | 105 | wt | | 0.0290 | 8.79 | 0.0025 |
| 18 | 3.78 | 158 | 3 | 75 | pale | | 0.0239 | 7.67 | 0.0018 |
| 19 | 2.98 | 130 | 1 | 70 | pale | | 0.0229 | 10.74 | 0.0025 |
| 20 | 8.33 | 296 | 3 | 70 | pale | bleaching | 0.0281 | 7.56 | 0.0021 |
| 22 | 11.5 | 460 | 1 | 117 | pale | bleaching | 0.0251 | 3.03 | 0.0008 |
| 24 | 9.42 | 369 | 1 | 155 | wt | | 0.0255 | 10.62 | 0.0027 |
| 25 | 15.9 | 565 | 1 | 170 | wt | | 0.0282 | 9.54 | 0.0027 |
| 26 | 8.07 | 343 | 2 | 155 | wt | | 0.0235 | 15.37 | 0.0036 |
| 28 | 11.7 | 411 | 2 | 65 | pale | bleaching | 0.0286 | 6.90 | 0.0020 |
| 29 | 11.6 | 420 | 1 | 117 | pale | Bleaching | 0.0277 | 3.53 | 0.0010 |
| 31 | 8.21 | 307 | 2 | 153 | wt | | 0.0267 | 12.79 | 0.0034 |
| 32 | 4.03 | 175 | 1 | 70 | pale | | 0.0230 | 18.86 | 0.0043 |
| 34 | 4.81 | 203 | 1 | 107 | pale | | 0.0237 | 20.58 | 0.0049 |
| 35 | 7.86 | 307 | 3 | 130 | pale | | 0.0256 | 11.45 | 0.0029 |
| 36 | 4.90 | 206 | 2 | 95 | pale | | 0.0238 | 22.65 | 0.0054 |
| 37 | 13.9 | 475 | 1 | 135 | wt | | 0.0293 | 4.82 | 0.0014 |
| 38 | 16.6 | 614 | 1 | 90 | pale | bleaching | 0.0271 | 3.31 | 0.0009 |
| 39 | 14.9 | 560 | 1 | 112 | wt | bleaching | 0.0267 | 6.08 | 0.0016 |
| 40 | 24.5 | 843 | | | | | 0.0292 | 9.80 | 0.0029 |
| 41 | 8.86 | 343 | 1 | 115 | wt | | 0.0258 | 2.93 | 0.0008 |
| 42 | 6.93 | 289 | 1 | | wt | | 0.0240 | 3.32 | 0.0008 |
| 43 | 11.3 | 433 | 136 | 135 | wt | | 0.0261 | 6.73 | 0.0018 |
| 44 | 10.0 | 341 | 2 | 135 | wt | | 0.0294 | 6.49 | 0.0019 |
| 45 | 9.40 | 327 | 2 | 135 | wt | | 0.0287 | 8.51 | 0.0024 |
| 46 | 9.18 | 284 | 2 | 115 | wt | | 0.0323 | 15.69 | 0.0051 |
| | | | | | | average | 0.027 | 9.60 | 0.0025 |

wt = wild-type

Tobacco plants (cv. Samsun NN) transformed with pVDH321 revealed in the greenhouse a pattern of development comparable to pMOG1010 transgenic plants (Table 6).

Figures 1, 32:
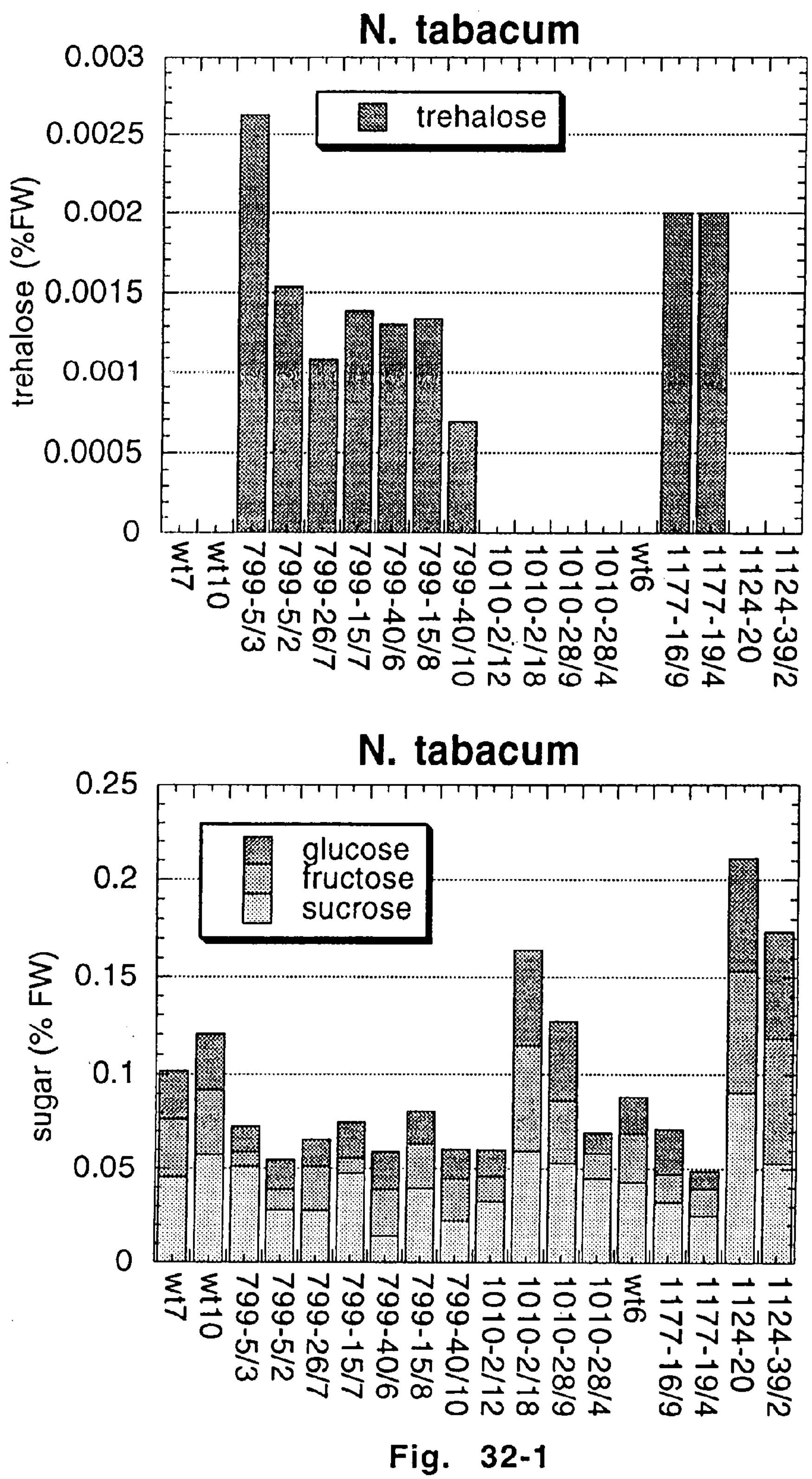
Figures 2, 32:
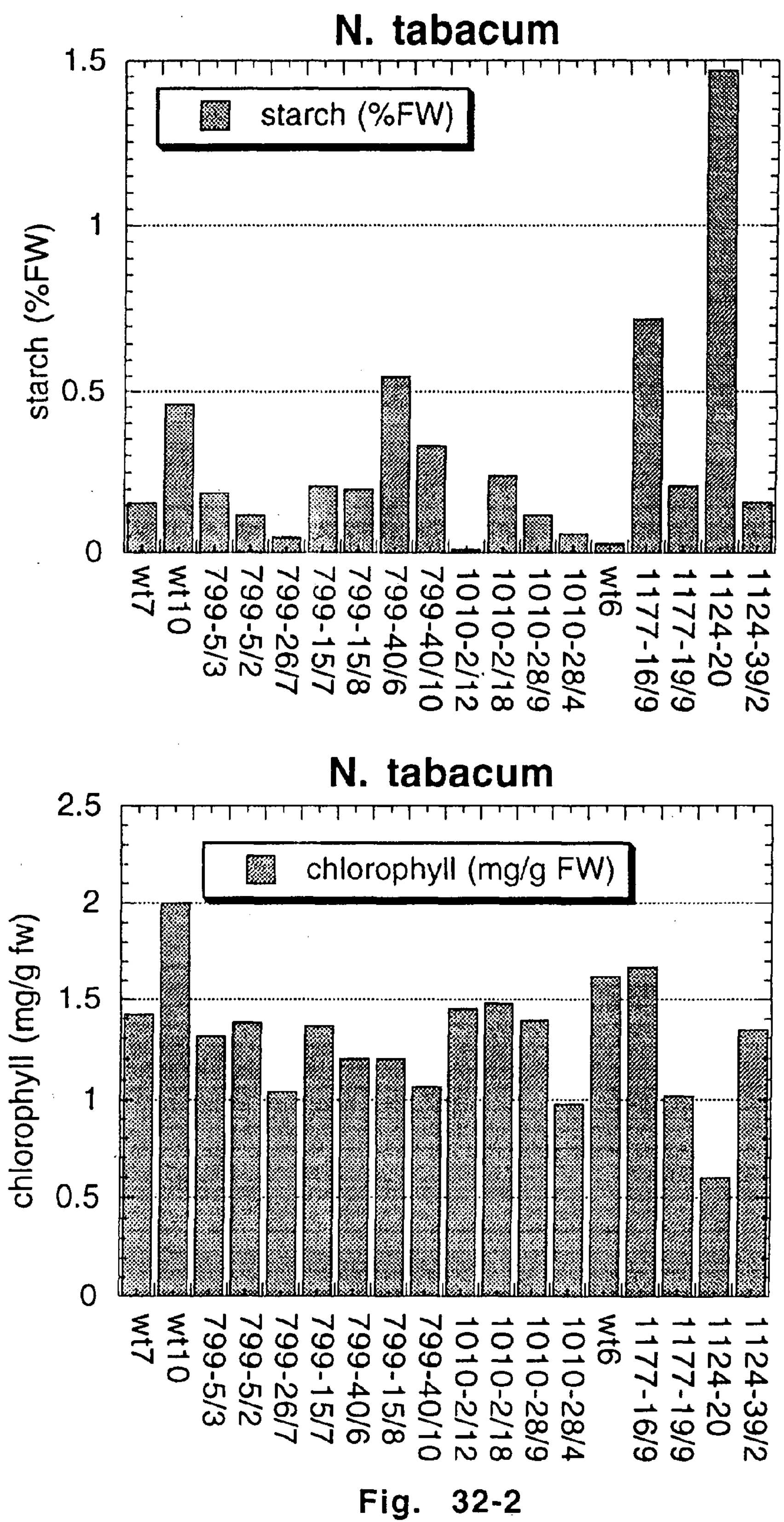

Plants transgenic for pMOG1010 (35S-TPP) and pMOG1124 (PC-TPP) were analyzed on carbohydrates, chlorophyll, trehalose and starch FIGS. 32 A-D. For chlorophyll data see also Table 6a.

TABLE 6a

| Chlorophyll content of N. tabacum leaves ($T_0$) transgenic for PC-TPP | | |
|---|---|---|
| sample | Chlorophyll (mg/g leaf) | Leaf phenotype |
| control 1 | 1.56 | wild-type |
| control 2 | 1.40 | wild-type |
| control 3 | 1.46 | wild-type |
| control 4 | 1.56 | wild-type |
| control 5 | 1.96 | wild-type |
| PC TPP 12 | 0.79 | bleaching |
| PC TPP 22 | 0.76 | bleaching |
| PC TPP 25 | 1.30 | wild-type |
| PC TPP 37 | 0.86 | wild-type |
| PC TPP 38 | 0.74 | bleaching |

Note:

light conditions during growth will influence the determined levels of chlorophyll significantly. The calculated amounts of chlorophyll may thus only be compared between plants harvested and analyzed within one experiment!

Example 3

Isolation of Gene Fragments Encoding Trehalose-6-Phosphate Synthases from *Selaginella legidophylla* and *Helianthus annuus*

Comparison of the TPS protein sequences from *E. coli* and *S. cerevisiae* revealed the presence of several conserved regions. These regions were used to design degenerated primers which were tested in PCR amplification reactions using genomic DNA of *E. coli* and yeast as a template. A PCR program was used with a temperature ramp between the annealing and elongation step to facilitate annealing of the degenerate primers.

PCR amplification was performed using primer sets TPSdeg 1/5 and TPSdeg 2/5 using cDNA of *Selaginella lepidophylla* as a template.

Degenerated primers used (IUB code):

```
TPSdeg1:
GAY ITI ATI TGG RTI CAY GAY TAY CA    (SEQ ID NO:7)

TPSdeg2:
TIG GIT KIT TYY TIC AYA YIC CIT TYC C (SEQ ID NO:8)

TPSdeg5:
GYI ACI ARR TTC ATI CCR TCI C         (SEQ ID NO:9)
```

PCR fragments of the expected size were cloned and sequenced. Since a large number of homologous sequences were isolated, Southern blot analysis was used to determine which clones hybridized with *Selaginella* genomic DNA. Two clones were isolated, clone 8 of which the sequence is given in SEQ ID NO: 42 (PCR primer combination 1/5) and clone 43 of which the sequence is given in SEQ ID NO: 44 (PCR primer combination 2/5) which on the level of amino acids revealed regions with a high percentage of identity to the TPS genes from *E. coli* and yeast.

Figures 3, 35:
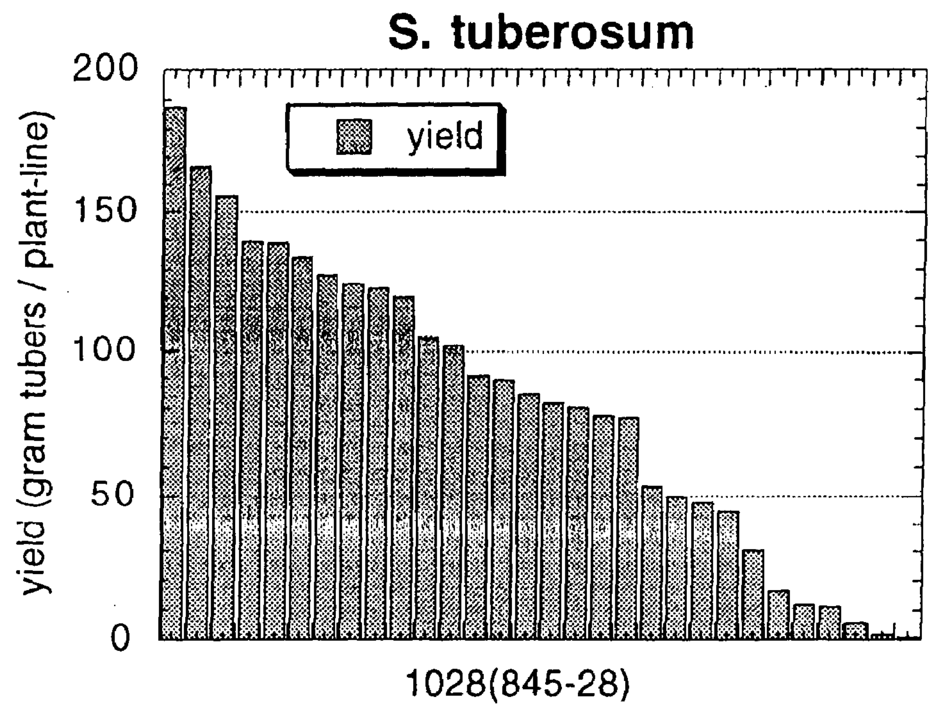
FIGS. 3A and 3B. Lineup of plant derived TPS encoding sequences compared with the $TPS_{yeast}$ sequence using the Wisconsin GCG sequence analysis package (Devereux et al. (1984) A comprehensive set of sequence analysis programs of the VAX. Nucl. Acids Res., 12, 387).

One TPS gene fragment was isolated from *Helianthus annuus* (sunflower) using primer combination TPSdeg 2/5 in a PCR amplification with genomic DNA of *H. annuus* as a template. Sequence and Southern blot analysis confirmed the homology with the TPS genes from *E. coli*, yeast and *Selaginella*. Comparison of these sequences with EST sequences (expressed sequence tags) from various organisms, see Table 6b and SEQ ID NOS 45-53 and 41, indicated the presence of highly homologous genes in rice and *Arabidopsis*, which supports our invention that most plants contain TPS homologous genes (FIGS. 3A and 3B).

TABLE 6b

| dbest ID. | Genbank Accession No. | Organism | Function |
|---|---|---|---|
| 35567 | D22143 | *Oryza sativa* | TPS |
| 58199 | D35348 | *Caenorhabditis elegans* | TPS |
| 60020 | D36432 | *Caenorhabditis elegans* | TPS |
| 87366 | T36750 | *Saccharomyces cerevisiae* | TPS |
| 35991 | D22344 | *Oryza sativa* | TPS |
| 57576 | D34725 | *Caenorhabditis elegans* | TPS |
| 298273 | H37578 | *Arabidopsis thaliana* | TPS |
| 298289 | H37594 | *Arabidopsis thaliana* | TPS |
| 315344 | T76390 | *Arabidopsis thaliana* | TPS |
| 315675 | T76758 | *Arabidopsis thaliana* | TPS |
| 317475 | R65023 | *Arabidopsis thaliana* | TPS |
| 71710 | D40048 | *Oryza sativa* | TPS |
| 401677 | D67869 | *Caenorhabditis elegans* | TPS |
| 322639 | T43451 | *Arabidopsis thaliana* | TPS |
| 76027 | D41954 | *Oryza sativa* | TPP |

TABLE 6b-continued

| dbest ID. | Genbank Accession No. | Organism | Function |
|---|---|---|---|
| 296689 | H35994 | *Arabidopsis thaliana* | TPP |
| 297478 | H36783 | *Arabidopsis thaliana* | TPP |
| 300237 | T21695 | *Arabidopsis thaliana* | TPP |
| 680701 | AA054930 | *Brugia malayi* | trehalase |
| 693476 | C12818 | *Caenorhabditis elegans* | trehalase |
| 311652 | T21173 | *Arabidopsis thaliana* | TPP |
| 914068 | AA273090 | *Brugia malayi* | trehalase |
| 43328 | T17578 | *Saccharomyces cerevisiae* | TPP |
| 267495 | H07615 | *Brassica napus* | trehalase |
| 317331 | R64855 | *Arabidopsis thaliana* | TPP |
| 15008 | T00368 | *Caenorhabditis elegans* | trehalase |
| 36717 | D23329 | *Oryza sativa* | TPP |
| 71650 | D39988 | *Oryza sativa* | TPP |
| 147057 | D49134 | *Oryza sativa* | TPP |
| 401537 | D67729 | *Caenorhabditis elegans* | trehalase |
| 680728 | AA054884 | *Brugia malayi* | trehalase |
| 694414 | C13756 | *Caenorhabditis elegans* | trehalase |
| 871371 | AA231986 | *Brugia malayi* | trehalase |
| 894468 | AA253544 | *Brugia malayi* | trehalase |
| 86985 | T36369 | *Saccharomyces cerevisiae* | TPP |

Example 4

Isolation of Plant TPS and TPP Genes from *Nicotiana Tabacum*

Figure 5:
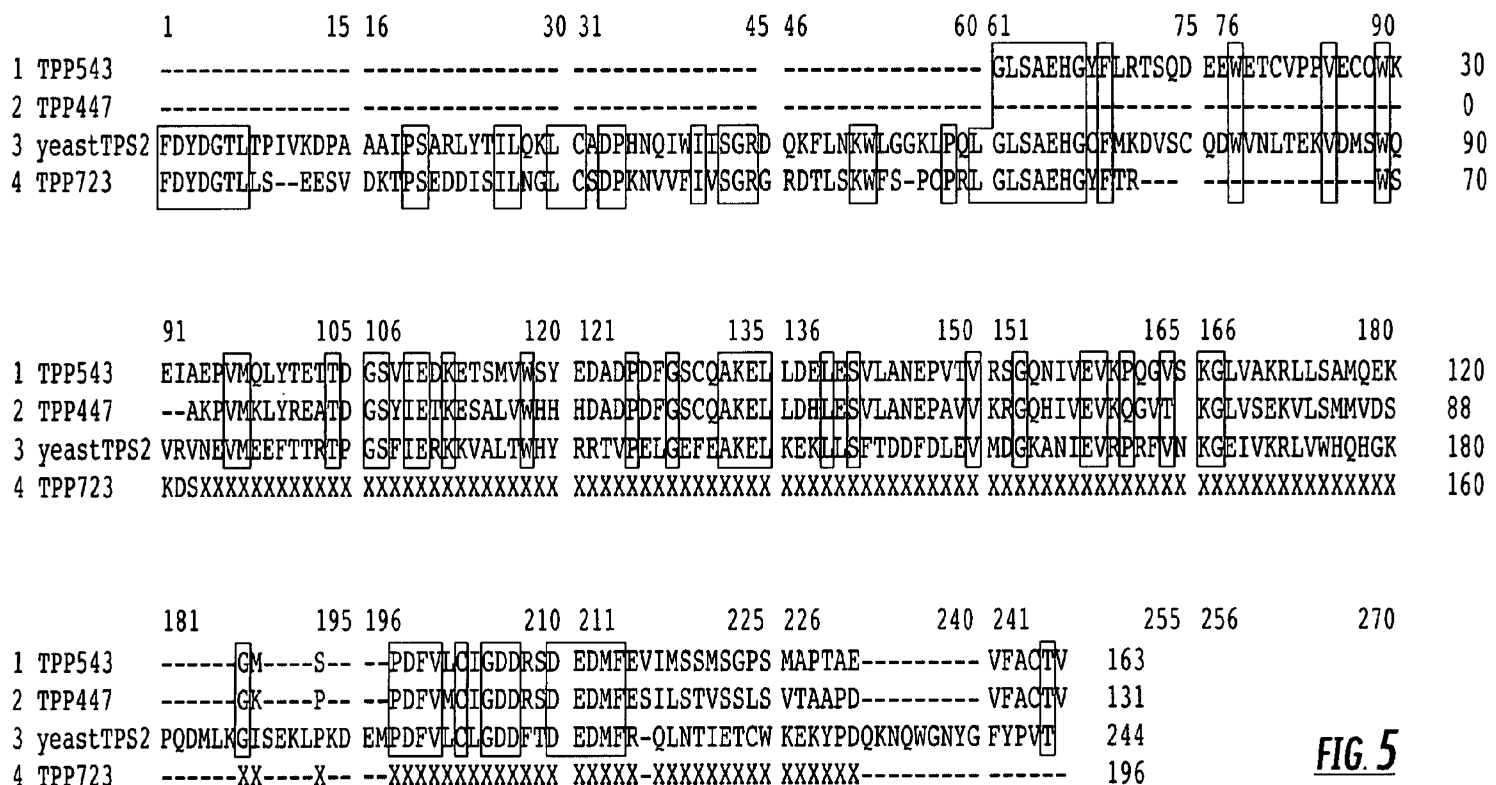
FIG. 5. Alignment of PCR amplified tobacco TPP cDNA fragments with the TPP encoding yeast TPS2 gene. Boxes indicate identity between amino-acids of all four listed sequences.

Fragments of plant TPS- and TPP-encoding cDNA were isolated using PCR on cDNA derived from tobacco leaf total RNA preparations. The column "nested" in Table 7 indicates if a second round of PCR amplification was necessary with primer set 3 and 4 to obtain the corresponding DNA fragment. Primers have been included in the sequence listing (Table 7). Subcloning and subsequent sequence analysis of the DNA fragments obtained with the primer sets mentioned revealed substantial homology to known TPS genes (FIGS. 4 & 5).

TABLE 7

Amplification of plant derived TPS and TPP cDNAs

| TPS-cDNA | primer 1 | primer 2 | nested | primer 3 | primer 4 |
|---|---|---|---|---|---|
| "825" bp SEQ ID NO 22 & 23 | Tre-TPS-14 SEQ ID NO 30 | Deg 1 SEQ ID NO 7 | No | | |
| "840" bp SEQ ID NO 18 & 19 | Tre-TPS-14 SEQ ID NO 30 | Tre-TPS-12 SEQ ID NO 31 | Yes | Tre-TPS-13 SEQ ID NO 32 | Deg 5 SEQ ID NO 9 |
| "630" bp SEQ ID NO 20 & 21 | Tre-TPS-14 SEQ ID NO 30 | Tre-TPS-12 SEQ ID NO 31 | Yes | Deg 2 SEQ ID NO 8 | Deg 5 SEQ ID NO 9 |

| TPP-cDNA | primer 1 | primer 2 | nested |
|---|---|---|---|
| "723" bp SEQ ID NO 16 & 17 | Tre-TPP-5 SEQ ID NO 35 | Tre-TPP-16 SEQ ID NO 38 | No |
| "543" bp SEQ ID NO 14 | Tre-TPP-7 SEQ ID NO 36 | Tre-TPP-16 SEQ ID NO 38 | No |
| "447" bp SEQ ID NO 12 | Tre-TPP-11 SEQ ID NO 37 | Tre-TPP-16 SEQ ID NO 38 | No |

Example 5

Isolation of a Bipartite TPS/TPP Gene from *Helianthus Annuus* and *Nicotiana Tabacum*

Using the sequence information of the TPS gene fragment from sunflower (*Helianthus annuus*), a full length sunflower TPS clone was obtained using RACE-PCR technology.

Sequence analysis of this full length clone and alignment with TPS2 from yeast (FIG. 6) and TPS and TPP encoding sequences indicated the isolated clone encodes a TPS/TPP bipartite enzyme (SEQ ID NO: 24, 26 and 28). The bipartite clone isolated (PMOG1192) was deposited at the Central Bureau for Strain collections under the rules of the Budapest treaty with accession number CBS692.97 at Apr. 21, 1997. Subsequently, we investigated if other plant species also contain TPS/TPP bipartite clones. A bipartite TPS/TPP cDNA was amplified from tobacco. A DNA product of the expected size (i.e. 1.5 kb) was detected after PCR with primers TPS deg1/FRE-TPP-16 and nested with TPS deg2/TRE-TPP-15 (SEQ ID NO: 33). An identical band appeared with PCR with TPS deg1/TRE-TPP-6 (SEQ ID NO: 34) and nested with TPS deg2/TRE-TPP-15. The latter fragment was shown to hybridize to the sunflower bipartite cDNA in a Southern blot experiment. Additionally, using computer database searches, an *Arabidopsis* bipartite clone was identified (SEQ ID NO: 39)

Example 6

Expression of Plant Derived TPS Genes in Plants

Further proof for the function of the TPS genes from sunflower and *Selaginella lepidophylla* was obtained by isolating their corresponding full-length cDNA clones and subsequent expression of these clones in plants under control of the 35S CaMV promoter. Accumulation of trehalose by expression of the *Seliganella* enzyme has been reported by Zentella and Iturriaga (1996) (Plant Physiol. 111. Abstract 88).

Example 7

Genes Encoding TPS and TPP from Monocot Species

A computer search in Genbank sequences revealed the presence of several rice EST-sequences homologous to TPS1 and TPS2 from yeast (FIG. 7) which are included in the sequence listing (SEQ ID NO: 41, 51, 52 and 53).

Example 8

Isolation Human TPS Gene

A TPS gene was isolated from human cDNA. A PCR reaction was performed on human cDNA using the degenerated TPS primers deg2 and deg5. This led to the expected TPS fragment of 0.6 kb. Sequence analysis (SEQ ID NO: 10) and comparison with the TPSyeast sequence indicated that isolated sequence encodes a homologous TPS protein (FIG. 8).

Example 9

Inhibition of Endogenous TPS Expression by Anti-Sense Inhibition

The expression of endogenous TPS genes can be inhibited by the anti-sense expression of a homologous TPS gene under control of promoter sequences which drive the expression of such an anti-sense TPS gene in cells or tissue where the inhibition is desired. For this approach, it is preferred to use a fully identical sequence to the TPS gene which has to be suppressed although it is not necessary to express the entire coding region in an anti-sense expression vector. Fragments of such a coding region have also shown to be functional in the anti-sense inhibition of gene-expression. Alternatively, heterologous genes can be used for the anti-sense approach when these are sufficiently homologous to the endogenous gene.

Binary vectors similar to pMOG845 and pMOG1010 can be used ensuring that the coding regions of the introduced genes which are to be suppressed are introduced in the reverse orientation. All promoters which are suitable to drive expression of genes in target tissues are also suitable for the anti-sense expression of genes.

Example 10

Inhibition of Endogenous TPP Expression by Anti-Sense Inhibition

Similar to the construction of vectors which can be used to drive anti-sense expression of tps in cells and tissues (Example 9), vectors can be constructed which drive the anti-sense expression of TPP genes.

Example 11

Trehalose Accumulation in Wild-Type Tobacco and Potato Plants Grown on Validamycin A Evidence for the presence of a trehalose biosynthesis pathway in tobacco was obtained by culturing wild-type plants in the presence of $10^{-3}$M of the trehalase inhibitor Validamycin A. The treated plants accumulated very small amounts of trehalose, up to 0.0021% (fw). Trehalose accumulation was never detected in any control plants cultured without inhibitor. Similar data were obtained with wild-type microtubers cultured in the presence of Validamycin A. Ten out of seventeen lines accumulated on average 0.001% trehalose (fw)/ (Table 4). No trehalose was observed in microtubers which were induced on medium without Validamycin A.

Example 12

Trehalose Accumulation in Potato Plants Transgenic for Astrehalase

Figure 9:
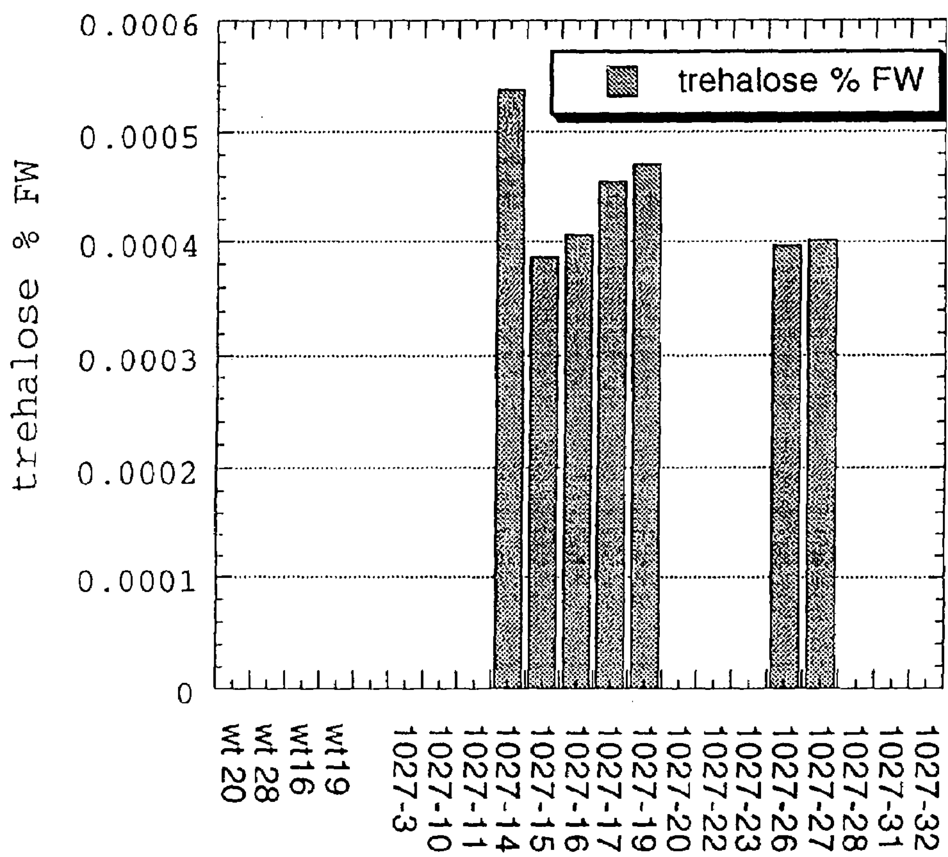
FIG. 9. Trehalose accumulation in tubers of pMOG1027 (35S astrehalase) transgenic potato plants.

Further proof for the presence of endogenous trehalose biosynthesis genes was obtained by transforming wild-type potato plants with a 35S CaMV anti-sense trehalase construct (SEQ ID NO: 54 and 55, pMOG1027; described in WO 96/21030). A potato shoot transgenic for pMOG1027 showed to accumulate trehalose up to 0.008% on a fresh weight basis. The identity of the trehalose peak observed was confirmed by specifically breaking down the accumulated trehalose with the enzyme trehalase. Tubers of some pMOG1027 transgenic lines showed to accumulate small amounts of trehalose (FIG. 9).

Example 13

Inhibition of Plant Hexokinase Activity by Trehalose-6-Phosphate

To demonstrate the regulatory effect of trehalose-6-phosphate on hexokinase activity, plant extracts were prepared and tested for hexokinase activity in the absence and presence of trehalose-6-phosphate.

Figure 10:
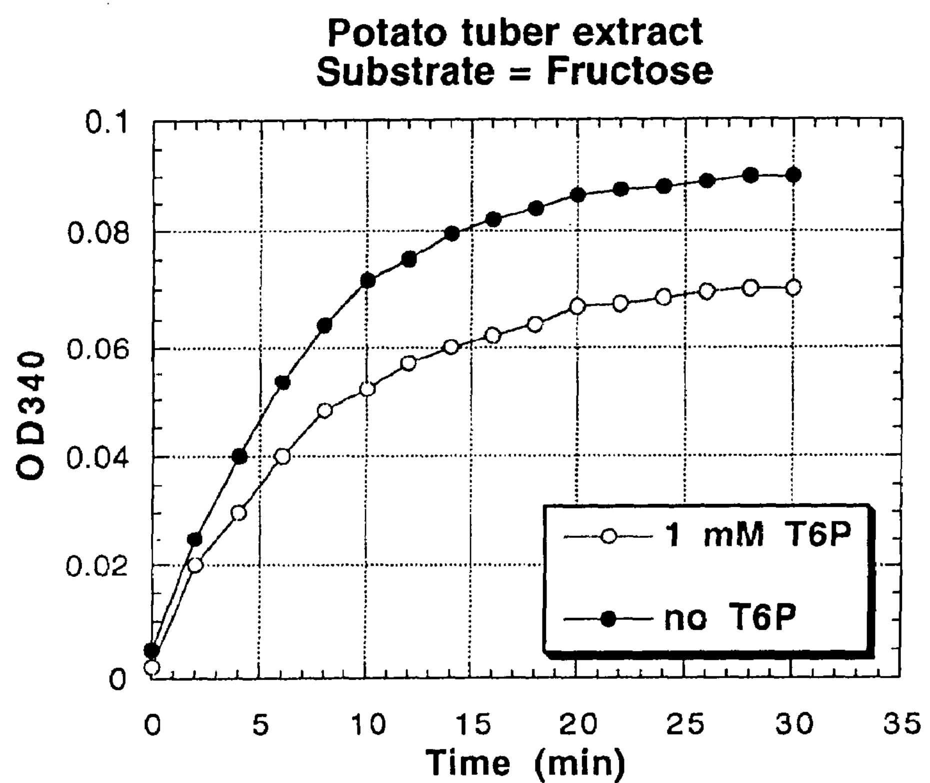
FIG. 10. Hexokinase activity of a wild-type potato tuber (*Solanum tuberosum* cv. Kardal) extract with and without the addition of trehalose-6-phosphate.
Figure 11:
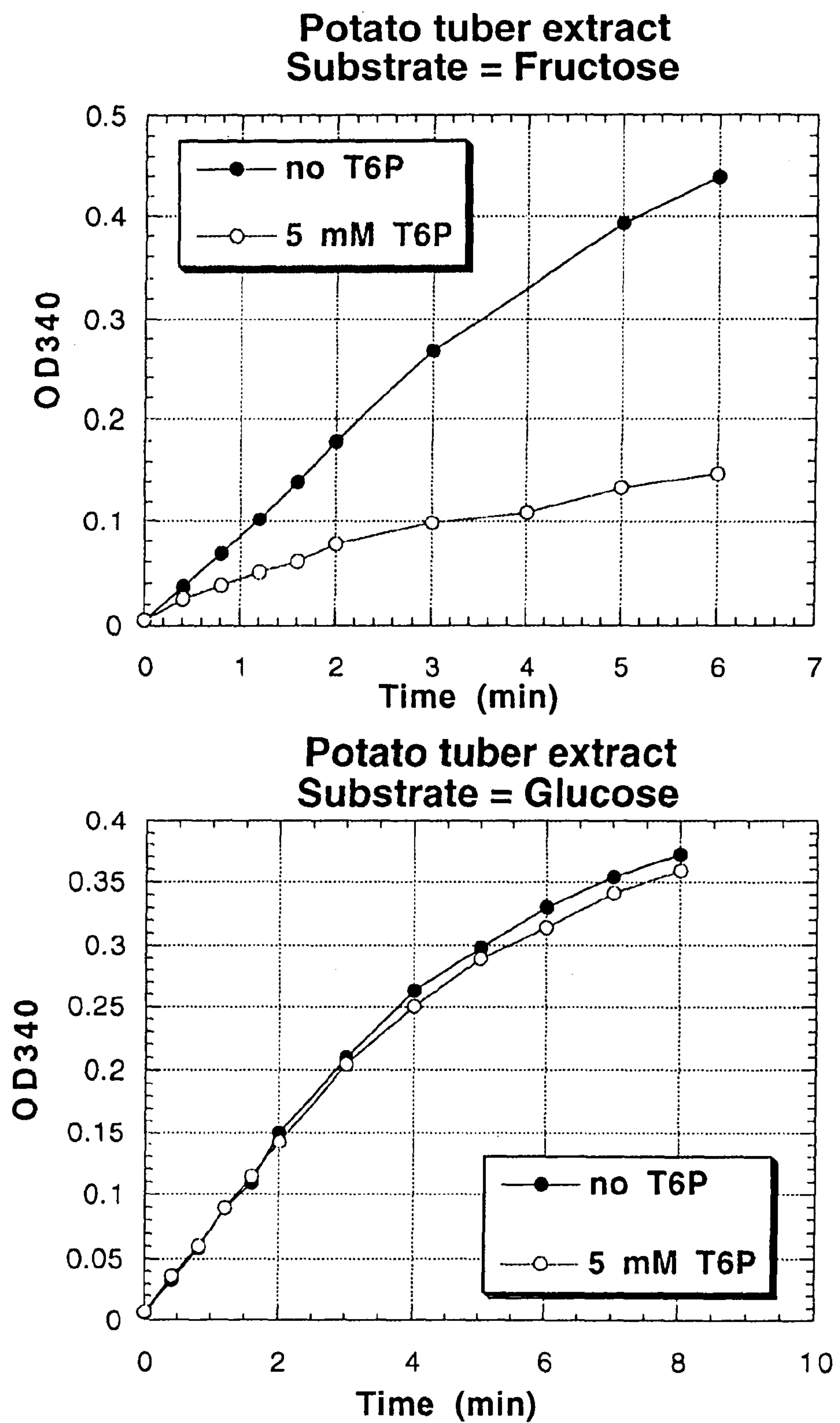
FIG. 11. Hexokinase activity of a wild-type potato tuber (*Solanum tuberosum* cv. Kardal) extract with and without the addition of trehalose-6-phosphate. Fructose or glucose is used as a substrate for the assay.
Figure 13:
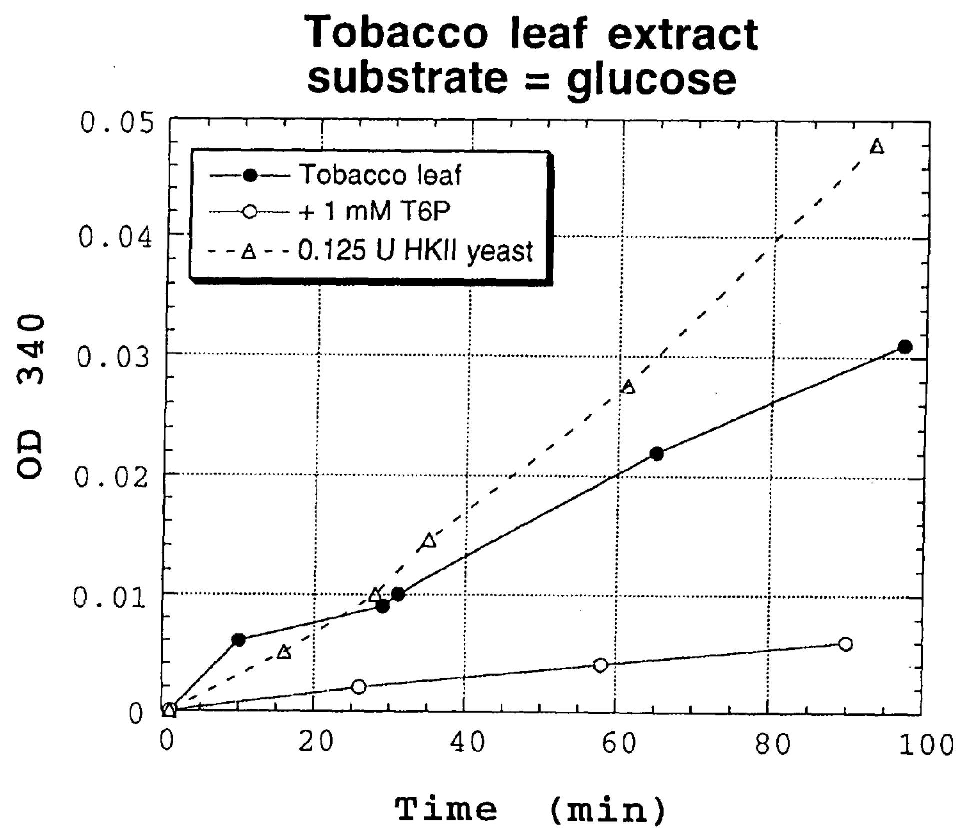
FIG. 13. Plot of a tobacco hexokinase activity measurement.

Potato tuber extracts were assayed using fructose (FIG. 10, FIG. 11) and glucose (FIG. 11) as substrate. The potato tuber assay using 1 mM T-6-P and fructose as substrate was performed according to Gancedo et al. (1997) J. Biol. Chem. 252, 4443. The following assays on tobacco, rice and maize were performed according to the assay described in the section experimental. Tobacco leaf extracts were assayed using fructose (FIG. 12) and glucose (FIG. 12, FIG. 13) as substrate. Rice leaf extracts were assayed using fructose and glucose (FIG. 14) as substrate. Maize leaf extracts were assayed using fructose and glucose (FIG. 15) as substrate.

Example 14

Inhibition of Hexokinase Activity in Animal Cell Cultures by Trehalose-6-Phosphate To demonstrate the regulation of hexokinase activity in animal cells, total cell extracts were prepared from mouse hybridoma cell cultures. A hexokinase assay was performed using glucose or fructose as substrate under conditions as described by Gancedo et al. (see above). Mouse hybridoma cells were subjected to osmotic shock by exposing a cell pellet to 20% sucrose, followed by distilled water. This crude protein extract was used in the hexokinase assay (50 μl) extract corresponding to ca. 200 μg protein).

TABLE 8

Inhibition of animal hexokinase activity for T-6-P

| Substrate | Concentration (mM) | T6P (ODU/ min) | V0 (ODU/ min) | V2 (ODU/min) | Inhibition (%) |
|---|---|---|---|---|---|
| Glucose | 2 | 0.83 | 0.0204 | 0.0133 | 35 |
| Glucose | 20 | 0.83 | 0.0214 | 0.0141 | 35 |
| Glucose | 100 | 0.83 | 0.0188 | 0.0125 | 34 |
| Fructose | 20 | 0.23 | 0.0207 | 0.0205 | 1 |
| Fructose | 20 | 0.43 | 0.0267 | 0.0197 | 26 |
| Fructose | 20 | 0.83 | 0.0234 | 0.0151 | 35 |
| Fructose | 20 | 1.67 | 0.0246 | 0.0133 | 46 |

The data obtained clearly showed that hexokinase activity in mouse cell extracts is inhibited by trehalose-6-phosphate. The T-6-P concentration range in which this effect is noted is comparable to what has been observed in crude plant extracts. No difference is noted in the efficiency of hexokinase inhibition by trehalose-6-phosphate using glucose or fructose as substrate for the enzyme.

Example 15

Photosynthesis and Respiration of TPS and TPP Expressing Tobacco Plants

Using tobacco plants transgenic for 35S-TPP (1010-5), PC-TPS (1318-10 and 1318-37) and wild-type Samsun NN plants, effects of expression of these genes on photosynthesis and respiration were determined in leaves.

Measurements were performed in a gas exchange-experimental set-up. Velocities of gas-exchange were calculated on the basis of differences in concentration between ingoing and outgoing air using infra-red gas-analytical equipment. Photosynthesis and respiration were measured from identical leaves. From each transgenic plant, the youngest, fully matured leaf was used (upper-leaf) and a leaf that was 3-4 leaf-"stores" lower (lower-leaf).

Photosynthesis was measured as a function of the photosynthetic active light intensity (PAR) from 0-975 μmol·$m^{-2}s^{-1}$ (200 Watt $m^{-2}$), in four-fold at $CO_2$-concentrations of 350 vpm and 950 vpm.

Respiration was measured using two different time-scales. Measurements performed during a short dark-period after the photosynthesis experiments are coded RD in table 9. These values reflect instantaneous activity since respiration varies substantially during the dark-period. Therefor, the values for the entire night-period were also summed as shown in Table 10 (only measured at 350 vpm $CO_2$).

TABLE 9

Rate of photosynthesis and respiration, STD is standard deviation

| | | 350 ppm | | 950 ppm | |
|---|---|---|---|---|---|
| | | micromol/m²/s | STD | micromol/m²/s | STD |
| Upper leaf | | | | | |
| Wild-type | RD | 0.0826 | 0.048 | 1.016 | 0.142 |
| | EFF | 0.060 | 0.004 | 0.087 | 0.004 |
| | AMAX | 11.596 | 0.588 | 19.215 | 0.942 |
| 1010-5 | RD | 0.873 | 0.060 | 1.014 | 0.134 |
| | EFF | 0.059 | 0.002 | 0.090 | 0.007 |
| | AMAX | 12.083 | 1.546 | 18.651 | 1.941 |
| 1318-10 | RD | 0.974 | 0.076 | 1.078 | 0.108 |
| | EFF | 0.064 | 0.003 | 0.088 | 0.008 |
| | AMAX | 16.261 | 2.538 | 24.154 | 1.854 |
| 1318-37 | RD | 1.067 | 0.140 | 1.204 | 0.116 |
| | EFF | 0.061 | 0.002 | 0.084 | 0.011 |
| | AMAX | 16.818 | 2.368 | 25.174 | 2.093 |
| Lower leaf | | | | | |
| Wild-type | RD | 0.0438 | 0.079 | 0.526 | 0.112 |
| | EFF | 0.068 | 0.002 | 0.085 | 0.004 |
| | AMAX | 6.529 | 1.271 | 11.489 | 1.841 |
| 1010-5 | RD | 0.455 | 0.068 | 0.562 | 0.118 |
| | EFF | 0.064 | 0.002 | 0.085 | 0.006 |
| | AMAX | 8.527 | 0.770 | 13.181 | 1.038 |
| 1318-10 | RD | 0.690 | 0.057 | 0.828 | 0.086 |
| | EFF | 0.064 | 0.008 | 0.085 | 0.005 |
| | AMAX | 11.562 | 1.778 | 20.031 | 1.826 |
| 1318-37 | RD | 0.767 | 0.033 | 0.918 | 0.099 |
| | EFF | 0.073 | 0.006 | 0.103 | 0.004 |
| | AMAX | 13.467 | 1.818 | 19.587 | 1.681 |

TABLE 10

Respiration during 12 hour dark period (mmol $CO_2$)

| | Upper leaf | STD | Lower leaf | STD |
|---|---|---|---|---|
| Wild-type | 25.17 | 0.82 | 13.19 | 1.98 |
| 1010-5 | 30.29 | 5.09 | 13.08 | 1.52 |
| 1318-10 | 28.37 | 4.50 | 20.47 | 0.87 |
| 1318-37 | 32.53 | 2.01 | 17.7 | 1.03 |

In contrast to the respiration in the upper-leaves, in lower leaves the respiration of TPS transgenic plants is significantly higher than for wild-type and TPP plants (Table 10) indicating a higher metabolic activity. The decline in respiration during aging of the leaves is significantly less for TPS transgenic plants.

Also, the photosynthetic characteristics differed significantly between on the one hand TPS transgenic plants and on the other hand TPP transgenic and wild-type control plants. The AMAX values (maximum of photosynthesis at light saturation), efficiency of photosynthesis (EFF) and the respiration velocity during a short dark-period after the photosynthetic measurements (RD) are shown in table 9. On average, the upper TPS leaves had a 35% higher AMAX value compared to the TPP and wild-type leaves. The lower leaves show even a higher increased rate of photosynthesis (88%).

To exclude that differences in light-absorption were causing the different photosynthetic rates, absorption values were measured with a SPAD-502 (Minolta). No significant differences in absorption were measured (Table 11).

TABLE 11

| Absorbtion values of transgenic lines | | |
|---|---|---|
| Absorbtion (%) | Upper-leaf | Lower-leaf |
| Wild-type Samsun NN | 84 | 83 |
| 1010-5 | 84 | 82 |
| 1318-10 | 85 | 86 |
| 1318-37 | 86 | 86 |

Example 16

Chlorophyll-Fluorescence of TPS and TPP Expressing Tobacco Plants

Using tobacco plants transgenic for 35S-TPP (1010-5), PC-TPS (1318-10 and 1318-37) and wild-type Samsun NN plants, effects of expressing these genes were determined on chlorophyll fluorescence of leaf material. Two characteristics of fluorescence were measured:

1) ETE (electron transport efficiency), as a measure for the electron transport velocity and the generation of reducing power, and 2) Non-photochemical quenching, a measure for energy-dissipation caused by the accumulation of assimilates.

Plants were grown in a greenhouse with additional light of 100 $\mu$mol·m$^{-2}$·s$^{-1}$ (04:00-20:00 hours). Day/night T=21° C./18° C.; R.H.±75%. During a night-period preceding the measurements (duration 16 hours), two plants of each genotype were transferred to the dark and two plants to the light (±430 $\mu$mol m$^{-2}$·s$^{-1}$, 20° C., R.H.±70%). The youngest fully matured leaf was measured. The photochemical efficiency of PSII (photosystem II) and the "non-photochemical quenching" parameters were determined as a function of increasing, light intensity. At each light intensity, a 300 sec. stabilisation time was taken. Measurements were performed at 5, 38, 236, 422 and 784 $\mu$mol m$^{-2}$·s$^{-1}$ PAR with a frequency of 3 light-flashes min$^{-1}$, 350 ppm $CO_2$ and 20% $O_2$. Experiments were replicated using identical plants, reversing the pretreatment from dark to light and vice versa. The fluorescence characteristics are depicted in FIG. 16.

The decrease in electron-transport efficiency (ETE) was comparable between TPP and wild-type plants. TPS plants clearly responded less to a increase of light intensity. This difference was most clear in the light pretreatment. These observations are in agreement with the "non-photochemical" quenching data. TPS plants clearly responded less to the additional supply of assimilates by light compared to TPP and wild-type plants. In the case of TPS plants, the negative regulation of accumulating assimilates on photosynthesis was significantly reduced.

Example 17

Export and Allocation of Assimilates in TPS and RPP Expressing Tobacco Plants

Using tobacco plants transgenic for 35S-TPP (1010-5) and PC-TPS (1318-37), 1) the export of carbon-assimilates from a fully grown leaf (indicating "relative source activity", Koch (1996) Annu. Rev. Plant Physiol. Plant. Mol. Biol. 47, 509 and 2) the net accumulation of photo-assimilates in sinks ("relative sink activity"), during a light and a dark-period, were determined.

Developmental stage of the plants: flowerbuds just visible. Labelling technique used: Steady-state high abundance 13C-labelling of photosynthetic products (De Visser et al. (1997) Plant Cell Environ 20, 37). Of both genotypes, 8 plants, using a fully grown leaf, were labelled with 5.1 atom % $^{13}CO_2$ during a light-period (10 hours), when appropriate followed by a dark-period (14 hours). After labelling, plants were split in: 1) shoot-tip, 2) young growing leaf, 3) young fully developed leaf (above the leaf being labelled), 4) young stem (above the leaf being labelled), 5) labelled leaf, 6) petiole and base of labelled leaf, 7) old, senescing leaf, 8) other and oldest leaves lower than the labelled leaf. 9) stem lower than the labelled leaf, 10) root-tips. Number, fresh and dry weight and $^{13}$C percentage (atom % $^{13}$C) of carbon were determined. Next to general parameters as biomass, dry matter and number of leaves, calculated were: 1) Export of C out of the labelled leaf, 2) the relative contribution of imported C in plant parts; 3) the absolute amount of imported C in plant parts; 4) the relative distribution of imported C during a light period and a complete light and dark-period.

The biomass above soil of the TPP transgenics was 27% larger compared to the TPS transgenics ($P<0.001$); also the root-system of the TPP transgenics were better developed. The TPP plants revealed a significant altered dry matter distribution, +39% leaf and +10% stem biomass compared to TPS plants. TPS plants had a larger number of leaves, but a smaller leaf-area per leaf. Total leaf area per TPS plant was comparable with wild-type (0.4 $m_2$ plant$^{-1}$).

—Relative Source Activity of a Fully Developed Leaf

The net export rate of photosynthates out of the labelled leaf is determined by the relative decrease of the % "new C" during the night (for TPP 39% and for TPS 56%) and by the total fixated amount present in the plant using the amount of "new C" in the plant (without the labelled leaf) as a measure. After a light period, TPP leaves exported 37% compared to 51% for TPS leaves (Table 11). In a following dark-period, this percentage increased to respectively 52% and 81%. Both methods support the conclusion that TPS transgenic plants have a significantly enhanced export rate of photosynthetic products compared to the TPP transgenic plants.

—Absolute Amount of "New c", in Plant Parts

Export by TPS transgenics was significantly higher compared to TPP transgenics. Young growing TPS leaves import C stronger compared to young growing TPP leaves.

—Relative Increase of "New c" in Plant Parts: Sink-Strength

The relative contribution of "new C" to the concerning plant part is depicted in FIG. 17. This percentage is a measure for the sink-strength. A significant higher sink-strength was present in the TPS transgenics, especially in the shoot-top, the stem above and beneath the labelled leaf and the petiole of the labelled leaf.

TABLE 11

Source activity of a full grown labelled leaf: C accumulation and -export. Nett daily accumulation and export of C-assimilates in labelled leaf and the whole plant (above soil) after steady-state 13$^{c}$-labelling during a light period (day). N = 4: LSD values indicated the smallest significant differences for P < 0.05

| | | Source activity grown leaf | | | |
|---|---|---|---|---|---|
| Time (end of) | Transgene | new C in source leaf (% of total C in leaf) | nett C export during night % of "Day" | new C in source leaf (% of new C in plant) | nett C export to plant (% of total new C) |
| Day | TPS | 17.8 | — | 48.7 | 51 |
| | TPP | 22.6 | — | 63.0 | 37 |
| Day + night | TPS | 7.8 | 56 | 16.6 | 81 |
| | TPP | 13.8 | 39 | 48.4 | 52 |
| LSD 0.05 | | 2.4 | | 6.1 | |

—Relative Distribution, within the Plant, of "New C" Between the Plant Parts: Relative Sink Strength The distribution of fixed carbon between plant organs (FIG. 18) confirmed the above mentioned conclusions. TPS transgenic plants revealed a relative large export of assimilates to the shoot-top, the young growing leaf (day) and even the oldest leaf (without axillary meristems), and to the young and old stem.

Example 18

Lettuce

Performance of Lettuce Plants Transgenic for PC-TPS and PC-TPP

Constructs used in lettuce transformation experiments: PC-TPS and PC-TPP. PC-TPS transgenics were rescued during regeneration by culturing explants on 60 g/l sucrose. The phenotypes of both TPS and TPP transgenic plants are clearly distinguishable from wild-type controls; TPS transgenic plants have thick, dark-green leaves and TPP transgenic plants have light-green leaves with a smoother leaf-edge when compared to wild-type plants.

The morphology of the leaves, and most prominent the leaf-edges, was clearly affected by the expression of TPS and TPP. Leaves transgenic for PC-TPS were far more "notched" than the PC-TPP transgenic leaves that had a more smooth and round morphology (FIG. 19). Leaf extracts of transgenic lettuce lines were analyzed for sugars and starch (FIGS. 20A-D).

Example 19

Sugarbeet

Performance of Sugarbeet Plants Transgenic for PC-TPS and PC-TPP

Constructs used in sugarbeet transformation experiments: PC-TPS and PC-TPP. Transformation frequencies obtained with both the TPS and the TPP construct were comparable to controls. The phenotypes of both TPS and TPP transgenic plants were clearly distinguishable from wild-type controls; TPS transgenic plants had thick, dark-green leaves and TPP transgenic plants had light-green colored leaves with slightly taller petioles when compared to wild-type plants (FIG. 21). Taproot diameter was determined for all plants after ca. 8 weeks of growth in the greenhouse. Some PC-TPS transgenic lines having a leaf size similar to the control plants showed a significant larger diameter of the tap-root (FIG. 22). PC-TPP transgenic lines formed a smaller taproot compared to the non-transgenic controls. Leaf extracts of transgenic sugar-beet lines were analyzed for sugars and starch (FIGS. 20 A-D).

Example 20

*Arabidopsis*

Performance of *Arabidopsis* Plants Transgenic for PC-TPS and PC-TPP

Constructs used in *Arabidopsis* transformation experiments: PC-TPS and PC-TPP. The phenotypes of both TPS and TPP transgenic plants were clearly distinguishable from wild-type controls; TPS transgenic plants had thick, dark-green leaves and TPP transgenic plants had larger, bleaching leaves when compared to wild-type plants. Plants with high levels of TPP expression did not set seed.

Example 21

Potato

Performance of *Solanum Tuberosum* Plants Transgenic for TPS and TPP Constructs Construct: 35S-TPS pMOG799

Plants transgenic for pMOG799 were grown in the greenhouse and tuber-yield was determined (FIG. 23). The majority of the transgenic plants showed smaller leaf sizes when compared to wild-type controls. Plants with smaller leaf-sizes yielded less tuber-mass compared to control lines (FIG. 25).

Construct: 35S-TPP pMOG1010 and PC-TPP pMOG1124

Plants transgenic for PMOG 1010 and pMOG1124 were grown in the greenhouse and tuber-yield was determined. Tuber-yield (FIG. 24) was comparable or less than the wild-type control lines (FIG. 25).

Construct: PC-TPS pMOG1093

Plants transgenic for pMOG1093 were grown in the greenhouse and tuber-yield was determined. A number of transgenic lines having leaves with a size comparable to wild-type (B-C) and that were slightly darker green in colour yielded more tuber-mass compared to control plants (FIG. 26). Plants with leaf sizes smaller (D-G) than control plants yielded less tuber-mass.

Construct: Pat-TPP pMOG1128

Microtubers were induced in vitro on explants of pat-TPP transgenic plants. The average fresh weight biomass of the microtubers formed was substantially lower compared to the control lines.

Construct: Pat-TPS pMOG845

Plants transgenic for pMOG 845 were grown in the greenhouse and tuber-yield was determined. Three Pat-TPS lines produced more tuber-mass compared to control lines (FIG. 27).

Construct: PC TPS Pat TPS; pMOG1129(845-11/22/28)

Plants expressing PC TPS and Pat-TPS simultaneously were generated by retransforming Pat-TPS lines (resistant against kanamycin) with construct pMOG1129, harboring a PC TPS construct and a hygromycin resistance marker gene, resulting in genotypes pMOG1129(845-11), pMOG1129 (845-22) and pMOG1129(845-28). Tuber-mass yield varied between almost no yield up to yield comparable or higher then control plants (FIGS. 28 A-C).

Example 22

Tobacco

Performance of *N. tabacum* Plants Transgenic for TPS and TPP Constructs

Root System

Tobacco plants transgenic for 35S TPP (pMOG1010) or 35S TPS (pMOG799) were grown in the greenhouse. Root size was determined just before flowering. Lines transgenic for pMOG1010 revealed a significantly smaller/larger root size compared to pMOG795 and non-transgenic wild-type tobacco plants.

Influence of Expressing TPS and/or TPP on Flowering

Tobacco plants transgenic for 35S-TPS, PC-TPS, 35S-TPP or PC-TPP were cultured in the greenhouse. Plants expressing high levels of the TPS gene revealed significantly slower growth rates compared to wild-type plants. Flowering and senescence of the lower leaves was delayed in these plants resulting in a stay-green phenotype of the normally senescing leaves. Plants expressing high levels of the TPP gene did not make any flowers or made aberrant, not fully developing flower buds resulting in sterility.

Influence of Expressing TPS and/or TPP on Seed Setting

Tobacco plants transgenic for 35S-TPS, PC-TPS, 35S-TPP or PC-TPP were cultured in the greenhouse. Plants expressing high levels of the TPP gene revealed poor or no development of flowers and absence of seed-setting.

Influence of Expressing TPS and/or TPP on Seed Germination

Tobacco plants transgenic for 35S TPP (pMOG11010) or PC TPP were grown in the greenhouse. Some of the transgenic lines, having low expression levels of the transgene, did flower and set seed. Upon germination of S1 seed, a significantly reduced germination frequency was observed (or germination was absent) compared to S1 seed derived from wild-type plants (Table 12).

TABLE 12

Germination of transgenic 35S-TPP seeds

| Seedlot | Bleaching | Rel. (TPPmRNA) | Germination |
|---|---|---|---|
| 1010-2 | + | 15.8 | delayed |
| 1010-3 | − | 5.3 | delayed |
| 1010-4 | + | 4.2 | delayed |
| 1010-5 | + | 5.2 | delayed |
| 1010-6 | + | 3.9 | delayed |
| 1010-7 | − | 2.8 | delayed |
| 1010-8 | + | 6.5 | delayed |
| 1010-9 | + | 4.6 | delayed |
| 1010-10 | − | 1.9 | normal |
| 1010-11 | − | 5.7 | normal |
| 1010-12 | + | 1.4 | normal |
| 1010-14 | − | 0.1 | normal |
| 1010-15 | − | 0.3 | normal |
| 1010-18 | + | 5.6 | delayed |
| 1010-20 | + | 6.4 | delayed |
| 1010-21 | + | 9.5 | delayed |
| 1010-22 | + | 8.8 | not |
| 1010-23 | − | 4.5 | normal |
| 1010-24 | − | 10.2 | delayed |
| 1010-25 | − | 4.7 | delayed (less) |
| 1010-27 | − | 4.8 | normal |
| 1010-28 | + | 22.1 | delayed |
| 1010-31 | + | 9.4 | delayed (less) |
| 1010-32 | − | 0.3 | delayed (less) |
| 1010-33 | + | 14.7 | delayed |

Influence of Expressing TPS and/or TPP on Seed Yield

Seed-yield was determined for S1 plants transgenic for pMOG1010-5. On average, pMOG1010-5 yielded 4.9 g seed/plant (n=8) compared to 7.8 g seed/plant (n=8) for wild-type plants. The “1000-grain” weight is 0.06 g for line pMOG1010-5 compared to 0.08 g for wild-type Samsun NN. These data can be explained by a reduced export of carbohydrates from the source leaves, leading to poor development of seed “sink” tissue.

Influence of TPS and TPP Expression on Leaf Morphology

Segments of greenhouse grown PC-TPS transgenic, PC-TPP transgenic and non-transgenic control tobacco leaves were fixed, embedded in plastic and coupes were prepared to study cell structures using light-microscopy. Cell structures and morphology of cross-sections of the PC-TPP transgenic plants were comparable to those observed in control plants. Cross-sections of PC-TPS transgenics revealed that the spongy parenchyme cell-layer constituted of 7 layers of cells compared to 3 layers in wild-type and TPP transgenic plants (FIGS. 29A and B). This finding agrees with our observation that TPS transgenic plant lines form thicker and more rigid leaves compared to TPP and control plants.

Example 23

Inhibition of Cold-Sweetening by the Expression of Trehalose Phosphate Synthase Transgenic potato plants (*Solanum tuberosum* cv. Kardal) were generated harbouring the TPS gene under control of the potato tuber-specific patatin promoter (pMOG845; Example 1). Transgenic plants and wild-type control plants were grown in the greenhouse and tubers were harvested. Samples of tuber material were taken for sugar analysis directly after harvesting and after 6 months of storage at 4° C. Data resulting from the HPLC-PED analysis are depicted in FIG. 30.

What is clearly shown is that potato plants transgenic for $TPS_{E.coli}$ have a lower amount of total sugar (glucose, fructose and sucrose) accumulating in tubers directly after harvesting. After a storage period of 6 months at 4° C., the increase in soluble sugars is significantly less in the transgenic lines compared to the wild-type control lines.

Example 24

Improved Performance of 358 TPS 358 TPP (pMOG851) Transgenic Tobacco Plants Under Drought Stress Transgenic tobacco plants were engineered harbouring both the TPS and TPP gene from *E. coli* under control of the 35S CaMV promoter. The expression of the TPS and TPP genes was verified in the lines obtained using Northern blot and enzyme activity measurements. pMOG851-2 was shown to accumulate 0.008 mg trehalose·$g^{-1}$ fw and pMOGB51-5 accumulated 0.09 mg trehalose·$g^{-1}$ fw. Expression of both genes had a pronounced effect on plant morphology and growth performance under drought stress. When grown under drought stress imposed by limiting water supply, the two transgenic tobacco lines tested, pMOGS51-2 and pMOG851-5, yielded total dry weights that were 28% (P<0.01) and 39% (P<0.001) higher than those of wild-type tobacco. These increases in dry weight were due mainly to increased leaf production: leaf dry weights were up to 85% higher for pMOG851-5 transgenic plants. No significant differences were observed under well-watered conditions.

Drought Stress Experiments

F1 seeds obtained from self-fertilization of primary transformants pMOG851-2 and pMOG851-5 (Goddijn et al. (1997) Plant Physiol. 113, 181) were used in this study. Seeds were sterilized for 10 minutes in 20% household bleach, rinsed five times in sterile water, and sown on half-strength Murashige and Skoog medium containing 10 g·$L^{-1}$ sucrose and 100 mg·$L^{-1}$ kanamycin. Wildtype SR1 seeds were sown on plates without kanamycin. After two weeks seedlings from all lines were transferred to soil (sandy loam), and grown in a growth chamber at 22° C. at approximately 100 μE·$m^{-2}$ light intensity, 14 h·$d^{-1}$. All plants were grown in equal amounts of soil, in 3.8 liter pots. The plants were watered daily with half-strength Hoagland's nutrient solution. The seedlings of pMOG851-2 and pMOG851-5 grew somewhat slower than the wildtype seedlings. Since we considered it most important to start the experiments at equal developmental stage, we initiated the drought stress treatments of each line when the seedlings were at equal height (10 cm), at an equal developmental stage (4-leaves), and at equal dry weight (as measured from two additional plants of each line). This meant that the onset of pMOG851-2 treatment was two days later than wildtype, and that of pMOG851-5 seven days later than wildtype. From each line, six plants were subjected to drought stress, while four were kept under well-watered conditions as controls. The wildtype tobacco plants were droughted by maintaining them around the wilting point: when the lower half of the leaves were wilted, the plants were given so much nutrient solution that the plants temporarily regained turgor. In practice, this meant supplying 50 ml of nutrient solution every three days; the control plants were watered daily to keep them at field capacity. The pMOG851-2 and pMOG851-5 plants were then watered in the exact same way as wildtype, i.e., they were supplied with equal amounts of nutrient solution and after equal time intervals as wildtype. The stem height was measured regularly during the entire study period. All plants were harvested on the same day (32 d after the onset of treatment for the wildtype plants), as harvesting the transgenic plants at a later stage would complicate the comparison of the plant lines. At the time of harvest the total leaf area was measured using a Delta-T Devices leaf area meter (Santa Clara, Calif.). In addition, the fresh weight and dry weight of the leaves, stems and roots was determined.

A second experiment was done essentially in the same way, to analyze the osmotic potential of the plants. After 35 days of drought stress, samples from the youngest mature leaves were taken at the beginning of the light period (n=3).

Air-Drying of Detached Leaves

The water loss from air-dried detached leaves was measured from well-watered, four-week old pMOG851-2, pMOG851-5 and wildtype plants. Per plant line, five plants were used, and from each plant the two youngest mature leaves were detached and airdried at 25% relative humidity. The fresh weight of each leaf was measured over 32 hours. At the time of the experiment samples were taken from comparable, well-watered leaves, for osmotic potential measurements and determination of soluble sugar contents.

Osmotic Potential Measurements

Leaf samples for osmotic potential analysis were immediately stored in capped 1 ml syringes and frozen on dry ice. Just before analysis the leaf sap was squeezed into a small vial, mixed, and used to saturate a paper disc. The osmotic potential was then determined in Wescor C52 chambers, using a Wescor HR-33T dew point microvolt meter.

Chlorophyll Fluorescence

Chlorophyll fluorescence of the wildtype, pMOG851-2 and pMOG851-5 plants was measured for each plant line after 20 days of drought treatment, using a pulse modulation (PAM) fluorometer (Walz, Effeltrich, Germany). Before the measurements, the plants were kept in the dark for two hours, followed by a one-hour light period. Subsequently, the youngest mature leaf was dark-adapted for 20 minutes. At the beginning of each measurement, a small (0.05 μmol $m^{-2}$ $s^{-1}$ modulated at 1.6 KHz) measuring light beam was turned on, and the minimal fluorescence level ($F_0$) was measured. The maximal fluorescence level ($F_m$) was then measured by applying a: saturation light pulse of 4000 μmol $m^{-2}$ $s^{-1}$, 800 ms in duration. After another 20 s, when the signal was relaxed to near $F_0$, brief saturating pulses of actinic light (800 ms in length, 4000 μmol $m^{-2}$ $s^{-1}$) were given repetitively for 30 s with 2 s dark intervals. The photochemical ($q_Q$) and non-photochemical ($q_E$) quenching components were determined from the fluorescence/time curve according to Bolhar-Nordenkampf and Oquist (1993). At the moment of measurement, the leaves in question were not visibly wilted. Statistical data were obtained by one-way analysis of variance using the program Number Cruncher Statistical System (Dr. J. L. Hintze, 865 East 400 North, Kaysville, Utah 84037, USA).

Chlorophyll fluorescence analysis of drought-stressed plants showed a higher photochemical quenching ($q_Q$) and a higher ratio of variable fluorescence over maximal fluorescence ($F_v/F_m$) in pMOG851-5, indicating a more efficiently working photosynthetic machinery (Table 13).

TABLE 13

Chlorophyll fluorescence parameters of wild-type (wt) and trehalose-accumulating (pMOG851-2, pMOG851-5) transgenic tobacco plants. P (probability) values were obtained from ANOVA tests analyzing differences per plant line between plants grown under well-watered (control) or dry conditions, as well as differences between each of the transgenic lines and WT, grown under well-watered or dry conditions. $F_m$: maximal fluorescence; $F_v$: variable fluorescence ($F_m$-$F_0$): $q_Q$: photochemical quenching: $q_E$: non-photochemical quenching. $F_m$, $F_v$ are expressed in arbitrary units (chart mm).

| | | WT | pMOG851-1 | pMOG851-5 | 8-51-2/WT | 815-5 |
|---|---|---|---|---|---|---|
| $F_m$ | control | 174.4 | 180.4 | 175.6 | ns | ns |
| | dry | 151.5 | 155.7 | 167.8 | ns | 0.0068 |
| | P(ctrl.dry) | 0.0004 | 0.0000 | ns | | |
| $F_v$ | Control | 134.6 | 143.3 | 142.8 | ns | ns |
| | dry | 118.4 | 122.1 | 135.6 | ns | 0.0011 |
| | P (ctrl.dry) | 0.006 | 0.0000 | ns | | |
| $F_v/F_m$ | control | 0.771 | 0.794 | 0.813 | 0.059 | 0.0052 |
| | dry | 0.782 | 0.784 | 0.809 | ns | 0.0016 |
| | P (ctrl.dry) | Ns | Ns | Ns | | |
| $q_E$ | control | 15.2 | 23.8 | 29.9 | 0.259 | 0.0085 |
| | dry | 25.4 | 21.6 | 23.5 | ns | ns |
| | P (ctrl.dry) | 0.048 | ns | ns | | |
| $q_Q$ | control | 91.3 | 92.4 | 90.4 | ns | ns |
| | dry | 73.69 | 78.5 | 92.75 | ns | 0.0005 |
| | P (ctrl.dry) | 0.005 | 0.006 | ns | | |

Carbohydrate Analysis

At the time of harvest, pMOG851-5 plants contained 0.2 mg·g$^{-1}$ dry weight trehalose, whereas in pMOG851-2 and wildtype the trehalose levels were below the detection limit, under both stressed and unstressed conditions. The trehalose content in pMOG851-5 plants was comparable in stressed and unstressed plants (0.19 and 0.20 mg·g$^{-1}$ dry weight, respectively). Under well-watered conditions, the levels of glucose and fructose were twofold higher in pMOG851-5 plants than in wildtype. Leaves of stressed pMOG851-5 plants contained about threefold higher levels of each of the four nonstructural carbohydrates starch, sucrose, glucose and fructose, than leaves of stressed wildtype plants. In pMOG851-2 leaves, carbohydrate levels, like chlorophyll fluorescence values, did not differ significantly from those in wildtype. Stressed plants of all lines contained increased levels of glucose and fructose compared to unstressed plants.

Osmotic Potential of Drought Stressed and Control Plants

During a second, similar experiment under greenhouse conditions, the transgenic plants showed the same phenotypes as described above, and again the pMOG851-5 plants showed much less reduction in growth under drought stress than pMOG851-2 and wildtype plants. The osmotic potential in leaves of droughted pMOG851-5 plants (−1.77±0.39 Mpa) was significantly lower (P=0.017) than in wildtype leaves (−1.001±0.08 Mpa); pMOG851-2 showed intermediate values (−1.12±0.05 Mpa). Similarly, under well-watered conditions the osmotic potential of pMOG851-5 plants (−0.79±0.05 Mpa) was significantly lower (P=0.038) than that of wildtype leaves (−0.62±0.03 Mpa), with pMOG851-2 having intermediate values (−0.70±0.01 Mpa).

Airdrying of Detached Leaves

Leaves of pMOG851-2, pMOG851-5 and wildtype were detached and their fresh weight was measured over 32 hours of airdrying. Leaves of pMOG851-2 and pMOG851-5 plants lost significantly less water (P<0.05) than wildtype leaves: after 32 h leaves of pMOG851-5 and pMOG851-2 had 41% and 41% of their fresh weight left, respectively, compared to 30% for wildtype. At the time of the experiment samples were taken from comparable, well-watered leaves for osmotic potential determination and analysis of trehalose, sucrose, glucose and fructose. The two transgenic lines had lower osmotic potentials than wildtype (P<0.05), with pMOG851-5 having the lowest water potential (−0.63±0.03 Mpa), wildtype the highest (−0.51±0.02 Mpa) and pMOG851-2 intermediate (−0.57±0.04 Mpa). The levels of all sugars tested were significantly higher in leaves of pMOG851-5 plants than for wildtype leaves resulting in a threefold higher level of the four sugars combined (P=0.002). pMOG851-2 plants contained twofold higher levels of the four sugars combined (P=0.09). The trehalose levels were 0.24±0.02 mg·g$^{-1}$ DW in pMOG851-5 plants, and below detection in pMOG851-2 and wildtype.

Example 25

Performance of TPS and TPP Transgenic Lettuce Plant Lines Under Drought Stress Primary TPS and TPP transformants and wild-type control plants were subjected to drought-stress. Lines transgenic for TPP reached their wilting point first, then control plants, followed by TPS transgenic plants indicating that TPS transgenic lines, as observed in other plant species, have a clear advantage over the TPP and wild-type plants during drought stress.

Example 26

Bolting of Lettuce Plants is Affected in Plants Transgenic for PC-TPS or PC-TPP Bolting of lettuce is reduced in plants transgenic for PC-TPP (Table 14). Plant lines transgenic for PC-TPS show enhanced bolting compared to wild-type lettuce plants.

TABLE 14

| Bolting of lettuce plants | | | | | | |
|---|---|---|---|---|---|---|
| PC-TPP lines | Total # of plants | 1. Normal bolting | 2. Reduced bolting | 3. Visible inflorescence | 4. Possible fasciation | 5. Completely vegetative |
| 1A | 4 | | | | | 4 |
| 2A | 3 | | | | 1 | 2 |
| 3A | 2 | 2 | | | | |
| 4A | 5 | 1 | 1 | 1 | 2 | |
| 5A | 5 | | 1 | 1 | | 3 |
| 7A | 1 | | 1 | | | |
| 8A | 5 | 4 | 1 | | | |
| 9A | 5 | 5 | | | | |
| 10A | 3 | | 1 | | | 2 |
| 11A | 5 | | | 2 | | 3 |
| 12A | 4 | | | | | 4 |
| Control | 5 | 5 | | | | |

Example 27

Performance of Tomato Plants Transgenic for TPS and TPP

Constructs used in tomato transformation experiments: 35S TPP, PC-TPS, PC-TPS as-trehalase, PC-TPP, E8-TPS, E8-TPP, E8TPS E8 as-trehalase. Plants transgenic for the TPP gene driven by the plastocyanin promoter and 35S promoter revealed phenotypes similar to those observed in other plants: bleaching of leaves, reduced formation of flowers or absent flower formation leading to small fruits or absence of fruits. A small number of 35S-TPP transgenic lines generated extreme large fruits. Those fruits revealed enhanced outgrow of the pericarp. Plants transgenic for the TPS gene driven by the plastocyanin promoter and 35S promoter did not form small lancet shaped leaves. Some severely stunted plants did form small dark-green leaves. Plants transgenic for PC-TPS and PC-as-trehalase did form smaller and darker green leaves as compared to control plants.

The colour and leaf-edge of the 35S or PC driven TPS and TPP transgenic plants were clearly distinguishable similar to what is observed in other crops.

Plants harbouring the TPS and TPP gene under control of the fruit-specific E8 promoter did not show any phenotypical differences compared to wild-type fruits. Plants transgenic for E8 TPS E8 astrehalase produced aberrant fruits with a yellow skin and incomplete ripening.

Example 28

Performance of Potato Plants Transgenic for as-Trehalase and/or TPS

Constructs: 35S as-trehalase (pMOG1027) and 35S as-trehalase Pat TPS (PMOG1027(845-11/22/28).

Plants expressing 35S as-trehalase and pat-TPS simultaneously were generated by retransforming pat-TPS lines (resistant against kanamycin) with construct pMOG1027, harbouring the 35S as-trehalase construct and a hygromycin resistance marker gene, resulting in genotypes pMOG1027 (845-11), pMOG1027(845-22) and pMOG1027(845-28). Microtubers were induced in vitro and fresh weight of the microtubers was determined. The average fresh weight yield was increased for transgenic lines harbouring pMOG1027 (pMOG845-11/22/28). The fresh weight biomass of microtubers obtained from lines transgenic for pMOG1027 only was slightly higher then wild-type control plants. Resulting plants were grown in the greenhouse and tuber yield was determined (FIG. 33). Lines transgenic for 35S as-trehalase or a combination of 35S as-trehalase and pat-TPS yielded significantly more tuber-mass compared to control lines. Starch determination revealed no difference in starch content of tubers produced by plant lines having a higher yield (FIG. 34). A large number of the 1027(845-11/22/28) lines produced tubers above the soil out of the axillary buds of the leaves indicating a profound influence of the constructs used on plant development. Plant lines transgenic for 35S as-trehalase only did not form tubers above the soil.

Constructs: Pat as-trehalase (pMOG1028) and Pat as-trehalase Pat TPS (pMOG1028 845-11/22/28)

Plants expressing Pat as-trehalase and Pat-TPS simultaneously were generated by retransforming Pat-TPS lines (resistant against kanamycin) with construct pMOG1028, harboring the Pat as-trehalase construct and a hygromycin resistance marker gene, resulting in genotypes pMOG1028 (845-11), pMOG1028(845-22) and pMOG1028(845-28). Plants were grown in the greenhouse and tuber yield was determined (FIGS. 35 A-E). A number of pMOG1028 transgenic lines yielded significantly more tuber-mass compared to control lines. Individual plants transgenic for both Pat TPS and Pat as-trehalase revealed a varying tuber-yield from almost no yield up to a yield comparable to or higher then the control lines (FIGS. 35 A-E).

Construct: PC as-Trehalase (pMOG1092)

Plants transgenic for pMOG1092 were grown in the greenhouse and tuber-yield was determined. Several lines formed darker-green leaves compared to controls. Tuber-yield was significantly enhanced compared to non-transgenic plants (FIG. 36).

Construct: PC as-Trehalase PC-TPS (PMOG 1130)

Plants transgenic for pMOG 1130 were grown in the greenhouse and tuber-yield was determined. Several transgenic lines developed small dark-green leaves and severely stunted growth indicating that the phenotypic effects observed when plants are transformed with TPS is more severe when the as-trehalase gene is expressed simultaneously (see Example 21). Tuber-mass yield varied between almost no yield up to significantly more yield compared to control plants (FIG. 37).

Example 29

Overexpression of a Potato Trehalase cDNA in *N. Tabacum*

Construct: de35S CaMV trehalase (pMOG1078)

Primary tobacco transformants transgenic for pMOG1078 revealed a phenotype different from wild-type tobacco, some transgenics have a dark-green leaf colour and a thicker leaf (the morphology of the leaf is not lancet-shaped) indicating an influence of trehalase gene-expression on plant metabolism. Seeds of selfed primary transformants were sown and selected on kanamycin. The phenotype showed to segregate in a mendelian fashion in the S1 generation.

DEPOSITS

The following deposits were made under the Budapest Treaty. The clones were deposited at the Centraal Bureau voor Schimnelcultures, Oosterstraat 1, P.O. Box 273, 3740 AG Baarn, The Netherlands on Apr. 21, 1997 and received the following numbers:

| | | |
|---|---|---|
| *Escherichia coli* | DH5alpha/pMOG1192 | CBS 692.97 |
| | DH5alpha/pMOG1240 | CBS 693.97 |
| | DH5alpha/pMOG1241 | CBS 694.97 |
| | DH5alpha/pMOG1242 | CBS 695.97 |
| | DH5alpha/pMOG1243 | CBS 696.97 |
| | DH5alpha/pMOG1244 | CBS 697.97 |
| | DH5alpha/pMOG1245 | CBS 698.97 |

Deposited Clones:

pMOG1192 harbors the *Helianchus annuus* TPS/TPP bipartite cDNA inserted in the multi-copy vector PGEM-T (Promega).

pMOG1240 harbors the tobacco TPS "825" bp cDNA fragment inserted in pCRscript (Stratagene).

pMOG1241 harbors the tobacco TPS "840" bp cDNA fragment inserted in pGEM-T (Promega).

pMOG1242 harbors the tobacco TPS "630" bp cDNA fragment inserted in pGEM-T (Promega).

pMOG1243 harbors the tobacco TPP "543", bp cDNA fragment inserted in pGEM-T (Promega).

pMOG1244 harbors the tobacco TPP "723" bp cDNA fragment inserted in a pUC18 plasmid.

pMOG1245 harbors the tobacco TPP "447" bp fragment inserted in PGEM-T (Promega).

List of Relevant pMOG### and pVDH### Clones

1. Binary Vectors pMOG23 Binary vector (ca. 10 Kb) harboring the NPTII selection marker pMOG22 Derivative of pMOG23, the NPTII-gene has been replaced by the HPT-gene which confers resistance to hygromycine pVDH 275 Binary vector derived from pMOG23, harbors a plastocyanin promoter-nos terminator expression cassette.

pMOG402 Derivative of pMOG23, a point-mutation in the NPTII-gene has been restored, no KpnI restriction site present in the polylinker pMOG800 Derivative of pMOG402 with restored KpnI site in polylinker 2. TPS/TPP Expression Constructs pMOG 799 35S-TPS-3'nos[1]

pMOG 810 idem with Hyg marker pMOG 845 Pat-TPS-3'PotPiII pMOG 925 idem with Hyg marker pMOG 851 35S-TPS-3'nos 35S-TPP(atg)[2]

pMOG 1010 de35S CaMV any leader TPP(gtg), PotPiII pMOG 1142 idem with Hyg marker pMOG 1093 Plastocyanin-TPS-3'nos pMOG 1129 idem with Hyg marker pMOG 1177 Plastocyanin-TPS-3'PotPiII 3'nos pVDH 318 Identical to pMOG 1177

Functionally identical to pMOG1093 pMOG 1124 Plastocyanin-TPP(gtg) 3'PotPiII 3'nos pVDH 321 Identical to pMOG1124 pMOG 1128 Patatin TPP(gtg) 3'PotPiII pMOG 1140 E8-TPS-3'nos pMOG 1141 E8-TPP(gtg)-3'PotPiII 3. Trehalase Constructs pMOG 1028 Patatin as-trehalase 3'PotPiII, Hygromycin resistance marker pMOG 1078 de35S CaMV amv leader trehalase 3'nos pMOG 1090 de35S CaMV amv leader as-trehalase 3'nos pMOG 1027 idem with Hyg marker pMOG 1092 Plastocyanin-as trehalase-3'nos pMOG 1130 Plastocyanin-as trehalase-3'nos Plastocyanin-TPS-3'nos pMOG 1153 E8-TPS-3'nos E8-as trehalase-3'PotPiII 1. All constructs harbour the NPTII selection marker unless noted otherwise 2. Two types of TPP constructs have been used as described in Goddijn et al. (1997) Plant Physiol. 133, 181.

The invention claimed is:

1. A method of stimulating carbon flow in a plant, the method comprising transforming a plant cell or plant tissue with a nucleic acid encoding a trehalose phosphate synthase gene, thereby producing a transformed plant cell or a transformed plant tissue, wherein the gene is driven by a promoter which functions in the plant to drive expression of the gene, regenerating a transformant from the transformed plant cell or the transformed plant tissue, growing up the transformant into the plant, and selecting for the plant having stimulated carbon flow.

2. A method for the modification of source-sink relations in a plant the method comprising transforming a plant cell or plant tissue with a nucleic acid encoding a trehalose phosphate synthase gene, thereby producing a transformed plant cell or a transformed plant tissue, wherein the gene is driven by a promoter which functions in the plant to drive expression of the gene, regenerating a transformant from the transformed plant cell or the transformed plant tissue, growing up the transformant into the plant, and selecting for the plant having modified source-sink relations.

3. A method for modification of metabolism in a plant, the method comprising transforming a plant cell or plant tissue with a nucleic acid encoding a trehalose phosphate synthase gene, thereby producing a transformed plant cell or a transformed plant tissue, wherein the gene is driven by a promoter which functions in the plant to drive expression of the gene, regenerating a transformant from the transformed plant cell or the transformed plant tissue, growing up the transformant into the plant, and selecting for the plant having modified metabolism.

4. A method of stimulating photosynthesis in a plant cell comprising increasing the intracellular availability of trehalose-6-phosphate, wherein increasing the intracellular availability of trehalose-6-phosphate comprises transforming the plant cell with a nucleic acid encoding trehalose phosphate synthase operably linked to a promoter in sense orientation, and selecting for the plant having stimulated photosynthesis.

5. A method of obtaining a dwarfed plant comprising increasing the intracellular availability of trehalose-6-phosphate, wherein increasing the intracellular availability of trehalose-6-phosphate comprises transforming the plant cell with a nucleic acid encoding trehalose phosphate synthase operably linked to a promoter in sense orientation, and selecting for the plant having dwarfed.

6. A method of reducing cold sweetening in a plant comprising increasing the intracellular availability of trehalose-6-phosphate, wherein increasing the intracellular availability of trehalose-6-phosphate comprises transforming the plant cell with a nucleic acid encoding trehalose phosphate synthase operably linked to a promoter in sense orientation, and selecting for the plant having reduced cold sweetening.

7. A method for stimulation of carbon flow, the method comprising transforming cells or tissues of the plant with a nucleic acid encoding a trehalose-6-phosphate phosphatase operably linked to a promoter in sense orientation, regenerating transformants from the transformed cells or tissues, and growing up said transformants into plants, and selecting for the plant having stimulated carbon flow.

8. A method of claim 7, wherein the source of the trehalose-6-phosphate phosphatase is selected from the group consisting of microorganisms, plants or animals.

9. A method of claim 8, wherein the source of the trehalose-6-phosphate phosphatase is from plants.

10. A method for the modification of source-sink relations in a plant, the method comprising transforming cells or tissues of the plant with a nucleic acid encoding a trehalose-6-phosphate phosphatase operably linked to a promoter in sense orientation, regenerating transformants from the transformed cells or tissues, and growing up said transformants into plants, and selecting for the plant having modified source-sink relations.

11. A method of claim 10, wherein the source of the trehalose-6-phosphate phosphatase is selected from the group consisting of microorganisms, plants or animals.

12. A method of claim 11, wherein the source of the trehalose-6-phosphate phosphatase is from plants.

13. A method for modification of metabolism in a plant, the method comprising transforming cells or tissues of the plant with a nucleic acid encoding a trehalose-6-phosphate phosphatase gene operably linked to a promoter in sense orientation, regenerating transformants from the transformed cells or tissues, and growing up said transformants into plants, and selecting for the plant having modified metabolism.

14. A method of claim 13, wherein the source of the trehalose-6-phosphate phosphatase is selected from the group consisting of microorganisms, plants or animals.

15. A method of claim 14, wherein the source of the trehalose-6-phosphate phosphatase is from plants.

* * * * *